United States Patent
Liu et al.

(10) Patent No.: US 9,624,485 B2
(45) Date of Patent: Apr. 18, 2017

(54) GENETIC INCORPORATION OF UNNATURAL AMINO ACIDS INTO PROTEINS IN MAMMALIAN CELLS

(75) Inventors: Wenshe Liu, College Station, TX (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 1269 days.

(21) Appl. No.: 12/311,545

(22) PCT Filed: Oct. 17, 2007

(86) PCT No.: PCT/US2007/022232
§ 371 (c)(1),
(2), (4) Date: Jul. 14, 2009

(87) PCT Pub. No.: WO2008/073184
PCT Pub. Date: Jun. 19, 2008

(65) Prior Publication Data
US 2010/0021963 A1    Jan. 28, 2010

Related U.S. Application Data

(60) Provisional application No. 60/853,008, filed on Oct. 18, 2006, provisional application No. 60/923,458, filed on Apr. 12, 2007.

(51) Int. Cl.
    C12N 5/00      (2006.01)
    C12N 9/00      (2006.01)
    C12P 21/02     (2006.01)

(52) U.S. Cl.
    CPC .............. C12N 9/93 (2013.01); C12P 21/02 (2013.01)

(58) Field of Classification Search
    CPC ...................................................... C12P 21/00
    See application file for complete search history.

(56) References Cited

U.S. PATENT DOCUMENTS

| | | | |
|---|---|---|---|
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,129,333 B2 | 10/2006 | Schultz et al. | |
| 7,183,082 B2 | 2/2007 | Schultz et al. | |
| 7,199,222 B2 | 4/2007 | Shultz et al. | |
| 7,217,809 B2 | 5/2007 | Schultz et al. | |
| 7,238,510 B2 | 7/2007 | Schultz et al. | |
| 7,262,040 B2 | 8/2007 | Schultz et al. | |
| 7,566,555 B2* | 7/2009 | Yokoyama et al. | 435/183 |
| 7,888,063 B2* | 2/2011 | Deiters et al. | 435/68.1 |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0136513 A1 | 6/2005 | Zhang et al. | |
| 2005/0208536 A1 | 9/2005 | Schultz et al. | |
| 2005/0227318 A1 | 10/2005 | Alfonta et al. | |
| 2005/0272121 A1 | 12/2005 | Xie et al. | |
| 2006/0063244 A1 | 3/2006 | Schultz et al. | |
| 2006/0068478 A1 | 3/2006 | Schultz et al. | |
| 2006/0073507 A1 | 4/2006 | Deiters et al. | |
| 2006/0110784 A1 | 5/2006 | Deiters et al. | |
| 2006/0110796 A1 | 5/2006 | Schultz et al. | |
| 2006/0134746 A1* | 6/2006 | Deiters et al. | 435/69.1 |
| 2006/0160175 A1 | 7/2006 | Anderson et al. | |
| 2006/0177900 A1 | 8/2006 | Anderson et al. | |
| 2006/0234367 A1 | 10/2006 | Schultz et al. | |
| 2006/0246509 A1 | 11/2006 | Deiters et al. | |
| 2007/0009990 A1 | 1/2007 | Alfonta et al. | |
| 2007/0020634 A1 | 1/2007 | Anderson et al. | |
| 2007/0042461 A1 | 2/2007 | Anderson et al. | |
| 2007/0111193 A1 | 5/2007 | Zhang et al. | |
| 2007/0154952 A1 | 7/2007 | Chin et al. | |
| 2007/0166791 A1 | 7/2007 | Chin et al. | |
| 2007/0172915 A1 | 7/2007 | Schultz et al. | |
| 2007/0178448 A1 | 8/2007 | Tsao et al. | |
| 2007/0184517 A1 | 8/2007 | Schultz et al. | |
| 2007/0238152 A1 | 10/2007 | Wang et al. | |
| 2008/0146781 A1 | 6/2008 | Cho et al. | |

(Continued)

FOREIGN PATENT DOCUMENTS

| | | |
|---|---|---|
| WO | WO 2004/094593 A2 | 11/2004 |
| WO | WO 2006/110182 | 12/2006 |
| WO | WO 2007/103490 | 9/2007 |

OTHER PUBLICATIONS

Pear et al. Production of high-titer helper-free retroviruses by transient transfection. Proc Natl Acad Sci U S A. Sep. 15, 1993;90(18):8392-6.*
Hino et al. (2005) "Protein photo-cross-linking in mammalian cells by site-specific incorporation of a photoreactive amino acid." *Nature Methods*, 2(3): 201-206.
Liu et al. (2007) "Genetic incorporation of unnatural amino acids into proteins in mammalian cells." *Nature Methods*, 4(3): 239-244.
Alfonta et al. (2003) "Site-Specific Incorporation of a Redox-Active Amino Acid into Proteins," *Journal of the American Chemistry Society*, 125:14662-14663.
Anderson et al. (2004) "An expanded genetic code with a functional quadruplet codon," *Proceedings of the National Academy of Sciences, USA*, 101(20): 7566-7571.
Chin et al. (2003) "An expanded eukaryotic genetic code," *Science*, 301: 964-967.

(Continued)

*Primary Examiner* — Catherine S Hibbert
(74) *Attorney, Agent, or Firm* — Quine Intellectual Property Law Group PC

(57) ABSTRACT

The invention relates to orthogonal pairs of tRNAs and aminoacyl-tRNA synthetases that can incorporate unnatural amino acids into proteins in mammalian host cells, for example, primate host cells and rodent host cells. The invention provides, for example but not limited to, translation systems that include host cells (e.g., primate or rodent cells), orthogonal aminoacyl-tRNA synthetases derived from eubacterial synthetases, orthogonal tRNAs, and the unnatural amino acid. The invention also relates to methods for producing proteins of interest comprising at least one unnatural amino acid in mammalian host cell systems.

10 Claims, 47 Drawing Sheets

(56) References Cited

U.S. PATENT DOCUMENTS

2010/0158879 A1* 6/2010 Sisk et al. ............... 424/93.21
2013/0245230 A1* 9/2013 Dieters et al. ........... 530/387.3

OTHER PUBLICATIONS

Chin et al. (2003) "Progress toward an expanded eukaryotic genetic code," *Chemistry & Biology*, 10: 511-519.

Liu and Schultz (2006) "Recombinant Expression of Selectively Sulfated Proteins in *E. coli*," *Nature Biotechnology*, 24(11): 1436-1440.

Monahan et al. (2003) "Site-specific incorporation of unnatural amino acids into receptors expressed in Mammalian cells," *Chemistry & Biology*, 10(6): 573-580.

Sakamoto et al. (2002) "Site-specific incorporation of an unnatural amino acid into proteins in mammalian cells," *Nucleic Acids Research*, 30(31): 4692-4699.

Santoro et al. (2003) "An archaebacteria-derived glutamyl-tRNA synthetase and tRNA pair for unnatural amino acid mutagenesis of proteins in *Escherichia coli*," *Nucleic Acids Research*, 31(23): 6700-6709.

Summerer et al. (2006) "A Genetically Encoded Fluorescent Amino Acid," *Proceedings of the National Academy of Sciences, USA*, 103(26): 9785-9789.

Wang and Schultz (2005) "Expanding the Genetic Code," *Angewandte Chemie Int. Ed.*, 44(1): 34-66.

Wang and Schultz (2002), "Expanding the Genetic Code," *Chem. Commun.*, 1: 1-11.

Wang et al. (2001) "Expanding the genetic code of *Escherichia coli*," *Science*, 292: 498-500.

Wang et al. (2004) "Evolution of new nonantibody proteins via iterative somatic hypermutation," *Proceedings of the National Academy of Sciences, USA*, 101(48): 16745-16749.

Wang et al. (2006) "A Genetically Encoded Fluorescent Amino Acid," *Journal of the American Chemistry Society*, 128(27): 8738-8739.

Wang et al. (2006) "Expanding the Genetic Code," *Annu. Rev. Biophys. Biomol. Struct.*, 35: 225-249.

Wu et al. (2004) "A genetically encoded photocaged amino acid," *Journal of the American Chemistry Society*, 126: 14306-14307.

Xie and Schultz (2006) "A Chemical Toolkit for Proteins—an Expanded Genetic Code," *Nature Reviews: Molecular Cell Biology*, 7(10): 775-782.

Xie and Schultz (2005) "Adding Amino Acids to the Genetic Repertoire," *Current Opinion in Chemical Biology*, 9(6): 548-554.

Xie and Schultz (2005) "An Expanding Genetic Code," *Methods* 36(3): 227-238.

Zhang et al. (2004) "A new strategy for the synthesis of glycoproteins," *Science*, 303, 371-373.

Zhang et al. (2004) "Selective incorporation of 5-hydroxytryptophan into proteins in mammalian cells," *Proceedings of the National Academy of Sciences, USA*, 101: 8882-8887.

Hawko & Francklyn (2001) "Covariation of a specificity-determining structural motif in an aminoacyl-tRNA synthetase and a tRNA identity element," *Biochemistry*, 40(7):1930-1936.

Philipson et al. (2001) "Incorporation of caged systeine and caged tyrosine into a transmembrane segment of the nicotinic Ach receptor." *American Journal of Physiology and Cell Physiology*, 281: C195-C206.

* cited by examiner

| Structure Number | Name (abbreviation) | Structure |
|---|---|---|
| 1 | *p*-methoxy-L-phenylalanine (pMpa)<br><br>also termed:<br>O-methyl-L-tyrosine<br>O-Me-L-tyrosine<br>O-MeY | 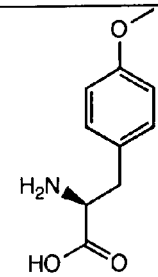 |
| 2 | *p*-acetyl-L-phenylalanine (pApa)<br><br>also termed:<br>*p*-acyl-L-phenylalanine<br>*p*-acetylPhe | 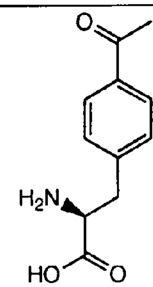 |
| 3 | *p*-benzoyl-L-phenylalanine (pBpa)<br><br>also termed:<br>*p*-benzophenone<br>*p*-benzoylPhe | 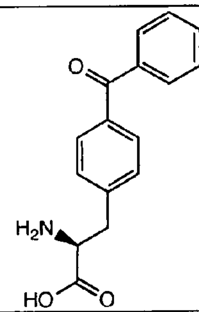 |
| 4 | *p*-iodo-L-phenylalanine (pIpa)<br><br>also termed<br>*p*-iodo-tyrosine | 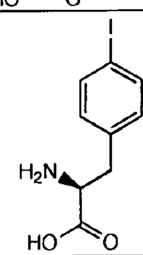 |
| 5 | *p*-azido-L-phenylalanine (pAzpa)<br><br>also termed:<br>*p*-azidoPhe | 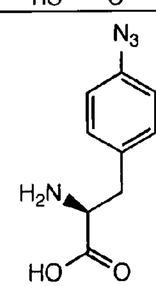 |

Fig. 1

| Structure Number | Name (abbreviation) | Structure |
|---|---|---|
| 6 | p-propargyloxyphenylalanine (pPpa)<br><br>also termed:<br>pPRO-Phe<br>pPR<br>2-amino-3-[4-(prop-2-ynyloxy)phenyl]-propionic acid according to IUPAC nomenclature | 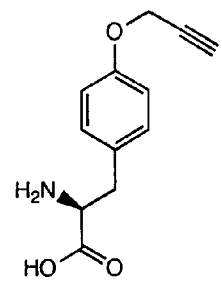 |
| 7 | α-aminocaprylic acid<br><br>also termed:<br>alpha-aminocaprylic acid<br>2-aminocaprylic acid<br>2-aminooctanoic acid<br>or "C8" | 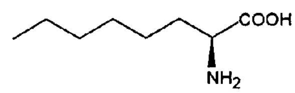 |
| 8 | o-nitrobenzylcysteine (o-NBC or nbC) | 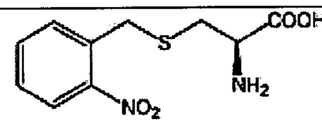 |
| 9 | 1,5-dansylalanine<br><br>also termed:<br>2-amino-3-(5-dimethylamino-naphthalene-1-sulfonylamino)-propionic acid according to IUPAC nomenclature | 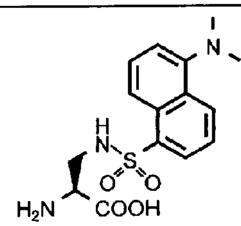 |
| 10 | o-nitrobenzylserine (o-NBS or nbS) | 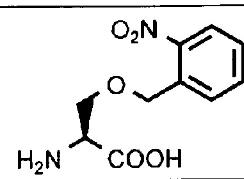 |

Fig. 1 Cont.

Nucleotide and Amino Acid Sequences

| SEQ ID NO and Description | SEQUENCE |
|---|---|
| SEQ ID NO: 1<br>E. coli suppressor tRNA$^{Leu5}_{CUA}$ | GCCCGGAUGGUGGAAUCGGUAGACACAAGGGAUUCUAAAUCCCUCGGCGUUCGCGCUGU<br>GCGGGUUCAAGUCCCGCUCCGGGUACCA |
| SEQ ID NO: 2<br>E. coli suppressor tyrosyl-tRNA (Ec-tRNA$^{Tyr}$) | GGTGGGGTTCCCGAGCGGCCAAAGGGAGCAGACTCTAAATCTGCCGTCATCGACTTCGA<br>AGGTTCGAATCCTTCCCCCACCACCA |
| SEQ ID NO: 3<br>Bacillus stearothermophilus amber suppressor tyrosyl-tRNA(CUA) (Bs-tRNA$^{Tyr}_{CUA}$) | GGAGGGGTAGCGAAGTGGCTAAACGCGGCGGACTCTAAATCCGCTCCCTTTGGGTTCGG<br>CGGTTCGAATCCGTCCCCCTCCA |
| SEQ ID NO: 4<br>Wild-type E. coli leucyl-tRNA synthetase (Ec LeuRS) amino acid sequence | MQEQYRPEEIESKVQLHWDEKRTFEVTEDESKEKYYCLSMLPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWYYARYTCPQYKEGMLDSEAANYWLPVDIYIGGI<br>EHAIMHLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |

Fig. 16

| SEQ ID NO and Description | SEQUENCE |
|---|---|
| SEQ ID NO: 5<br><br>Wild-type *E. coli* leucyl-tRNA synthetase (*Ec*LeuRS) nucleotide sequence | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTA<br>TGCTTCCCTATCCTTCTGGTCGACTACACATGGGCCACGTACGTAACTACACCATCGGT<br>GACGTGATCGCCCGCTACCAGCATATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCAACGAACAAGTTATCGACGGCTGCTGCTGG<br>CGCTGCGATACCAAAGTTGAACGTAAAGAGATCCCGCAGTGGTTTATCAAAATCAATGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTACGTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCCGTGAAACCGACACTTTCGACAC<br>CTTTATGGAGTCCTCCTGGTACTATGCGCGCTACACTTGCCCGCAGTACAAGAAGGTA<br>TGCTGGATTCCGAAGCGGCTAACTACTGGCTGCCGGTGGATATCTACATTGGTGGTATT<br>GAACACGCCATTATGCACCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGACCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |
| SEQ ID NO: 6<br><br>*E. coli* wild-type TyrRS (synthetase) | MASSNLIKQLQERGLVAQVTDEEALAERLAQGPIALYCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYDFACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |

Fig. 16 cont.

| SEQ ID NO and Description | SEQUENCE |
|---|---|
| SEQ ID NO: 7<br><br>E. coli wild-type TyrRS (synthetase) polynucleotide | ATGGCAAGCAGTAACTTGATTAAACAATTGCAAGAGCGGGGGCTGGTAGCCCAGGTGAC<br>GGACGAGGAAGCGTTAGCAGAGCGACTGGCGCAAGGCCCGATCGCGCTCTATTGCGGCT<br>TCGATCCTACCGCTGACAGCTTGCATTTGGGGCATCTTGTTCCATTGTTATGCCTGAAA<br>CGCTTCCAGCAGGCGGGCCACAAGCCGGTTGCGCTGGTAGGCGGCGCGACGGGTCTGAT<br>TGGCGACCCGAGCTTCAAAGCTGCCGAGCGTAAGCTGAACACCGAAGAAACTGTTCAGG<br>AGTGGGTGGACAAAATCCGTAAGCAGGTTGCCCCGTTCCTCGATTTCGACTGTGGAGAA<br>AACTCTGCTATCGCGGCGAACAACTATGACTGGTTCGGCAATATGAATGTGCTGACCTT<br>CCTGCGCGATATTGGCAAACACTTCTCCGTTAACCAGATGATCAACAAAGAAGCGGTTA<br>AGCAGCGTCTCAACCGTGAAGATCAGGGGATTTCGTTCACTGAGTTTTCCTACAACCTG<br>TTGCAGGGTTATGACTTCGCCTGTCTGAACAAACAGTACGGTGTGGTGCTGCAAATTGG<br>TGGTTCTGACCAGTGGGGTAACATCACTTCTGGTATCGACCTGACCCGTCGTCTGCATC<br>AGAATCAGGTGTTTGGCCTGACCGTTCCGCTGATCACTAAAGCAGATGGCACCAAATTT<br>GGTAAAACTGAAGGCGGCGCAGTCTGGTTGGATCCGAAGAAACCAGCCCGTACAAATT<br>CTACCAGTTCTGGATCAACACTGCGGATGCCGACGTTTACCGCTTCCTGAAGTTCTTCA<br>CCTTTATGAGCATTGAAGAGATCAACGCCCTGGAAGAAGAAGATAAAAACAGCGGTAAA<br>GCACCGCGCGCCCAGTATGTACTGGCGGAGCAGGTGACTCGTCTGGTTCACGGTGAAGA<br>AGGTTTACAGGCGGCAAAACGTATTACCGAATGCCTGTTCAGCGGTTCTTTGAGTGCGC<br>TGAGTGAAGCGGACTTCGAACAGCTGGCGCAGGACGGCGTACCGATGGTTGAGATGGAA<br>AAGGGCGCAGACCTGATGCAGGCACTGGTCGATTCTGAACTGCAACCTTCCCGTGGTCA<br>GGCACGTAAAACTATCGCCTCCAATGCCATCACCATTAACGGTGAAAAACAGTCCGATC<br>CTGAATACTTCTTTAAAGAAGAAGATCGTCTGTTTGGTCGTTTTACCTTACTGCGTCGC<br>GGTAAAAAGAATTACTGTCTGATTTGCTGGAAATAA |
| SEQ ID NO: 8<br><br>pOMeTyrRS-1 Synthetase polynucleotide | ATGGCAAGCAGTAACTTGATTAAACAATTGCAAGAGCGGGGGCTGGTAGCCCAGGTGAC<br>GGACGAGGAAGCGTTAGCAGAGCGACTGGCGCAAGGCCCGATCGCCACTCGTGTGTGGCT<br>TCGATCCTACCGCTGACAGCTTGCATTTGGGGCATCTTGTTCCATTGTTATGCCTGAAA<br>CGCTTCCAGCAGGCGGGCCACAAGCCGGTTGCGCTGGTAGGCGGCGCGACGGGTCTGAT<br>TGGCGACCCGAGCTTCAAAGCTGCCGAGCGTAAGCTGAACACCGAAGAAACTGTTCAGG<br>AGTGGGTGGACAAAATCCGTAAGCAGGTTGCCCCGTTCCTCGATTTCGACTGTGGAGAA<br>AACTCTGCTATCGCGGCCAATAATTATGACTGGTTCGGCAATATGAATGTGCTGACCTT<br>CCTGCGCGATATTGGCAAACACTTCTCCGTTAACCAGATGATCAACAAAGAAGCGGTTA<br>AGCAGCGTCTCAACCGTGAAGATCAGGGGATTTCGTTCACTGAGTTTTCCTACAACCTG<br>CTGCAGGGTTATAGTATGGCCTGTTTGAACAAACAGTACGGTGTGGTGCTGCAAATTGG<br>TGGTTCTGACCAGTGGGGTAACATCACTTCTGGTATCGACCTGACCCGTCGTCTGCATC<br>AGAATCAGGTGTTTGGCCTGACCGTTCCGCTGATCACTAAAGCAGATGGCACCAAATTT<br>GGTAAAACTGAAGGCGGCGCAGTCTGGTTGGATCCGAAGAAACCAGCCCGTACAAATT<br>CTACCAGTTCTGGATCAACACTGCGGATGCCGACGTTTACCGCTTCCTGAAGTTCTTCA<br>CCTTTATGAGCATTGAAGAGATCAACGCCCTGGAAGAAGAAGATAAAAACAGCGGTAAA<br>GCACCGCGCGCCCAGTATGTACTGGCGGAGCAGGTGACTCGTCTGGTTCACGGTGAAGA<br>AGGTTTACAGGCGGCAAAACGTATTACCGAATGCCTGTTCAGCGGTTCTTTGAGTGCGC<br>TGAGTGAAGCGGACTTCGAACAGCTGGCGCAGGACGGCGTACCGATGGTTGAGATGGAA<br>AAGGGCGCAGACCTGATGCAGGCACTGGTCGATTCTGAACTGCAACCTTCCCGTGGTCA<br>GGCACGTAAAACTATCGCCTCCAATGCCATCACCATTAACGGTGAAAAACAGTCCGATC<br>CTGAATACTTCTTTAAAGAAGAAGATCGTCTGTTTGGTCGTTTTACCTTACTGCGTCGC<br>GGTAAAAAGAATTACTGTCTGATTTGCTGGAAATAA |

Fig. 16 cont.

| SEQ ID NO and Description | SEQUENCE |
|---|---|
| SEQ ID NO: 9<br><br>pOMeTyrRS-2 Synthetase polynucleotide | ATGGCAAGCAGTAACTTGATTAAACAATTGCAAGAGCGGGGGCTGGTAGCCCAGGTGAC<br>GGACGAGGAAGCGTTAGCAGAGCGACTGGCGCAAGGCCCGATCGCACTCACTTGTGGCT<br>TCGATCCTACCGCTGACAGCTTGCATTTGGGGCATCTTGTTCCATTGTTATGCCTGAAA<br>CGCTTCCAGCAGGCGGGCCACAAGCCGGTTGCGCTGGTAGGCGGCGCGACGGGTCTGAT<br>TGGCGACCCGAGCTTCAAAGCTGCCGAGCGTAAGCTGAACACCGAAGAAACTGTTCAGG<br>AGTGGGTGGACAAAATCCGTAAGCAGGTTGCCCCGTTCCTCGATTTCGACTGTGGAGAA<br>AACTCTGCTATCGCGGCCAATAATTATGACTGGTTCAGCAATATGAATGTGCTGACCTT<br>CCTGCGCGATATTGGCAAACACTTCTCCGTTAACCAGATGATCAACAAAGAAGCGGTTA<br>AGCAGCGTCTCAACCGTGAAGATCAGGGGATTTCGTTCACTGAGTTTTCCTACAACCTG<br>CTGCAGGGTTATACGTATGCCTGTCTGAACAAACAGTACGGTGTGGTGCTGCAAATTGG<br>TGGTTCTGACCAGTGGGGTAACATCACTTCTGGTATCGACCTGACCCGTCGTCTGCATC<br>AGAATCAGGTGTTTGGCCTGACCGTTCCGCTGATCACTAAAGCAGATGGCACCAAATTT<br>GGTAAAACTGAAGGCGGCGCAGTCTGGTTGGATCCGAAGAAAACCAGCCCGTACAAATT<br>CTACCAGTTCTGGATCAACACTGCGGATGCCGACGTTTACCGCTTCCTGAAGTTCTTCA<br>CCTTTATGAGCATTGAAGAGATCAACGCCCTGGAAGAAGAAGATAAAAACAGCGGTAAA<br>GCACCGCGCGCCCAGTATGTACTGGCGGAGCAGGTGACTCGTCTGGTTCACGGTGAAGA<br>AGGTTTACAGGCGGCAAAACGTATTACCGAATGCCTGTTCAGCGGTTCTTTGAGTGCGC<br>TGAGTGAAGCGGACTTCGAACAGCTGGCGCAGGACGGCGTACCGATGGTTGAGATGGAA<br>AAGGGCGCAGACCTGATGCAGGCACTGGTCGATTCTGAACTGCAACCTTCCCGTGGTCA<br>GGCACGTAAAACTATCGCCTCCAATGCCATCACCATTAACGGTGAAAAACAGTCCGATC<br>CTGAATACTTCTTTAAAGAAGAAGATCGTCTGTTTGGTCGTTTTACCTTACTGCGTCGC<br>GGTAAAAAGAATTACTGTCTGATTTGCTGGAAATAA |
| SEQ ID NO: 10<br><br>pOMeTyrRS-3 Synthetase polynucleotide | ATGGCAAGCAGTAACTTGATTAAACAATTGCAAGAGCGGGGGCTGGTAGCCCAGGTGAC<br>GGACGAGGAAGCGTTAGCAGAGCGACTGGCGCAAGGCCCGATCGCACTCGTGTGTGGCT<br>TCGATCCTACCGCTGACAGCTTGCATTTGGGGCATCTTGTTCCATTGTTATGCCTGAAA<br>CGCTTCCAGCAGGCGGGCCACAAGCCGGTTGCGCTGGTAGGCGGCGCGACGGGTCTGAT<br>TGGCGACCCGAGCTTCAAAGCTGCCGAGCGTAAGCTGAACACCGAAGAAACTGTTCAGG<br>AGTGGGTGGACAAAATCCGTAAGCAGGTTGCCCCGTTCCTCGATTTCGACTGTGGAGAA<br>AACTCTGCTATCGCGGCCAATAATTATGACTGGTTCGGCAATATGAATGTGCTGACCTT<br>CCTGCGCGATATTGGCAAACACTTCTCCGTTAACCAGATGATCAACAAAGAAGCGGTTA<br>AGCAGCGTCTCAACCGTGAAGATCAGGGGATTTCGTTCACTGAGTTTTCCTACAACCTG<br>CTGCAGGGTTATAGTATGGCCTGTTTGAACAAACAGTACGGTGTGGTGCTGCAAATTGG<br>TGGTTCTGACCAGTGGGGTAACATCACTTCTGGTATCGACCTGACCCGTCGTCTGCATC<br>AGAATCAGGTGTTTGGCCTGACCGTTCCGCTGATCACTAAAGCAGATGGCACCAAATTT<br>GGTAAAACTGAAGGCGGCGCAGTCTGGTTGGATCCGAAGAAAACCAGCCCGTACAAATT<br>CTACCAGTTCTGGATCAACACTGCGGATGCCGACGTTTACCGCTTCCTGAAGTTCTTCA<br>CCTTTATGAGCATTGAAGAGATCAACGCCCTGGAAGAAGAAGATAAAAACAGCGGTAAA<br>GCACCGCGCGCCCAGTATGTACTGGCGGAGCAGGTGACTCGTCTGGTTCACGGTGAAGA<br>AGGTTTACAGGCGGCAAAACGTATTACCGAATGCCTGTTCAGCGGTTCTTTGAGTGCGC<br>TGAGTGAAGCGGACTTCGAACAGCTGGCGCAGGACGGCGTACCGATGGTTGAGATGGAA<br>AAGGGCGCAGACCTGATGCAGGCACTGGTCGATTCTGAACTGCAACCTTCCCGTGGTCA<br>GGCACGTAAAACTATCGCCTCCAATGCCATCACCATTAACGGTGAAAAACAGTCCGATC<br>CTGAATACTTCTTTAAAGAAGAAGATCGTCTGTTTGGTCGTTTTACCTTACTGCGTCGC<br>GGTAAAAAGAATTACTGTCTGATTTGCTGGAAATAA |

Fig. 16 cont.

| SEQ ID NO and Description | SEQUENCE |
|---|---|
| SEQ ID NO: 11<br><br>pOMeTyrRS-4<br>Synthetase<br>polynucleotide | ATGGCAAGCAGTAACTTGATTAAACAATTGCAAGAGCGGGGGCTGGTAGCCCAGGTGAC<br>GGACGAGGAAGCGTTAGCAGAGCGACTGGCGCAAGGCCCGATCGCACTCGTGTGTGGCT<br>TCGATCCTACCGCTGACAGCTTGCATTTGGGGCATCTTGTTCCATTGTTATGCCTGAAA<br>CGCTTCCAGCAGGCGGGCCACAAGCCGGTTGCGCTGGTAGGCGGCGCGACGGGTCTGAT<br>TGGCGACCCGAGCTTCAAAGCTGCCGAGCGTAAGCTGAACACCGAAGAAACTGTTCAGG<br>AGTGGGTGGACAAAATCCGTAAGCAGGTTGCCCCGTTCCTCGATTTCGACTGTGGAGAA<br>AACTCTGCTATCGCGGCCAATAATTATGACTGGTTCGGCAATATGAATGTGCTGACCTT<br>CCTGCGCGATATTGGCAAACACTTCTCCGTTAACCAGATGATCAACAAAGAAGCGGTTA<br>AGCAGCGTCTCAACCGTGAAGATCAGGGGATTTCGTTCACTGAGTTTTCCTACAACCTG<br>CTGCAGGGTTATAGTATGGCCTGTTTGAACAAACAGTACGGTGTGGTGCTGCAAATTGG<br>TGGTTCTGACCAGTGGGGTAACATCACTTCTGGTATCGACCTGACCCGTCGTCTGCATC<br>AGAATCAGGTGTTTGGCCTGACCGTTCCGCTGATCACTAAAGCAGATGGCACCAAATTT<br>GGTAAAACTGAAGGCGGCGCAGTCTGGTTGGATCCGAAGAAAACCAGCCCGTACAAATT<br>CTACCAGTTCTGGATCAACACTGCGGATGCCGACGTTTACCGCTTCCTGAAGTTCTTCA<br>CCTTTATGAGCATTGAAGAGATCAACGCCCTGGAAGAAGAAGATAAAAACAGCGGTAAA<br>GCACCGCGCGCCCAGTATGTACTGGCGGAGCAGGTGACTCGTCTGGTTCACGGTGAAGA<br>AGGTTTACAGGCGGCAAAACGTATTACCGAATGCCTGTTCAGCGGTTCTTTGAGTGCGC<br>TGAGTGAAGCGGACTTCGAACAGCTGGCGCAGGACGGCGTACCGATGGTTGAGATGGAA<br>AAGGGCGCAGACCTGATGCAGGCACTGGTCGATTCTGAACTGCAACCTTCCCGTGGTCA<br>GGCACGTAAAACTATCGCCTCCAATGCCATCACCATTAACGGTGAAAAACAGTCCGATC<br>CTGAATACTTCTTTAAAGAAGAAGATCGTCTGTTTGGTCGTTTTACCTTACTGCGTCGC<br>GGTAAAAAGAATTACTGTCTGATTTGCTGGAAATAA |
| SEQ ID NO: 12<br><br>pOMeTyrRS-5<br>Synthetase<br>polynucleotide | ATGGCAAGCAGTAACTTGATTAAACAATTGCAAGAGCGGGGGCTGGTAGCCCAGGTGAC<br>GGACGAGGAAGCGTTAGCAGAGCGACTGGCGCAAGGCCCGATCGCACTCACGTGTGGCT<br>TCGATCCTACCGCTGACAGCTTGCATTTGGGGCATCTTGTTCCATTGTTATGCCTGAAA<br>CGCTTCCAGCAGGCGGGCCACAAGCCGGTTGCGCTGGTAGGCGGCGCGACGGGTCTGAT<br>TGGCGACCCGAGCTTCAAAGCTGCCGAGCGTAAGCTGAACACCGAAGAAACTGTTCAGG<br>AGTGGGTGGACAAAATCCGTAAGCAGGTTGCCCCGTTCCTCGATTTCGACTGTGGAGAA<br>AACTCTGCTATCGCGGCCAATAATTATGACTGGTTCGGCAATATGAATGTGCTGACCTT<br>CCTGCGCGATATTGGCAAACACTTCTCCGTTAACCAGATGATCAACAAAGAAGCGGTTA<br>AGCAGCGTCTCAACCGTGAAGATCAGGGGATTTCGTTCACTGAGTTTTCCTACAGCCTG<br>CTGCAGGGTTATACGATGGCCTGTCTGAACAAACAGTACGGTGTGGTGCTGCAAATTGG<br>TGGTTCTGACCAGTGGGGTAACATCACTTCTGGTATCGACCTGACCCGTCGTCTGCATC<br>AGAATCAGGTGTTTGGCCTGACCGTTCCGCTGATCACTAAAGCAGATGGCACCAAATTT<br>GGTAAAACTGAAGGCGGCGCAGTCTGGTTGGATCCGAAGAAAACCAGCCCGTACAAATT<br>CTACCAGTTCTGGATCAACACTGCGGATGCCGACGTTTACCGCTTCCTGAAGTTCTTCA<br>CCTTTATGAGCATTGAAGAGATCAACGCCCTGGAAGAAGAAGATAAAAACAGCGGTAAA<br>GCACCGCGCGCCCAGTATGTACTGGCGGAGCAGGTGACTCGTCTGGTTCACGGTGAAGA<br>AGGTTTACAGGCGGCAAAACGTATTACCGAATGCCTGTTCAGCGGTTCTTTGAGTGCGC<br>TGAGTGAAGCGGACTTCGAACAGCTGGCGCAGGACGGCGTACCGATGGTTGAGATGGAA<br>AAGGGCGCAGACCTGATGCAGGCACTGGTCGATTCTGAACTGCAACCTTCCCGTGGTCA<br>GGCACGTAAAACTATCGCCTCCAATGCCATCACCATTAACGGTGAAAAACAGTCCGATC<br>CTGAATACTTCTTTAAAGAAGAAGATCGTCTGTTTGGTCGTTTTACCTTACTGCGTCGC<br>GGTAAAAAGAATTACTGTCTGATTTGCTGGAAATAA |
| SEQ ID NO: 13<br><br>pOMeTyrRS-6<br>(active site)<br>Synthetase<br>polynucleotide | CGGGGGCTGGTAGCCCAGGTGACGGACGAGGAAGCGTTAGCAGAGCGACTGGCGCAAGG<br>CCCGATCGCACTCACTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>AGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGTATGCCTGTCTGAACAAACAG<br>TACGGTGTG |

Fig. 16 cont.

| SEQ ID NO and Description | SEQUENCE |
|---|---|
| SEQ ID NO: 14<br><br>pOMeTyrRS-7 (active site) Synthetase polynucleotide | CGGGGGCTGGTACCCCAGGTGACGGACGAGGAAGCGTTAGCAGAGCGACTGGCGCAAGG<br>CCCGATCGCACTCACTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>AGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGTATGCCTGTCTGAACAAACAG<br>TACGGTGTG |
| SEQ ID NO: 15<br><br>pOMeTyrRS-8 (active site) Synthetase polynucleotide | CGGGGGCTGGTAGCCCAGGTGACGGACGAGGAAGCGTTAGCAGAGCGACTGGCGCAAGG<br>CCCGATCGCACTCACTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>AGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGTATGCCTGTCTGAACAAACAG<br>TACGGTGTG |
| SEQ ID NO: 16<br><br>pOMeTyrRS-9 (active site) Synthetase polynucleotide | CGGGGGCTGGTAGCCCAGGTGACGGACGAGGAAGCGTTAGCAGAGCGACTGGCGCAAGG<br>CCCGATCGCACTCACTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATTCGTATGCCTGTGCGAACAAACAG<br>TACGGTGTG |
| SEQ ID NO: 17<br><br>pOMeTyrRS-10 (active site) Synthetase polynucleotide | CGGGGGCTGGTAGCCCAGGTGACGGACGAGGAAGCGTTAGCAGAGCGACTGGCGCAAGG<br>CCCGATCGCACTCACTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>AGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGTATGCCTGTCTGAACAAACAG<br>TACGGTGTG |
| SEQ ID NO: 18<br><br>pOMeTyrRS-11 (active site) Synthetase polynucleotide | CGGGGGCTGGTACCCCAGGTGACGGACGAGGAAGCGTTAGCAGAGCGACTGGCGCAAGG<br>CCCGATCGCACTCCTTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATTCTATTGCCTGTTCGAACAAACAG<br>TACGGTGTG |

Fig. 16 cont.

| SEQ ID NO and Description | SEQUENCE |
|---|---|
| SEQ ID NO: 19<br><br>pOMeTyrRS-12 (active site) Synthetase polynucleotide | CGGGGGCTGGTAGCCCAGGTGACGGACGAGGAAGCGTTAGCAGAGCGACTGGCGCAAGG<br>CCCGATCGCACTCGTGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATAGTATTGCCTGTTTGAACAAACAG<br>TACGGTGTG |
| SEQ ID NO: 20<br><br>pOMeTyrRS-13 (active site) Synthetase polynucleotide | CGGGGGCTGGTACCCCAGGTGACGGACGAGGAAGCGTTAGCAGAGCGACTGGCGCAAGG<br>CCCGATCGCACTCGTGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATAGTATTGCCTGTTTGAACAAACAG<br>TACGGTGTG |
| SEQ ID NO: 21<br><br>pOMeTyrRS-14 (active site) Synthetase polynucleotide | CGGGGGCTGGTAGCCCAGGTGACGGACGAGGAAGCGTTAGCAGAGCGACTGGCGCAAGG<br>CCCGATCGCACTCTGGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATTGTTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATATGCGTGCCTGTGAGAACAAACAG<br>TACGGTGTG |
| SEQ ID NO: 22<br><br>p-acetyl-Phe-1 (active site) Synthetase polynucleotide | CGGGGGCTGGTAGCCCAGGTGACGGACGAGGAAGCGTTAGCAGAGCGACTGGCGCAAGG<br>CCCGATCGCACTCATTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGGTCAGGGGATTTCGT<br>TCACTGAGTTTTCCTACAACCTGCTGCAGGGTTATGGTATGGCCTGTGCTAACAAACAG<br>TACGGTGTGGTGCTGCAAATTGGTGGTTCTGACCAATGGGGTAACATCACTTCTGGTAT<br>CGACCTGACCCGTCGTCTGCATCAGAATCAGGTG |
| SEQ ID NO: 23<br><br>pBenzophenone-1 (active site) Synthetase polynucleotide | CAGGTGACGGACGAGGAAGCGTTAGCAGAGCGACTGGCGCAAGGCCCGATCGCACTCGG<br>TTGTGGCTTCGATCCTACCGCTGACAGCTTGCATTTGGGGCATCTTGTTCCATTGTTAT<br>GCCTGAAACGCTTCCAGCAGGCGGGCCACAAGCCGGTTGCGCTGGTAGGCGGCGCGACG<br>GGTCTGATTGGCGACCCGAGCTTCAAAGCTGCCGAGCGTAAGCTGAACACCGAAGAAAC<br>TGTTCAGGAGTGGGTGGACAAAATCCGTAAGCAGGTTGCCCCGTTCCTCGATTTCGACT<br>GTGGAGAAAACTCTGCTATCGCGGCCAATAATTATGACTGGTTCGGCAATATGAATGTG<br>CTGACCTTCCTGCGCGATATTGGCAAACACTTCTCCGTTAACCAGATGATCAACAAAGA<br>AGCGGTTAAGCAGCGTCTCAACCGTGAAGATCAGGGGATTTCGTTCACTGAGTTTTCCT<br>ACAACCTGCTGCAGGGTTATGGTTTTGCCTGTTTGAACAAACAGTACGGTGTGGTGCTG<br>CAAATTGGTGGTTCTGACCAGTGGGGTAACATCACTTCTGGTATCGACCTGACCCGTCG<br>TCTGCATCAGAATCAGGTG |

Fig. 16 cont.

| SEQ ID NO and Description | SEQUENCE |
|---|---|
| SEQ ID NO: 24<br><br>pBenzophenone-2 (active site) Synthetase polynucleotide | GCGTTAGCAGAGCGACTGGCGCAAGGCCCGATCGCACTCGGGTGTGGCTTCGATCCTAC CGCTGACAGCTTGCATTTGGGGCATCTTGTTCCATTGTTATGCCTGAAACGCTTCCAGC AGGCGGGCCACAAGCCGGTTGCGCTGGTAGGCGGCGCGACGGGTCTGATTGGCGACCCG AGCTTCAAAGCTGCCGAGCGTAAGCTGAACACCGAAGAAACTGTTCAGGAGTGGGTGGA CAAAATCCGTAAGCAGGTTGCCCCGTTCCTCGATTTCGACTGTGGAGAAAACTCTGCTA TCGCGGCCAATAATTATGACTGGTTCGGCAATATGAATGTGCTGACCTTCCTGCGCGAT ATTGGCAAACACTTCTCCGTTAACCAGATGATCAACAAAGAAGCGGTTAAGCAGCGTCT CAACCGTGAAGATCAGGGGATTTCGTTCACTGAGTTTTCCTACAACCTGCTGCAGGGTT ATGGTTATGCCTGTATGAACAAACAGTACGGTGTGGTGCTGCAAATTGGTGGTTCTGAC CAGTGGGGTAACATCACTTCTGGTATCGACCTGACCCGTCGTCTGCATCAGAATCAGGT G |
| SEQ ID NO: 25<br><br>pAzidoPhe-1 (active site) Synthetase polynucleotide | GGGCTGGTAGCCCAGGTGACGGACGNAGAAGCGTTAGCAGAGCGACTGGCGCAAGGCCC GATCGCACTCCTTTGTGGCTTCGATCCTACCGCTGACAGCTTGCATTTGGGGCATCTTG TTCCATTGTTATGCCTGAAACGCTTCCAGCAGGCGGGCCACAAGCCGGTTGCGCTGGTA GGCGGCGCGACGGGTCTGATTGGCGACCCGAGCTTCAAAGCTGCCGAGCGTAAGCTGAA CACCGAAGAAACTGTTCAGGAGTGGGTGGACAAAATCCGTAAGCAGGTTGCCCCGTTCC TCGATTTCGACTGTGGAGAAAACTCTGCTATCGCGGCCAATAATTATGACTGGTTCGGC AATATGAATGTGCTGACCTTCCTGCGCGATATTGGCAAACACTTCTCCGTTAACCAGAT GATCAACAAAGAAGCGGTTAAGCAGCGTCTCAACCGTGAAGATCAGGGGATTTCGTTCA CTGAGTTTTCCTACAACCTGCTGCAGGGTTATTCTATGGCCTGTGCGAACAAACAGTAC GGTGTGGTGCTGCAAATTGGTGGTTCTGACCAGTGGGGTAACATCACTTCTGGTATCGA CCTGACCCGTCGTCTGCATCANAATCANGTG |
| SEQ ID NO: 26<br><br>pAzidoPhe-2 (active site) Synthetase polynucleotide | TTAGCAGAGCGACTGGCGCAAGGCCCGATCGCACTCGTTTGTGGCTTCGATCCTACCGC TGACAGCTTGCATTTGGGGCATCTTGTTCCATTGTTATGCCTGAAACGCTTCCAGCAGG CGGGCCACAAGCCGGTTGCGCTGGTAGGCGGCGCGACGGGTCTGATTGGCGACCCGAGC TTCAAAGCTGCCGAGCGTAAGCTGAACACCGAAGAAACTGTTCAGGAGTGGGTGGACAA AATCCGTAAGCAGGTTGCCCCGTTCCTCGATTTCGACTGTGGAGAAAACTCTGCTATCG CGGCCAATAATTATGACTGGTTCGGCAATATGAATGTGCTGACCTTCCTGCGCGATATT GGCAAACACTTCTCCGTTAACCAGATGATCAACAAAGAAGCGGTTAAGCAGCGTCTCAA CCGTGAAGATCAGGGGATTTCGTTCACTGAGTTTTCCTACAACCTGCTGCAGGGTTATT CTGCGGCCTGTGCGAACAAACAGTACGGTGTGGTGCTGCAAATTGGTGGTTCTGACCAG TGGGGTAACATCACTTCTGGTATCGACCTGACCCGTCGTCTGCATCAGAATCAGGTG |
| SEQ ID NO: 27<br><br>pAzidoPhe-3 (active site) Synthetase polynucleotide | GACGAGGAAGCGTTAGCAGAGCGACTGGCGCAAGGCCCGATCGCACTCCTGTGTGGCTT CGATCCTACCGCTGACAGCTTGCATTTGGGGCATCTTGTTCCATTGTTATGCCTGAAAC GCTTCCAGCAGGCGGGCCACAAGCCGGTTGCGCTGGTAGGCGGCGCGACGGGTCTGATT GGCGACCCGAGCTTCAAAGCTGCCGAGCGTAAGCTGAACACCGAAGAAACTGTTCAGGA GTGGGTGGACAAAATCCGTAAGCAGGTTGCCCCGTTCCTCGATTTCGACTGTGGAGAAA ACTCTGCTATCGCGGCCAATAATTATGACTGGTTCGGCAATATGAATGTGCTGACCTTC CTGCGCGATATTGGCAAACACTTCTCCGTTAACCAGATGATCAACAAANAAGCGGTTAA GCAGCGTCTCAACCGTGAAGATCAGGGGATTTCGTTCACTGAGTTTTCCTACAACCTGC TGCAGGGTTATTCGGCTGCCTGTGCGAACAAACAGTACGGNGNGGNGCTGCAAATTGGN GGTTCTGACCAGGGGGTAACATCACTTCTGGTATCGACCTGACCCGTCGTCTGCATCA AAATCAGGTG |
| SEQ ID NO: 28<br><br>pAzidoPhe-4 (active site) Synthetase polynucleotide | GCGTTAGCAGAGCGACTGGCGCAAGGCCCGATCGCACTCGTTTGTGGCTTCGATCCTAC CGCTGACAGCTTGCATTTGGGGCATCTTGTTCCATTGTTGTGCCTGAAACGCTTCCAGC AGGCGGGCCACAAGCCGGTTGCGCTGGTAGGCGGCGCGACGGGTCTGATTGGCGACCCG AGCTTCAAAGCTGCCGAGCGTAAGCTGAACACCGAAGAAACTGTTCAGGAGTGGGTGGA CAAAATCCGTAAGCAGGTTGCCCCGTTCCTCGATTTCGACTGTGGAGAAAACTCTGCTA TCGCGGCCAATAATTATGACTGGTTCGGCAATATGAATGTGCTGACCTTCCTGCGCGAT ATTGGCAAACACTTCTCCGTTAACCAGATGATCAACAAAGAAGCGGTTAAGCAGCGTCT CAACCGTGAAGATCAGGGGATTTCGTTCACTGAGTTTTCCTACAACCTGCTGCAGGGTT ATAGTGCGGCCTGTGTTAACAAACAGTACGGTGTGGTGCTGCAAATTGGTGGTTCTGAC CAGTGGGGTAACATCACTTCTGGTATCGACCTGACCCGTCGTCTGCATCAGAATCANGT G |

Fig. 16 cont.

| SEQ ID NO and Description | SEQUENCE |
|---|---|
| SEQ ID NO: 29<br><br>pAzidoPhe-5 (active site) Synthetase polynucleotide | GACGAGGAAGCGTTAGCAGAGCGACTGGCGCAAGGCCCGATCGCACTCATTTGTGGCTT<br>CGATCCTACCGCTGACAGCTTGCATTTGGGGCATCTTGTTCCATTGTTATGCCTGAAAC<br>GCTTCCAGCAGGCGGGCCACAAGCCGGTTGCGCTGGTAGGCGGCGCGACGGGTCTGATT<br>GGCGACCCGAGCTTCAAAGCTGCCGAGCGTAAGCTGAACACCGAAGAAACTGTTCAGGA<br>GTGGGTGGACAAAATCCGTAAGCAGGTTGCCCCGTTCCTCGATTTCGACTGTGGAGAAA<br>ACTCTGCTATCGCGGCCAATGATTATGACTGGTTCGGCAATATGAATGTGCTGACCTTC<br>CTGCGCGATATTGGCAAACACTTCTCCGTTAACCAGATGATCAACAAAGAAGCGGTTAA<br>GCAGCGTCTCAACCGTGAAGATCAGGGGATTTCGTTCACTGAGTTTTCCTACAACCTGC<br>TGCAGGGTTATAATTTTGCCTGTGTGAACAAACAGTACGGTGTGGTGCTGCAAATTGGT<br>GGTTCTGACCAGTGGGGTAACATCACTTCTGGTATCGACCTGACCCGTCGTCTGCATCA<br>GAATCAGGTG |
| SEQ ID NO: 30<br><br>pAzidoPhe-6 (active site) Synthetase polynucleotide | CGACTGGCGCAAGGCCCGATCGCACTCACGTGTGGCTTCGATCCTACCGCTGACAGCTT<br>GCATTTGGGGCATCTTGTTCCATTGTTATGCCTGAAACGCTTCCAGCAGGCGGGCCACA<br>AGCCGGTTGCGCTGGTAGGCGGCGCGACGGGTCTGATTGGCGACCCGAGCTTCAAAGCT<br>GCCGAGCGTAAGCTGAACACCGAAGAAACTGTTCAGGAGTGGGTGGACAAAATCCGTAA<br>GCAGGTTGCCCCGTTCCTCGATTTCGACTGTGGAGAAAACTCTGCTATCGCGGCCAATA<br>ATTATGACTGGTTCGGCAATATGAATGTGCTGACCTTCCTGCGCGATATTGGCAAACAC<br>TTCTCCGTTAACCAGATGATCAACAAAGAAGCGGTTAAGCAGCGTCTCAACCGTGAAGA<br>TCAGGGGATTTCGTTCACTGAGTTTTCCTACAATCTGCTGCAGGGTTATTCGGCTGCCT<br>GTCTTAACAAACAGTACGGTGTGGTGCTGCAAATTGGTGGTTCTGACCAGTGGGGTAAC<br>ATCACTTCTGGTATCGACCTGACCCGTCGTCTGCATCAGAATCAGGTG |
| SEQ ID NO: 31<br><br>pPR-EcRS-1 (propargyloxypheny lalanine synthetase) (active site) Synthetase polynucleotide | CGGGGGCTGGTANCCCAGGTGACGGACGAGGAAGCGTTAGCAGAGCGACTGGCGCAAGG<br>CCCGATCGCACTCGGGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATTCTATGGCCTGTTTGAACAAACAG<br>TACGGTGTGGTGCTGCAAATTGGTGGTTCTGACCAGTGGGGTAACATCACTTCTGGTAT<br>CGACCTGANCCGTCGTCTGCATCAGAATCAGGTG |
| SEQ ID NO: 32<br><br>pPR-EcRS -2 (active site) Synthetase polynucleotide | CGGGGGCTGGTAGCCCAGGTGACGGACGAGGAAGCGTTAGCAGAGCGACTGGCGCAAGG<br>CCCGATCGCACTCACGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAATCTGCTGCAGGGTTATTCGGCTGCCTGTCTTAACAAACAG<br>TACGGTGTGGTGCTGCAAATTGGTGGTTCTGACCAGTGGGGTAACATCACTTCTGGTAT<br>CGAACCTGANCCGTCGTCTGCATCAAAATCAAGTG |
| SEQ ID NO: 33<br><br>pPR-EcRS -3 (active site) Synthetase polynucleotide | CGGGGGCTGGTACCCCAAGTGACGGACGAGGAAACGTTAGCAGAGCGACTGGCGCAAGG<br>CCCGATCGCACTCTCTTGTGGCTTCGATCCTACCGCTGACAGCTTGCATTTGGGGCATC<br>TTGTTCCATTGTTATGCCTGAAACGCTTCCAGCAGGCAGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGATGGCCTGTGTGAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |

Fig. 16 cont.

| SEQ ID NO and Description | SEQUENCE |
|---|---|
| SEQ ID NO: 34<br><br>pPR-EcRS -4 (active site) Synthetase polynucleotide | CGGGGGCTGGTAGCCCAGGTGACGGACGAGGAAGCGTTAGCAGAGCGACTGGCGCAAGG<br>CCCGATCGCACTCGCGTGCGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAGGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATTCTTATGCCTGTCTTAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |
| SEQ ID NO: 35<br><br>pPR-EcRS-5 (active site) Synthetase polynucleotide | CGGGGGCTGGTAGCCCAGGTGACGGACGAGGAAGCGTTAGCAGAGCGACTGGCGCAAGG<br>CCCGATCGCACTCGCGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGATGGCCTGTTGTAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |
| SEQ ID NO: 36<br><br>pPR-EcRS-6 (active site) Synthetase polynucleotide | CGGGGGCTGGTACCCCAAGTGACGGACGAGGAAGCGTTAGCAGAGCGACTGGCGCAAGG<br>CCCGATCGCACTCACGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCGCTGAGTTTTCCTACAACCTGCTGCAGGGTTATACGTTTGCCTGTATGAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |
| SEQ ID NO: 37<br><br>pPR-EcRS-7 (active site) Synthetase polynucleotide | GTGACGGACGAGGAAGCGTTAGCAGAGCGACTGGCGCAAGGCCCGATCGCACTCACGTG<br>TGGCTTCGATCCTACCGCTGACAGCTTGCATTTGGGGCATCTTGTTCCATTGTTATGCC<br>TGAAACGCTTCCAGCAGGCGGGCCACAAGCCGGTTGCGCTGGTAGGCGGCGCGACGGGT<br>CTGATTGGCGACCCGAGCTTCAAAGCTGCCGAGCGTAAGCTGAACACCGAAGAAACTGT<br>TCAGGAGTGGGTGGACAAAATCCGTAAGCAGGTTGCCCCGTTCCTCGATTTCGACTGTG<br>GAGAAAACTCTGCTATCGCGGCCAATAATTATGACTGGTTCGGCAATATGAATGTGCTG<br>ACCTTCCTGCGCGATATTGGCAAACACTTCTCCGTTAACCAGATGATCAACAAAGAAGC<br>GGTTAAGCAGCGTCTCAACCGTGAAGATCAGGGGATTTCGTTCACTGAGTTTTCCTACA<br>ATCTGCTGCAGGGTTATTCGGCTGCCTGTCTTAACAAACAGTACGGTGTGGTGCTGCAA<br>ATTGGTGGTTCTGACCAGTGGGGTAACATCACTTCTGGTATCGACCTGACCCGTCGTCT<br>GCATCAGAATCAGGTG |
| SEQ ID NO: 38<br><br>pPR-EcRS-8 (active site) Synthetase polynucleotide | CGGGGGCTGGTAGCCCAGGTGACGGACGAGGAAGCGTTAGCAGAGCGACTGGCGCAAGG<br>CCCGATCGCACTCGTTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATTCGATGCCTGTACGAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |

Fig. 16 cont.

| SEQ ID NO and Description | SEQUENCE |
|---|---|
| SEQ ID NO: 39<br><br>pPR-EcRS-9 (active site) Synthetase polynucleotide | CGGGGGCTGGTANCCCAAGTGACGGACGGGGAAGCGTTAGCAGAGCGACTGGCGCAAGG<br>CCCGATCGCACTCAGTTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATCTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATAGTTTTGCCTGTCTGAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |
| SEQ ID NO: 40<br><br>pPR-EcRS-10 (active site) Synthetase polynucleotide | CGGGGGCTGGTAGCCCAGGTGACGGACGAGGAAGCGTTAGCAGAGCGACTGGCGCAAGG<br>CCCGATCGCACTCACGTGTGGCTTCGATCCTACCGCTGACAGCTTGCATTTGGGGCATC<br>TTGTTCCATTGTTATGCCTGAAACGCTTCCAGCAGGCGGGCCACAAGCCGGTTGCGCTG<br>GTAGGCGGCGCGACGGGTCTGATTGGCGACCCGAGCTTCAAAGCTGCCGAGCGTAAGCT<br>GAACACCGAAGAAACTGTTCAGGAGTGGGTGGACAAAATCCGTAAGCAGGTTGCCCCGT<br>TCCTCGATTTCGACTGTGGAGAAAACTCTGCTATCGCGGCCAATAATTATGACTGGTTC<br>GGCAATATGAATGTGCTGACCTTCCTGCGCGATATTGGCAAACACTTCTCCGTTAACCA<br>GATGATCAACAAAGAAGCGGTTAAGCAGCGTCTCAACCGTGAAGATCAGGGGATTTCGT<br>TCACTGAGTTTTCCTACAACCTGCTGCAGGGTTATACGTTTGCCTGTACTAACAAACAG<br>TACGGTGTGGTGCTGCAAATTGGTGGTTCTGACCAGTGGGGTAACATCACTTCTGGTAT<br>CGACCTGACCCGTCGTCTGCATCAGAATCAGGTG |

Fig. 16 cont.

| SEQ ID NO and Description | SEQUENCE |
|---|---|
| SEQ ID NO: 41<br><br>1,5-dansylalanine aminoacyl-tRNA synthetase clone B8 nucleotide sequence | ATGGAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>CTAATCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGTCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACTCTAGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTGCTGGATTTATGCGCGCTACACTTGCCCGCAGTACAAAGAAGGTA<br>TGCTGGATTCCGAAGCGGCTAACTACTGGCTGCCGGTGGATATCGGTATTGGTGGTATT<br>GAACACGCCATTATGACGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 42<br><br>1,5-dansylalanine aminoacyl-tRNA synthetase T252A nucleotide sequence | ATGGAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>CTAATCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGTCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACGCGTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACTCTAGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTGCTGGATTTATGCGCGCTACACTTGCCCGCAGTACAAAGAAGGTA<br>TGCTGGATTCCGAAGCGGCTAACTACTGGCTGCCGGTGGATATCGGTATTGGTGGTATT<br>GAACACGCCATTATGACGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGCCGTATCGTGAAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAAGCGGCC |

Fig. 16 cont.

| SEQ ID NO and Description | SEQUENCE |
|---|---|
| SEQ ID NO: 43<br><br>1,5-dansylalanine aminoacyl-tRNA synthetase V338A nucleotide sequence | ATGGAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>CTAATCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGTCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGCGCCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACTCTAGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTGCTGGATTTATGCGCGCTACACTTGCCCGCAGTACAAAGAAGGTA<br>TGCTGGATTCCGAAGCGGCTAACTACTGGCTGCCGGTCGGATATCGGTATTGGTGGTATT<br>GAACACGCCATTATGACGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAAGCGGCC |

Fig. 16 cont.

| SEQ ID NO and Description | SEQUENCE |
|---|---|
| SEQ ID NO: 44<br><br>o-nitrobenzylserine aminoacyl-tRNA synthetase clone G2-6 nucleotide sequence | ATCTCGAAGCACACGAAACTTTTTCCTTCCTTCATTCACGCACACTACTCTCTAATGAG<br>CAACGGTATACGGCCTTCCTTCCAGTTACTTGAATTTGAAATAAAAAAAAGTTTGCTGT<br>CTTGCTATCAAGTATAAATAGACCTGCAATTATTAATCTTTTGTTTCCTCGTCATTGTT<br>CTCGTTCCCTTTCTTCCTTGTTTCTTTTTCTGCACAATATTTCAAGCTATACCAAGCAT<br>ACAATCAACTGAATTCAGTATGGAAGAGCAATACCGCCCGGAAGAGATAGAATCCAAAG<br>TACAGCTTCATTGGGATGAGAAGCGCACATTTGAAGTAACCGAAGACGAGGGCAAAGAG<br>AAGTATTACTGCCTGTCTTGGTCGCCCTATCCTTCTGGTCGACTACACATGGGCCACGT<br>ACGTAACTACACCATCGGTGACGTGATCGCCCGCTACCAGCGTATGCTGGGCAAAAACG<br>TCCTGCAGCCGATCGGCTGGGACGCGTTTGGTCTGCCTGCGGAAGGCGCGGCGGTGAAA<br>AACAACACCGCTCCGGCACCGTGGACGTACGACAACATCGCGTATATGAAAAACCAGCT<br>CAAAATGCTGGGCTTTGGTTATGACTGGAGCCGCGAGCTGGCAACCTGTACGCCGGAAT<br>ACTACCGTTGGGAACAGAAATTCTTCACCGAGCTGTATAAAAAGGCCTGGTATATAAG<br>AAGACTTCTGCGGTCAACTGGTGTCCGAACGACCAGACCGTACTGGCGAACGAACAAGT<br>TATCGACGGCTGCTGCTGGCGCTGCGATACCAAAGTTGAACGTAAAGAGATCCCGCAGT<br>GGTTTATCAAAATCACTGCTTACGCTGACGAGCTGCTCAACGATCTGGATAAACTGGAT<br>CACTGGCCAGACACCGTTAAAACCATGCAGCGTAACTGGATCGGTCGTTCCGAAGGCGT<br>GGAGATCACCTTCAACGTTAACGACTATGACAACACGCTGACCGTTTACGCTTCCCGCC<br>CGGACACCTTTATGGGTTGTACCTACCTGGCGGTAGCTGCGGGTCATCCGCTGGCGCAG<br>AAAGCGGCGGAAAATAATCCTGAACTGGCGGCCTTTATTGACGAATGCCGTAACACCAA<br>AGTTGCCGAAGCTGAAATGCGACGATGGAGAAAAAAGGCGTCGATACTGGCTTTAAAG<br>CGGTTCACCCATTAACGGGCGAAGAAATTCCCGTTTGGGCAGCAAACTTCGTATTGATG<br>GAGTACGGCACGGGCGCAGTTATGGCGGTACCGGGGCACGACCAGCGCGACTACGAGTT<br>TGCCTCTAAATACGGCCTGAACATCAAACCGGTTATCCTGGCAGCTGACGGCTCTGAGC<br>CAGATCTTTCTCAGCAAGCCCTGACTGAAAAAGGCGTGCTGTTCAACTCTGGCGAGTTC<br>AACGGTCTTGACCATGAAGCGGCCTTCAACGCCATCGCCGATAAACTGACTGCGATGGG<br>CGTTGGCGAGCGTAAAGTGAACTACCGCCTGCGCGACTGGGGTGTTTCCCGTCAGCGTT<br>ACTGGGGCGCGCCGATTCCGATGGTGACTCTAGAAGACGGTACCGTAATGCCGACCCCG<br>GACGACCAGCTGCCGGTGATCCTGCCGGAAGATGTGGTAATGGACGGCATTACCAGCCC<br>GATTAAAGCAGATCCGGAGTGGGCGAAAACTACCGTTAACGGTATGCCAGCACTGCGTG<br>AAACCGACACTTTCGACACCTTTATGGAGTCCTGCTGGATTTATGCGCGCTACACTTGC<br>CCGCAGTACAAAGAAGGTATGCTGGATTCCGAAGCGGCTAACTACTGGCTGCCGGTGGA<br>TATCGCGATTGGTGGTATTGAACACGCCATTATGGGGCTGCTCTACTTCCGCTTCTTCC<br>ACAAACTGATGCGTGATGCAGGCATGGTGAACTCTGACGAACCAGCGAAACAGTTGCTG<br>TGTCAGGGTATGGTGCTGGCAGATGCCTTCTACTATGTTGGCGAAAACGGCGAACGTAA<br>CTGGGTTTCCCCGGTTGATGCTATCGTTGAACGTGACGAGAAAGGCCGTATCGTGAAAG<br>CGAAAGATGCGGCAGGCCATGAACTGGTTTATACCGGCATAAGCAAAATGTCCAAGTCG<br>AAGAACAACGGTATCGACCCGCAGGTGATGGTTGAACGTTACGGCGCGGACACCGTTCG<br>TCTGTTTATGATGTTTGCTTCTCCGGCTGATATGACTCTCGAATGGCAGGAATCCGGTG<br>TGGAAGGGGCTAACCGCTTCCTGAAACGTGCCTGGAAACTGGTTTACGGCACACAGCA<br>AAAGGTGATGTTGCGGCACTGAACGTTGATGCGCTGACTGAAAATCAGAAAGCGCTGCG<br>TCGCGATGTGCATAAAACGATCGCTAAAGTGACCGATGATATCGGCCGTCGTCAGACCT<br>TCAACACCGCAATTGCGGCGATTATGGAGCTGATGAACAAACTGGCGAAAGCACCAACC<br>GATGGCGAGCAGGATCGCGCTCTGATGCAGGAAGCACTGCTGGCCGTTGTCCGTATGCT<br>TAACCCGTTCACCCCGCACATCTGCTTCACGCTGTGGCAGGAACTGAAAGGCGAAGGCG<br>ATATCGACAACGCGCCGTGGCCGGTTGCTGACGAAAAAGCGATGGTGGAAGACTCCACG<br>CTGGTCGTGGTGCAGGTTAACGGTAAAGTCCGTGCCAAAATCACCGTTCCGGTGGACGC<br>AACGGAAGAACAGGTTCGCGAACGTGCTGGCCAGGAACATCTGGTAGCAAAATATCTTG<br>ATGGCGTTACTGTACGTAAAGTGATTTACGTACCAGGTAAACTCCTCAATCTGGTCGTT<br>GGCTAAGCGGCC |

| SEQ ID NO and Description | SEQUENCE |
|---|---|
| SEQ ID NO: 45<br><br>α-aminocaprylic acid aminoacyl-tRNA synthetase isolate-1D7 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>CTGCGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCCTTATGCGCGCTACACTTGCCCGCAGTACAAAGAAGGTA<br>TGCTGGATTCCGAAGCGGCTAACTACTGGCTGCCGGTGGATATCGTTATTGGTGGTATT<br>GAACACGCCATTATGGGGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 46<br><br>α-aminocaprylic acid aminoacyl-tRNA synthetase isolate-1G8 (C8-RS) nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>TGATGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCTGTATGCGCGCTACACTTGCCCGCAGTACAAAGAAGGTA<br>TGCTGGATTCCGAAGCGGCTAACTACTGGCTGCCGGTGGATATCCTGATTGGTGGTATT<br>GAACACGCCATTATGGGGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 47<br><br>α-aminocaprylic acid aminoacyl-tRNA synthetase isolate-2F2 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTC<br>ATCCTCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGACGGCATTACCAGCCCGATTAAAGCAGATCCGGAG<br>TGGGCGAAAACTACCGTTAACGGTATGCCAGCACTGCCGTGAAACCGACACTTTCGACAC<br>CTTTATGGAGTCCTCCTGGGCGTATGCGCGCTACACTTGCCCGCAGTACAAAGAAGGTA<br>TGCTGGATTCCGAAGCGGCTAACTACTGGCTGCCGGTGGATATCATGATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 48<br><br>α-aminoaprylic acid aminoacyl-tRNA synthetase isolate-2F5 nucleic acid sequence (derived from wild-type E. coli leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>TGTATCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCTGTATGCGCGCTACACTTGCCCGCAGTACAAAGAAGGTA<br>TGCTGGATTCCGAAGCGGCTAACTACTGGCTGCCGGTGGATATCCTGATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 49<br><br>O-methyl tyrosine aminoacyl-tRNA synthetase isolate-3A7 (OMeYRS) nucleic acid sequence (derived from wild-type *E. coli* leucyl tRNA-synthetase), | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTT<br>TGGAGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCGTTATGCGCGCTACACTTGCCCGCAGTACAAAGAAGGTA<br>TGCTGGATTCCGAAGCGGCTAACTACTGGCTGCCGGTGGATATCGCTATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 50<br><br>O-methyl tyrosine aminoacyl-tRNA synthetase isolate-3A2 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTA<br>TGGAGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCGCGATTAAAGCAGATCCGGAG<br>TGGGCGAAAACTACCGTTAACGGTATGCCAGCACTGCCGTGAAACCGACACTTTCGACAC<br>CTTTATGGAGTCCTCCTGGCGTTATGCGCGCTACACTTGCCCGCAGTACAAAGAAGGTA<br>TGCTGGATTCCGAAGCGGCTAACTACTGGCTGCCGGTGGATATCTTTATTGGTGGTATT<br>GAACACGCCATTATGGGGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 51<br><br>O-methyl tyrosine aminoacyl-tRNA synthetase isolate-3F11 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTT<br>TGGAGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCGTTATGCGCGCTACACTTGCCCGCAGTACAAAGAAGGTA<br>TGCTGGATTCCGAAGCGGCTAACTACTGGCTGCCGGTGGATATCTGTATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 52<br><br>O-methyl tyrosine aminoacyl-tRNA synthetase isolate-3E7 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTT<br>TTGAGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCGTTATGCGCGCTACACTTGCCCGCAGTACAAAGAAGGTA<br>TGCTGGATTCCGAAGCGGCTAACTACTGGCTGCCGGTGGATATCACGATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 53<br><br>o-nitrobenzyl cysteine aminoacyl-tRNA synthetase isolate-1A3 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>GGGAGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGCGGTATGCGCGCTACACTTGCCCGCAGTACAAAGAAGGTA<br>TGCTGGATTCCGAAGCGGCTAACTACTGGCTGCCGGTGGATATCCTGATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGGTTTCCCCGGTTGAT<br>GCTATCGTTGAACGTGACGAGAAAGGCCGTATCGTGAAAGCGAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

| SEQ ID NO and Description | SEQUENCE |
|---|---|
| SEQ ID NO: 54<br><br>o-nitrobenzyl cysteine aminoacyl-tRNA synthetase isolate-3A12 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>GTTGGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGGCTTATGCGCGCTACACTTGCCCGCAGTACAAAGAAGGTA<br>TGCTGGATTCCGAAGCGGCTAACTACTGGCTGCCGGTGGATATCCTTATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 55<br><br>o-nitrobenzyl cysteine aminoacyl-tRNA synthetase isolate-3H11 (nbCRS) nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTT<br>GGTCGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGATTTATGCGCGCTACACTTGCCCGCAGTACAAAGAAGGTA<br>TGCTGGATTCCGAAGCGGCTAACTACTGGCTGCCGGTGGATATCGCGATTGGTGGTATT<br>GAACACGCCATTATGGGCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTGAACGTTACGGCGCGGACACCGTTCGTCTGTTTATGATGTTTGCT<br>TCTCCGGCTGATATGACTCTCGAATGCAGGAATCCGGTGTGGAAGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |

Fig. 16 cont.

| SEQ ID NO and Description | SEQUENCE |
|---|---|
| SEQ ID NO: 56<br><br>o-nitrobenzyl cysteine aminoacyl-tRNA synthetase isolate-4E1 nucleic acid sequence (derived from wild-type *E. coli* leucyl tRNA-synthetase) | ATGCAAGAGCAATACCGCCCGGAAGAGATAGAATCCAAAGTACAGCTTCATTGGGATGA<br>GAAGCGCACATTTGAAGTAACCGAAGACGAGAGCAAAGAGAAGTATTACTGCCTGTCTG<br>GTACGCCCTATCCTTCTGGTCGACTACACATGGGCCACGTACGTAACTACACCATCGGT<br>GACGTGATCGCCCGCTACCAGCGTATGCTGGGCAAAAACGTCCTGCAGCCGATCGGCTG<br>GGACGCGTTTGGTCTGCCTGCGGAAGGCGCGGCGGTGAAAAACAACACCGCTCCGGCAC<br>CGTGGACGTACGACAACATCGCGTATATGAAAAACCAGCTCAAAATGCTGGGCTTTGGT<br>TATGACTGGAGCCGCGAGCTGGCAACCTGTACGCCGGAATACTACCGTTGGGAACAGAA<br>ATTCTTCACCGAGCTGTATAAAAAAGGCCTGGTATATAAGAAGACTTCTGCGGTCAACT<br>GGTGCCCGAACGACCAGACCGTACTGGCGAACGAACAAGTTATCGACGGCTGCTGCTGG<br>CGCTGCGATACCAAAGTTGAACGTAAAGAGATCCCGCAGTGGTTTATCAAAATCACTGC<br>TTACGCTGACGAGCTGCTCAACGATCTGGATAAACTGGATCACTGGCCAGACACCGTTA<br>AAACCATGCAGCGTAACTGGATCGGTCGTTCCGAAGGCGTGGAGATCACCTTCAACGTT<br>AACGACTATGACAACACGCTGACCGTTTACACTACCCGCCCGGACACCTTTATGGGTTG<br>TACCTACCTGGCCGGTAGCTGCGGGTCATCCGCTGGCGCAGAAAGCGGCGGAAAATAATC<br>CTGAACTGGCGGCCTTTATTGACGAATGCCGTAACACCAAAGTTGCCGAAGCTGAAATG<br>GCGACGATGGAGAAAAAAGGCGTCGATACTGGCTTTAAAGCGGTTCACCCATTAACGGG<br>CGAAGAAATTCCCGTTTGGGCAGCAAACTTCGTATTGATGGAGTACGGCACGGGCGCAG<br>TTATGGCGGTACCGGGGCACGACCAGCGCGACTACGAGTTTGCCTCTAAATACGGCCTG<br>AACATCAAACCGGTTATCCTGGCAGCTGACGGCTCTGAGCCAGATCTTTCTCAGCAAGC<br>CCTGACTGAAAAAGGCGTGCTGTTCAACTCTGGCGAGTTCAACGGTCTTGACCATGAAG<br>CGGCCTTCAACGCCATCGCCGATAAACTGACTGCGATGGGCGTTGGCGAGCGTAAAGTG<br>AACTACCGCCTGCGCGACTGGGGTGTTTCCCGTCAGCGTTACTGGGGCGCGCCGATTCC<br>GATGGTGACGCTGGAAGACGGTACCGTAATGCCGACCCCGGACGACCAGCTGCCGGTGA<br>TCCTGCCGGAAGATGTGGTAATGGACGGCATTACCAGCCCGATTAAAGCAGATCCGGAG<br>TGGGCGAAAACTACCGTTAACGGTATGCCAGCACTGCGTGAAACCGACACTTTCGACAC<br>CTTTATGGAGTCCTCCTGGTGGTATGCGCGCTACACTTGCCCGCAGTACAAAGAAGGTA<br>TGCTGGATTCCGAAGCGGCTAACTACTGGCTGCCGGTGGATATCCTTATTGGTGGTATT<br>GAACACGCCATTATGGGTCTGCTCTACTTCCGCTTCTTCCACAAACTGATGCGTGATGC<br>AGGCATGGTGAACTCTGACGAACCAGCGAAACAGTTGCTGTGTCAGGGTATGGTGCTGG<br>CAGATGCCTTCTACTATGTTGGCGAAAACGGCGAACGTAACTGGGTTTCCCCGGTTGAT<br>GCTATCGTTGAACGTGACGAGAAAGGCCGTATCGTGAAAGCGAAAGATGCGGCAGGCCA<br>TGAACTGGTTTATACCGGCATGAGCAAAATGTCCAAGTCGAAGAACAACGGTATCGACC<br>CGCAGGTGATGGTTAACGTTACGGCGCGGACACCGTTCGTCTGTTTATGATGTTTGCT<br>TCTCCGGCTGATATGACTCTCGAATGGCAGGAATCCGGTGTGGAAGGGGCTAACCGCTT<br>CCTGAAACGTGTCTGGAAACTGGTTTACGAGCACACAGCAAAAGGTGATGTTGCGGCAC<br>TGAACGTTGATGCGCTGACTGAAAATCAGAAAGCGCTGCGTCGCGATGTGCATAAAACG<br>ATCGCTAAAGTGACCGATGATATCGGCCGTCGTCAGACCTTCAACACCGCAATTGCGGC<br>GATTATGGAGCTGATGAACAAACTGGCGAAAGCACCAACCGATGGCGAGCAGGATCGCG<br>CTCTGATGCAGGAAGCACTGCTGGCCGTTGTCCGTATGCTTAACCCGTTCACCCCGCAC<br>ATCTGCTTCACGCTGTGGCAGGAACTGAAAGGCGAAGGCGATATCGACAACGCGCCGTG<br>GCCGGTTGCTGACGAAAAAGCGATGGTGGAAGACTCCACGCTGGTCGTGGTGCAGGTTA<br>ACGGTAAAGTCCGTGCCAAAATCACCGTTCCGGTGGACGCAACGGAAGAACAGGTTCGC<br>GAACGTGCTGGCCAGGAACATCTGGTAGCAAAATATCTTGATGGCGTTACTGTACGTAA<br>AGTGATTTACGTACCAGGTAAACTCCTCAATCTGGTCGTTGGCTAA |
| SEQ ID NO: 57<br><br>OMeTyrRS-1 Synthetase Amino acid (aa) | MASSNLIKQLQERGLVAQVTDEEALAERLAQGPIALVCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSMACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |

Fig. 16 cont.

| SEQ ID NO and Description | SEQUENCE |
|---|---|
| SEQ ID NO: 58<br><br>OMeTyrRS-2<br>Synthetase<br>Amino acid (aa) | MASSNLIKQLQERGLVAQVTDEEALAERLAQGPIALTCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYTMACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 59<br><br>OMeTyrRS-3<br>Synthetase<br>Amino acid (aa) | MASSNLIKQLQERGLVAQVTDEEALAERLAQGPIALTCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYTYACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 60<br><br>OMeTyrRS-4<br>Synthetase<br>Amino acid (aa) | MASSNLIKQLQERGLVAQVTDEEALAERLAQGPIALLCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSMACSNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 61<br><br>OMeTyrRS-5<br>Synthetase<br>Amino acid (aa) | MASSNLIKQLQERGLVAQVTDEEALAERLAQGPIALLCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSMACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 62<br><br>OMeTyrRS-6<br>Synthetase<br>Amino acid (aa) | MASSNLIKQLQERGLVAQVTDEEALAERLAQGPIALTCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYRMACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 63<br><br>p-acetylPheRS-1<br>Synthetase<br>Amino acid (aa) | MASSNLIKQLQERGLVAQVTDEEALAERLAQGPIALICGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYGMACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 64<br><br>p-acetylPheRS-2<br>Synthetase<br>Amino acid (aa) | MASSNLIKQLQERGLVAQVTDEEALAERLAQGPIALICGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREGQGISFTEFSYNL<br>LQGYGMACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |

Fig. 16 cont.

| SEQ ID NO and Description | SEQUENCE |
|---|---|
| SEQ ID NO: 65<br><br>p-benzoylPheRS-1 Synthetase<br>Amino acid (aa) | MASSNLIKQLQERGLVAQVTDEEALAERLAQGPIALGCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYGFACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 66<br><br>p-benzoylPheRS-2 Synthetase<br>Amino acid (aa) | MASSNLIKQLQERGLVAQVTDEEALAERLAQGPIALGCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYGYACMNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 67<br><br>p-azidoPheRS-1 Synthetase<br>Amino acid (aa) | MASSNLIKQLQERGLVAQVTDEEALAERLAQGPIALLCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSMACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 68<br><br>p-azidoPheRS-2 Synthetase<br>Amino acid (aa) | MASSNLIKQLQERGLVAQVTDEEALAERLAQGPIALVCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSAACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 69<br><br>p-azidoPheRS-3 Synthetase<br>Amino acid (aa) | MASSNLIKQLQERGLVAQVTDEEALAERLAQGPIALLCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSAACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 70<br><br>p-azidoPheRS-4 Synthetase<br>Amino acid (aa) | MASSNLIKQLQERGLVAQVTDEEALAERLAQGPIALVCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSAACVNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 71<br><br>p-azidoPheRS-5 Synthetase<br>Amino acid (aa) | MASSNLIKQLQERGLVAQVTDEEALAERLAQGPIALICGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYNFACVNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |

Fig. 16 cont.

| SEQ ID NO and Description | SEQUENCE |
|---|---|
| SEQ ID NO: 72<br><br>p-azidoPheRS-6 Synthetase<br>Amino acid (aa) | MASSNLIKQLQERGLVAQVTDEEALAERLAQGPIALTCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSAACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 73<br><br>pPR-EcRS-1 Synthetase<br>p-propargyloxy-phenylalanine synthetase<br>Amino acid (aa) | MASSNLIKQLQERGLVAQVTDEEALAERLAQGPIALGCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSMACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 74<br><br>pPR-EcRS-2 Synthetase<br>Amino acid (aa) | MASSNLIKQLQERGLVAQVTDEEALAERLAQGPIALTCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSAACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 75<br><br>pPR-EcRS-3 Synthetase<br>Amino acid (aa) | MASSNLIKQLQERGLVAQVTDEEALAERLAQGPIALSCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYTMACVNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 76<br><br>pPR-EcRS-4 Synthetase<br>Amino acid (aa) | MASSNLIKQLQERGLVAQVTDEEALAERLAQGPIALACGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSYACLNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 77<br><br>pPR-EcRS-5 Synthetase<br>Amino acid (aa) | MASSNLIKQLQERGLVAQVTDEEALAERLAQGPIALACGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYTMACCNKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |

Fig. 16 cont.

| SEQ ID NO and Description | SEQUENCE |
|---|---|
| SEQ ID NO: 78<br><br>pPR-EcRS-6 Synthetase<br>Amino acid (aa) | MASSNLIKQLQERGLVAQVTDEEALAERLAQGPIALTCGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYTFACMNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |
| SEQ ID NO: 79<br><br>pPR-EcRS-7 Synthetase<br>Amino acid (aa) | MASSNLIKQLQERGLVAQVTDEEALAERLAQGPIALTCGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYSVACLNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |
| SEQ ID NO: 80<br><br>pPR-EcRS-8 Synthetase<br>Amino acid (aa) | MASSNLIKQLQERGLVAQVTDEEALAERLAQGPIALVCGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYSMACTNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |
| SEQ ID NO: 81<br><br>pPR-EcRS-9 Synthetase<br>Amino acid (aa) | MASSNLIKQLQERGLVAQVTDEEALAERLAQGPIALSCGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYSFACLNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |
| SEQ ID NO: 82<br><br>pPR-EcRS-10 Synthetase<br>Amino acid (aa) | MASSNLIKQLQERGLVAQVTDEEALAERLAQGPIALTCGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYTFACTNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |
| SEQ ID NO: 83<br><br>p-iodoPheRS-1 Synthetase<br>Amino acid (aa) | MASSNLIKQLQERGLVAQVTDEEALAERLAQGPIALVCGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYSYACLNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |
| SEQ ID NO: 84<br><br>p-iodoPheRS-2 Synthetase<br>Amino acid (aa) | MASSNLIKQLQERGLVAQVTDEEALAERLAQGPIALICGFDPTADSLHLGHLVPLLCLK RFQQAGHKPVALVGGATGLIGDPSFKAAERKLNTEETVQEWVDKIRKQVAPFLDFDCGE NSAIAANNYDWFGNMNVLTFLRDIGKHFSVNQMINKEAVKQRLNREDQGISFTEFSYNL LQGYSMACLNKQYGVVLQIGGSDQWGNITSGIDLTRRLHQNQVFGLTVPLITKADGTKF GKTEGGAVWLDPKKTSPYKFYQFWINTADADVYRFLKFFTFMSIEEINALEEEDKNSGK APRAQYVLAEQVTRLVHGEEGLQAAKRITECLFSGSLSALSEADFEQLAQDGVPMVEME KGADLMQALVDSELQPSRGQARKTIASNAITINGEKQSDPEYFFKEEDRLFGRFTLLRR GKKNYCLICWK |

Fig. 16 cont.

| SEQ ID NO and Description | SEQUENCE |
|---|---|
| SEQ ID NO: 85<br><br>p-iodoPheRS-3 Synthetase Amino acid (aa) | MASSNLIKQLQERGLVAQVTDEEALAERLAQGPIALVCGFDPTADSLHLGHLVPLLCLK<br>RFQQAGHKPVALVGGATGLIGDPSFKAAERKLNTEETVQEWVDKIRKQVAPFLDFDCGE<br>NSAIAANNYDWFGNMNVLTFLRDIGKHFSVNQMINKEAVKQRLNREDQGISFTEFSYNL<br>LQGYSMACANKQYGVVLQIGGSDQWGNITSGIDLTRRLHQNQVFGLTVPLITKADGTKF<br>GKTEGGAVWLDPKKTSPYKFYQFWINTADADVYRFLKFFTFMSIEEINALEEEDKNSGK<br>APRAQYVLAEQVTRLVHGEEGLQAAKRITECLFSGSLSALSEADFEQLAQDGVPMVEME<br>KGADLMQALVDSELQPSRGQARKTIASNAITINGEKQSDPEYFFKEEDRLFGRFTLLRR<br>GKKNYCLICWK |
| SEQ ID NO: 86<br><br>α-aminocaprylic acid aminoacyl-tRNA synthetase isolate-1D7 amino acid sequence (derived from wild-type E. coli leucyl tRNA-synthetase) | MQEQYRPEEIESKVQLHWDEKRTFEVTEDESKEKYYCLSAAPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWPYARYTCPQYKEGMLDSEAANYWLPVDIVIGGI<br>EHAIMGLLYFRFFHKLMRDAGMVNSDEPAKQLLCQGMVLADAFYVVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 87<br><br>α-aminocaprylic acid aminoacyl-tRNA synthetase isolate-1G8 (C8-RS) amino acid sequence (derived from wild-type E. coli leucyl tRNA-synthetase) | MQEQYRPEEIESKVQLHWDEKRTFEVTEDESKEKYYCLSVMPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWLYARYTCPQYKEGMLDSEAANYWLPVDILIGGI<br>EHAIMGLLYFRFFHKLMRDAGMVNSDEPAKQLLCQGMVLADAFYVVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 88<br><br>α-aminocaprylic acid aminoacyl-tRNA synthetase isolate-2F2 amino acid sequence (derived from wild-type E. coli leucyl tRNA-synthetase) | MQEQYRPEEIESKVQLHWDEKRTFEVTEDESKEKYYCLSHPPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWAYARYTCPQYKEGMLDSEAANYWLPVDIMIGGI<br>EHAIMGLLYFRFFHKLMRDAGMVNSDEPAKQLLCQGMVLADAFYVVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |

Fig. 16 cont.

| SEQ ID NO and Description | SEQUENCE |
|---|---|
| SEQ ID NO: 89<br><br>α-aminocaprylic acid aminoacyl-tRNA synthetase isolate-2F5 amino acid sequence (derived from wild-type *E. coli* leucyl tRNA-synthetase) | MQEQYRPEEIESKVQLHWDEKRTFEVTEDESKEKYYCLSVYPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWLYARYTCPQYKEGMLDSEAANYWLPVDILIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 90<br><br>O-methyl tyrosine aminoacyl-tRNA synthetase (OMeYRS) isolate-3A7 amino acid sequence (derived from wild-type *E. coli* leucyl tRNA-synthetase), | MQEQYRPEEIESKVQLHWDEKRTFEVTEDESKEKYYCLSLEPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWRYARYTCPQYKEGMLDSEAANYWLPVDIAIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 91<br><br>O-methyl tyrosine aminoacyl-tRNA synthetase isolate-3A2 amino acid sequence (derived from wild-type *E. coli* leucyl tRNA-synthetase) | MQEQYRPEEIESKVQLHWDEKRTFEVTEDESKEKYYCLSMEPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWRYARYTCPQYKEGMLDSEAANYWLPVDIFIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |

Fig. 16 cont.

| SEQ ID NO and Description | SEQUENCE |
|---|---|
| SEQ ID NO: 92<br><br>O-methyl tyrosine aminoacyl-tRNA synthetase isolate-3F11 amino acid sequence (derived from wild-type E. coli leucyl tRNA-synthetase) | MQEQYRPEEIESKVQLHWDEKRTFEVTEDESKEKYYCLSLEPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWRYARYTCPQYKEGMLDSEAANYWLPVDICIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 93<br><br>O-methyl tyrosine aminoacyl-tRNA synthetase isolate-3E7 amino acid sequence (derived from wild-type E. coli leucyl tRNA-synthetase) | MQEQYRPEEIESKVQLHWDEKRTFEVTEDESKEKYYCLSFEPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWRYARYTCPQYKEGMLDSEAANYWLPVDITIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 94<br><br>o-nitrobenzyl cysteine aminoacyl-tRNA synthetase isolate-1A3 amino acid sequence (derived from wild-type E. coli leucyl tRNA-synthetase) | MQEQYRPEEIESKVQLHWDEKRTFEVTEDESKEKYYCLSGEPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWRYARYTCPQYKEGMLDSEAANYWLPVDILIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |

Fig. 16 cont.

| SEQ ID NO and Description | SEQUENCE |
|---|---|
| SEQ ID NO: 95<br><br>o-nitrobenzyl cysteine aminoacyl-tRNA synthetase isolate-3A12 amino acid sequence (derived from wild-type *E. coli* leucyl tRNA-synthetase) | MQEQYRPEEIESKVQLHWDEKRTFEVTEDESKEKYYCLSGWPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWAYARYTCPQYKEGMLDSEAANYWLPVDILIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 96<br><br>o-nitrobenzyl cysteine aminoacyl-tRNA synthetase (nbCRS) isolate-3H11 amino acid sequence (derived from wild-type *E. coli* leucyl tRNA-synthetase) | MQEQYRPEEIESKVQLHWDEKRTFEVTEDESKEKYYCLSWSPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWIYARYTCPQYKEGMLDSEAANYWLPVDIAIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 97<br><br>o-nitrobenzyl cysteine aminoacyl-tRNA synthetase isolate-4E1 amino acid sequence (derived from wild-type *E. coli* leucyl tRNA-synthetase) | MQEQYRPEEIESKVQLHWDEKRTFEVTEDESKEKYYCLSGTPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESSWWYARYTCPQYKEGMLDSEAANYWLPVDILIGGI<br>EHAIMGLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |

Fig. 16 cont.

| SEQ ID NO and Description | SEQUENCE |
|---|---|
| SEQ ID NO: 98<br><br>1,5-dansylalanine aminoacyl-tRNA synthetase clone B8 amino acid sequence (derived from wild-type *E. coli* leucyl-tRNA synthetase) | MEEQYRPEEIESKVQLHWDEKRTFEVTEDESKEKYYCLSANPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESCWIYARYTCPQYKEGMLDSEAANYWLPVDIGIGGI<br>EHAIMTLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 99<br><br>1,5-dansylalanine aminoacyl-tRNA synthetase T252A amino acid sequence (derived from wild-type *E. coli* leucyl-tRNA synthetase) | MEEQYRPEEIESKVQLHWDEKRTFEVTEDESKEKYYCLSANPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDAFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESCWIYARYTCPQYKEGMLDSEAANYWLPVDIGIGGI<br>EHAIMTLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 100<br><br>1,5-dansylalanine aminoacyl-tRNA synthetase V338A amino acid sequence (derived from wild-type *E. coli* leucyl-tRNA synthetase) | MEEQYRPEEIESKVQLHWDEKRTFEVTEDESKEKYYCLSANPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYTTRPDTFMGCTYLAVAAGHPLAQKAAENNPELAAFIDECRNTKVAEAEM<br>ATMEKKGVDTGFKAVHPLTGEEIPVWAANFVLMEYGTGAVMAAPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESCWIYARYTCPQYKEGMLDSEAANYWLPVDIGIGGI<br>EHAIMTLLYFRFFHKLMRDAGMVNSDEPAKQLLCQGMVLADAFYYVGENGERNWVSPVD<br>AIVERDEKGRIVKAKDAAGHELVYTGMSKMSKSKNNGIDPQVMVERYGADTVRLFMMFA<br>SPADMTLEWQESGVEGANRFLKRVWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |

Fig. 16 cont.

| SEQ ID NO and Description | SEQUENCE |
|---|---|
| SEQ ID NO: 101<br><br>o-nitrobenzylserine aminoacyl-tRNA synthetase clone G2-6 amino acid sequence (derived from wild-type E. coli leucyl-tRNA synthetase) | MEEQYRPEEIESKVQLHWDEKRTFEVTEDEGKEKYYCLSWSPYPSGRLHMGHVRNYTIG<br>DVIARYQRMLGKNVLQPIGWDAFGLPAEGAAVKNNTAPAPWTYDNIAYMKNQLKMLGFG<br>YDWSRELATCTPEYYRWEQKFFTELYKKGLVYKKTSAVNWCPNDQTVLANEQVIDGCCW<br>RCDTKVERKEIPQWFIKITAYADELLNDLDKLDHWPDTVKTMQRNWIGRSEGVEITFNV<br>NDYDNTLTVYASRPDTFMGCTYLAVAAGHPLAQKAAENNPELAAFIDECRNTKVAEAEM<br>ATMEKKGVDTGFKAVHPLTGEEIPVWAANFVLMEYGTGAVMAVPGHDQRDYEFASKYGL<br>NIKPVILAADGSEPDLSQQALTEKGVLFNSGEFNGLDHEAAFNAIADKLTAMGVGERKV<br>NYRLRDWGVSRQRYWGAPIPMVTLEDGTVMPTPDDQLPVILPEDVVMDGITSPIKADPE<br>WAKTTVNGMPALRETDTFDTFMESCWIYARYTCPQYKEGMLDSEAANYWLPVDIAIGGI<br>EHAIMGLLYFRFFHKLMRDAGMVNSDEPAKQLLCQGMVLADAFYVVGENGERNWVSPVD<br>AIVERDEKGRIVKAKDAAGHELVYTGISKMSKSKNNGIDPQVMVERYGADTVRLFMMFA<br>SPADMTLEWQESGVEGANRFLKRAWKLVYEHTAKGDVAALNVDALTENQKALRRDVHKT<br>IAKVTDDIGRRQTFNTAIAAIMELMNKLAKAPTDGEQDRALMQEALLAVVRMLNPFTPH<br>ICFTLWQELKGEGDIDNAPWPVADEKAMVEDSTLVVVQVNGKVRAKITVPVDATEEQVR<br>ERAGQEHLVAKYLDGVTVRKVIYVPGKLLNLVVG |
| SEQ ID NO: 102<br><br>GFP peptide, where Y denotes the wild-type tyrosine amino acid position | FSVSGEGEGDATYGK |
| SEQ ID NO: 103<br><br>GFP peptide, where Y* denotes the unnatural amino acid position | FSVSGEGEGDATY GK |
| SEQ ID NO: 104<br><br>5'-flanking sequence of the human tRNA$^{Tyr}$ gene | AGCGCTCCGGTTTTTCTGTGCTGAACCTCAGGGGACGCCGACACACGTACACGTC |
| SEQ ID NO: 105<br><br>5'-flanking sequence for E. coli suppressor tRNA$^{Leu5}$ CUA transcription in mammalian cells | gatccgaccgtgtgcttggcagaac |
| SEQ ID NO: 106<br><br>3'-flanking sequence for E. coli suppressor tRNA$^{Leu5}$ CUA transcription in mammalian cells | gtccttttttg |

SEQUENCE LISTING

<160> NUMBER OF SEQ ID NOS: 106

<210> SEQ ID NO 1
<211> LENGTH: 87
<212> TYPE: RNA

<213> ORGANISM: Artificial
<220> FEATURE:
<223> OTHER INFORMATION: mutant suppressor tRNA Leu5 CUA

<400> SEQUENCE: 1

```
gcccggaugg uggaaucggu agacacaagg gauucuaaau cccucggcgu ucgcgcugug    60
cggguucaag ucccgcuccg gguacca                                        87
```

<210> SEQ ID NO 2
<211> LENGTH: 85
<212> TYPE: DNA
<213> ORGANISM: Escherichia coli

<400> SEQUENCE: 2

```
ggtggggttc ccgagcggcc aaagggagca gactctaaat ctgccgtcat cgacttcgaa    60
ggttcgaatc cttcccccac cacca                                          85
```

<210> SEQ ID NO 3
<211> LENGTH: 82
<212> TYPE: DNA
<213> ORGANISM: Artificial
<220> FEATURE:
<223> OTHER INFORMATION: mutant suppressor tyrosyl-tRNA(CUA)

<400> SEQUENCE: 3

```
ggaggggtag cgaagtggct aaacgcggcg gactctaaat ccgctccctt tgggttcggc    60
ggttcgaatc cgtccccctc ca                                             82
```

<210> SEQ ID NO 4
<211> LENGTH: 860
<212> TYPE: PRT
<213> ORGANISM: Escherichia coli

<400> SEQUENCE: 4

```
Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Met Leu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190
```

```
Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
                260                 265                 270

Glu Asn Asn Pro Glu Leu Ala Ala Phe Ile Asp Glu Cys Arg Asn Thr
                275                 280                 285

Lys Val Ala Glu Ala Glu Met Ala Thr Met Glu Lys Lys Gly Val Asp
            290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
                355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Tyr Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Tyr Ile
            515                 520                 525

Gly Gly Ile Glu His Ala Ile Met His Leu Leu Tyr Phe Arg Phe Phe
530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605
```

| | | | | | | | | | | | | | |
|---|---|---|---|---|---|---|---|---|---|---|---|---|---|
|Gly|His|Glu|Leu|Val|Tyr|Thr|Gly|Met|Ser|Lys|Met|Ser|Lys Ser Lys|
| |610| | | |615| | | |620| | | | |

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Val Glu Gly Ala Asn Arg Phe Leu Lys Arg
        660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly
850                 855                 860

<210> SEQ ID NO 5
<211> LENGTH: 2583
<212> TYPE: DNA
<213> ORGANISM: Escherichia coli

<400> SEQUENCE: 5
atgcaagagc aataccgccc ggaagagata gaatccaaag tacagcttca ttgggatgag     60
aagcgcacat ttgaagtaac cgaagacgag agcaaagaga agtattactg cctgtctatg    120
cttccctatc cttctggtcg actacacatg ggccacgtac gtaactacac catcggtgac    180
gtgatcgccc gctaccagca tatgctgggc aaaaacgtcc tgcagccgat cggctgggac    240
gcgtttggtc tgcctgcgga aggcgcggcg gtgaaaaaca caccgctcc ggcaccgtgg    300 acgtacgaca catcgcgta tatgaaaaac cagctcaaaa tgctgggctt tggttatgac    360
tggagccgcg agctggcaac ctgtacgccg gaatactacc gttgggaaca gaaattcttc    420
accgagctgt ataaaaaagg cctggtatat aagaagactt ctgcggtcaa ctggtgcccg    480
aacgaccaga ccgtactggc gaacgaacaa gttatcgacg gctgctgctg cgctgcgat    540 accaaagttg aacgtaaaga gatcccgcag tggtttatca aaatcaatgc ttacgctgac    600
gagctgctca cgatctgga taaactggat cactggccag acaccgttaa accatgcag    660 cgtaactgga tcggtcgttc cgaaggcgtg gagatcacct tcaacgttaa cgactatgac    720

-continued

```
aacacgctga ccgtttacac tacccgcccg gacaccttta tgggttgtac ctacctggcg    780
gtacgtgcgg gtcatccgct ggcgcagaaa gcggcggaaa ataatcctga actggcggcc    840
tttattgacg aatgccgtaa caccaaagtt gccgaagctg aaatggcgac gatggagaaa    900
aaaggcgtcg atactggctt taaagcggtt cacccattaa cgggcgaaga aattcccgtt    960
tgggcagcaa acttcgtatt gatggagtac ggcacgggcg cagttatggc ggtaccgggg   1020
cacgaccagc gcgactacga gtttgcctct aaatacggcc tgaacatcaa accggttatc   1080
ctggcagctg acggctctga gccagatctt tctcagcaag ccctgactga aaaggcgtg    1140
ctgttcaact ctggcgagtt caacggtctt gaccatgaag cggccttcaa cgccatcgcc   1200
gataaactga ctgcgatggg cgttggcgag cgtaaagtga actaccgcct gcgcgactgg   1260
ggtgtttccc gtcagcgtta ctggggcgcg ccgattccga tggtgacgct ggaagacggt   1320
accgtaatgc cgaccccgga cgaccagctg ccggtgatcc tgccggaaga tgtggtaatg   1380
gacggcatta ccagcccgat taaagcagat ccggagtggg cgaaaactac cgttaacggt   1440
atgccagcac tgcgtgaaac cgacactttc gacaccttta tggagtcctc ctggtactat   1500
gcgcgctaca cttgcccgca gtacaaagaa ggtatgctgg attccgaagc ggctaactac   1560
tggctgccgg tggatatcta cattggtggt attgaacacg ccattatgca cctgctctac   1620
ttccgcttct tccacaaact gatgcgtgat gcaggcatgg tgaactctga cgaaccagcg   1680
aaacagttgc tgtgtcaggg tatggtgctg gcagatgcct tctactatgt tggcgaaaac   1740
ggcgaacgta actgggtttc cccggttgat gctatcgttg aacgtgacga aaaggccgt    1800
atcgtgaaag cgaaagatgc ggcaggccat gaactggttt ataccggcat gagcaaaatg   1860
tccaagtcga gaacaacgg tatcgacccg caggtgatgg ttgaacgtta cggcgcggac    1920
accgttcgtc tgtttatgat gtttgcttct ccggctgata tgactctcga atggcaggaa   1980
tccggtgtgg aaggggctaa ccgcttcctg aaacgtgtct ggaaactggt ttacgagcac   2040
acagcaaaag gtgatgttgc ggcactgaac gttgatgcgc tgactgaaaa tcagaaagcg   2100
ctgcgtcgcg atgtgcataa aacgatcgct aaagtgaccg atgatatcgg ccgtcgtcag   2160
accttcaaca ccgcaattgc ggcgattatg gagctgatga caaactggc gaaagcacca    2220
accgatggcg agcaggaccg cgctctgatg caggaagcac tgctggccgt tgtccgtatg   2280
cttaacccgt tcaccccgca catctgcttc acgcgtgggc aggaactgaa aggcgaaggc   2340
gatatcgaca cgcgccgtg gccggttgct gacgaaaaag cgatggtgga agactccacg    2400
ctggtcgtgg tgcaggttaa cggtaaagtc cgtgccaaaa tcaccgttcc ggtggacgca   2460
acggaagaac aggttcgcga acgtgctggc caggaacatc tggtagcaaa atatcttgat   2520
ggcgttactg tacgtaaagt gatttacgta ccaggtaaac tcctcaatct ggtcgttggc   2580
taa                                                                 2583
```

<210> SEQ ID NO 6
<211> LENGTH: 424
<212> TYPE: PRT
<213> ORGANISM: Escherichia coli

<400> SEQUENCE: 6

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30
```

```
Pro Ile Ala Leu Tyr Cys Gly Phe Asp Pro Thr Ala Asp Ser Leu His
            35                  40                  45

Leu Gly His Leu Val Pro Leu Leu Cys Leu Lys Arg Phe Gln Gln Ala
 50                  55                  60

Gly His Lys Pro Val Ala Leu Val Gly Ala Thr Gly Leu Ile Gly
 65                  70                  75                  80

Asp Pro Ser Phe Lys Ala Ala Glu Arg Lys Leu Asn Thr Glu Thr
                 85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
            210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 7
<211> LENGTH: 1275
<212> TYPE: DNA
```

<213> ORGANISM: Escherichia coli

<400> SEQUENCE: 7

```
atggcaagca gtaacttgat taaacaattg caagagcggg ggctggtagc ccaggtgacg      60
gacgaggaag cgttagcaga gcgactggcg caaggcccga tcgcgctcta ttgcggcttc     120
gatcctaccg ctgacagctt gcatttgggg catcttgttc cattgttatg cctgaaacgc     180
ttccagcagg cgggccacaa gccggttgcg ctggtaggcg cgcgacggg tctgattggc      240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg cgaacaacta tgactggttc ggcaatatga atgtgctgac cttcctgcgc     420
gatattggca acacttctc cgttaaccag atgatcaaca agaagcggt taagcagcgt       480
ctcaaccgtg aagatcaggg gatttcgttc actgagtttt cctacaacct gttgcagggt     540
tatgacttcg cctgtctgaa caaacagtac ggtgtggtgc tgcaaattgg tggttctgac     600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa accagcccgt acaaattcta ccagttctgg     780
atcaacactg cggatgccga cgtttaccgc ttcctgaagt tcttcacctt tatgagcatt     840
gaagagatca acgccctgga agaagaagat aaaaacagcg gtaaagcacc gcgcgcccag     900
tatgtactgg cggagcaggt gactcgtctg gttcacggtg aagaaggttt acaggcggca     960
aaacgtatta ccgaatgcct gttcagcggt tctttgagtg cgctgagtga agcggacttc    1020
gaacagctgg cgcaggacgg cgtaccgatg gttgagatgg aaaagggcgc agacctgatg    1080
caggcactgt cgattctga actgcaacct tcccgtggtc aggcacgtaa aactatcgcc     1140
tccaatgcca tcaccattaa cggtgaaaaa cagtccgatc tgaatactt cttttaagaa    1200
gaagatcgtc tgtttggtcg ttttacctta ctgcgtcgcg gtaaaagaa ttactgtctg     1260
atttgctgga aataa                                                    1275
```

<210> SEQ ID NO 8
<211> LENGTH: 1275
<212> TYPE: DNA
<213> ORGANISM: Artificial
<220> FEATURE:
<223> OTHER INFORMATION: mutant synthetase

<400> SEQUENCE: 8

```
atggcaagca gtaacttgat taaacaattg caagagcggg ggctggtagc ccaggtgacg      60
gacgaggaag cgttagcaga gcgactggcg caaggcccga tcgcactcgt gtgtggcttc     120
gatcctaccg ctgacagctt gcatttgggg catcttgttc cattgttatg cctgaaacgc     180
ttccagcagg cgggccacaa gccggttgcg ctggtaggcg cgcgacggg tctgattggc      240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg ccaataatta tgactggttc ggcaatatga atgtgctgac cttcctgcgc     420
gatattggca acacttctc cgttaaccag atgatcaaca agaagcggt taagcagcgt       480
ctcaaccgtg aagatcaggg gatttcgttc actgagtttt cctacaacct gctgcagggt     540
tatagtatgg cctgtttgaa caaacagtac ggtgtggtgc tgcaaattgg tggttctgac     600
cagtggggta acatcacttc tggtatcgac ctgacccgtc gtctgcatca gaatcaggtg     660
```

```
tttggcctga ccgttccgct gatcactaaa gcagatggca ccaaatttgg taaaactgaa    720
ggcggcgcag tctggttgga tccgaagaaa accagcccgt acaaattcta ccagttctgg    780
atcaacactg cggatgccga cgtttaccgc ttcctgaagt tcttcacctt tatgagcatt    840
gaagagatca acgccctgga agaagaagat aaaaacagcg gtaaagcacc gcgcgcccag    900
tatgtactgg cggagcaggt gactcgtctg gttcacggtg aagaaggttt acaggcggca    960
aaacgtatta ccgaatgcct gttcagcggt tctttgagtg cgctgagtga agcggacttc   1020
gaacagctgg cgcaggacgg cgtaccgatg gttgagatgg aaaagggcgc agacctgatg   1080
caggcactgg tcgattctga actgcaacct cccgtggtc aggcacgtaa aactatcgcc    1140
tccaatgcca tcaccattaa cggtgaaaaa cagtccgatc ctgaatactt ctttaaagaa   1200
gaagatcgtc tgtttggtcg ttttacctta ctgcgtcgcg gtaaaaagaa ttactgtctg   1260
atttgctgga aataa                                                    1275

<210> SEQ ID NO 9
<211> LENGTH: 1275
<212> TYPE: DNA
<213> ORGANISM: Artificial
<220> FEATURE:
<223> OTHER INFORMATION: mutant synthetase

<400> SEQUENCE: 9
atggcaagca gtaacttgat taaacaattg caagagcggg ggctggtagc ccaggtgacg     60
gacgaggaag cgttagcaga gcgactggcg caaggcccga tcgcactcac ttgtggcttc    120
gatcctaccg ctgacagctt gcatttgggg catcttgttc cattgttatg cctgaaacgc    180
ttccagcagg cgggccacaa gccggttgcg ctggtaggcg cgcgacggg tctgattggc    240 gaccccgagct tcaaagctgc cgagcgtaag ctgaacaccg aagaaactgt tcaggagtgg    300
gtggacaaaa tccgtaagca ggttgccccg ttcctcgatt tcgactgtgg agaaaactct    360
gctatcgcgg ccaataatta tgactggttc agcaatatga atgtgctgac cttcctgcgc    420
gatattggca acacttctc cgttaaccag atgatcaaca agaagcggt taagcagcgt     480 ctcaaccgtg aagatcaggg gatttcgttc actgagtttt cctacaacct gctgcagggt    540
tatacgtatg cctgtctgaa caaacagtac ggtgtggtgc tgcaaattgg tggttctgac    600
cagtggggta acatcacttc tggtatcgac ctgacccgtc gtctgcatca gaatcaggtg    660
tttggcctga ccgttccgct gatcactaaa gcagatggca ccaaatttgg taaaactgaa    720
ggcggcgcag tctggttgga tccgaagaaa accagcccgt acaaattcta ccagttctgg    780
atcaacactg cggatgccga cgtttaccgc ttcctgaagt tcttcacctt tatgagcatt    840
gaagagatca acgccctgga agaagaagat aaaaacagcg gtaaagcacc gcgcgcccag    900
tatgtactgg cggagcaggt gactcgtctg gttcacggtg aagaaggttt acaggcggca    960
aaacgtatta ccgaatgcct gttcagcggt tctttgagtg cgctgagtga agcggacttc   1020
gaacagctgg cgcaggacgg cgtaccgatg gttgagatgg aaaagggcgc agacctgatg   1080
caggcactgg tcgattctga actgcaacct cccgtggtc aggcacgtaa aactatcgcc    1140
tccaatgcca tcaccattaa cggtgaaaaa cagtccgatc ctgaatactt ctttaaagaa   1200
gaagatcgtc tgtttggtcg ttttacctta ctgcgtcgcg gtaaaaagaa ttactgtctg   1260
atttgctgga aataa                                                    1275

<210> SEQ ID NO 10
```

<211> LENGTH: 1275
<212> TYPE: DNA
<213> ORGANISM: Artificial
<220> FEATURE:
<223> OTHER INFORMATION: mutant synthetase

<400> SEQUENCE: 10

```
atggcaagca gtaacttgat taaacaattg caagagcggg ggctggtagc ccaggtgacg      60
gacgaggaag cgttagcaga gcgactggcg caaggcccga tcgcactcgt gtgtggcttc     120
gatcctaccg ctgacagctt gcatttgggg catcttgttc cattgttatg cctgaaacgc     180
ttccagcagg cgggccacaa gccggttgcg ctggtaggcg gcgcgacggg tctgattggc     240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg ccaataatta tgactggttc ggcaatatga atgtgctgac cttcctgcgc     420
gatattggca acacttctc cgttaaccag atgatcaaca agaagcggt taagcagcgt      480
ctcaaccgtg aagatcaggg gatttcgttc actgagtttt cctacaacct gctgcagggt     540
tatagtatgg cctgtttgaa caaacagtac ggtgtggtgc tgcaaattgg tggttctgac     600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa ccagcccgt acaaattcta ccagttctgg     780
atcaacactg cggatgccga cgtttaccgc ttcctgaagt tcttcacctt tatgagcatt     840
gaagagatca cgccctgga agaagaagat aaaaacagcg gtaaagcacc gcgcgcccag     900
tatgtactgg cggagcaggt gactcgtctg gttcacggtg aagaaggttt acaggcggca     960
aaacgtatta ccgaatgcct gttcagcggt tctttgagtg cgctgagtga agcggacttc    1020
gaacagctgg cgcaggacgg cgtaccgatg gttgagatgg aaaagggcgc agacctgatg    1080
caggcactgg tcgattctga actgcaacct tcccgtggtc aggcacgtaa aactatcgcc    1140
tccaatgcca tcaccattaa cggtgaaaaa cagtccgatc tgaatactt ctttaaagaa     1200
gaagatcgtc tgtttggtcg ttttaccta ctgcgtcgcg gtaaaaagaa ttactgtctg    1260
atttgctgga aataa                                                     1275
```

<210> SEQ ID NO 11
<211> LENGTH: 1275
<212> TYPE: DNA
<213> ORGANISM: Artificial
<220> FEATURE:
<223> OTHER INFORMATION: mutant synthetase

<400> SEQUENCE: 11

```
atggcaagca gtaacttgat taaacaattg caagagcggg ggctggtagc ccaggtgacg      60
gacgaggaag cgttagcaga gcgactggcg caaggcccga tcgcactcgt gtgtggcttc     120
gatcctaccg ctgacagctt gcatttgggg catcttgttc cattgttatg cctgaaacgc     180
ttccagcagg cgggccacaa gccggttgcg ctggtaggcg gcgcgacggg tctgattggc     240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg ccaataatta tgactggttc ggcaatatga atgtgctgac cttcctgcgc     420
gatattggca acacttctc cgttaaccag atgatcaaca agaagcggt taagcagcgt      480
ctcaaccgtg aagatcaggg gatttcgttc actgagtttt cctacaacct gctgcagggt     540
```

```
tatagtatgg cctgtttgaa caaacagtac ggtgtggtgc tgcaaattgg tggttctgac     600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa accagcccgt acaaattcta ccagttctgg     780
atcaacactg cggatgccga cgtttaccgc ttcctgaagt tcttcacctt tatgagcatt     840
gaagagatca acgccctgga agaagaagat aaaaacagcg gtaaagcacc gcgcgcccag     900
tatgtactgg cggagcaggt gactcgtctg gttcacggtg aagaaggttt acaggcggca     960
aaacgtatta ccgaatgcct gttcagcggt tctttgagtg cgctgagtga agcggacttc    1020
gaacagctgg cgcaggacgg cgtaccgatg gttgagatgg aaaagggcgc agacctgatg    1080
caggcactgg tcgattctga actgcaacct tcccgtggtc aggcacgtaa aactatcgcc    1140
tccaatgcca tcaccattaa cggtgaaaaa cagtccgatc ctgaatactt ctttaaagaa    1200
gaagatcgtc tgtttggtcg ttttaccctta ctgcgtcgcg gtaaaaagaa ttactgtctg    1260
atttgctgga aataa                                                    1275
```

<210> SEQ ID NO 12
<211> LENGTH: 1275
<212> TYPE: DNA
<213> ORGANISM: Artificial
<220> FEATURE:
<223> OTHER INFORMATION: mutant synthetase

<400> SEQUENCE: 12

```
atggcaagca gtaacttgat taaacaattg caagagcggg ggctggtagc ccaggtgacg      60
gacgaggaag cgttagcaga gcgactggcg caaggcccga tcgcactcac gtgtggcttc     120
gatcctaccg ctgacagctt gcatttgggg catcttgttc cattgttatg cctgaaacgc     180
ttccagcagg cgggccacaa gccggttgcg ctggtaggcg cgcgacgggt tctgattggc     240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg ccaataatta tgactggttc ggcaatatga atgtgctgac cttcctgcgc     420
gatattggca acacttctc cgttaaccag atgatcaaca agaagcggt taagcagcgt     480 ctcaaccgtg aagatcaggg gatttcgttc actgagtttt cctacagcct gctgcagggt     540
tatacgatgg cctgtctgaa caaacagtac ggtgtggtgc tgcaaattgg tggttctgac     600
cagtggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga tccgaagaaa accagcccgt acaaattcta ccagttctgg     780
atcaacactg cggatgccga cgtttaccgc ttcctgaagt tcttcacctt tatgagcatt     840
gaagagatca acgccctgga agaagaagat aaaaacagcg gtaaagcacc gcgcgcccag     900
tatgtactgg cggagcaggt gactcgtctg gttcacggtg aagaaggttt acaggcggca     960
aaacgtatta ccgaatgcct gttcagcggt tctttgagtg cgctgagtga agcggacttc    1020
gaacagctgg cgcaggacgg cgtaccgatg gttgagatgg aaaagggcgc agacctgatg    1080
caggcactgg tcgattctga actgcaacct tcccgtggtc aggcacgtaa aactatcgcc    1140
tccaatgcca tcaccattaa cggtgaaaaa cagtccgatc ctgaatactt ctttaaagaa    1200
gaagatcgtc tgtttggtcg ttttaccctta ctgcgtcgcg gtaaaaagaa ttactgtctg    1260
```
atttgctgga aataa 1275

<210> SEQ ID NO 13
<211> LENGTH: 540
<212> TYPE: DNA
<213> ORGANISM: Artificial
<220> FEATURE:
<223> OTHER INFORMATION: mutant synthetase

<400> SEQUENCE: 13

```
cgggggctgg tagcccaggt gacggacgag gaagcgttag cagagcgact ggcgcaaggc    60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtgagaaaaa ctctgctatc gcggccaata attatgactg gttcagcaat   360
atgaatgtgc tgaccttcct gcgcgatatt ggcaaacact tctccgttaa ccagatgatc   420
aacaaagaag cggttaagca gcgtctcaac cgtgaagatc agggatttc gttcactgag   480
ttttcctaca acctgctgca gggttatacg tatgcctgtc tgaacaaaca gtacggtgtg   540
```

<210> SEQ ID NO 14
<211> LENGTH: 540
<212> TYPE: DNA
<213> ORGANISM: Artificial
<220> FEATURE:
<223> OTHER INFORMATION: mutant synthetase

<400> SEQUENCE: 14

```
cgggggctgg tacccaggt gacggacgag gaagcgttag cagagcgact ggcgcaaggc     60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtgagaaaaa ctctgctatc gcggccaata attatgactg gttcagcaat   360
atgaatgtgc tgaccttcct gcgcgatatt ggcaaacact tctccgttaa ccagatgatc   420
aacaaagaag cggttaagca gcgtctcaac cgtgaagatc agggatttc gttcactgag   480
ttttcctaca acctgctgca gggttatacg tatgcctgtc tgaacaaaca gtacggtgtg   540
```

<210> SEQ ID NO 15
<211> LENGTH: 540
<212> TYPE: DNA
<213> ORGANISM: Artificial
<220> FEATURE:
<223> OTHER INFORMATION: mutant synthetase

<400> SEQUENCE: 15

```
cgggggctgg tagcccaggt gacggacgag gaagcgttag cagagcgact ggcgcaaggc    60
ccgatcgcac tcacttgtgg cttcgatcct accgctgaca gcttgcattt ggggcatctt   120
gttccattgt tatgcctgaa acgcttccag caggcgggcc acaagccggt tgcgctggta   180
ggcggcgcga cgggtctgat tggcgacccg agcttcaaag ctgccgagcg taagctgaac   240
accgaagaaa ctgttcagga gtgggtggac aaaatccgta agcaggttgc cccgttcctc   300
gatttcgact gtgagaaaaa ctctgctatc gcggccaata attatgactg gttcagcaat   360
```

```
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
tttccctaca acctgctgca gggttatacg tatgcctgtc tgaacaaaca gtacggtgtg    540
```

```
<210> SEQ ID NO 16
<211> LENGTH: 540
<212> TYPE: DNA
<213> ORGANISM: Artificial
<220> FEATURE:
<223> OTHER INFORMATION: mutant synthetase

<400> SEQUENCE: 16
cgggggctgg tagcccaggt gacggacgag gaagcgttag cagagcgact ggcgcaaggc     60
ccgatcgcac tcacttgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
tttccctaca acctgctgca gggttattcg tatgcctgtg cgaacaaaca gtacggtgtg    540
```

```
<210> SEQ ID NO 17
<211> LENGTH: 540
<212> TYPE: DNA
<213> ORGANISM: Artificial
<220> FEATURE:
<223> OTHER INFORMATION: mutant synthetase

<400> SEQUENCE: 17
cgggggctgg tagcccaggt gacggacgag gaagcgttag cagagcgact ggcgcaaggc     60
ccgatcgcac tcacttgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcagcaat    360
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
tttccctaca acctgctgca gggttatacg tatgcctgtc tgaacaaaca gtacggtgtg    540
```

```
<210> SEQ ID NO 18
<211> LENGTH: 540
<212> TYPE: DNA
<213> ORGANISM: Artificial
<220> FEATURE:
<223> OTHER INFORMATION: mutant synthetase

<400> SEQUENCE: 18
cgggggctgg tacccaggt gacggacgag gaagcgttag cagagcgact ggcgcaaggc      60
ccgatcgcac tcctttgtgg cttcgatcct accgctgaca gcttgcattt ggggcatctt    120
gttccattgt tatgcctgaa acgcttccag caggcgggcc acaagccggt tgcgctggta    180
```

```
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact ctccgttaa ccagatgatc     420 aacaaagaag cggttaagca gcgtctcaac cgtgaagatc aggggatttc gttcactgag    480
ttttcctaca acctgctgca gggttattct attgcctgtt cgaacaaaca gtacggtgtg    540

<210> SEQ ID NO 19
<211> LENGTH: 540
<212> TYPE: DNA
<213> ORGANISM: Artificial
<220> FEATURE:
<223> OTHER INFORMATION: mutant synthetase

<400> SEQUENCE: 19
cgggggctgg tagcccaggt gacggacgag gaagcgttag cagagcgact ggcgcaaggc     60
ccgatcgcac tcgtgtgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact ctccgttaa ccagatgatc     420 aacaaagaag cggttaagca gcgtctcaac cgtgaagatc aggggatttc gttcactgag    480
ttttcctaca acctgctgca gggttatagt attgcctgtt tgaacaaaca gtacggtgtg    540

<210> SEQ ID NO 20
<211> LENGTH: 540
<212> TYPE: DNA
<213> ORGANISM: Artificial
<220> FEATURE:
<223> OTHER INFORMATION: mutant synthetase

<400> SEQUENCE: 20
cgggggctgg tacccaggt gacggacgag gaagcgttag cagagcgact ggcgcaaggc      60
ccgatcgcac tcgtgtgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact ctccgttaa ccagatgatc     420 aacaaagaag cggttaagca gcgtctcaac cgtgaagatc aggggatttc gttcactgag    480
ttttcctaca acctgctgca gggttatagt attgcctgtt tgaacaaaca gtacggtgtg    540

<210> SEQ ID NO 21
<211> LENGTH: 540
<212> TYPE: DNA
<213> ORGANISM: Artificial
<220> FEATURE:
<223> OTHER INFORMATION: mutant synthetase

<400> SEQUENCE: 21
cgggggctgg tagcccaggt gacggacgag gaagcgttag cagagcgact ggcgcaaggc     60
```

```
ccgatcgcac tctggtgtgg cttcgatcct accgctgaca gcttgcattt ggggcatctt      120
gttccattgt tatgcctgaa acgcttccag caggcgggcc acaagccggt tgcgctggta      180
ggcggcgcga cgggtctgat tggcgacccg agcttcaagg ctgccgagcg taagctgaac      240
accgaagaaa ctgttcagga gtgggtggac aaaatccgta agcaggttgc cccgttcctc      300
gatttcgact gtggagaaaa ctctgctatc gcggccaatt gttatgactg gttcggcaat      360
atgaatgtgc tgaccttcct gcgcgatatt ggcaaacact ctccgttaa ccagatgatc       420 aacaaagaag cggttaagca gcgtctcaac cgtgaagatc aggggatttc gttcactgag      480
ttttcctaca acctgctgca gggttatatg cgtgcctgtg agaacaaaca gtacggtgtg      540
```

<210> SEQ ID NO 22
<211> LENGTH: 624
<212> TYPE: DNA
<213> ORGANISM: Artificial
<220> FEATURE:
<223> OTHER INFORMATION: mutant synthetase

<400> SEQUENCE: 22

```
cgggggctgg tagcccaggt gacggacgag gaagcgttag cagagcgact ggcgcaaggc       60
ccgatcgcac tcatttgtgg cttcgatcct accgctgaca gcttgcattt ggggcatctt      120
gttccattgt tatgcctgaa acgcttccag caggcgggcc acaagccggt tgcgctggta      180
ggcggcgcga cgggtctgat tggcgacccg agcttcaaag ctgccgagcg taagctgaac      240
accgaagaaa ctgttcagga gtgggtggac aaaatccgta agcaggttgc cccgttcctc      300
gatttcgact gtggagaaaa ctctgctatc gcggccaata attatgactg gttcggcaat      360
atgaatgtgc tgaccttcct gcgcgatatt ggcaaacact ctccgttaa ccagatgatc       420 aacaaagaag cggttaagca gcgtctcaac cgtgaaggtc aggggatttc gttcactgag      480
ttttcctaca acctgctgca gggttatggt atggcctgtg ctaacaaaca gtacggtgtg      540
gtgctgcaaa ttggtggttc tgaccaatgg ggtaacatca cttctggtat cgacctgacc      600
cgtcgtctgc atcagaatca ggtg                                             624
```

<210> SEQ ID NO 23
<211> LENGTH: 609
<212> TYPE: DNA
<213> ORGANISM: Artificial
<220> FEATURE:
<223> OTHER INFORMATION: mutant synthetase

<400> SEQUENCE: 23

```
caggtgacgg acgaggaagc gttagcagag cgactggcgc aaggcccgat cgcactcggt       60
tgtggcttcg atcctaccgc tgacagcttg catttgggga tcttgttcc attgttatgc       120 ctgaaacgct tccagcaggc gggccacaag ccggttgcgc tggtaggcgg cgcgacgggt      180
ctgattggcg acccgagctt caaagctgcc gagcgtaagc tgaacaccga gaaaactgtt      240
caggagtggg tggacaaaat ccgtaagcag gttgccccgt tcctcgattt cgactgtgga      300
gaaaactctg ctatcgcggc caataattat gactggttcg gcaatatgaa tgtgctgacc      360
ttcctgcgcg atattggcaa acacttctcc gttaaccaga tgatcaacaa gaagcggtt      420 aagcagcgtc tcaaccgtga agatcagggg atttcgttca ctgagttttc ctacaacctg      480
ctgcagggtt atggttttgc ctgtttgaac aaacagtacg gtgtggtgct gcaaattggt      540
ggttctgacc agtggggtaa catcacttct ggtatcgacc tgacccgtcg tctgcatcag      600
```

```
                                                                    aatcaggtg                                                        609

<210> SEQ ID NO 24
<211> LENGTH: 591
<212> TYPE: DNA
<213> ORGANISM: Artificial
<220> FEATURE:
<223> OTHER INFORMATION: mutant synthetase

<400> SEQUENCE: 24
gcgttagcag agcgactggc gcaaggcccg atcgcactcg ggtgtggctt cgatcctacc     60
gctgacagct tgcatttggg gcatcttgtt ccattgttat gcctgaaacg cttccagcag    120
gcgggccaca agccggttgc gctggtaggc ggcgcgacgg gtctgattgg cgacccgagc    180
ttcaaagctg ccgagcgtaa gctgaacacc gaagaaactg ttcaggagtg ggtggacaaa    240
atccgtaagc aggttgcccc gttcctcgat ttcgactgtg agaaaactc tgctatcgcg     300
gccaataatt atgactggtt cggcaatatg aatgtgctga ccttcctgcg cgatattggc    360
aaacacttct ccgttaacca gatgatcaac aaagaagcgg ttaagcagcg tctcaaccgt    420
gaagatcagg ggatttcgtt cactgagttt tcctacaacc tgctgcaggg ttatggttat    480
gcctgtatga caaacagta cggtgtggtg ctgcaaattg gtggttctga ccagtggggt     540
aacatcactt ctggtatcga cctgacccgt cgtctgcatc agaatcaggt g             591

<210> SEQ ID NO 25
<211> LENGTH: 621
<212> TYPE: DNA
<213> ORGANISM: Artificial
<220> FEATURE:
<223> OTHER INFORMATION: mutant synthetase
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t

<400> SEQUENCE: 25
gggctggtag cccaggtgac ggacgnagaa gcgttagcag agcgactggc gcaaggcccg     60
atcgcactcc tttgtggctt cgatcctacc gctgacagct tgcatttggg gcatcttgtt    120
ccattgttat gcctgaaacg cttccagcag gcgggccaca agccggttgc gctggtaggc    180
ggcgcgacgg gtctgattgg cgacccgagc ttcaaagctg ccgagcgtaa gctgaacacc    240
gaagaaactg ttcaggagtg ggtggacaaa atccgtaagc aggttgcccc gttcctcgat    300
ttcgactgtg agaaaactc tgctatcgcg gccaataatt atgactggtt cggcaatatg     360
aatgtgctga ccttcctgcg cgatattggc aaacacttct ccgttaacca gatgatcaac    420
aaagaagcgg ttaagcagcg tctcaaccgt gaagatcagg ggatttcgtt cactgagttt    480
tcctacaacc tgctgcaggg ttattctatg gcctgtgcga caaacagta cggtgtggtg     540
ctgcaaattg gtggttctga ccagtggggt aacatcactt ctggtatcga cctgacccgt    600
cgtctgcatc anaatcangt g                                              621

<210> SEQ ID NO 26
<211> LENGTH: 588
```

<212> TYPE: DNA
<213> ORGANISM: Artificial
<220> FEATURE:
<223> OTHER INFORMATION: mutant synthetase

<400> SEQUENCE: 26

```
ttagcagagc gactggcgca aggcccgatc gcactcgttt gtggcttcga tcctaccgct    60
gacagcttgc atttggggca tcttgttcca ttgttatgcc tgaaacgctt ccagcaggcg   120
ggccacaagc cggttgcgct ggtaggcggc gcgacgggtc tgattggcga cccgagcttc   180
aaagctgccg agcgtaagct gaacaccgaa gaaactgttc aggagtgggt ggacaaaatc   240
cgtaagcagg ttgccccgtt cctcgatttc gactgtggag aaaactctgc tatcgcggcc   300
aataattatg actggttcgg caatatgaat gtgctgacct tcctgcgcga tattggcaaa   360
cacttctccg ttaaccagat gatcaacaaa gaagcggtta agcagcgtct caaccgtgaa   420
gatcagggga tttcgttcac tgagttttcc tacaacctgc tgcagggtta ttctgcggcc   480
tgtgcgaaca acagtacgg tgtggtgctg caaattggtg ttctgacca gtggggtaac   540
atcacttctg gtatcgacct gacccgtcgt ctgcatcaga atcaggtg                588
```

<210> SEQ ID NO 27
<211> LENGTH: 600
<212> TYPE: DNA
<213> ORGANISM: Artificial
<220> FEATURE:
<223> OTHER INFORMATION: mutant synthetase
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t

<400> SEQUENCE: 27

```
gacgaggaag cgttagcaga gcgactggcg caaggcccga tcgcactcct gtgtggcttc    60
gatcctaccg ctgacagctt gcatttgggg catcttgttc cattgttatg cctgaaacgc   120
ttccagcagg cgggccacaa gccggttgcg ctggtaggcg gcgcgacggg tctgattggc   180
gacccgagct tcaaagctgc cgagcgtaag ctgaacaccg aagaaactgt tcaggagtgg   240
gtggacaaaa tccgtaagca ggttgccccg ttcctcgatt tcgactgtgg agaaaactct   300
gctatcgcgg ccaataatta tgactggttc ggcaatatga atgtgctgac cttcctgcgc   360
gatattggca aacacttctc cgttaaccag atgatcaaca anaagcggt taagcagcgt   420
ctcaaccgtg aagatcaggg gatttcgttc actgagtttt cctacaacct gctgcagggt   480
tattcggctg cctgtgcgaa caaacagtac ggngnggngc tgcaaattgg nggttctgac   540
caggggggta acatcacttc tggtatcgac ctgacccgtc gtctgcatca aaatcaggtg   600
```

<210> SEQ ID NO 28

<211> LENGTH: 591
<212> TYPE: DNA
<213> ORGANISM: Artificial
<220> FEATURE:
<223> OTHER INFORMATION: mutant synthetase
<220> FEATURE:
<221> NAME/KEY: misc_feature
<222> LOCATION: (588)..(588)
<223> OTHER INFORMATION: n is a, c, g, or t

<400> SEQUENCE: 28

| | | | | | |
|---|---|---|---|---|---|
| gcgttagcag | agcgactggc | gcaaggcccg | atcgcactcg | tttgtggctt | cgatcctacc | 60 |
| gctgacagct | tgcatttggg | gcatcttgtt | ccattgttgt | gcctgaaacg | cttccagcag | 120 |
| gcgggccaca | agccggttgc | gctggtaggc | ggcgcgacgg | gtctgattgg | cgacccgagc | 180 |
| ttcaaagctg | ccgagcgtaa | gctgaacacc | gaagaaactg | ttcaggagtg | ggtggacaaa | 240 |
| atccgtaagc | aggttgcccc | gttcctcgat | ttcgactgtg | gagaaaactc | tgctatcgcg | 300 |
| gccaataatt | atgactggtt | cggcaatatg | aatgtgctga | ccttcctgcg | cgatattggc | 360 |
| aaacacttct | ccgttaacca | gatgatcaac | aagaagcgg | ttaagcagcg | tctcaaccgt | 420 |
| gaagatcagg | ggatttcgtt | cactgagttt | cctacaaccc | tgctgcaggg | ttatagtgcg | 480 |
| gcctgtgtta | acaaacagta | cggtgtggtg | ctgcaaattg | tggttctga | ccagtggggt | 540 |
| aacatcactt | ctggtatcga | cctgacccgt | cgtctgcatc | agaatcangt | g | 591 |

<210> SEQ ID NO 29
<211> LENGTH: 600
<212> TYPE: DNA
<213> ORGANISM: Artificial
<220> FEATURE:
<223> OTHER INFORMATION: mutant synthetase

<400> SEQUENCE: 29

| | | | | | |
|---|---|---|---|---|---|
| gacgaggaag | cgttagcaga | gcgactggcg | caaggcccga | tcgcactcat | tgtgtggcttc | 60 |
| gatcctaccg | ctgacagctt | gcatttgggg | catcttgttc | cattgttatg | cctgaaacgc | 120 |
| ttccagcagg | cgggccacaa | gccggttgcg | ctggtaggcg | gcgcgacggg | tctgattggc | 180 |
| gacccgagct | tcaaagctgc | cgagcgtaag | ctgaacaccg | aagaaactgt | tcaggagtgg | 240 |
| gtggacaaaa | tccgtaagca | ggttgccccg | ttcctcgatt | tcgactgtgg | agaaaactct | 300 |
| gctatcgcgg | ccaatgatta | tgactggttc | ggcaatatga | atgtgctgac | cttcctgcgc | 360 |
| gatattggca | aacacttctc | cgttaaccag | atgatcaaca | agaagcggt | taagcagcgt | 420 |
| ctcaaccgtg | aagatcaggg | gatttcgttc | actgagtttt | cctacaacct | gctgcagggt | 480 |
| tataattttg | cctgtgtgaa | caaacagtac | ggtgtggtgc | tgcaaattgg | tggttctgac | 540 |
| cagtggggta | acatcacttc | tggtatcgac | ctgacccgtc | gtctgcatca | gaatcaggtg | 600 |

<210> SEQ ID NO 30
<211> LENGTH: 579
<212> TYPE: DNA
<213> ORGANISM: Artificial
<220> FEATURE:
<223> OTHER INFORMATION: mutant synthetase

<400> SEQUENCE: 30

| | | | | | |
|---|---|---|---|---|---|
| cgactggcgc | aaggcccgat | cgcactcacg | tgtggcttcg | atcctaccgc | tgacagcttg | 60 |
| catttggggc | atcttgttcc | attgttatgc | ctgaaacgct | tccagcaggc | gggccacaag | 120 |
| ccggttgcgc | tggtaggcgg | cgcgacgggt | ctgattggcg | acccgagctt | caaagctgcc | 180 |
| gagcgtaagc | tgaacaccga | agaaactgtt | caggagtggg | tggacaaaat | ccgtaagcag | 240 |

```
gttgccccgt tcctcgattt cgactgtgga gaaaactctg ctatcgcggc caataattat    300
gactggttcg gcaatatgaa tgtgctgacc ttcctgcgcg atattggcaa acacttctcc    360
gttaaccaga tgatcaacaa agaagcggtt aagcagcgtc tcaaccgtga agatcagggg    420
atttcgttca ctgagttttc ctacaatctg ctgcagggtt attcggctgc ctgtcttaac    480
aaacagtacg gtgtggtgct gcaaattggt ggttctgacc agtggggtaa catcacttct    540
ggtatcgacc tgacccgtcg tctgcatcag aatcaggtg                           579
```

<210> SEQ ID NO 31
<211> LENGTH: 624
<212> TYPE: DNA
<213> ORGANISM: Artificial
<220> FEATURE:
<223> OTHER INFORMATION: mutant synthetase
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t

<400> SEQUENCE: 31

```
cgggggctgg tancccaggt gacggacgag gaagcgttag cagagcgact ggcgcaaggc     60
ccgatcgcac tcgggtgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
ttttcctaca acctgctgca gggttattct atggcctgtt tgaacaaaca gtacggtgtg    540
gtgctgcaaa ttggtggttc tgaccagtgg ggtaacatca cttctggtat cgacctganc    600
cgtcgtctgc atcagaatca ggtg                                           624
```

<210> SEQ ID NO 32
<211> LENGTH: 625
<212> TYPE: DNA
<213> ORGANISM: Artificial
<220> FEATURE:
<223> OTHER INFORMATION: mutant synthetase
<220> FEATURE:
<221> NAME/KEY: misc_feature
<222> LOCATION: (600)..(600)
<223> OTHER INFORMATION: n is a, c, g, or t

<400> SEQUENCE: 32

```
cgggggctgg tagcccaggt gacggacgag gaagcgttag cagagcgact ggcgcaaggc     60
ccgatcgcac tcacgtgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
```

```
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
ttttcctaca atctgctgca gggttattcg gctgcctgtc ttaacaaaca gtacggtgtg    540
gtgctgcaaa ttggtggttc tgaccagtgg ggtaacatca cttctggtat cgaacctgan    600
ccgtcgtctg catcaaaatc aagtg                                          625
```

<210> SEQ ID NO 33
<211> LENGTH: 624
<212> TYPE: DNA
<213> ORGANISM: Artificial
<220> FEATURE:
<223> OTHER INFORMATION: mutant synthetase

<400> SEQUENCE: 33

```
cgggggctgg taccccaagt gacggacgag gaaacgttag cagagcgact ggcgcaaggc     60
ccgatcgcac tctcttgtgg cttcgatcct accgctgaca gcttgcattt ggggcatctt    120
gttccattgt tatgcctgaa acgcttccag caggcaggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
ttttcctaca acctgctgca gggttatacg atggcctgtg tgaacaaaca gtacggtgtg    540
gtgctgcaaa ttggtggttc tgaccagtgg ggtaacatca cttctggtat cgacctgacc    600
cgtcgtctgc atcagaatca ggtg                                           624
```

<210> SEQ ID NO 34
<211> LENGTH: 624
<212> TYPE: DNA
<213> ORGANISM: Artificial
<220> FEATURE:
<223> OTHER INFORMATION: mutant synthetase

<400> SEQUENCE: 34

```
cgggggctgg tagcccaggt gacggacgag gaagcgttag cagagcgact ggcgcaaggc     60
ccgatcgcac tcgcgtgcgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaagg ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact tctccgttaa ccagatgatc    420
aacaaagaag cggttaagca gcgtctcaac cgtgaagatc aggggatttc gttcactgag    480
ttttcctaca acctgctgca gggttattct tatgcctgtc ttaacaaaca gtacggtgtg    540
gtgctgcaaa ttggtggttc tgaccagtgg ggtaacatca cttctggtat cgacctgacc    600
cgtcgtctgc atcagaatca ggtg                                           624
```

<210> SEQ ID NO 35
<211> LENGTH: 624
<212> TYPE: DNA
<213> ORGANISM: Artificial

```
<220> FEATURE:
<223> OTHER INFORMATION: mutant synthetase

<400> SEQUENCE: 35
cgggggctgg tagcccaggt gacggacgag gaagcgttag cagagcgact ggcgcaaggc      60
ccgatcgcac tcgcgtgtgg cttcgatcct accgctgaca gcttgcattt ggggcatctt     120
gttccattgt tatgcctgaa acgcttccag caggcgggcc acaagccggt tgcgctggta     180
ggcggcgcga cgggtctgat tggcgacccg agcttcaaag ctgccgagcg taagctgaac     240
accgaagaaa ctgttcagga gtgggtggac aaaatccgta agcaggttgc cccgttcctc     300
gatttcgact gtggagaaaa ctctgctatc gcggccaata attatgactg gttcggcaat     360
atgaatgtgc tgaccttcct gcgcgatatt ggcaaacact tctccgttaa ccagatgatc     420
aacaaagaag cggttaagca gcgtctcaac cgtgaagatc aggggatttc gttcactgag     480
ttttcctaca acctgctgca gggttatacg atggcctgtt gtaacaaaca gtacggtgtg     540
gtgctgcaaa ttggtggttc tgaccagtgg ggtaacatca cttctggtat cgacctgacc     600
cgtcgtctgc atcagaatca ggtg                                            624

<210> SEQ ID NO 36
<211> LENGTH: 624
<212> TYPE: DNA
<213> ORGANISM: Artificial
<220> FEATURE:
<223> OTHER INFORMATION: mutant synthetase

<400> SEQUENCE: 36
cgggggctgg taccccaagt gacggacgag gaagcgttag cagagcgact ggcgcaaggc      60
ccgatcgcac tcacgtgtgg cttcgatcct accgctgaca gcttgcattt ggggcatctt     120
gttccattgt tatgcctgaa acgcttccag caggcgggcc acaagccggt tgcgctggta     180
ggcggcgcga cgggtctgat tggcgacccg agcttcaaag ctgccgagcg taagctgaac     240
accgaagaaa ctgttcagga gtgggtggac aaaatccgta agcaggttgc cccgttcctc     300
gatttcgact gtggagaaaa ctctgctatc gcggccaata attatgactg gttcggcaat     360
atgaatgtgc tgaccttcct gcgcgatatt ggcaaacact tctccgttaa ccagatgatc     420
aacaaagaag cggttaagca gcgtctcaac cgtgaagatc aggggatttc gttcgctgag     480
ttttcctaca acctgctgca gggttatacg tttgcctgta tgaacaaaca gtacggtgtg     540
gtgctgcaaa ttggtggttc tgaccagtgg ggtaacatca cttctggtat cgacctgacc     600
cgtcgtctgc atcagaatca ggtg                                            624

<210> SEQ ID NO 37
<211> LENGTH: 606
<212> TYPE: DNA
<213> ORGANISM: Artificial
<220> FEATURE:
<223> OTHER INFORMATION: mutant synthetase

<400> SEQUENCE: 37
gtgacggacg aggaagcgtt agcagagcga ctggcgcaag gcccgatcgc actcacgtgt      60
ggcttcgatc ctaccgctga cagcttgcat ttggggcatt tgttccattg ttatgcctg     120 aaacgcttcc agcaggcggg ccacaagccg gttgcgctgg taggcggcgc gacgggtctg     180
attggcgacc cgagcttcaa agctgccgag cgtaagctga acaccgaaga aactgttcag     240
gagtgggtgg acaaaatccg taagcaggtt gccccgttcc tcgatttcga ctgtggagaa     300
```

```
aactctgcta tcgcggccaa taattatgac tggttcggca atatgaatgt gctgaccttc    360
ctgcgcgata ttggcaaaca cttctccgtt aaccagatga tcaacaaaga agcggttaag    420
cagcgtctca accgtgaaga tcaggggatt tcgttcactg agttttccta caatctgctg    480
cagggttatt cggctgcctg tcttaacaaa cagtacggtg tggtgctgca aattggtggt    540
tctgaccagt ggggtaacat cacttctggt atcgacctga cccgtcgtct gcatcagaat    600
caggtg                                                              606

<210> SEQ ID NO 38
<211> LENGTH: 624
<212> TYPE: DNA
<213> ORGANISM: Artificial
<220> FEATURE:
<223> OTHER INFORMATION: mutant synthetase

<400> SEQUENCE: 38
cgggggctgg tagcccaggt gacggacgag gaagcgttag cagagcgact ggcgcaaggc     60
ccgatcgcac tcgtttgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatttcgact gtggagaaaa ctctgctatc gcggccaata attatgactg gttcggcaat    360
atgaatgtgc tgaccttcct gcgcgatatt ggcaaacact ctccgttaa ccagatgatc     420 aacaaagaag cggttaagca gcgtctcaac cgtgaagatc aggggatttc gttcactgag    480
ttttcctaca acctgctgca gggttattcg atggcctgta cgaacaaaca gtacggtgtg    540
gtgctgcaaa ttggtggttc tgaccagtgg ggtaacatca cttctggtat cgacctgacc    600
cgtcgtctgc atcagaatca ggtg                                          624

<210> SEQ ID NO 39
<211> LENGTH: 624
<212> TYPE: DNA
<213> ORGANISM: Artificial
<220> FEATURE:
<223> OTHER INFORMATION: mutant synthetase
<220> FEATURE:
<221> NAME/KEY: misc_feature
<222> LOCATION: (13)..(13)
<223> OTHER INFORMATION: n is a, c, g, or t

<400> SEQUENCE: 39
cgggggctgg tancccaagt gacggacggg gaagcgttag cagagcgact ggcgcaaggc     60
ccgatcgcac tcagttgtgg cttcgatcct accgctgaca gcttgcattt ggggcatctt    120
gttccattgt tatgcctgaa acgcttccag caggcgggcc acaagccggt tgcgctggta    180
ggcggcgcga cgggtctgat tggcgacccg agcttcaaag ctgccgagcg taagctgaac    240
accgaagaaa ctgttcagga gtgggtggac aaaatccgta agcaggttgc cccgttcctc    300
gatctcgact gtggagaaaa ctctgctatc gcggccaata attatgactg gttcggcaat    360
atgaatgtgc tgaccttcct gcgcgatatt ggcaaacact ctccgttaa ccagatgatc     420 aacaaagaag cggttaagca gcgtctcaac cgtgaagatc aggggatttc gttcactgag    480
ttttcctaca acctgctgca gggttatagt tttgcctgtc tgaacaaaca gtacggtgtg    540
gtgctgcaaa ttggtggttc tgaccagtgg ggtaacatca cttctggtat cgacctgacc    600
cgtcgtctgc atcagaatca ggtg                                          624
```

<210> SEQ ID NO 40
<211> LENGTH: 624
<212> TYPE: DNA
<213> ORGANISM: Artificial
<220> FEATURE:
<223> OTHER INFORMATION: mutant synthetase

<400> SEQUENCE: 40

| | | | | | |
|---|---|---|---|---|---|
| cgggggctgg | tagcccaggt | gacggacgag | gaagcgttag | cagagcgact | ggcgcaaggc | 60 |
| ccgatcgcac | tcacgtgtgg | cttcgatcct | accgctgaca | gcttgcattt | ggggcatctt | 120 |
| gttccattgt | tatgcctgaa | acgcttccag | caggcgggcc | acaagccggt | tgcgctggta | 180 |
| ggcggcgcga | cgggtctgat | tggcgacccg | agcttcaaag | ctgccgagcg | taagctgaac | 240 |
| accgaagaaa | ctgttcagga | gtgggtggac | aaaatccgta | agcaggttgc | ccgttcctc | 300 |
| gatttcgact | gtggagaaaa | ctctgctatc | gcggccaata | attatgactg | gttcggcaat | 360 |
| atgaatgtgc | tgaccttcct | gcgcgatatt | ggcaaacact | tctccgttaa | ccagatgatc | 420 |
| aacaaagaag | cggttaagca | gcgtctcaac | cgtgaagatc | aggggatttc | gttcactgag | 480 |
| ttttcctaca | acctgctgca | gggttatacg | tttgcctgta | ctaacaaaca | gtacggtgtg | 540 |
| gtgctgcaaa | ttggtggttc | tgaccagtgg | ggtaacatca | cttctggtat | cgacctgacc | 600 |
| cgtcgtctgc | atcagaatca | ggtg | | | | 624 |

<210> SEQ ID NO 41
<211> LENGTH: 2583
<212> TYPE: DNA
<213> ORGANISM: Artificial
<220> FEATURE:
<223> OTHER INFORMATION: mutant synthetase

<400> SEQUENCE: 41

| | | | | | |
|---|---|---|---|---|---|
| atggaagagc | aataccgccc | ggaagagata | gaatccaaag | tacagcttca | ttgggatgag | 60 |
| aagcgcacat | ttgaagtaac | cgaagacgag | agcaaagaga | agtattactg | cctgtctgct | 120 |
| aatccctatc | cttctggtcg | actacacatg | ggccacgtac | gtaactacac | catcggtgac | 180 |
| gtgatcgccc | gctaccagcg | tatgctgggc | aaaaacgtcc | tgcagccgat | cggctgggac | 240 |
| gcgtttggtc | tgcctgcgga | aggcgcggcg | gtgaaaaaca | acaccgctcc | ggcaccgtgg | 300 |
| acgtacgaca | catcgcgta | tatgaaaaac | cagctcaaaa | tgctgggctt | tggttatgac | 360 |
| tggagccgcg | agctggcaac | ctgtacgccg | gaatactacc | gttgggaaca | gaaattcttc | 420 |
| accgagctgt | ataaaaaagg | cctggtatat | aagaagactt | ctgcggtcaa | ctggtgtccg | 480 |
| aacgaccaga | ccgtactggc | gaacgaacaa | gttatcgacg | gctgctgctg | gcgctgcgat | 540 |
| accaaagttg | aacgtaaaga | gatcccgcag | tggtttatca | aaatcactgc | ttacgctgac | 600 |
| gagctgctca | cgatctgga | taaactggat | cactggccag | acaccgttaa | accatgcag | 660 |
| cgtaactgga | tcggtcgttc | cgaaggcgtg | gagatcacct | tcaacgttaa | cgactatgac | 720 |
| aacacgctga | ccgtttacac | tacccgcccg | gacacctta | tgggttgtac | ctacctggcg | 780 |
| gtagctgcgg | tcatccgct | ggcgcagaaa | gcggcggaaa | taatcctga | actggcggcc | 840 |
| tttattgacg | aatgccgtaa | caccaaagtt | gccgaagctg | aaatggcgac | gatggagaaa | 900 |
| aaaggcgtcg | atactggctt | taaagcggtt | cacccattaa | cgggcgaaga | aattcccgtt | 960 |
| tgggcagcaa | acttcgtatt | gatggagtac | ggcacgggcg | cagttatggc | ggtaccgggg | 1020 |
| cacgaccagc | gcgactacga | gtttgcctct | aaatacggcc | tgaacatcaa | accggttatc | 1080 |

```
ctggcagctg acggctctga gccagatctt tctcagcaag ccctgactga aaaggcgtg    1140
ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260
ggtgttccc gtcagcgtta ctggggcgcg ccgattccga tggtgactct agaagacggt    1320
accgtaatgc cgaccccgga cgaccagctg ccggtgatcc tgccggaaga tgtggtaatg    1380
gacggcatta ccagcccgat aaagcagat ccggagtggg cgaaaactac cgttaacggt    1440
atgccagcac tgcgtgaaac cgacactttc gacacctta tggagtcctg ctggatttat    1500
gcgcgctaca cttgcccgca gtacaaagaa ggtatgctgg attccgaagc ggctaactac    1560
tggctgccgg tggatatcgg tattggtggt attgaacacg ccattatgac gctgctctac    1620
ttccgcttct tccacaaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc ccggttgat gctatcgttg aacgtgacga gaaaggccgt    1800
atcgtgaaag cgaaagatgc ggcaggccat gaactggttt ataccggcat gagcaaaatg    1860
tccaagtcga agaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aaggggctaa ccgcttcctg aaacgtgtct ggaaactggt ttacgagcac    2040
acagcaaaag gtgatgttgc ggcactgaac gttgatgcgc tgactgaaaa tcagaaagcg    2100
ctgcgtcgcg atgtgcataa aacgatcgct aaagtgaccg atgatatcgg ccgtcgtcag    2160
accttcaaca ccgcaattgc ggcgattatg gagctgatga caaactggc gaaagcacca    2220
accgatggcg agcaggatcg cgctctgatg caggaagcac tgctggccgt tgtccgtatg    2280
cttaacccgt tcacccgca catctgcttc acgctgtggc aggaactgaa aggcgaaggc    2340
gatatcgaca cgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                  2583
```

<210> SEQ ID NO 42
<211> LENGTH: 2589
<212> TYPE: DNA
<213> ORGANISM: Artificial
<220> FEATURE:
<223> OTHER INFORMATION: mutant synthetase

<400> SEQUENCE: 42

```
atggaagagc ataccgcccc ggaagagata gaatccaaag tacagcttca ttgggatgag      60
aagcgcacat ttgaagtaac cgaagacgag agcaaagaga agtattactg cctgtctgct     120
aatccctatc cttctggtcg actacacatg ggccacgtac gtaactacac catcggtgac     180
gtgatcgccc gctaccagcg tatgctgggc aaaaacgtcc tgcagccgat cggctgggac     240
gcgtttggtc tgcctgcgga aggcgcgcg gtgaaaaaca caccgctcc ggcaccgtgg     300
acgtacgaca acatcgcgta tgaaaaaac cagctcaaaa tgctgggctt tggttatgac     360
tggagccgcg agctgcaac ctgtacgccg aatactacc gttgggaaca gaaattcttc     420
accgagctgt ataaaaaagg cctggtatat aagaagactt ctgcggtcaa ctggtgtccg     480
aacgaccaga ccgtactggc gaacgaacaa gttatcgacg gctgctgctg gcgctgcgat    540
```

```
accaaagttg aacgtaaaga gatcccgcag tggtttatca aaatcactgc ttacgctgac    600
gagctgctca acgatctgga taaactggat cactggccag acaccgttaa aaccatgcag    660
cgtaactgga tcggtcgttc cgaaggcgtg gagatcacct tcaacgttaa cgactatgac    720
aacacgctga ccgtttacac tacccgcccg gacgcgttta tgggttgtac ctacctggcg    780
gtagctgcgg gtcatccgct ggcgcagaaa gcggcggaaa ataatcctga actggcggcc    840
tttattgacg aatgccgtaa caccaaagtt gccgaagctg aaatggcgac gatggagaaa    900
aaaggcgtcg atactggctt taaagcggtt cacccattaa cgggcgaaga aattcccgtt    960
tgggcagcaa acttcgtatt gatggagtac ggcacgggcg cagttatggc ggtaccgggg   1020
cacgaccagc gcgactacga gtttgcctct aaatacggcc tgaacatcaa accggttatc   1080
ctggcagctg acggctctga gccagatctt tctcagcaag ccctgactga aaaggcgtg    1140 ctgttcaact ctggcgagtt caacggtctt gaccatgaag cggccttcaa cgccatcgcc   1200
gataaactga ctgcgatggg cgttggcgag cgtaaagtga actaccgcct gcgcgactgg   1260
ggtgtttccc gtcagcgtta ctggggcgcg ccgattccga tggtgactct agaagacggt   1320
accgtaatgc cgaccccgga cgaccagctg ccggtgatcc tgccggaaga gtggtaatg   1380 gacggcatta ccagcccgat aaagcagat  ccggagtggg cgaaaactac cgttaacggt   1440
atgccagcac tgcgtgaaac cgacactttc gacaccttta tggagtcctg ctggatttat   1500
gcgcgctaca cttgcccgca gtacaaagaa ggtatgctgg attccgaagc ggctaactac   1560
tggctgccgg tggatatcgg tattggtggt attgaacacg ccattatgac gctgctctac   1620
ttccgcttct tccacaaact gatgcgtgat gcaggcatgg tgaactctga cgaaccagcg   1680
aaacagttgc tgtgtcaggg tatggtgctg gcagatgcct tctactatgt tggcgaaaac   1740
ggcgaacgta actgggtttc cccggttgat gctatcgttg aacgtgacga gaaaggccgt   1800
atcgtgaaag cgaaagatgc ggcaggccat gaactggttt ataccggcat gagcaaaatg   1860
tccaagtcga agaacaacgg tatcgacccg caggtgatgg ttgaacgtta cggcgcggac   1920
accgttcgtc tgtttatgat gttgcttct ccggctgata tgactctcga atggcaggaa   1980
tccggtgtgg aaggggctaa ccgcttcctg aaacgtgtct ggaaactggt ttacgagcac   2040
acagcaaaag gtgatgttgc ggcactgaac gttgatgcgc tgactgaaaa tcagaaagcg   2100
ctgcgtcgcg atgtgcataa aacgatcgct aaagtgaccg atgatatcgg ccgtcgtcag   2160
accttcaaca ccgcaattgc ggcgattatg gagctgatga caaactggc gaaagcacca   2220 accgatggcg agcaggatcg cgctctgatg caggaagcac tgctggccgt tgtccgtatg   2280
cttaacccgt tcaccccgca catctgcttc acgctgtggc aggaactgaa aggcgaaggc   2340
gatatcgaca acgcgccgtg gccggttgct gacgaaaaag cgatggtgga agactccacg   2400
ctggtcgtgg tgcaggttaa cggtaaagtc cgtgccaaaa tcaccgttcc ggtggacgca   2460
acggaagaac aggttcgcga acgtgctggc aggaacatc tggtagcaaa atatcttgat   2520
ggcgttactg tacgtaaagt gatttacgta ccaggtaaac tcctcaatct ggtcgttggc   2580
taagcggcc                                                           2589

<210> SEQ ID NO 43
<211> LENGTH: 2589
<212> TYPE: DNA
<213> ORGANISM: Artificial
<220> FEATURE:
<223> OTHER INFORMATION: mutant synthetase
```

<400> SEQUENCE: 43

```
atggaagagc aataccgccc ggaagagata gaatccaaag tacagcttca ttgggatgag      60
aagcgcacat ttgaagtaac cgaagacgag agcaaagaga agtattactg cctgtctgct     120
aatccctatc cttctggtcg actacacatg ggccacgtac gtaactacac catcggtgac     180
gtgatcgccc gctaccagcg tatgctgggc aaaaacgtcc tgcagccgat cggctgggac     240
gcgtttggtc tgcctgcgga aggcgcgcg gtgaaaaaca acaccgctcc ggcaccgtgg       300
acgtacgaca acatcgcgta tatgaaaaac cagctcaaaa tgctgggctt tggttatgac     360
tggagccgcg agctggcaac ctgtacgccg aatactacc gttgggaaca gaaattcttc      420
accgagctgt ataaaaaagg cctggtatat aagaagactt ctgcggtcaa ctggtgtccg     480
aacgaccaga ccgtactggc gaacgaacaa gttatcgacg ctgctgctg gcgctgcgat      540
accaaagttg aacgtaaaga gatcccgcag tggtttatca aaatcactgc ttacgctgac     600
gagctgctca cgatctggat aaactggat cactggccag acaccgttaa aaccatgcag      660
cgtaactgga tcggtcgttc cgaaggcgtg agatcaccct tcaacgttaa cgactatgac     720
aacacgctga ccgtttacac tacccgcccg gacacctta tgggttgtac ctacctggcg      780
gtagctgcgg gtcatccgct ggcgcagaaa gcggcggaaa ataatcctga actggcggcc     840
tttattgacg aatgccgtaa caccaaagtt gccgaagctg aaatggcgac gatggagaaa     900
aaaggcgtcg atactggctt taaagcggtt cacccattaa cgggcgaaga aattcccgtt     960
tgggcagcaa acttcgtatt gatggagtac ggcacgggcg cagttatggc ggcgccgggg    1020
cacgaccagc gcgactacga gtttgcctct aaatacggcc tgaacatcaa ccggttatc    1080
ctggcagctg acggctctga gccagatctt tctcagcaag ccctgactga aaaaggcgtg    1140
ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260
ggtgttccc gtcagcgtta ctggggcgcg ccgattccga tggtgactct agaagacggt    1320
accgtaatgc cgaccccgga cgaccagctg ccggtgatcc tgccggaaga tgtggtaatg    1380
gacggcatta ccagcccgat taaagcagat ccggagtggg cgaaaactac cgttaacggt    1440
atgccagcac tgcgtgaaac cgacactttc gacacctta tggagtcctg ctggattat    1500
gcgcgctaca cttgcccgca gtacaaagaa ggtatgctgg attccgaagc ggctaactac    1560
tggctgccgg tggatatcgg tattggtggt attgaacacg ccattatgac gctgctctac    1620
ttccgcttct tccacaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc cccggttgat gctatcgttg aacgtgacga aaaggccgt    1800
atcgtgaaag cgaaagatgc ggcaggccat gaactggttt ataccggcat gagcaaaatg    1860
tccaagtcga gaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aaggggctaa ccgcttcctg aaacgtgtct ggaaactggt ttacgagcac    2040
acagcaaaag gtgatgttgc ggcactgaac gttgatgcgc tgactgaaaa tcagaaagcg    2100
ctgcgtcgcg atgtgcataa aacgatcgct aaagtgaccg atgatatcgg ccgtcgtcag    2160
accttcaaca ccgcaattgc ggcgattatg gagctgatga caaaactggc gaaagcacca    2220
accgatggcg agcaggatcg cgctctgatg caggaagcac tgctggccgt tgtccgtatg    2280
cttaacccgt tcaccccgca catctgcttc acgctgtggc aggaactgaa aggcgaaggc    2340
```

```
gatatcgaca acgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taagcggcc                                                            2589
```

<210> SEQ ID NO 44
<211> LENGTH: 2844
<212> TYPE: DNA
<213> ORGANISM: Artificial
<220> FEATURE:
<223> OTHER INFORMATION: mutant synthetase

<400> SEQUENCE: 44

```
atctcgaagc acacgaaact ttttccttcc ttcattcacg cacactactc tctaatgagc      60
aacggtatac ggccttcctt ccagttactt gaatttgaaa taaaaaaaag tttgctgtct     120
tgctatcaag tataaataga cctgcaatta ttaatctttt gtttcctcgt cattgttctc     180
gttccctttc ttccttgttt ctttttctgc acaatatttc aagctatacc aagcatacaa     240
tcaactgaat tcagtatgga agagcaatac cgcccggaag atagaatcc caaagtacag     300 cttcattggg atgagaagcg cacatttgaa gtaaccgaag acgagggcaa agagaagtat     360
tactgcctgt cttggtcgcc ctatccttct ggtcgactac acatgggcca cgtacgtaac     420
tacaccatcg gtgacgtgat cgcccgctac cagcgtatgc tgggcaaaaa cgtcctgcag     480
ccgatcggct gggacgcgtt tggtctgcct gcggaaggcg cggcggtgaa aaacaacacc     540
gctccggcac cgtggacgta cgacaacatc gcgtatatga aaaccagct caaaatgctg     600 ggctttggtt atgactggag ccgcgagctg gcaacctgta cgccggaata ctaccgttgg     660
gaacagaaat tcttcaccga gctgtataaa aaaggcctgg tatataagaa gacttctgcg     720
gtcaactggt gtccgaacga ccagaccgta ctggcgaacg aacaagttat cgacggctgc     780
tgctggcgct gcgataccaa agttgaacgt aaagagatcc gcagtggtt tatcaaaatc     840 actgcttacg ctgacgagct gctcaacgat ctggataaac tggatcactg gccagacacc     900
gttaaaacca tgcagcgtaa ctggatcggt cgttccgaag gcgtggagat caccttcaac     960
gttaacgact atgacaacac gctgaccgtt tacgcttccc gcccggacac ctttatgggt    1020
tgtacctacc tggcggtagc tgcgggtcat ccgctggcgc agaaagcggc ggaaaataat    1080
cctgaactgg cggcctttat tgacgaatgc cgtaacacca agttgccga agctgaaatg    1140 gcgacgatgg agaaaaagg cgtcgatact ggctttaaag cggttcaccc attaacgggc    1200
gaagaaattc ccgtttgggc agcaaacttc gtattgatgg agtacggcac gggcgcagtt    1260
atggcggtac cggggcacga ccagcgcgac tacgagtttg cctctaaata cggcctgaac    1320
atcaaaccgg ttatcctggc agctgacggc tctgagccag atctttctca gcaagccctg    1380
actgaaaaag gcgtgctgtt caactctggc gagttcaacg tcttgacca tgaagcggcc    1440 ttcaacgcca tcgccgataa actgactgcg atgggcgttg gcagcgtaa agtgaactac    1500 cgcctgcgcg actgggtgt ttcccgtcag cgttactggg gcgcgccgat tccgatggtg    1560
actctagaag acggtaccgt aatgccgacc ccggacgacc agctgccggt gatcctgccg    1620
gaagatgtgg taatgacgg cattaccagc ccgattaaag cagatccgga gtgggcgaaa    1680
actaccgtta acggtatgcc agcactgcgt gaaaccgaca ctttcgacac ctttatggag    1740
```

| | |
|---|---:|
| tcctgctgga tttatgcgcg ctacacttgc ccgcagtaca agaaggtat gctggattcc | 1800 |
| gaagcggcta actactggct gccggtggat atcgcgattg gtggtattga acacgccatt | 1860 |
| atggggctgc tctacttccg cttcttccac aaactgatgc gtgatgcagg catggtgaac | 1920 |
| tctgacgaac cagcgaaaca gttgctgtgt cagggtatgg tgcctggcaga tgccttctac | 1980 |
| tatgttggcg aaaacggcga acgtaactgg gtttccccgg ttgatgctat cgttgaacgt | 2040 |
| gacgagaaag gccgtatcgt gaaagcgaaa gatgcggcag ccatgaact ggtttatacc | 2100 |
| ggcataagca aaatgtccaa gtcgaagaac aacggtatcg acccgcaggt gatggttgaa | 2160 |
| cgttacggcg cggacaccgt tcgtctgttt atgatgtttg cttctccggc tgatatgact | 2220 |
| ctcgaatggc aggaatccgg tgtggaaggg gctaaccgct tcctgaaacg tgcctggaaa | 2280 |
| ctggtttacg agcacacagc aaaaggtgat gttgcggcac tgaacgttga tgcgctgact | 2340 |
| gaaaatcaga aagcgctgcg tcgcgatgtg cataaaacga tcgctaaagt gaccgatgat | 2400 |
| atcggccgtc gtcagacctt caacaccgca attgcggcga ttatggagct gatgaacaaa | 2460 |
| ctggcgaaag caccaaccga tggcgagcag gatcgcgctc tgatgcagga agcactgctg | 2520 |
| gccgttgtcc gtatgcttaa cccgttcacc ccgcacatct gcttcacgct gtggcaggaa | 2580 |
| ctgaaaggca aggcgatat cgacaacgcg ccgtggccgg ttgctgacga aaaagcgatg | 2640 |
| gtggaagact ccacgctggt cgtggtgcag gttaacggta agtccgtgc caaaatcacc | 2700 |
| gttccggtgg acgaacgga gaacaggtt cgcgaacgtg ctggccagga acatctggta | 2760 |
| gcaaaatatc ttgatggcgt tactgtacgt aaagtgattt acgtaccagg taaactcctc | 2820 |
| aatctggtcg ttggctaagc ggcc | 2844 |

```
<210> SEQ ID NO 45
<211> LENGTH: 2583
<212> TYPE: DNA
<213> ORGANISM: Artificial
<220> FEATURE:
<223> OTHER INFORMATION: mutant synthetase

<400> SEQUENCE: 45
```

| | |
|---|---:|
| atgcaagagc ataccgcccc ggaagagata gaatccaaag tacagcttca ttgggatgag | 60 |
| aagcgcacat ttgaagtaac cgaagacgag agcaaagaga agtattactg cctgtctgct | 120 |
| gcgccctatc cttctggtcg actacacatg ggccacgtac gtaactacac catcggtgac | 180 |
| gtgatcgccc gctaccagcg tatgctgggc aaaaacgtcc tgcagccgat cggctgggac | 240 |
| gcgtttggtc tgcctgcgga aggcgcggcg gtgaaaaaca caccgctcc ggcaccgtgg | 300 |
| acgtacgaca catcgcgta tgaaaaaac cagctcaaaa tgctgggctt tggttatgac | 360 |
| tggagccgcg agctggcaac ctgtacgccg gaatactacc gttgggaaca gaaattcttc | 420 |
| accgagctgt ataaaaaagg cctggtatat aagaagactt ctgcggtcaa ctggtgcccg | 480 |
| aacgaccaga ccgtactggc gaacgaacaa gttatcgacg ctgctgctg gcgctgcgat | 540 |
| accaaagttg aacgtaaaga gatcccgcag tggtttatca aaatcactgc ttacgctgac | 600 |
| gagctgctca cgatctgga taaactggat cactggccag acaccgttaa accatgcag | 660 |
| cgtaactgga tcggtcgttc cgaaggcgtg agatcacct tcaacgttaa cgactatgac | 720 |
| aacacgctga ccgtttacac taccgcccg gacacctta tgggttgtac ctacctggcg | 780 |
| gtagctgcgg gtcatccgct ggcgcagaaa gcggcggaaa taatcctga actggcggcc | 840 |
| tttattgaca atgccgtaa caccaaagtt gccgaagctg aaatggcgac gatggagaaa | 900 |
| aaaggcgtcg atactggctt taagcggtt cacccattaa cgggcgaaga aattccgtt | 960 |

```
tgggcagcaa acttcgtatt gatggagtac ggcacgggcg cagttatggc ggtaccgggg    1020
cacgaccagc gcgactacga gtttgcctct aaatacggcc tgaacatcaa accggttatc    1080
ctggcagctg acggctctga gccagatctt tctcagcaag ccctgactga aaaaggcgtg    1140
ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260
ggtgtttccc gtcagcgtta ctggggcgcg ccgattccga tggtgacgct ggaagacggt    1320
accgtaatgc cgaccccgga cgaccagctg ccggtgatcc tgccggaaga tgtggtaatg    1380
gacggcatta ccagcccgat aaagcagat ccggagtggg cgaaaactac cgttaacggt    1440
atgccagcac tgcgtgaaac cgacactttc gacaccttta tggagtcctc ctggccttat    1500
gcgcgctaca cttgcccgca gtacaaagaa ggtatgctgg attccgaagc ggctaactac    1560
tggctgccgg tggatatcgt tattggtggt attgaacacg ccattatggg gctgctctac    1620
ttccgcttct tccacaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc cccggttgat gctatcgttg aacgtgacga aaaggccgt    1800 atcgtgaaag cgaaagatgc ggcaggccat gaactggttt ataccggcat gagcaaaatg    1860
tccaagtcga gaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aagggctaa ccgcttcctg aaacgtgtct ggaaactggt ttacgagcac    2040
acagcaaaag gtgatgttgc ggcactgaac gttgatgcgc tgactgaaaa tcagaaagcg    2100
ctgcgtcgcg atgtgcataa aacgatcgct aaagtgaccg atgatatcgg ccgtcgtcag    2160
accttcaaca ccgcaattgc ggcgattatg gagctgatga caaactggc gaaagcacca    2220 accgatggcg agcaggatcg cgctctgatg caggaagcac tgctggccgt tgtccgtatg    2280
cttaacccgt tcacccgca catctgcttc acgctgtggc aggaactgaa aggcgaaggc    2340
gatatcgaca cgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                  2583
```

<210> SEQ ID NO 46
<211> LENGTH: 2583
<212> TYPE: DNA
<213> ORGANISM: Artificial
<220> FEATURE:
<223> OTHER INFORMATION: mutant synthetase

<400> SEQUENCE: 46

```
atgcaagagc ataccgccc ggaagagata gaatccaaag tacagcttca ttgggatgag     60
aagcgcacat ttgaagtaac cgaagacgag agcaaagaga agtattactg cctgtctgtg    120 atgcccatc cttctggtcg actacacatg ggccacgtac gtaactacac catcggtgac    180
gtgatcgccc gctaccagcg tatgctgggc aaaaacgtcc tgcagccgat cggctgggac    240
gcgtttggtc tgcctgcgga aggcgcgcg gtgaaaaaca caccgctcc ggcaccgtgg    300 acgtacgaca acatcgcgta tatgaaaaac cagctcaaaa tgctgggctt tggttatgac    360
```

```
tggagccgcg agctggcaac ctgtacgccg aatactacc gttgggaaca gaaattcttc    420
accgagctgt ataaaaaagg cctggtatat aagaagactt ctgcggtcaa ctggtgcccg    480
aacgaccaga ccgtactggc gaacgaacaa gttatcgacg gctgctgctg gcgctgcgat    540
accaaagttg aacgtaaaga gatcccgcag tggtttatca aaatcactgc ttacgctgac    600
gagctgctca acgatctgga taaactggat cactggccag acaccgttaa aaccatgcag    660
cgtaactgga tcggtcgttc cgaaggcgtg gagatcacct tcaacgttaa cgactatgac    720
aacacgctga ccgtttacac tacccgcccg gacaccttta tgggttgtac ctacctggcg    780
gtagctgcgg gtcatccgct ggcgcagaaa gcggcggaaa ataatcctga actggcggcc    840
tttattgacg aatgccgtaa caccaaagtt gccgaagctg aaatggcgac gatggagaaa    900
aaaggcgtcg atactggctt taaagcggtt cacccattaa cgggcgaaga aattcccgtt    960
tgggcagcaa acttcgtatt gatggagtac ggcacgggcg cagttatggc ggtaccgggg   1020
cacgaccagc gcgactacga gtttgcctct aaatacggcc tgaacatcaa accggttatc   1080
ctggcagctg acggctctga gccagatctt tctcagcaag ccctgactga aaaggcgtg    1140
ctgttcaact ctggcgagtt caacggtctt gaccatgaag cggccttcaa cgccatcgcc   1200
gataaactga ctgcgatggg cgttggcgag cgtaaagtga actaccgcct cgcgactgg    1260
ggtgtttccc gtcagcgtta ctggggcgcg ccgattccga tggtgacgct ggaagacggt   1320
accgtaatgc cgaccccgga cgaccagctg ccggtgatcc tgccggaaga tgtggtaatg   1380
gacggcatta ccagcccgat taaagcagat ccggagtggg cgaaaactac cgttaacggt   1440
atgccagcac tgcgtgaaac cgacactttc gaccccttta tggagtcctc ctggctgtat   1500
gcgcgctaca cttgcccgca gtacaaagaa ggtatgctgg attccgaagc ggctaactac   1560
tggctgccgg tggatatcct gattggtggt attgaaacacg ccattatggg gctgctctac   1620
ttccgcttct ccacaaaact gatgcgtgat gcaggcatgg tgaactctga cgaaccagcg   1680
aaacagttgc tgtgtcaggg tatggtgctg gcagatgcct tctactatgt tggcgaaaac   1740
ggcgaacgta actgggttttc cccggttgat gctatcgttg aacgtgacga gaaaggccgt   1800
atcgtgaaag cgaaagatgc ggcaggccat gaactggttt ataccggcat gagcaaaatg   1860
tccaagtcga agaacaacgg tatcgacccg caggtgatgg ttgaacgtta cggcgcggac   1920
accgttcgtc tgtttatgat gtttgcttct ccggctgata tgactctcga atggcaggaa   1980
tccggtgtgg aaggggctaa ccgcttcctg aaacgtgtct ggaaactggt ttacgagcac   2040
acagcaaaag gtgatgttgc ggcactgaac gttgatgcgc tgactgaaaa tcagaaagcg   2100
ctgcgtcgcg atgtgcataa aacgatcgct aaagtgaccg atgatatcgg ccgtcgtcag   2160
accttcaaca ccgcaattgc ggcgattatg gagctgatga caaaactggc gaaagcacca   2220
accgatggcg agcaggatcg cgctctgatg caggaagcac tgctggccgt tgtccgtatg   2280
cttaacccgt tcacccgca catctgcttc acgctgtggc aggaactgaa aggcgaaggc   2340
gatatcgaca cgcgccgtg gccggttgct gacgaaaaag cgatggtgga agactccacg   2400
ctggtcgtgg tgcaggttaa cggtaaagtc cgtgccaaaa tcaccgttcc ggtggacgca   2460
acggaagaac aggttcgcga acgtgctggc caggaacatc tggtagcaaa atatcttgat   2520
ggcgttactg tacgtaaagt gatttacgta ccaggtaaac tcctcaatct ggtcgttggc   2580
taa                                                                 2583
```

<210> SEQ ID NO 47
<211> LENGTH: 2583

<212> TYPE: DNA
<213> ORGANISM: Artificial
<220> FEATURE:
<223> OTHER INFORMATION: mutant synthetase

<400> SEQUENCE: 47

```
atgcaagagc aataccgccc ggaagagata gaatccaaag tacagcttca ttgggatgag      60
aagcgcacat ttgaagtaac cgaagacgag agcaaagaga agtattactg cctgtctcat     120
cctccctatc cttctggtcg actacacatg ggccacgtac gtaactacac catcggtgac     180
gtgatcgccc gctaccagcg tatgctgggc aaaaacgtcc tgcagccgat cggctgggac     240
gcgtttggtc tgcctgcgga aggcgcggcg gtgaaaaaca caccgctcc ggcaccgtgg      300
acgtacgaca acatcgcgta tatgaaaaac cagctcaaaa tgctgggctt tggttatgac     360
tggagccgcg agctggcaac ctgtacgccg aatactacc gttgggaaca gaaattcttc      420
accgagctgt ataaaaaagg cctggtatat aagaagactt ctgcggtcaa ctggtgcccg     480
aacgaccaga ccgtactggc gaacaacaa gttatcgacg ctgctgctg gcgctgcgat       540
accaaagttg aacgtaaaga gatcccgcag tggtttatca aaatcactgc ttacgctgac     600
gagctgctca cgatctgga taaactggat cactggccag acaccgttaa accatgcag      660
cgtaactgga tcggtcgttc cgaaggcgtg gagatcacct tcaacgttaa cgactatgac     720
aacacgctga ccgtttacac tacccgcccg gacacctta tgggttgtac ctacctggcg      780
gtagctgcgg gtcatccgct ggcgcagaaa gcggcggaaa ataatcctga actggcggcc     840
tttattgacg aatgccgtaa caccaaagtt gccgaagctg aaatggcgac gatggagaaa     900
aaaggcgtcg atactggctt taaagcggtt cacccattaa cgggcgaaga aattcccgtt     960
tgggcagcaa acttcgtatt gatggagtac ggcacgggcg cagttatggc ggtaccgggg    1020
cacgaccagc gcgactacga gtttgcctct aaatacggcc tgaacatcaa accggttatc    1080
ctggcagctg acggctctga gccagatctt tctcagcaag ccctgactga aaaaggcgtg    1140
ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260
ggtgtttccc gtcagcgtta ctggggcgcg ccgattccga tggtgacgct ggaagacggt    1320
accgtaatgc cgaccccgga cgaccagctg ccggtgatcc tgccggaaga tgtggtaatg    1380
gacggcatta ccagcccgat taagcagat ccggagtggg cgaaaactac cgttaacggt     1440
atgccagcac tgcgtgaaac cgacactttc gacaccttta tggagtcctc ctgggcgtat    1500
gcgcgctaca cttgcccgca gtacaaagaa ggtatgctgg attccgaagc ggctaactac    1560
tggctgccgg tggatatcat gattggtggt attgaacacg ccattatggg tctgctctac    1620
ttccgcttct tccacaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc cccgttgat gctatcgttg aacgtgacga gaaaggccgt     1800
atcgtgaaag cgaaagatgc ggcaggccat gaactggttt ataccggcat gagcaaaatg    1860
tccaagtcga agaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aagggctaa ccgcttcctg aacgtgtct ggaaactggt ttacgagcac      2040
acagcaaaag gtgatgttgc ggcactgaac gttgatgcgc tgactgaaaa tcagaaagcg    2100
ctgcgtcgcg atgtgcataa aacgatcgct aaagtgacca tgatatcgg ccgtcgtcag     2160
```

| | | |
|---|---|---|
| accttcaaca ccgcaattgc ggcgattatg gagctgatga acaaactggc gaaagcacca | 2220 |
| accgatggcg agcaggatcg cgctctgatg caggaagcac tgctggccgt tgtccgtatg | 2280 |
| cttaacccgt tcaccccgca catctgcttc acgctgtggc aggaactgaa aggcgaaggc | 2340 |
| gatatcgaca acgcgccgtg gccggttgct gacgaaaaag cgatggtgga agactccacg | 2400 |
| ctggtcgtgg tgcaggttaa cggtaaagtc cgtgccaaaa tcaccgttcc ggtggacgca | 2460 |
| acggaagaac aggttcgcga acgtgctggc caggaacatc tggtagcaaa atatcttgat | 2520 |
| ggcgttactg tacgtaaagt gatttacgta ccaggtaaac tcctcaatct ggtcgttggc | 2580 |
| taa | 2583 |

<210> SEQ ID NO 48
<211> LENGTH: 2583
<212> TYPE: DNA
<213> ORGANISM: Artificial
<220> FEATURE:
<223> OTHER INFORMATION: mutant synthetase

<400> SEQUENCE: 48

| | | |
|---|---|---|
| atgcaagagc aataccgccc ggaagagata gaatccaaag tacagcttca ttgggatgag | 60 |
| aagcgcacat ttgaagtaac cgaagacgag agcaaagaga agtattactg cctgtctgtg | 120 |
| tatccctatc cttctggtcg actacacatg ggccacgtac gtaactacac catcggtgac | 180 |
| gtgatcgccc gctaccagcg tatgctgggc aaaaacgtcc tgcagccgat cggctgggac | 240 |
| gcgtttggtc tgcctgcgga aggcgcggcg gtgaaaaaca caccgctcc ggcaccgtgg | 300 |
| acgtacgaca catcgcgta tatgaaaaac cagctcaaaa tgctgggctt tggttatgac | 360 |
| tggagccgcg agctggcaac ctgtacgccg gaatactacc gttgggaaca gaaattcttc | 420 |
| accgagctgt ataaaaaagg cctggtatat aagaagactt ctgcggtcaa ctggtgcccg | 480 |
| aacgaccaga ccgtactggc gaacgaacaa gttatcgacg ctgctgctg cgctgcgat | 540 |
| accaaagttg aacgtaaaga gatcccgcag tggttttatca aaatcactgc ttacgctgac | 600 |
| gagctgctca acgatctgga taaactggat cactggccag acaccgttaa aaccatgcag | 660 |
| cgtaactgga tcggtcgttc cgaaggcgtg gagatcacct tcaacgttaa cgactatgac | 720 |
| aacacgctga ccgtttacac tacccgcccg gacaccttta tgggttgtac ctacctggcg | 780 |
| gtagctgcgg tcatccgct ggcgcagaaa gcggcggaaa taatcctga actggcggcc | 840 |
| tttattgacg aatgccgtaa caccaaagtt gccgaagctg aaatggcgac gatggagaaa | 900 |
| aaaggcgtcg atactggctt taagcggtt cacccattaa cggcgaaga aattcccgtt | 960 |
| tgggcagcaa acttcgtatt gatggagtac ggcacgggcg cagttatggc ggtaccgggg | 1020 |
| cacgaccagc gcgactacga gtttgcctct aaatacggcc tgaacatcaa ccggttatc | 1080 |
| ctggcagctg acggctctga ccagatcttt ctcagcaag ccctgactga aaaggcgtg | 1140 |
| ctgttcaact ctggcgagtt caacggtctt gaccatgaag cggccttcaa cgccatcgcc | 1200 |
| gataaactga ctgcgatggg cgttggcgag cgtaaagtga actaccgcct gcgcgactgg | 1260 |
| ggtgttttccc gtcagcgtta ctggggcgcg ccgattccga tggtgacgct ggaagacggt | 1320 |
| accgtaatgc cgaccccgga cgaccagctg ccggtgatcc tgccggaaga tgtggtaatg | 1380 |
| gacggcatta ccagcccgat taaagcagat ccggagtggg cgaaaactac cgttaacggt | 1440 |
| atgccagcac tgcgtgaaac cgacacttc gacaccttta tggagtcctc ctggctgtat | 1500 |
| gcgcgctaca cttgcccgca gtacaaagaa ggtatgctgg attccgaagc ggctaactac | 1560 |
| tggctgccgg tggatatcct gattggtggt attgaacacg ccattatggg tctgctctac | 1620 |

```
ttccgcttct tccacaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc cccggttgat gctatcgttg aacgtgacga gaaaggccgt    1800
atcgtgaaag cgaaagatgc ggcaggccat gaactggttt ataccggcat gagcaaaatg    1860
tccaagtcga agaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aagggctaa ccgcttcctg aaacgtgtct ggaaactggt ttacgagcac    2040
acagcaaaag gtgatgttgc ggcactgaac gttgatgcgc tgactgaaaa tcagaaagcg    2100
ctgcgtcgcg atgtgcataa acgatcgct aaagtgaccg atgatatcgg ccgtcgtcag    2160
accttcaaca ccgcaattgc ggcgattatg gagctgatga caaactggc gaaagcacca    2220 accgatggcg agcaggatcg cgctctgatg caggaagcac tgctggccgt tgtccgtatg    2280
cttaacccgt tcaccccgca catctgcttc acgctgtggc aggaactgaa aggcgaaggc    2340
gatatcgaca acgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                  2583

<210> SEQ ID NO 49
<211> LENGTH: 2583
<212> TYPE: DNA
<213> ORGANISM: Artificial
<220> FEATURE:
<223> OTHER INFORMATION: mutant synthetase

<400> SEQUENCE: 49
atgcaagagc aataccgccc ggaagagata gaatccaaag tacagcttca ttgggatgag      60
aagcgcacat ttgaagtaac cgaagacgag agcaaagaga agtattactg cctgtctttg     120
gagccctatc cttctggtcg actacacatg ggccacgtac gtaactacac catcggtgac     180
gtgatcgccc gctaccagcg tatgctgggc aaaaacgtcc tgcagccgat cggctgggac     240
gcgtttggtc tgcctgcgga aggcgcgcg gtgaaaaaca caccgctcc ggcaccgtgg     300 acgtacgaca catcgcgta tatgaaaaac cagctcaaaa tgctgggctt tggttatgac     360
tggagccgca gctggcaac ctgtacgccg gaatactacc gttgggaaca gaaattcttc     420
accgagctgt ataaaaaagg cctggtatat aagaagactt ctgcggtcaa ctggtgcccg     480
aacgaccaga ccgtactggc gaacaacaa gttatcgacg ctgctgctg gcgctgcgat     540 accaaagttg aacgtaaaga gatcccgcag tggtttatca aaatcactgc ttacgctgac     600
gagctgctca cgatctgga taaactggat cactggccag acaccgttaa accatgcag     660 cgtaactgga tcggtcgttc cgaaggcgtg gagatcacct tcaacgttaa cgactatgac     720
aacacgctga ccgtttacac taccgccccg gacaccttta tgggttgtac ctacctggcg     780
gtagctgcgg tcatccgct ggcgcagaaa gcggcggaaa ataatcctga actggcggcc     840
tttattgacg aatgccgtaa caccaaagtt gccgaagctg aaatggcgac gatggagaaa     900
aaaggcgtcg atactggctt taagcggtt cacccattaa cggcgaaga attcccgtt      960 tgggcagcaa acttcgtatt gatggagtac ggcacgggcg cagttatggc ggtaccgggg    1020
```

```
cacgaccagc gcgactacga gtttgcctct aaatacggcc tgaacatcaa accggttatc    1080
ctggcagctg acggctctga gccagatctt tctcagcaag ccctgactga aaaaggcgtg    1140
ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260 ggtgttccc gtcagcgtta ctggggcgcg ccgattccga tggtgacgct ggaagacggt    1320
accgtaatgc cgaccccgga cgaccagctg ccggtgatcc tgccggaaga tgtggtaatg    1380
gacggcatta ccagcccgat aaagcagat ccggagtggg cgaaaactac cgttaacggt    1440
atgccagcac tgcgtgaaac cgacactttc gaccctta tggagtcctc ctggcgttat    1500
gcgcgctaca cttcccgca gtacaaagaa ggtatgctgg attccgaagc ggctaactac    1560
tggctgccgg tggatatcgc tattggtggt attgaacacg ccattatggg tctgctctac    1620
ttccgcttct ccacaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc cccggttgat gctatcgttg aacgtgacga aaaggccgt    1800 atcgtgaaag cgaaagatgc ggcaggccat gaactggttt ataccggcat gagcaaaatg    1860
tccaagtcga gaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aaggggctaa ccgcttcctg aaacgtgtct ggaaactggt ttacgagcac    2040
acagcaaaag gtgatgttgc ggcactgaac gttgatgcgc tgactgaaaa tcagaaagcg    2100
ctgcgtcgcg atgtgcataa aacgatcgct aaagtgaccg atgatatcgg ccgtcgtcag    2160
accttcaaca ccgcaattgc ggcgattatg gagctgatga caaactggc gaaagcacca    2220 accgatggcg agcaggatcg cgctctgatg caggaagcac tgctggccgt tgtccgtatg    2280
cttaacccgt tcacccccgca catctgcttc acgctgtggc aggaactgaa aggcgaaggc    2340
gatatcgaca cgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                 2583
```

<210> SEQ ID NO 50  
<211> LENGTH: 2583  
<212> TYPE: DNA  
<213> ORGANISM: Artificial  
<220> FEATURE:  
<223> OTHER INFORMATION: mutant synthetase

<400> SEQUENCE: 50

```
atgcaagagc aataccgccc ggaagagata gaatccaaag tacagcttca ttgggatgag     60
aagcgcacat ttgaagtaac cgaagacgag agcaaagaga agtattactg cctgtctatg    120
gagccctatc cttctggtcg actacacatg ggccacgtac gtaactacac catcggtgac    180
gtgatcgccc gctaccagcg tatgctgggc aaaaacgtcc tgcagccgat cggctgggac    240
gcgtttggtc tgcctgcgga aggcgcggcg gtgaaaaaca acaccgctcc ggcaccgtgg    300
acgtacgaca acatcgcgta tatgaaaaac cagctcaaaa tgctgggctt tggttatgac    360
tggagccgcg agctggcaac ctgtacgccg gaatactacc gttgggaaca gaaattcttc    420
accgagctgt ataaaaaagg cctggtatat aagaagactt ctgcggtcaa ctggtgcccg    480
```

```
aacgaccaga ccgtactggc gaacgaacaa gttatcgacg gctgctgctg gcgctgcgat    540
accaaagttg aacgtaaaga gatcccgcag tggtttatca aaatcactgc ttacgctgac    600
gagctgctca acgatctgga taaactggat cactggccag acaccgttaa aaccatgcag    660
cgtaactgga tcggtcgttc cgaaggcgtg gagatcacct tcaacgttaa cgactatgac    720
aacacgctga ccgtttacac tacccgcccg gacaccttta tgggttgtac ctacctggcg    780
gtagctgcgg gtcatccgct ggcgcagaaa gcggcggaaa ataatcctga actggcggcc    840
tttattgacg aatgccgtaa caccaaagtt gccgaagctg aaatggcgac gatggagaaa    900
aaaggcgtcg atactggctt taaagcggtt cacccattaa cgggcgaaga aattcccgtt    960
tgggcagcaa acttcgtatt gatggagtac ggcacgggcg cagttatggc ggtaccgggg   1020
cacgaccagc gcgactacga gtttgcctct aaatacggcc tgaacatcaa accggttatc   1080
ctggcagctg acggctctga gccagatctt tctcagcaag ccctgactga aaaaggcgtg   1140
ctgttcaact ctggcgagtt caacggtctt gaccatgaag cggccttcaa cgccatcgcc   1200
gataaactga ctgcgatggg cgttggcgag cgtaaagtga actaccgcct gcgcgactgg   1260
ggtgtttccc gtcagcgtta ctggggcgcg ccgattccga tggtgacgct ggaagacggt   1320
accgtaatgc cgaccccgga cgaccagctg ccggtgatcc tgccggaaga tgtggtaatg   1380
gacggcatta ccagcccgat taaagcagat ccggagtggg cgaaaactac cgttaacggt   1440
atgccagcac tgcgtgaaac cgacactttc gacaccttta tggagtcctc ctggcgttat   1500
gcgcgctaca cttgcccgca gtacaaagaa ggtatgctgg attccgaagc ggctaactac   1560
tggctgccgg tggatatctt tattggtggt attgaacacg ccattatggg gctgctctac   1620
ttccgcttct tccacaaact gatgcgtgat gcaggcatgg tgaactctga cgaaccagcg   1680
aaacagttgc tgtgtcaggg tatggtgctg gcagatgcct tctactatgt tggcgaaaac   1740
ggcgaacgta actgggtttc cccggttgat gctatcgttg aacgtgacga gaaaggccgt   1800
atcgtgaaag cgaaagatgc ggcaggccat gaactggttt ataccggcat gagcaaaatg   1860
tccaagtcga gaacaacgg tatcgacccg caggtgatgg ttgaacgtta cggcgcggac   1920
accgttcgtc tgtttatgat gtttgcttct ccggctgata tgactctcga atggcaggaa   1980
tccggtgtgg aagggctaa ccgcttcctg aaacgtgtct ggaaactggt ttacgagcac   2040
acagcaaaag gtgatgttgc ggcactgaac gttgatgcgc tgactgaaaa tcagaaagcg   2100
ctgcgtcgcg atgtgcataa aacgatcgct aaagtgaccg atgatatcgg ccgtcgtcag   2160
accttcaaca ccgcaattgc ggcgattatg agctgatga caaaactggc gaaagcacca   2220
accgatggcg agcaggatcg cgctctgatg caggaagcac tgctggccgt tgtccgtatg   2280
cttaacccgt tcaccccgca catctgcttc acgctgtggc aggaactgaa aggcgaaggc   2340
gatatcgaca acgcgccgtg gccggttgct gacgaaaaag cgatggtgga agactccacg   2400
ctggtcgtgg tgcaggttaa cggtaaagtc cgtgccaaaa tcaccgttcc ggtggacgca   2460
acggaagaac aggttcgcga acgtgctggc caggaacatc tggtagcaaa atatcttgat   2520
ggcgttactg tacgtaaagt gatttacgta ccaggtaaac tcctcaatct ggtcgttggc   2580
taa                                                                 2583
```

<210> SEQ ID NO 51
<211> LENGTH: 2583
<212> TYPE: DNA
<213> ORGANISM: Artificial
<220> FEATURE:

<223> OTHER INFORMATION: mutant synthetase

<400> SEQUENCE: 51

| | | | | | |
|---|---|---|---|---|---|
| atgcaagagc | aataccgccc | ggaagagata | gaatccaaag | tacagcttca | ttgggatgag | 60 |
| aagcgcacat | ttgaagtaac | cgaagacgag | agcaaagaga | agtattactg | cctgtctttg | 120 |
| gagccctatc | cttctggtcg | actacacatg | ggccacgtac | gtaactacac | catcggtgac | 180 |
| gtgatcgccc | gctaccagcg | tatgctgggc | aaaaacgtcc | tgcagccgat | cggctgggac | 240 |
| gcgtttggtc | tgcctgcgga | aggcgcggcg | gtgaaaaaca | caccgctcc | ggcaccgtgg | 300 |
| acgtacgaca | catcgcgta | tatgaaaaac | cagctcaaaa | tgctgggctt | tggttatgac | 360 |
| tggagccgcg | agctggcaac | ctgtacgccg | gaatactacc | gttgggaaca | gaaattcttc | 420 |
| accgagctgt | ataaaaaagg | cctggtatat | aagaagactt | ctgcggtcaa | ctggtgcccg | 480 |
| aacgaccaga | ccgtactggc | gaacgaacaa | gttatcgacg | gctgctgctg | cgctgcgat | 540 |
| accaaagttg | aacgtaaaga | gatcccgcag | tggtttatca | aaatcactgc | ttacgctgac | 600 |
| gagctgctca | acgatctgga | taaactggat | cactggccag | acaccgttaa | accatgcag | 660 |
| cgtaactgga | tcggtcgttc | cgaaggcgtg | gagatcacct | tcaacgttaa | cgactatgac | 720 |
| aacacgctga | ccgtttacac | tacccgcccg | gacacctta | tgggttgtac | ctacctggcg | 780 |
| gtagctgcgg | tcatccgct | ggcgcagaaa | gcggcggaaa | ataatcctga | actggcggcc | 840 |
| tttattgacg | aatgccgtaa | caccaaagtt | gccgaagctg | aaatggcgac | gatggagaaa | 900 |
| aaaggcgtcg | atactggctt | taaagcggtt | cacccattaa | cgggcgaaga | aattcccgtt | 960 |
| tgggcagcaa | acttcgtatt | gatggagtac | ggcacgggcg | cagttatggc | ggtaccgggg | 1020 |
| cacgaccagc | gcgactacga | gtttgcctct | aaatacggcc | tgaacatcaa | accggttatc | 1080 |
| ctggcagctg | acgctctga | gccagatctt | tctcagcaag | ccctgactga | aaaaggcgtg | 1140 |
| ctgttcaact | ctggcgagtt | caacggtctt | gaccatgaag | cggccttcaa | cgccatcgcc | 1200 |
| gataaactga | ctgcgatggg | cgttggcgag | cgtaaagtga | actaccgcct | gcgcgactgg | 1260 |
| ggtgtttccc | gtcagcgtta | ctggggcgcg | ccgattccga | tggtgacgct | ggaagacggt | 1320 |
| accgtaatgc | cgaccccgga | cgaccagctg | ccggtgatcc | tgccggaaga | gtggtaatg | 1380 |
| gacggcatta | ccagcccgat | taaagcagat | ccggagtggg | cgaaaactac | cgttaacggt | 1440 |
| atgccagcac | tgcgtgaaac | cgacactttc | gacacctta | tggagtcctc | ctggcgttat | 1500 |
| gcgcgctaca | cttcccgca | gtacaaagaa | ggtatgctgg | attccgaagc | ggctaactac | 1560 |
| tggctgccgg | tggatatctg | tattggtggt | attgaacacg | ccattatggg | tctgctctac | 1620 |
| ttccgcttct | tccacaaact | gatgcgtgat | gcaggcatgg | tgaactctga | cgaaccagcg | 1680 |
| aaacagttgc | tgtgtcaggg | tatggtgctg | gcagatgcct | tctactatgt | tggcgaaaac | 1740 |
| ggcgaacgta | actgggtttc | cccggttgat | gctatcgttg | aacgtgacga | gaaaggccgt | 1800 |
| atcgtgaaag | cgaaagatgc | ggcaggccat | gaactggttt | ataccggcat | gagcaaaatg | 1860 |
| tccaagtcga | agaacaacgg | tatcgacccg | caggtgatgg | ttgaacgtta | cggcgcggac | 1920 |
| accgttcgtc | tgtttatgat | gtttgcttct | ccggctgata | tgactctcga | atggcaggaa | 1980 |
| tccggtgtgg | aaggggctaa | ccgcttcctg | aaacgtgtct | ggaaactggt | ttacgagcac | 2040 |
| acagcaaaag | gtgatgttgc | ggcactgaac | gttgatgcgc | tgactgaaaa | tcagaaagcg | 2100 |
| ctgcgtcgcg | atgtgcataa | aacgatcgct | aaagtgaccg | atgatatcgg | ccgtcgtcag | 2160 |
| accttcaaca | ccgcaattgc | ggcgattatg | gagctgatga | caaactggc | gaaagcacca | 2220 |
| accgatggcg | agcaggatcg | cgctctgatg | caggaagcac | tgctggccgt | tgtccgtatg | 2280 |

```
cttaacccgt tcaccccgca catctgcttc acgctgtggc aggaactgaa aggcgaaggc    2340
gatatcgaca acgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                 2583
```

<210> SEQ ID NO 52
<211> LENGTH: 2583
<212> TYPE: DNA
<213> ORGANISM: Artificial
<220> FEATURE:
<223> OTHER INFORMATION: mutant synthetase

<400> SEQUENCE: 52

```
atgcaagagc aataccgccc ggaagagata gaatccaaag tacagcttca ttgggatgag      60
aagcgcacat ttgaagtaac cgaagacgag agcaaagaga agtattactg cctgtctttt     120
gagccctatc cttctggtcg actacacatg ggccacgtac gtaactacac catcggtgac     180
gtgatcgccc gctaccagcg tatgctgggc aaaaacgtcc tgcagccgat cggctgggac     240
gcgtttggtc tgcctgcgga aggcgcgcg gtgaaaaaca caccgctcc ggcaccgtgg       300 acgtacgaca acatcgcgta tgaaaaaac cagctcaaaa tgctgggctt tggttatgac      360
tggagccgcg agctggcaac ctgtacgccg aatactacc gttgggaaca gaaattcttc      420
accgagctgt ataaaaaagg cctggtatat aagaagactt ctgcggtcaa ctggtgcccg    480
aacgaccaga ccgtactggc gaacgaacaa gttatcgacg ctgctgctg gcgctgcgat     540 accaaagttg aacgtaaaga gatcccgcag tggtttatca aaatcactgc ttacgctgac    600
gagctgctca cgatctggat aaactggat cactggccag acaccgttaa accatgcag      660 cgtaactgga tcggtcgttc cgaaggcgtg gagatcacct tcaacgttaa cgactatgac    720
aacacgctga ccgtttacac tacccgcccg gacaccttta tgggttgtac ctacctggcg    780
gtagctgcgg tcatccgct ggcgcagaaa gcggcgaaa ataatcctga actggcggcc     840
tttattgacg aatgccgtaa caccaaagtt gccgaagctg aaatggcgac gatggagaaa    900
aaaggcgtcg atactggctt taagcggtt cacccattaa cgggcgaaga aattcccgtt     960
tgggcagcaa acttcgtatt gatggagtac ggcacgggcg cagttatggc ggtaccgggg    1020
cacgaccagc gcgactacga gtttgcctct aaatacggcc tgaacatcaa accggttatc    1080
ctggcagctg acggctctga gccagatctt tctcagcaag ccctgactga aaaggcgtg     1140 ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260 ggtgttccc gtcagcgtta ctggggcgcg ccgattccga tggtgacgct ggaagacggt     1320
accgtaatgc cgaccccgga cgaccagctg ccggtgatcc tgccggaaga tgtggtaatg    1380
gacggcatta ccagcccgat taaagcagat ccggagtggg cgaaaactac cgttaacggt    1440
atgccagcac tgcgtgaaac cgacactttc gacaccttta tggagtcctc ctggcgttat    1500
gcgcgctaca cttgcccgca gtacaaagaa ggtatgctgg attccgaagc ggctaactac    1560
tggctgccgg tggatatcac gattggtggt attgaacacg ccattatggg tctgctctac    1620
ttccgcttct tccacaaact gatgcgtgat gcaggcatgg tgaactctga cgaaccagcg    1680
```

```
aaacagttgc tgtgtcaggg tatggtgctg gcagatgcct tctactatgt tggcgaaaac    1740
ggcgaacgta actgggtttc cccggttgat gctatcgttg aacgtgacga gaaaggccgt    1800
atcgtgaaag cgaaagatgc ggcaggccat gaactggttt ataccggcat gagcaaaatg    1860
tccaagtcga agaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aagggctaa ccgcttcctg aaacgtgtct ggaaactggt ttacgagcac     2040
acagcaaaag gtgatgttgc ggcactgaac gttgatgcgc tgactgaaaa tcagaaagcg    2100
ctgcgtcgcg atgtgcataa aacgatcgct aaagtgaccg atgatatcgg ccgtcgtcag    2160
accttcaaca ccgcaattgc ggcgattatg gagctgatga caaactggc gaaagcacca     2220
accgatggcg agcaggatcg cgctctgatg caggaagcac tgctggccgt tgtccgtatg    2280
cttaacccgt tcaccccgca catctgcttc acgctgtggc aggaactgaa aggcgaaggc    2340
gatatcgaca acgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                  2583
```

<210> SEQ ID NO 53
<211> LENGTH: 2583
<212> TYPE: DNA
<213> ORGANISM: Artificial
<220> FEATURE:
<223> OTHER INFORMATION: mutant synthetase

<400> SEQUENCE: 53

```
atgcaagagc aataccgccc ggaagagata gaatccaaag tacagcttca ttgggatgag     60
aagcgcacat ttgaagtaac cgaagacgag agcaaagaga agtattactg cctgtctggg    120
gagccctatc cttctggtcg actacacatg ggccacgtac gtaactacac catcggtgac    180
gtgatcgccc gctaccagcg tatgctgggc aaaaacgtcc tgcagccgat cggctgggac    240
gcgtttggtc tgcctgcgga aggcgcggcg gtgaaaaaca caccgctcc ggcaccgtgg     300
acgtacgaca catcgcgta tatgaaaaac cagctcaaaa tgctgggctt tggttatgac    360
tggagccgcg agctggcaac ctgtacgccg gaatactacc gttgggaaca gaaattcttc    420
accgagctgt ataaaaaagg cctggtatat aagaagactt ctgcggtcaa ctggtgcccg    480
aacgaccaga ccgtactggc gaacgaacaa gttatcgacg gctgctgctg gcgctgcgat    540
accaaagttg aacgtaaaga gatcccgcag tggtttatca aaatcactgc ttacgctgac    600
gagctgctca cgatctgga taaactggat cactggccag acaccgttaa aaccatgcag    660
cgtaactgga tcggtcgttc cgaaggcgtg gagatcacct tcaacgttaa cgactatgac    720
aacacgctga ccgtttacac tacccgcccg gacaccttta gggttgtac ctacctggcg     780
gtagctgcgg gtcatccgct ggcgcagaaa gcggcggaaa ataatcctga actggcggcc    840
tttattgacg aatgccgtaa caccaaagtt gccgaagctg aaatggcgac gatggagaaa    900
aaaggcgtcg atactggctt taagcggtt cacccattaa cgggcgaaga aattcccgtt     960
tgggcagcaa acttcgtatt gatggagtac ggcacgggcg cagttatggc ggtaccgggg    1020
cacgaccagc gcgactacga gtttgcctct aaatacggcc tgaacatcaa accgttatc    1080
ctggcagctg acggctctga gccagatctt tctcagcaag ccctgactga aaaggcgtg    1140
```

```
ctgttcaact ctggcgagtt caacggtctt gaccatgaag cggccttcaa cgccatcgcc    1200
gataaactga ctgcgatggg cgttggcgag cgtaaagtga actaccgcct gcgcgactgg    1260
ggtgtttccc gtcagcgtta ctggggcgcg ccgattccga tggtgacgct ggaagacggt    1320
accgtaatgc cgaccccgga cgaccagctg ccggtgatcc tgccggaaga tgtggtaatg    1380
gacggcatta ccagcccgat taaagcagat ccggagtggg cgaaaactac cgttaacggt    1440
atgccagcac tgcgtgaaac cgacactttc gacacccttta tggagtcctc ctggcggtat    1500
gcgcgctaca cttgcccgca gtacaaagaa ggtatgctgg attccgaagc ggctaactac    1560
tggctgccgg tggatatcct gattggtggt attgaacacg ccattatggg tctgctctac    1620
ttccgcttct ccacaaaact gatgcgtgat gcaggcatgg tgaactctga cgaaccagcg    1680
aaacagttgc tgtgtcaggg tatggtgctg gcagatgcct tctactatgt tggcgaaaac    1740
ggcgaacgta actgggtttc cccggttgat gctatcgttg aacgtgacga gaaaggccgt    1800
atcgtgaaag cgaaagatgc ggcaggccat gaactggttt ataccggcat gagcaaaatg    1860
tccaagtcga agaacaacgg tatcgacccg caggtgatgg ttgaacgtta cggcgcggac    1920
accgttcgtc tgtttatgat gtttgcttct ccggctgata tgactctcga atggcaggaa    1980
tccggtgtgg aaggggctaa ccgcttcctg aaacgtgtct ggaaactggt ttacgagcac    2040
acagcaaaag gtgatgttgc ggcactgaac gttgatgcgc tgactgaaaa tcagaaagcg    2100
ctgcgtcgcg atgtgcataa aacgatcgct aaagtgaccg atgatatcgg ccgtcgtcag    2160
accttcaaca ccgcaattgc ggcgattatg gagctgatga caaaactggc gaaagcacca    2220
accgatggcg agcaggatcg cgctctgatg caggaagcac tgctggccgt tgtccgtatg    2280
cttaacccgt tcacccccgca catctgcttc acgctgtggc aggaactgaa aggcgaaggc    2340
gatatcgaca acgcgccgtg gccggttgct gacgaaaaag cgatggtgga agactccacg    2400
ctggtcgtgg tgcaggttaa cggtaaagtc cgtgccaaaa tcaccgttcc ggtggacgca    2460
acggaagaac aggttcgcga acgtgctggc caggaacatc tggtagcaaa atatcttgat    2520
ggcgttactg tacgtaaagt gatttacgta ccaggtaaac tcctcaatct ggtcgttggc    2580
taa                                                                  2583
```

<210> SEQ ID NO 54
<211> LENGTH: 2583
<212> TYPE: DNA
<213> ORGANISM: Artificial
<220> FEATURE:
<223> OTHER INFORMATION: mutant synthetase

<400> SEQUENCE: 54

```
atgcaagagc aataccgccc ggaagagata gaatccaaag tacagcttca ttgggatgag      60
aagcgcacat ttgaagtaac cgaagacgag agcaaagaga agtattactg cctgtctggt     120
tggccctatc cttctggtcg actacacatg gccacgtac gtaactacac catcggtgac      180
gtgatcgccc gctaccagcg tatgctgggc aaaaacgtcc tgcagccgat cggctgggac     240
gcgtttggtc tgcctgcgga aggcgcggcg gtgaaaaaca caccgctcc ggcaccgtgg      300 acgtacgaca catcgcgta tatgaaaaac cagctcaaaa tgctgggctt tggttatgac      360
tggagccgcg agctggcaac ctgtacgccg gaatactacc gttgggaaca gaaattcttc     420
accgagctgt ataaaaaagg cctggtatat aagaagactt ctgcggtcaa ctggtgcccg     480
aacgaccaga ccgtactggc gaacgaacaa gttatcgacg gctgctgctg gcgctgcgat     540
```

| | | |
|---|---|---|
| accaaagttg aacgtaaaga gatcccgcag tggtttatca aaatcactgc ttacgctgac | 600 | |
| gagctgctca acgatctgga taaactggat cactggccag acaccgttaa aaccatgcag | 660 | |
| cgtaactgga tcggtcgttc cgaaggcgtg gagatcacct tcaacgttaa cgactatgac | 720 | |
| aacacgctga ccgtttacac tacccgcccg gacaccttta tggggttgtac ctacctggcg | 780 | |
| gtagctgcgg gtcatccgct ggcgcagaaa gcggcggaaa ataatcctga actggcggcc | 840 | |
| tttattgacg aatgccgtaa caccaaagtt gccgaagctg aaatggcgac gatggagaaa | 900 | |
| aaaggcgtcg atactggctt taaagcggtt cacccattaa cgggcgaaga aattcccgtt | 960 | |
| tgggcagcaa acttcgtatt gatggagtac ggcacgggcg cagttatggc ggtaccgggg | 1020 | |
| cacgaccagc gcgactacga gtttgcctct aaatacggcc tgaacatcaa accggttatc | 1080 | |
| ctggcagctg acggctctga gccagatctt tctcagcaag ccctgactga aaaggcgtg | 1140 | |
| ctgttcaact ctggcgagtt caacggtctt gaccatgaag cggccttcaa cgccatcgcc | 1200 | |
| gataaactga ctgcgatggg cgttggcgag cgtaaagtga actaccgcct gcgcgactgg | 1260 | |
| ggtgtttccc gtcagcgtta ctggggcgcg ccgattccga tggtgacgct ggaagacggt | 1320 | |
| accgtaatgc cgaccccgga cgaccagctg ccggtgatcc tgccggaaga tgtggtaatg | 1380 | |
| gacggcatta ccagcccgat taaagcagat ccggagtggg cgaaaactac cgttaacggt | 1440 | |
| atgccagcac tgcgtgaaac cgacactttc gacaccttta tggagtcctc ctgggcttat | 1500 | |
| gcgcgctaca cttgcccgca gtacaaagaa ggtatgctgg attccgaagc ggctaactac | 1560 | |
| tggctgccgg tggatatcct tattggtggt attgaacacg ccattatggg tctgctctac | 1620 | |
| ttccgcttct tccacaaact gatgcgtgat gcaggcatgg tgaactctga cgaaccagcg | 1680 | |
| aaacagttgc tgtgtcaggg tatggtgctg gcagatgcct tctactatgt tggcgaaaac | 1740 | |
| ggcgaacgta actgggtttc cccggttgat gctatcgttg aacgtgacga gaaaggccgt | 1800 | |
| atcgtgaaag cgaaagatgc ggcaggccat gaactggttt ataccggcat gagcaaaatg | 1860 | |
| tccaagtcga gaacaacgg tatcgacccg caggtgatgg ttgaacgtta cggcgcggac | 1920 | |
| accgttcgtc tgtttatgat gtttgcttct ccggctgata tgactctcga atggcaggaa | 1980 | |
| tccggtgtgg aaggggctaa ccgcttcctg aaacgtgtct ggaaactggt ttacgagcac | 2040 | |
| acagcaaaag gtgatgttgc ggcactgaac gttgatgcgc tgactgaaaa tcagaaagcg | 2100 | |
| ctgcgtcgcg atgtgcataa aacgatcgct aaagtgaccg atgatatcgg ccgtcgtcag | 2160 | |
| accttcaaca ccgcaattgc ggcgattatg gagctgatga caaactggc gaaagcacca | 2220 | |
| accgatggcg agcaggatcg cgctctgatg caggaagcac tgctggccgt tgtccgtatg | 2280 | |
| cttaacccgt tcaccccgca catctgcttc acgctgtggc aggaactgaa aggcgaaggc | 2340 | |
| gatatcgaca acgcgccgtg gccggttgct gacgaaaaag cgatggtgga agactccacg | 2400 | |
| ctggtcgtgg tgcaggttaa cggtaaagtc cgtgccaaaa tcaccgttcc ggtggacgca | 2460 | |
| acggaagaac aggttcgcga acgtgctggc caggaacatc tggtagcaaa atatcttgat | 2520 | |
| ggcgttactg tacgtaaagt gatttacgta ccaggtaaac tcctcaatct ggtcgttggc | 2580 | |
| taa | 2583 | |

<210> SEQ ID NO 55
<211> LENGTH: 2583
<212> TYPE: DNA
<213> ORGANISM: Artificial
<220> FEATURE:
<223> OTHER INFORMATION: mutant synthetase

<400> SEQUENCE: 55

```
atgcaagagc aataccgccc ggaagagata gaatccaaag tacagcttca ttgggatgag    60
aagcgcacat ttgaagtaac cgaagacgag agcaaagaga agtattactg cctgtcttgg   120
tcgccctatc cttctggtcg actacacatg ggccacgtac gtaactacac catcggtgac   180
gtgatcgccc gctaccagcg tatgctgggc aaaaacgtcc tgcagccgat cggctgggac   240
gcgtttggtc tgcctgcgga aggcgcggcg gtgaaaaaca acaccgctcc ggcaccgtgg   300
acgtacgaca acatcgcgta tatgaaaaac cagctcaaaa tgctgggctt tggttatgac   360
tggagccgcg agctggcaac ctgtacgccg gaatactacc gttgggaaca gaaattcttc   420
accgagctgt ataaaaaagg cctggtatat aagaagactt ctgcggtcaa ctggtgcccg   480
aacgaccaga ccgtactggc gaacgaacaa gttatcgacg gctgctgctg cgctgcgat   540 accaaagttg aacgtaaaga gatcccgcag tggtttatca aaatcactgc ttacgctgac   600
gagctgctca acgatctgga taaactggat cactggccag acaccgttaa aaccatgcag   660
cgtaactgga tcggtcgttc cgaaggcgtg gagatcacct tcaacgttaa cgactatgac   720
aacacgctga ccgtttacac tacccgcccg gacacctttt tgggttgtac ctacctggcg   780
gtagctgcgg gtcatccgct ggcgcagaaa gcggcggaaa ataatcctga actggcggcc   840
tttattgacg aatgccgtaa caccaaagtt gccgaagctg aaatggcgac gatggagaaa   900
aaaggcgtcg atactggctt taaagcggtt cacccattaa cgggcgaaga aattcccgtt   960
tgggcagcaa acttcgtatt gatggagtac ggcacgggcg cagttatggc ggtaccgggg  1020
cacgaccagc gcgactacga gtttgcctct aaatacggcc tgaacatcaa accggttatc  1080
ctggcagctg acggctctga gccagatctt tctcagcaag ccctgactga aaaaggcgtg  1140
ctgttcaact ctggcgagtt caacggtctt gaccatgaag cggccttcaa cgccatcgcc  1200
gataaactga ctgcgatggg cgttggcgag cgtaaagtga actaccgcct gcgcgactgg  1260 ggtgttttccc gtcagcgtta ctggggcgcg ccgattccga tggtgacgct ggaagacggt  1320
accgtaatgc cgaccccgga cgaccagctg ccggtgatcc tgccggaaga tgtggtaatg  1380
gacggcatta ccagcccgat taaagcagat ccggagtggg cgaaaactac cgttaacggt  1440
atgccagcac tgcgtgaaac cgacactttc gacaccttta tggagtcctc ctggatttat  1500
gcgcgctaca cttgcccgca gtacaaagaa ggtatgctgg attccgaagc ggctaactac  1560
tggctgccgg tggatatcgc gattggtggt attgaacacg ccattatggg gctgctctac  1620
ttccgcttct tccacaaact gatgcgtgat gcaggcatgg tgaactctga cgaaccagcg  1680
aaacagttgc tgtgtcaggg tatggtgctg gcagatgcct tctactatgt tggcgaaaac  1740
ggcgaacgta actgggtttc cccggttgat gctatcgttg aacgtgacga gaaaggccgt  1800
atcgtgaaag cgaaagatgc ggcaggccat gaactggttt ataccggcat gagcaaaatg  1860
tccaagtcga agaacaacgg tatcgacccg caggtgatgg ttgaacgtta cggcgcggac  1920
accgttcgtc tgtttatgat gtttgcttct ccggctgata tgactctcga atggcaggaa  1980
tccggtgtgg aaggggctaa ccgcttcctg aaacgtgtct ggaaactggt ttacgagcac  2040
acagcaaaag gtgatgttgc ggcactgaac gttgatgcgc tgactgaaaa tcagaaagcg  2100
ctgcgtcgcg atgtgcataa aacgatcgct aaagtgaccg atgatatcgg ccgtcgtcag  2160
accttcaaca ccgcaattgc ggcgattatg gagctgatga caaaactggc gaaagcacca  2220
accgatggcg agcaggatcg cgctctgatg caggaagcac tgctggccgt tgtccgtatg  2280
cttaacccgt tcaccccgca catctgcttc acgctgtggc aggaactgaa aggcgaaggc  2340
```

| | |
|---|---:|
| gatatcgaca acgcgccgtg gccggttgct gacgaaaaag cgatggtgga agactccacg | 2400 |
| ctggtcgtgg tgcaggttaa cggtaaagtc cgtgccaaaa tcaccgttcc ggtggacgca | 2460 |
| acggaagaac aggttcgcga acgtgctggc caggaacatc tggtagcaaa atatcttgat | 2520 |
| ggcgttactg tacgtaaagt gatttacgta ccaggtaaac tcctcaatct ggtcgttggc | 2580 |
| taa | 2583 |

<210> SEQ ID NO 56
<211> LENGTH: 2583
<212> TYPE: DNA
<213> ORGANISM: Artificial
<220> FEATURE:
<223> OTHER INFORMATION: mutant synthetase

<400> SEQUENCE: 56

| | |
|---|---:|
| atgcaagagc aataccgccc ggaagagata gaatccaaag tacagcttca ttgggatgag | 60 |
| aagcgcacat ttgaagtaac cgaagacgag agcaaagaga agtattactg cctgtctggt | 120 |
| acgccctatc cttctggtcg actacacatg ggccacgtac gtaactacac catcggtgac | 180 |
| gtgatcgccc gctaccagcg tatgctgggc aaaaacgtcc tgcagccgat cggctgggac | 240 |
| gcgtttggtc tgcctgcgga aggcgcgcg gtgaaaaaca acaccgctcc ggcaccgtgg | 300 |
| acgtacgaca acatcgcgta tatgaaaaac cagctcaaaa tgctgggctt tggttatgac | 360 |
| tggagccgcg agctggcaac ctgtacgccg gaatactacc gttgggaaca gaaattcttc | 420 |
| accgagctgt ataaaaaagg cctggtatat aagaagactt ctgcggtcaa ctggtgcccg | 480 |
| aacgaccaga ccgtactggc gaacgaacaa gttatcgacg ctgctgctg gcgctgcgat | 540 |
| accaaagttg aacgtaaaga gatcccgcag tggtttatca aaatcactgc ttacgctgac | 600 |
| gagctgctca cgatctggga taaactcgat cactggccag acaccgttaa accatgcag | 660 |
| cgtaactgga tcggtcgttc cgaaggcgtg gagatcacct tcaacgttaa cgactatgac | 720 |
| aacacgctga ccgtttacac taccgccccg gacacccttta tgggttgtac ctacctggcg | 780 |
| gtagctgcgg tcatccgct ggcgcagaaa gcggcggaaa ataatcctga actggcggcc | 840 |
| tttattgacg aatgccgtaa caccaaagtt gccgaagctg aaatggcgac gatggagaaa | 900 |
| aaaggcgtcg atactggctt taaagcggtt cacccattaa cgggcgaaga attcccgtt | 960 |
| tgggcagcaa acttcgtatt gatggagtac ggcacgggcg cagttatggc ggtaccgggg | 1020 |
| cacgaccagc gcgactacga gtttgcctct aaatacggcc tgaacatcaa accggttatc | 1080 |
| ctggcagctg acgctctga ccagatcttc tctcagcaag ccctgactga aaaggcgtg | 1140 |
| ctgttcaact ctggcgagtt caacggtctt gaccatgaag cggccttcaa cgccatcgcc | 1200 |
| gataaactga ctgcgatggg cgttggcgag cgtaaagtga actaccgcct gcgcgactgg | 1260 |
| ggtgtttccc gtcagcgtta ctggggcgcg ccgattccga tggtgacgct ggaagacggt | 1320 |
| accgtaatgc cgaccccga cgaccagctg ccggtgatcc tgccggaaga tgtggtaatg | 1380 |
| gacggcatta ccagcccgat taaagcagat ccggagtggg cgaaaactac cgttaacggt | 1440 |
| atgccagcac tgcgtgaaac cgacactttc gacacccttta tggagtcctc ctggtggtat | 1500 |
| gcgcgctaca cttgccccgca gtacaaagaa ggtatgctgg attccgaagc ggctaactac | 1560 |
| tggctgccgg tggatatcct tattggtggt attgaacacg ccattatggg tctgctctac | 1620 |
| ttccgcttct tccacaaact gatgcgtgat gcaggcatgg tgaactctga cgaaccagcg | 1680 |
| aaacagttgc tgtgtcaggg tatggtgctg gcagatgcct tctactatgt tggcgaaaac | 1740 |
| ggcgaacgta actgggtttc cccggttgat gctatcgttg aacgtgacga aaaggccgt | 1800 |

-continued

```
atcgtgaaag cgaaagatgc ggcaggccat gaactggttt ataccggcat gagcaaaatg   1860
tccaagtcga agaacaacgg tatcgacccg caggtgatgg ttgaacgtta cggcgcggac   1920
accgttcgtc tgtttatgat gtttgcttct ccggctgata tgactctcga atggcaggaa   1980
tccggtgtgg aagggctaa  ccgcttcctg aaacgtgtct ggaaactggt ttacgagcac   2040
acagcaaaag gtgatgttgc ggcactgaac gttgatgcgc tgactgaaaa tcagaaagcg   2100
ctgcgtcgcg atgtgcataa aacgatcgct aaagtgaccg atgatatcgg ccgtcgtcag   2160
accttcaaca ccgcaattgc ggcgattatg gagctgatga acaaactggc gaaagcacca   2220
accgatggcg agcaggatcg cgctctgatg caggaagcac tgctggccgt tgtccgtatg   2280
cttaacccgt tcaccccgca catctgcttc acgctgtggc aggaactgaa aggcgaaggc   2340
gatatcgaca cgcgccgtg  gccggttgct gacgaaaaag cgatggtgga agactccacg   2400
ctggtcgtgg tgcaggttaa cggtaaagtc cgtgccaaaa tcaccgttcc ggtggacgca   2460
acggaagaac aggttcgcga acgtgctggc caggaacatc tggtagcaaa atatcttgat   2520
ggcgttactg tacgtaaagt gatttacgta ccaggtaaac tcctcaatct ggtcgttggc   2580
taa                                                                  2583
```

<210> SEQ ID NO 57
<211> LENGTH: 424
<212> TYPE: PRT
<213> ORGANISM: Artificial
<220> FEATURE:
<223> OTHER INFORMATION: mutant synthetase

<400> SEQUENCE: 57

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Val Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
```

```
            210                 215                 220
Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 58
<211> LENGTH: 424
<212> TYPE: PRT
<213> ORGANISM: Artificial
<220> FEATURE:
<223> OTHER INFORMATION: mutant synthetase

<400> SEQUENCE: 58

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Thr Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
```

-continued

```
                145                 150                 155                 160
        Leu Asn Arg Glu Asp Gln Gly Ile Ser Phe Thr Glu Phe Ser Tyr Asn
                        165                 170                 175

Leu Leu Gln Gly Tyr Thr Met Ala Cys Leu Asn Lys Gln Tyr Gly Val
                    180                 185                 190

Val Leu Gln Ile Gly Gly Ser Asp Gln Trp Gly Asn Ile Thr Ser Gly
                195                 200                 205

Ile Asp Leu Thr Arg Arg Leu His Gln Asn Gln Val Phe Gly Leu Thr
            210                 215                 220

Val Pro Leu Ile Thr Lys Ala Asp Gly Thr Lys Phe Gly Lys Thr Glu
        225                 230                 235                 240

Gly Gly Ala Val Trp Leu Asp Pro Lys Lys Thr Ser Pro Tyr Lys Phe
                        245                 250                 255

Tyr Gln Phe Trp Ile Asn Thr Ala Asp Ala Asp Val Tyr Arg Phe Leu
                    260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
        305                 310                 315                 320

Lys Arg Ile Thr Glu Cys Leu Phe Ser Gly Ser Leu Ser Ala Leu Ser
                        325                 330                 335

Glu Ala Asp Phe Glu Gln Leu Ala Gln Asp Gly Val Pro Met Val Glu
                    340                 345                 350

Met Glu Lys Gly Ala Asp Leu Met Gln Ala Leu Val Asp Ser Glu Leu
                355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
        385                 390                 395                 400

Glu Asp Arg Leu Phe Gly Arg Phe Thr Leu Leu Arg Arg Gly Lys Lys
                        405                 410                 415

Asn Tyr Cys Leu Ile Cys Trp Lys
                    420
```

<210> SEQ ID NO 59
<211> LENGTH: 424
<212> TYPE: PRT
<213> ORGANISM: Artificial
<220> FEATURE:
<223> OTHER INFORMATION: mutant synthetase

<400> SEQUENCE: 59

```
        Met Ala Ser Ser Asn Leu Ile Lys Gln Leu Gln Glu Arg Gly Leu Val
        1                   5                   10                  15

Ala Gln Val Thr Asp Glu Glu Ala Leu Ala Glu Arg Leu Ala Gln Gly
                        20                  25                  30

Pro Ile Ala Leu Thr Cys Gly Phe Asp Pro Thr Ala Asp Ser Leu His
                    35                  40                  45

Leu Gly His Leu Val Pro Leu Cys Leu Lys Arg Phe Gln Gln Ala
                50                  55                  60

Gly His Lys Pro Val Ala Leu Val Gly Gly Ala Thr Gly Leu Ile Gly
        65                  70                  75                  80

Asp Pro Ser Phe Lys Ala Ala Glu Arg Lys Leu Asn Thr Glu Glu Thr
```

```
                85                  90                  95
Val Gln Glu Trp Val Asp Lys Ile Arg Lys Gln Val Ala Pro Phe Leu
                100                 105                 110

Asp Phe Asp Cys Gly Glu Asn Ser Ala Ile Ala Asn Asn Tyr Asp
        115                 120                 125

Trp Phe Gly Asn Met Asn Val Leu Thr Phe Leu Arg Asp Ile Gly Lys
        130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Tyr Ala Cys Leu Asn Lys Gln Tyr Gly Val
                180                 185                 190

Val Leu Gln Ile Gly Gly Ser Asp Gln Trp Gly Asn Ile Thr Ser Gly
                195                 200                 205

Ile Asp Leu Thr Arg Arg Leu His Gln Asn Gln Val Phe Gly Leu Thr
        210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
        290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 60
<211> LENGTH: 424
<212> TYPE: PRT
<213> ORGANISM: Artificial
<220> FEATURE:
<223> OTHER INFORMATION: mutant synthetase

<400> SEQUENCE: 60

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
```

```
                    20                  25                  30
        Pro Ile Ala Leu Leu Cys Gly Phe Asp Pro Thr Ala Asp Ser Leu His
                    35                  40                  45
        Leu Gly His Leu Val Pro Leu Leu Cys Leu Lys Arg Phe Gln Gln Ala
                    50                  55                  60
        Gly His Lys Pro Val Ala Leu Val Gly Gly Ala Thr Gly Leu Ile Gly
        65                      70                  75                  80
        Asp Pro Ser Phe Lys Ala Ala Glu Arg Lys Leu Asn Thr Glu Thr
                            85                  90                  95
        Val Gln Glu Trp Val Asp Lys Ile Arg Lys Gln Val Ala Pro Phe Leu
                        100                 105                 110
        Asp Phe Asp Cys Gly Glu Asn Ser Ala Ile Ala Ala Asn Asn Tyr Asp
                        115                 120                 125
        Trp Phe Gly Asn Met Asn Val Leu Thr Phe Leu Arg Asp Ile Gly Lys
                        130                 135                 140
        His Phe Ser Val Asn Gln Met Ile Asn Lys Glu Ala Val Lys Gln Arg
        145                     150                 155                 160
        Leu Asn Arg Glu Asp Gln Gly Ile Ser Phe Thr Glu Phe Ser Tyr Asn
                        165                 170                 175
        Leu Leu Gln Gly Tyr Ser Met Ala Cys Ser Asn Lys Gln Tyr Gly Val
                        180                 185                 190
        Val Leu Gln Ile Gly Gly Ser Asp Gln Trp Gly Asn Ile Thr Ser Gly
                        195                 200                 205
        Ile Asp Leu Thr Arg Arg Leu His Gln Asn Gln Val Phe Gly Leu Thr
                        210                 215                 220
        Val Pro Leu Ile Thr Lys Ala Asp Gly Thr Lys Phe Gly Lys Thr Glu
        225                     230                 235                 240
        Gly Gly Ala Val Trp Leu Asp Pro Lys Lys Thr Ser Pro Tyr Lys Phe
                        245                 250                 255
        Tyr Gln Phe Trp Ile Asn Thr Ala Asp Ala Asp Val Tyr Arg Phe Leu
                        260                 265                 270
        Lys Phe Phe Thr Phe Met Ser Ile Glu Glu Ile Asn Ala Leu Glu Glu
                        275                 280                 285
        Glu Asp Lys Asn Ser Gly Lys Ala Pro Arg Ala Gln Tyr Val Leu Ala
                        290                 295                 300
        Glu Gln Val Thr Arg Leu Val His Gly Glu Glu Gly Leu Gln Ala Ala
        305                     310                 315                 320
        Lys Arg Ile Thr Glu Cys Leu Phe Ser Gly Ser Leu Ser Ala Leu Ser
                        325                 330                 335
        Glu Ala Asp Phe Glu Gln Leu Ala Gln Asp Gly Val Pro Met Val Glu
                        340                 345                 350
        Met Glu Lys Gly Ala Asp Leu Met Gln Ala Leu Val Asp Ser Glu Leu
                        355                 360                 365
        Gln Pro Ser Arg Gly Gln Ala Arg Lys Thr Ile Ala Ser Asn Ala Ile
                        370                 375                 380
        Thr Ile Asn Gly Glu Lys Gln Ser Asp Pro Glu Tyr Phe Phe Lys Glu
        385                     390                 395                 400
        Glu Asp Arg Leu Phe Gly Arg Phe Thr Leu Leu Arg Arg Gly Lys Lys
                        405                 410                 415
        Asn Tyr Cys Leu Ile Cys Trp Lys
                        420

<210> SEQ ID NO 61
```

<211> LENGTH: 424
<212> TYPE: PRT
<213> ORGANISM: Artificial
<220> FEATURE:
<223> OTHER INFORMATION: mutant synthetase

<400> SEQUENCE: 61

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Leu Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380
```

```
Thr Ile Asn Gly Glu Lys Gln Ser Asp Pro Glu Tyr Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 62
<211> LENGTH: 424
<212> TYPE: PRT
<213> ORGANISM: Artificial
<220> FEATURE:
<223> OTHER INFORMATION: mutant synthetase

<400> SEQUENCE: 62

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Thr Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Arg Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320
```

```
Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420
```

<210> SEQ ID NO 63
<211> LENGTH: 424
<212> TYPE: PRT
<213> ORGANISM: Artificial
<220> FEATURE:
<223> OTHER INFORMATION: mutant synthetase

<400> SEQUENCE: 63

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
            85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
        130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
            165                 170                 175

Leu Leu Gln Gly Tyr Gly Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
            210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
            245                 250                 255
```

```
Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
275                 280                 285

Glu Asp Lys Asn Ser Gly Lys Ala Pro Arg Ala Gln Tyr Val Leu Ala
        290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 64
<211> LENGTH: 424
<212> TYPE: PRT
<213> ORGANISM: Artificial
<220> FEATURE:
<223> OTHER INFORMATION: mutant synthetase

<400> SEQUENCE: 64

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Gly Gln Gly Ile Ser Phe Thr Glu Phe Ser Tyr Asn
                165                 170                 175

Leu Leu Gln Gly Tyr Gly Met Ala Cys Ala Asn Lys Gln Tyr Gly Val
            180                 185                 190
```

```
Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
            290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 65
<211> LENGTH: 424
<212> TYPE: PRT
<213> ORGANISM: Artificial
<220> FEATURE:
<223> OTHER INFORMATION: mutant synthetase

<400> SEQUENCE: 65

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
            35                  40                  45

Leu Gly His Leu Val Pro Leu Leu Cys Leu Lys Arg Phe Gln Gln Ala
            50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125
```

-continued

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
            165                 170                 175

Leu Leu Gln Gly Tyr Gly Phe Ala Cys Ala Asn Lys Gln Tyr Gly Val
        180                 185                 190

Val Leu Gln Ile Gly Gly Ser Asp Gln Trp Gly Asn Ile Thr Ser Gly
    195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
        260                 265                 270

Lys Phe Phe Thr Phe Met Ser Ile Glu Glu Ile Asn Ala Leu Glu Glu
    275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
        340                 345                 350

Met Glu Lys Gly Ala Asp Leu Met Gln Ala Leu Val Asp Ser Glu Leu
    355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
        420

<210> SEQ ID NO 66
<211> LENGTH: 424
<212> TYPE: PRT
<213> ORGANISM: Artificial
<220> FEATURE:
<223> OTHER INFORMATION: mutant synthetase

<400> SEQUENCE: 66

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
            85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
            165                 170                 175

Leu Leu Gln Gly Tyr Gly Tyr Ala Cys Met Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420

<210> SEQ ID NO 67
<211> LENGTH: 424
<212> TYPE: PRT
<213> ORGANISM: Artificial
<220> FEATURE:
<223> OTHER INFORMATION: mutant synthetase

<400> SEQUENCE: 67

-continued

```
Met Ala Ser Ser Asn Leu Ile Lys Gln Leu Gln Glu Arg Gly Leu Val
1               5                   10                  15

Ala Gln Val Thr Asp Glu Ala Leu Ala Glu Arg Leu Ala Gln Gly
            20                  25                  30

Pro Ile Ala Leu Leu Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
        130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
        210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415
```

Asn Tyr Cys Leu Ile Cys Trp Lys
            420

<210> SEQ ID NO 68
<211> LENGTH: 424
<212> TYPE: PRT
<213> ORGANISM: Artificial
<220> FEATURE:
<223> OTHER INFORMATION: mutant synthetase

<400> SEQUENCE: 68

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

```
Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 69
<211> LENGTH: 424
<212> TYPE: PRT
<213> ORGANISM: Artificial
<220> FEATURE:
<223> OTHER INFORMATION: mutant synthetase

<400> SEQUENCE: 69

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Leu Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Ala Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285
```

-continued

```
Glu Asp Lys Asn Ser Gly Lys Ala Pro Arg Ala Gln Tyr Val Leu Ala
    290                 295                 300
Glu Gln Val Thr Arg Leu Val His Gly Glu Glu Gly Leu Gln Ala Ala
305                 310                 315                 320
Lys Arg Ile Thr Glu Cys Leu Phe Ser Gly Ser Leu Ser Ala Leu Ser
                325                 330                 335
Glu Ala Asp Phe Glu Gln Leu Ala Gln Asp Gly Val Pro Met Val Glu
            340                 345                 350
Met Glu Lys Gly Ala Asp Leu Met Gln Ala Leu Val Asp Ser Glu Leu
        355                 360                 365
Gln Pro Ser Arg Gly Gln Ala Arg Lys Thr Ile Ala Ser Asn Ala Ile
370                 375                 380
Thr Ile Asn Gly Glu Lys Gln Ser Asp Pro Glu Tyr Phe Phe Lys Glu
385                 390                 395                 400
Glu Asp Arg Leu Phe Gly Arg Phe Thr Leu Leu Arg Arg Gly Lys Lys
                405                 410                 415
Asn Tyr Cys Leu Ile Cys Trp Lys
            420
```

<210> SEQ ID NO 70
<211> LENGTH: 424
<212> TYPE: PRT
<213> ORGANISM: Artificial
<220> FEATURE:
<223> OTHER INFORMATION: mutant synthetase

<400> SEQUENCE: 70

```
Met Ala Ser Ser Asn Leu Ile Lys Gln Leu Gln Glu Arg Gly Leu Val
1               5                   10                  15
Ala Gln Val Thr Asp Glu Glu Ala Leu Ala Glu Arg Leu Ala Gln Gly
            20                  25                  30
Pro Ile Ala Leu Val Cys Gly Phe Asp Pro Thr Ala Asp Ser Leu His
        35                  40                  45
Leu Gly His Leu Val Pro Leu Leu Cys Leu Lys Arg Phe Gln Gln Ala
    50                  55                  60
Gly His Lys Pro Val Ala Leu Val Gly Gly Ala Thr Gly Leu Ile Gly
65                  70                  75                  80
Asp Pro Ser Phe Lys Ala Ala Glu Arg Lys Leu Asn Thr Glu Glu Thr
                85                  90                  95
Val Gln Glu Trp Val Asp Lys Ile Arg Lys Gln Val Ala Pro Phe Leu
            100                 105                 110
Asp Phe Asp Cys Gly Glu Asn Ser Ala Ile Ala Ala Asn Asn Tyr Asp
        115                 120                 125
Trp Phe Gly Asn Met Asn Val Leu Thr Phe Leu Arg Asp Ile Gly Lys
    130                 135                 140
His Phe Ser Val Asn Gln Met Ile Asn Lys Glu Ala Val Lys Gln Arg
145                 150                 155                 160
Leu Asn Arg Glu Asp Gln Gly Ile Ser Phe Thr Glu Phe Ser Tyr Asn
                165                 170                 175
Leu Leu Gln Gly Tyr Ser Ala Ala Cys Val Asn Lys Gln Tyr Gly Val
            180                 185                 190
Val Leu Gln Ile Gly Gly Ser Asp Gln Trp Gly Asn Ile Thr Ser Gly
        195                 200                 205
Ile Asp Leu Thr Arg Arg Leu His Gln Asn Gln Val Phe Gly Leu Thr
    210                 215                 220
```

```
Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 71
<211> LENGTH: 424
<212> TYPE: PRT
<213> ORGANISM: Artificial
<220> FEATURE:
<223> OTHER INFORMATION: mutant synthetase

<400> SEQUENCE: 71

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Ile Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asp Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160
```

```
Leu Asn Arg Glu Asp Gln Gly Ile Ser Phe Thr Glu Phe Ser Tyr Asn
                165                 170                 175

Leu Leu Gln Gly Tyr Asn Phe Ala Cys Val Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 72
<211> LENGTH: 424
<212> TYPE: PRT
<213> ORGANISM: Artificial
<220> FEATURE:
<223> OTHER INFORMATION: mutant synthetase

<400> SEQUENCE: 72

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95
```

-continued

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 73
<211> LENGTH: 424
<212> TYPE: PRT
<213> ORGANISM: Artificial
<220> FEATURE:
<223> OTHER INFORMATION: mutant synthetase

<400> SEQUENCE: 73

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
             35                  40                  45

Leu Gly His Leu Val Pro Leu Leu Cys Leu Lys Arg Phe Gln Gln Ala
 50                  55                  60

Gly His Lys Pro Val Ala Leu Val Gly Ala Thr Gly Leu Ile Gly
 65                  70                  75                  80

Asp Pro Ser Phe Lys Ala Ala Glu Arg Lys Leu Asn Thr Glu Glu Thr
                 85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
       130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
        210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 74
<211> LENGTH: 424
<212> TYPE: PRT

<213> ORGANISM: Artificial
<220> FEATURE:
<223> OTHER INFORMATION: mutant synthetase

<400> SEQUENCE: 74

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Ala Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
```

```
                385                 390                 395                 400
Glu Asp Arg Leu Phe Gly Arg Phe Thr Leu Leu Arg Arg Gly Lys Lys
                    405                 410                 415

Asn Tyr Cys Leu Ile Cys Trp Lys
            420

<210> SEQ ID NO 75
<211> LENGTH: 424
<212> TYPE: PRT
<213> ORGANISM: Artificial
<220> FEATURE:
<223> OTHER INFORMATION: mutant synthetase

<400> SEQUENCE: 75

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Ser Cys Gly Phe Asp Pro Thr Ala Asp Ser Leu His
                35                  40                  45

Leu Gly His Leu Val Pro Leu Leu Cys Leu Lys Arg Phe Gln Gln Ala
            50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Met Ala Cys Val Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
```

-continued

```
                325                 330                 335
Glu Ala Asp Phe Glu Gln Leu Ala Gln Asp Gly Val Pro Met Val Glu
            340                 345                 350
Met Glu Lys Gly Ala Asp Leu Met Gln Ala Leu Val Asp Ser Glu Leu
        355                 360                 365
Gln Pro Ser Arg Gly Gln Ala Arg Lys Thr Ile Ala Ser Asn Ala Ile
370                 375                 380
Thr Ile Asn Gly Glu Lys Gln Ser Asp Pro Glu Tyr Phe Phe Lys Glu
385                 390                 395                 400
Glu Asp Arg Leu Phe Gly Arg Phe Thr Leu Leu Arg Arg Gly Lys Lys
            405                 410                 415
Asn Tyr Cys Leu Ile Cys Trp Lys
            420

<210> SEQ ID NO 76
<211> LENGTH: 424
<212> TYPE: PRT
<213> ORGANISM: Artificial
<220> FEATURE:
<223> OTHER INFORMATION: mutant synthetase

<400> SEQUENCE: 76

Met Ala Ser Ser Asn Leu Ile Lys Gln Leu Gln Glu Arg Gly Leu Val
1               5                   10                  15
Ala Gln Val Thr Asp Glu Glu Ala Leu Ala Glu Arg Leu Ala Gln Gly
            20                  25                  30
Pro Ile Ala Leu Ala Cys Gly Phe Asp Pro Thr Ala Asp Ser Leu His
        35                  40                  45
Leu Gly His Leu Val Pro Leu Leu Cys Leu Lys Arg Phe Gln Gln Ala
    50                  55                  60
Gly His Lys Pro Val Ala Leu Val Gly Gly Ala Thr Gly Leu Ile Gly
65                  70                  75                  80
Asp Pro Ser Phe Lys Ala Ala Glu Arg Lys Leu Asn Thr Glu Glu Thr
                85                  90                  95
Val Gln Glu Trp Val Asp Lys Ile Arg Lys Gln Val Ala Pro Phe Leu
            100                 105                 110
Asp Phe Asp Cys Gly Glu Asn Ser Ala Ile Ala Ala Asn Asn Tyr Asp
        115                 120                 125
Trp Phe Gly Asn Met Asn Val Leu Thr Phe Leu Arg Asp Ile Gly Lys
    130                 135                 140
His Phe Ser Val Asn Gln Met Ile Asn Lys Glu Ala Val Lys Gln Arg
145                 150                 155                 160
Leu Asn Arg Glu Asp Gln Gly Ile Ser Phe Thr Glu Phe Ser Tyr Asn
                165                 170                 175
Leu Leu Gln Gly Tyr Ser Tyr Ala Cys Leu Asn Lys Gln Tyr Gly Val
            180                 185                 190
Val Leu Gln Ile Gly Gly Ser Asp Gln Trp Gly Asn Ile Thr Ser Gly
        195                 200                 205
Ile Asp Leu Thr Arg Arg Leu His Gln Asn Gln Val Phe Gly Leu Thr
    210                 215                 220
Val Pro Leu Ile Thr Lys Ala Asp Gly Thr Lys Phe Gly Lys Thr Glu
225                 230                 235                 240
Gly Gly Ala Val Trp Leu Asp Pro Lys Lys Thr Ser Pro Tyr Lys Phe
                245                 250                 255
Tyr Gln Phe Trp Ile Asn Thr Ala Asp Ala Asp Val Tyr Arg Phe Leu
```

```
                260             265                 270
Lys Phe Phe Thr Phe Met Ser Ile Glu Glu Ile Asn Ala Leu Glu Glu
            275                 280                 285
Glu Asp Lys Asn Ser Gly Lys Ala Pro Arg Ala Gln Tyr Val Leu Ala
            290                 295                 300
Glu Gln Val Thr Arg Leu Val His Gly Glu Gly Leu Gln Ala Ala
305                 310                 315                 320
Lys Arg Ile Thr Glu Cys Leu Phe Ser Gly Ser Leu Ser Ala Leu Ser
                325                 330                 335
Glu Ala Asp Phe Glu Gln Leu Ala Gln Asp Gly Val Pro Met Val Glu
            340                 345                 350
Met Glu Lys Gly Ala Asp Leu Met Gln Ala Leu Val Asp Ser Glu Leu
                355                 360                 365
Gln Pro Ser Arg Gly Gln Ala Arg Lys Thr Ile Ala Ser Asn Ala Ile
            370                 375                 380
Thr Ile Asn Gly Glu Lys Gln Ser Asp Pro Glu Tyr Phe Phe Lys Glu
385                 390                 395                 400
Glu Asp Arg Leu Phe Gly Arg Phe Thr Leu Leu Arg Arg Gly Lys Lys
                405                 410                 415
Asn Tyr Cys Leu Ile Cys Trp Lys
            420

<210> SEQ ID NO 77
<211> LENGTH: 424
<212> TYPE: PRT
<213> ORGANISM: Artificial
<220> FEATURE:
<223> OTHER INFORMATION: mutant synthetase

<400> SEQUENCE: 77

Met Ala Ser Ser Asn Leu Ile Lys Gln Leu Gln Glu Arg Gly Leu Val
1               5                   10                  15
Ala Gln Val Thr Asp Glu Glu Ala Leu Ala Glu Arg Leu Ala Gln Gly
                20                  25                  30
Pro Ile Ala Leu Ala Cys Gly Phe Asp Pro Thr Ala Asp Ser Leu His
            35                  40                  45
Leu Gly His Leu Val Pro Leu Leu Cys Leu Lys Arg Phe Gln Gln Ala
        50                  55                  60
Gly His Lys Pro Val Ala Leu Val Gly Gly Ala Thr Gly Leu Ile Gly
65                  70                  75                  80
Asp Pro Ser Phe Lys Ala Ala Glu Arg Lys Leu Asn Thr Glu Glu Thr
                85                  90                  95
Val Gln Glu Trp Val Asp Lys Ile Arg Lys Gln Val Ala Pro Phe Leu
            100                 105                 110
Asp Phe Asp Cys Gly Glu Asn Ser Ala Ile Ala Ala Asn Asn Tyr Asp
        115                 120                 125
Trp Phe Gly Asn Met Asn Val Leu Thr Phe Leu Arg Asp Ile Gly Lys
    130                 135                 140
His Phe Ser Val Asn Gln Met Ile Asn Lys Glu Ala Val Lys Gln Arg
145                 150                 155                 160
Leu Asn Arg Glu Asp Gln Gly Ile Ser Phe Thr Glu Phe Ser Tyr Asn
                165                 170                 175
Leu Leu Gln Gly Tyr Thr Met Ala Cys Cys Asn Lys Gln Tyr Gly Val
            180                 185                 190
Val Leu Gln Ile Gly Gly Ser Asp Gln Trp Gly Asn Ile Thr Ser Gly
```

```
                195                 200                 205
Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 78
<211> LENGTH: 424
<212> TYPE: PRT
<213> ORGANISM: Artificial
<220> FEATURE:
<223> OTHER INFORMATION: mutant synthetase

<400> SEQUENCE: 78

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
```

```
                130                 135                 140
His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Phe Ala Cys Met Asn Lys Gln Tyr Gly Val
                180                 185                 190

Val Leu Gln Ile Gly Gly Ser Asp Gln Trp Gly Asn Ile Thr Ser Gly
                195                 200                 205

Ile Asp Leu Thr Arg Arg Leu His Gln Asn Gln Val Phe Gly Leu Thr
                210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
                290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
                355                 360                 365

Gln Pro Ser Arg Gly Gln Ala Arg Lys Thr Ile Ala Ser Asn Ala Ile
                370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 79
<211> LENGTH: 424
<212> TYPE: PRT
<213> ORGANISM: Artificial
<220> FEATURE:
<223> OTHER INFORMATION: mutant synthetase

<400> SEQUENCE: 79

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
                20                  25                  30

Pro Ile Ala Leu Thr Cys Gly Phe Asp Pro Thr Ala Asp Ser Leu His
                35                  40                  45

Leu Gly His Leu Val Pro Leu Leu Cys Leu Lys Arg Phe Gln Gln Ala
                50                  55                  60

Gly His Lys Pro Val Ala Leu Val Gly Gly Ala Thr Gly Leu Ile Gly
```

```
                65                  70                  75                  80
Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
                100                 105                 110

Asp Phe Asp Cys Gly Glu Asn Ser Ala Ile Ala Ala Asn Asn Tyr Asp
                115                 120                 125

Trp Phe Gly Asn Met Asn Val Leu Thr Phe Leu Arg Asp Ile Gly Lys
                130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Val Ala Cys Leu Asn Lys Gln Tyr Gly Val
                180                 185                 190

Val Leu Gln Ile Gly Gly Ser Asp Gln Trp Gly Asn Ile Thr Ser Gly
                195                 200                 205

Ile Asp Leu Thr Arg Arg Leu His Gln Asn Gln Val Phe Gly Leu Thr
                210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
                275                 280                 285

Glu Asp Lys Asn Ser Gly Lys Ala Pro Arg Ala Gln Tyr Val Leu Ala
                290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
                355                 360                 365

Gln Pro Ser Arg Gly Gln Ala Arg Lys Thr Ile Ala Ser Asn Ala Ile
                370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
                420

<210> SEQ ID NO 80
<211> LENGTH: 424
<212> TYPE: PRT
<213> ORGANISM: Artificial
<220> FEATURE:
<223> OTHER INFORMATION: mutant synthetase

<400> SEQUENCE: 80

Met Ala Ser Ser Asn Leu Ile Lys Gln Leu Gln Glu Arg Gly Leu Val
```

```
1               5                   10                  15
Ala Gln Val Thr Asp Glu Glu Ala Leu Ala Glu Arg Leu Ala Gln Gly
            20                  25                  30
Pro Ile Ala Leu Val Cys Gly Phe Asp Pro Thr Ala Asp Ser Leu His
            35                  40                  45
Leu Gly His Leu Val Pro Leu Leu Cys Leu Lys Arg Phe Gln Gln Ala
50                  55                  60
Gly His Lys Pro Val Ala Leu Val Gly Ala Thr Gly Leu Ile Gly
65                  70                  75                  80
Asp Pro Ser Phe Lys Ala Ala Glu Arg Lys Leu Asn Thr Glu Thr
                85                  90                  95
Val Gln Glu Trp Val Asp Lys Ile Arg Lys Gln Val Ala Pro Phe Leu
            100                 105                 110
Asp Phe Asp Cys Gly Glu Asn Ser Ala Ile Ala Ala Asn Asn Tyr Asp
            115                 120                 125
Trp Phe Gly Asn Met Asn Val Leu Thr Phe Leu Arg Asp Ile Gly Lys
            130                 135                 140
His Phe Ser Val Asn Gln Met Ile Asn Lys Glu Ala Val Lys Gln Arg
145                 150                 155                 160
Leu Asn Arg Glu Asp Gln Gly Ile Ser Phe Thr Glu Phe Ser Tyr Asn
                165                 170                 175
Leu Leu Gln Gly Tyr Ser Met Ala Cys Thr Asn Lys Gln Tyr Gly Val
            180                 185                 190
Val Leu Gln Ile Gly Gly Ser Asp Gln Trp Gly Asn Ile Thr Ser Gly
            195                 200                 205
Ile Asp Leu Thr Arg Arg Leu His Gln Asn Gln Val Phe Gly Leu Thr
210                 215                 220
Val Pro Leu Ile Thr Lys Ala Asp Gly Thr Lys Phe Gly Lys Thr Glu
225                 230                 235                 240
Gly Gly Ala Val Trp Leu Asp Pro Lys Lys Thr Ser Pro Tyr Lys Phe
            245                 250                 255
Tyr Gln Phe Trp Ile Asn Thr Ala Asp Ala Asp Val Tyr Arg Phe Leu
            260                 265                 270
Lys Phe Phe Thr Phe Met Ser Ile Glu Glu Ile Asn Ala Leu Glu Glu
            275                 280                 285
Glu Asp Lys Asn Ser Gly Lys Ala Pro Arg Ala Gln Tyr Val Leu Ala
            290                 295                 300
Glu Gln Val Thr Arg Leu Val His Gly Glu Glu Gly Leu Gln Ala Ala
305                 310                 315                 320
Lys Arg Ile Thr Glu Cys Leu Phe Ser Gly Ser Leu Ser Ala Leu Ser
                325                 330                 335
Glu Ala Asp Phe Glu Gln Leu Ala Gln Asp Gly Val Pro Met Val Glu
            340                 345                 350
Met Glu Lys Gly Ala Asp Leu Met Gln Ala Leu Val Asp Ser Glu Leu
            355                 360                 365
Gln Pro Ser Arg Gly Gln Ala Arg Lys Thr Ile Ala Ser Asn Ala Ile
            370                 375                 380
Thr Ile Asn Gly Glu Lys Gln Ser Asp Pro Glu Tyr Phe Phe Lys Glu
385                 390                 395                 400
Glu Asp Arg Leu Phe Gly Arg Phe Thr Leu Leu Arg Arg Gly Lys Lys
                405                 410                 415
Asn Tyr Cys Leu Ile Cys Trp Lys
            420
```

<210> SEQ ID NO 81
<211> LENGTH: 424
<212> TYPE: PRT
<213> ORGANISM: Artificial
<220> FEATURE:
<223> OTHER INFORMATION: mutant synthetase

<400> SEQUENCE: 81

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ser Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365
```

```
Gln Pro Ser Arg Gly Gln Ala Arg Lys Thr Ile Ala Ser Asn Ala Ile
        370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 82
<211> LENGTH: 424
<212> TYPE: PRT
<213> ORGANISM: Artificial
<220> FEATURE:
<223> OTHER INFORMATION: mutant synthetase

<400> SEQUENCE: 82

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Thr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Phe Ala Cys Thr Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300
```

```
Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420
```

<210> SEQ ID NO 83
<211> LENGTH: 424
<212> TYPE: PRT
<213> ORGANISM: Artificial
<220> FEATURE:
<223> OTHER INFORMATION: mutant synthetase

<400> SEQUENCE: 83

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Tyr Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240
```

```
Gly Gly Ala Val Trp Leu Asp Pro Lys Lys Thr Ser Pro Tyr Lys Phe
            245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
            370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
            405                 410                 415

Asn Tyr Cys Leu Ile Cys Trp Lys
            420

<210> SEQ ID NO 84
<211> LENGTH: 424
<212> TYPE: PRT
<213> ORGANISM: Artificial
<220> FEATURE:
<223> OTHER INFORMATION: mutant synthetase

<400> SEQUENCE: 84

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ile Cys Gly Phe Asp Pro Thr Ala Asp Ser Leu His
            35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
            85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
            130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
            165                 170                 175
```

```
Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 85
<211> LENGTH: 424
<212> TYPE: PRT
<213> ORGANISM: Artificial
<220> FEATURE:
<223> OTHER INFORMATION: mutant synthetase

<400> SEQUENCE: 85

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110
```

```
Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 86
<211> LENGTH: 860
<212> TYPE: PRT
<213> ORGANISM: Artificial
<220> FEATURE:
<223> OTHER INFORMATION: mutant synthetase

<400> SEQUENCE: 86

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Ala Ala Pro Tyr Pro Ser Gly Arg Leu
        35                  40                  45
```

-continued

```
His Met Gly His Val Arg Asn Tyr Thr Ile Gly Asp Val Ile Ala Arg
    50                  55                  60
Tyr Gln Arg Met Leu Gly Lys Asn Val Leu Gln Pro Ile Gly Trp Asp
 65                  70                  75                  80
Ala Phe Gly Leu Pro Ala Glu Gly Ala Ala Val Lys Asn Asn Thr Ala
                 85                  90                  95
Pro Ala Pro Trp Thr Tyr Asp Asn Ile Ala Tyr Met Lys Asn Gln Leu
            100                 105                 110
Lys Met Leu Gly Phe Gly Tyr Asp Trp Ser Arg Glu Leu Ala Thr Cys
        115                 120                 125
Thr Pro Glu Tyr Tyr Arg Trp Glu Gln Lys Phe Phe Thr Glu Leu Tyr
    130                 135                 140
Lys Lys Gly Leu Val Tyr Lys Lys Thr Ser Ala Val Asn Trp Cys Pro
145                 150                 155                 160
Asn Asp Gln Thr Val Leu Ala Asn Glu Gln Val Ile Asp Gly Cys Cys
                165                 170                 175
Trp Arg Cys Asp Thr Lys Val Glu Arg Lys Glu Ile Pro Gln Trp Phe
            180                 185                 190
Ile Lys Ile Thr Ala Tyr Ala Asp Glu Leu Leu Asn Asp Leu Asp Lys
        195                 200                 205
Leu Asp His Trp Pro Asp Thr Val Lys Thr Met Gln Arg Asn Trp Ile
    210                 215                 220
Gly Arg Ser Glu Gly Val Glu Ile Thr Phe Asn Val Asn Asp Tyr Asp
225                 230                 235                 240
Asn Thr Leu Thr Val Tyr Thr Thr Arg Pro Asp Thr Phe Met Gly Cys
                245                 250                 255
Thr Tyr Leu Ala Val Ala Ala Gly His Pro Leu Ala Gln Lys Ala Ala
            260                 265                 270
Glu Asn Asn Pro Glu Leu Ala Ala Phe Ile Asp Glu Cys Arg Asn Thr
        275                 280                 285
Lys Val Ala Glu Ala Glu Met Ala Thr Met Glu Lys Lys Gly Val Asp
    290                 295                 300
Thr Gly Phe Lys Ala Val His Pro Leu Thr Gly Glu Glu Ile Pro Val
305                 310                 315                 320
Trp Ala Ala Asn Phe Val Leu Met Glu Tyr Gly Thr Gly Ala Val Met
                325                 330                 335
Ala Val Pro Gly His Asp Gln Arg Asp Tyr Glu Phe Ala Ser Lys Tyr
            340                 345                 350
Gly Leu Asn Ile Lys Pro Val Ile Leu Ala Ala Asp Gly Ser Glu Pro
        355                 360                 365
Asp Leu Ser Gln Gln Ala Leu Thr Glu Lys Gly Val Leu Phe Asn Ser
    370                 375                 380
Gly Glu Phe Asn Gly Leu Asp His Glu Ala Ala Phe Asn Ala Ile Ala
385                 390                 395                 400
Asp Lys Leu Thr Ala Met Gly Val Gly Glu Arg Lys Val Asn Tyr Arg
                405                 410                 415
Leu Arg Asp Trp Gly Val Ser Arg Gln Arg Tyr Trp Gly Ala Pro Ile
            420                 425                 430
Pro Met Val Thr Leu Glu Asp Gly Thr Val Met Pro Thr Pro Asp Asp
        435                 440                 445
Gln Leu Pro Val Ile Leu Pro Glu Asp Val Val Met Asp Gly Ile Thr
    450                 455                 460
```

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
            485                 490                 495

Ser Trp Pro Tyr Ala Arg Tyr Thr Cys Pro Gln Tyr Lys Glu Gly Met
        500                 505                 510

Leu Asp Ser Glu Ala Ala Asn Tyr Trp Leu Pro Val Asp Ile Val Ile
    515                 520                 525

Gly Gly Ile Glu His Ala Ile Met Gly Leu Leu Tyr Phe Arg Phe Phe
530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
    595                 600                 605

Gly His Glu Leu Val Tyr Thr Gly Met Ser Lys Met Ser Lys Ser Lys
610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
    675                 680                 685

Leu Asn Val Asp Ala Leu Thr Glu Asn Gln Lys Ala Leu Arg Arg Asp
690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
    755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
    835                 840                 845

Tyr Val Pro Gly Lys Leu Leu Asn Leu Val Val Gly
    850                 855                 860

<210> SEQ ID NO 87
<211> LENGTH: 860
<212> TYPE: PRT

<213> ORGANISM: Artificial
<220> FEATURE:
<223> OTHER INFORMATION: mutant synthetase

<400> SEQUENCE: 87

```
Met Gln Glu Gln Tyr Arg Pro Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Val Met Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
```

-continued

```
            385                 390                 395                 400
Asp Lys Leu Thr Ala Met Gly Val Gly Glu Arg Lys Val Asn Tyr Arg
                    405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
        450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Leu Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Leu Ile
            515                 520                 525

Gly Gly Ile Glu His Ala Ile Met Gly Leu Leu Tyr Phe Arg Phe Phe
        530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815
```

```
Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly
            850                 855                 860

<210> SEQ ID NO 88
<211> LENGTH: 860
<212> TYPE: PRT
<213> ORGANISM: Artificial
<220> FEATURE:
<223> OTHER INFORMATION: mutant synthetase

<400> SEQUENCE: 88

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser His Pro Pro Tyr Pro Ser Gly Arg Leu
            35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65              70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145             150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225             230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Lys Lys Gly Val Asp
    290                 295                 300

Thr Gly Phe Lys Ala Val His Pro Leu Thr Gly Glu Glu Ile Pro Val
305             310                 315                 320
```

```
Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
                355                 360                 365

Asp Leu Ser Gln Gln Ala Leu Thr Glu Lys Gly Val Leu Phe Asn Ser
370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
            450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ala Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Met Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
            690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735
```

```
Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly
            850                 855                 860

<210> SEQ ID NO 89
<211> LENGTH: 860
<212> TYPE: PRT
<213> ORGANISM: Artificial
<220> FEATURE:
<223> OTHER INFORMATION: mutant synthetase

<400> SEQUENCE: 89

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Val Tyr Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240
```

-continued

```
Asn Thr Leu Thr Val Tyr Thr Thr Arg Pro Asp Thr Phe Met Gly Cys
                245                 250                 255
Thr Tyr Leu Ala Val Ala Ala Gly His Pro Leu Ala Gln Lys Ala Ala
            260                 265                 270
Glu Asn Asn Pro Glu Leu Ala Ala Phe Ile Asp Glu Cys Arg Asn Thr
        275                 280                 285
Lys Val Ala Glu Ala Glu Met Ala Thr Met Glu Lys Lys Gly Val Asp
    290                 295                 300
Thr Gly Phe Lys Ala Val His Pro Leu Thr Gly Glu Ile Pro Val
305                 310                 315                 320
Trp Ala Ala Asn Phe Val Leu Met Glu Tyr Gly Thr Gly Ala Val Met
                325                 330                 335
Ala Val Pro Gly His Asp Gln Arg Asp Tyr Glu Phe Ala Ser Lys Tyr
            340                 345                 350
Gly Leu Asn Ile Lys Pro Val Ile Leu Ala Ala Asp Gly Ser Glu Pro
        355                 360                 365
Asp Leu Ser Gln Gln Ala Leu Thr Glu Lys Gly Val Leu Phe Asn Ser
    370                 375                 380
Gly Glu Phe Asn Gly Leu Asp His Glu Ala Ala Phe Asn Ala Ile Ala
385                 390                 395                 400
Asp Lys Leu Thr Ala Met Gly Val Gly Glu Arg Lys Val Asn Tyr Arg
                405                 410                 415
Leu Arg Asp Trp Gly Val Ser Arg Gln Arg Tyr Trp Gly Ala Pro Ile
            420                 425                 430
Pro Met Val Thr Leu Glu Asp Gly Thr Val Met Pro Thr Pro Asp Asp
        435                 440                 445
Gln Leu Pro Val Ile Leu Pro Glu Asp Val Val Met Asp Gly Ile Thr
    450                 455                 460
Ser Pro Ile Lys Ala Asp Pro Glu Trp Ala Lys Thr Thr Val Asn Gly
465                 470                 475                 480
Met Pro Ala Leu Arg Glu Thr Asp Thr Phe Asp Thr Phe Met Glu Ser
                485                 490                 495
Ser Trp Leu Tyr Ala Arg Tyr Thr Cys Pro Gln Tyr Lys Glu Gly Met
            500                 505                 510
Leu Asp Ser Glu Ala Ala Asn Tyr Trp Leu Pro Val Asp Ile Leu Ile
        515                 520                 525
Gly Gly Ile Glu His Ala Ile Met Gly Leu Leu Tyr Phe Arg Phe Phe
    530                 535                 540
His Lys Leu Met Arg Asp Ala Gly Met Val Asn Ser Asp Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
            580                 585                 590
Val Glu Arg Asp Glu Lys Gly Arg Ile Val Lys Ala Lys Asp Ala Ala
        595                 600                 605
Gly His Glu Leu Val Tyr Thr Gly Met Ser Lys Met Ser Lys Ser Lys
    610                 615                 620
Asn Asn Gly Ile Asp Pro Gln Val Met Val Glu Arg Tyr Gly Ala Asp
625                 630                 635                 640
Thr Val Arg Leu Phe Met Met Phe Ala Ser Pro Ala Asp Met Thr Leu
                645                 650                 655
Glu Trp Gln Glu Ser Gly Val Glu Gly Ala Asn Arg Phe Leu Lys Arg
```

```
               660                 665                 670
Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860

<210> SEQ ID NO 90
<211> LENGTH: 860
<212> TYPE: PRT
<213> ORGANISM: Artificial
<220> FEATURE:
<223> OTHER INFORMATION: mutant synthetase

<400> SEQUENCE: 90

Met Gln Glu Gln Tyr Arg Pro Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Leu Glu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
```

```
                165                 170                 175
Trp Arg Cys Asp Thr Lys Val Glu Arg Lys Glu Ile Pro Gln Trp Phe
                180                 185                 190
Ile Lys Ile Thr Ala Tyr Ala Asp Glu Leu Leu Asn Asp Leu Asp Lys
                195                 200                 205
Leu Asp His Trp Pro Asp Thr Val Lys Thr Met Gln Arg Asn Trp Ile
        210                 215                 220
Gly Arg Ser Glu Gly Val Glu Ile Thr Phe Asn Val Asn Asp Tyr Asp
225                 230                 235                 240
Asn Thr Leu Thr Val Tyr Thr Thr Arg Pro Asp Thr Phe Met Gly Cys
                245                 250                 255
Thr Tyr Leu Ala Val Ala Ala Gly His Pro Leu Ala Gln Lys Ala Ala
                260                 265                 270
Glu Asn Asn Pro Glu Leu Ala Ala Phe Ile Asp Glu Cys Arg Asn Thr
                275                 280                 285
Lys Val Ala Glu Ala Glu Met Ala Thr Met Glu Lys Lys Gly Val Asp
                290                 295                 300
Thr Gly Phe Lys Ala Val His Pro Leu Thr Gly Glu Glu Ile Pro Val
305                 310                 315                 320
Trp Ala Ala Asn Phe Val Leu Met Glu Tyr Gly Thr Gly Ala Val Met
                325                 330                 335
Ala Val Pro Gly His Asp Gln Arg Asp Tyr Glu Phe Ala Ser Lys Tyr
                340                 345                 350
Gly Leu Asn Ile Lys Pro Val Ile Leu Ala Ala Asp Gly Ser Glu Pro
                355                 360                 365
Asp Leu Ser Gln Gln Ala Leu Thr Glu Lys Gly Val Leu Phe Asn Ser
                370                 375                 380
Gly Glu Phe Asn Gly Leu Asp His Glu Ala Ala Phe Asn Ala Ile Ala
385                 390                 395                 400
Asp Lys Leu Thr Ala Met Gly Val Gly Glu Arg Lys Val Asn Tyr Arg
                405                 410                 415
Leu Arg Asp Trp Gly Val Ser Arg Gln Arg Tyr Trp Gly Ala Pro Ile
                420                 425                 430
Pro Met Val Thr Leu Glu Asp Gly Thr Val Met Pro Thr Pro Asp Asp
                435                 440                 445
Gln Leu Pro Val Ile Leu Pro Glu Asp Val Val Met Asp Gly Ile Thr
                450                 455                 460
Ser Pro Ile Lys Ala Asp Pro Glu Trp Ala Lys Thr Thr Val Asn Gly
465                 470                 475                 480
Met Pro Ala Leu Arg Glu Thr Asp Thr Phe Asp Thr Phe Met Glu Ser
                485                 490                 495
Ser Trp Arg Tyr Ala Arg Tyr Thr Cys Pro Gln Tyr Lys Glu Gly Met
                500                 505                 510
Leu Asp Ser Glu Ala Ala Asn Tyr Trp Leu Pro Val Asp Ile Ala Ile
                515                 520                 525
Gly Gly Ile Glu His Ala Ile Met Gly Leu Leu Tyr Phe Arg Phe Phe
                530                 535                 540
His Lys Leu Met Arg Asp Ala Gly Met Val Asn Ser Asp Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
                580                 585                 590
```

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860

<210> SEQ ID NO 91
<211> LENGTH: 860
<212> TYPE: PRT
<213> ORGANISM: Artificial
<220> FEATURE:
<223> OTHER INFORMATION: mutant synthetase

<400> SEQUENCE: 91

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Met Glu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

```
Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
            115                 120                 125

Thr Pro Glu Tyr Tyr Arg Trp Glu Gln Lys Phe Phe Thr Glu Leu Tyr
            130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
            195                 200                 205

Leu Asp His Trp Pro Asp Thr Val Lys Thr Met Gln Arg Asn Trp Ile
            210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
            245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
            275                 280                 285

Lys Val Ala Glu Ala Glu Met Ala Thr Met Glu Lys Lys Gly Val Asp
            290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
            370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
            450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Arg Tyr Ala Arg Tyr Thr Cys Pro Gln Tyr Lys Glu Gly Met
            500                 505                 510
```

```
Leu Asp Ser Glu Ala Ala Asn Tyr Trp Leu Pro Val Asp Ile Phe Ile
        515                 520                 525

Gly Gly Ile Glu His Ala Ile Met Gly Leu Leu Tyr Phe Arg Phe Phe
        530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
        580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
        820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
        850                 855                 860

<210> SEQ ID NO 92
<211> LENGTH: 860
<212> TYPE: PRT
<213> ORGANISM: Artificial
<220> FEATURE:
<223> OTHER INFORMATION: mutant synthetase

<400> SEQUENCE: 92

Met Gln Glu Gln Tyr Arg Pro Glu Glu Ile Glu Ser Lys Val Gln Leu
1               5                   10                  15
```

-continued

```
His Trp Asp Glu Lys Arg Thr Phe Glu Val Thr Glu Asp Ser Lys
             20                  25                  30

Glu Lys Tyr Tyr Cys Leu Ser Leu Glu Pro Tyr Pro Ser Gly Arg Leu
         35                  40                  45

His Met Gly His Val Arg Asn Tyr Thr Ile Gly Asp Val Ile Ala Arg
     50                  55                  60

Tyr Gln Arg Met Leu Gly Lys Asn Val Leu Gln Pro Ile Gly Trp Asp
 65                  70                  75                  80

Ala Phe Gly Leu Pro Ala Glu Gly Ala Ala Val Lys Asn Asn Thr Ala
                 85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
```

```
            435                 440                 445
Gln Leu Pro Val Ile Leu Pro Glu Asp Val Met Asp Gly Ile Thr
    450                 455                 460
Ser Pro Ile Lys Ala Asp Pro Glu Trp Ala Lys Thr Thr Val Asn Gly
465                 470                 475                 480
Met Pro Ala Leu Arg Glu Thr Asp Thr Phe Asp Thr Phe Met Glu Ser
                485                 490                 495
Ser Trp Arg Tyr Ala Arg Tyr Thr Cys Pro Gln Tyr Lys Glu Gly Met
            500                 505                 510
Leu Asp Ser Glu Ala Ala Asn Tyr Trp Leu Pro Val Asp Ile Cys Ile
            515                 520                 525
Gly Gly Ile Glu His Ala Ile Met Gly Leu Leu Tyr Phe Arg Phe Phe
            530                 535                 540
His Lys Leu Met Arg Asp Ala Gly Met Val Asn Ser Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
            580                 585                 590
Val Glu Arg Asp Glu Lys Gly Arg Ile Val Lys Ala Lys Asp Ala Ala
            595                 600                 605
Gly His Glu Leu Val Tyr Thr Gly Met Ser Lys Met Ser Lys Ser Lys
            610                 615                 620
Asn Asn Gly Ile Asp Pro Gln Val Met Val Glu Arg Tyr Gly Ala Asp
625                 630                 635                 640
Thr Val Arg Leu Phe Met Met Phe Ala Ser Pro Ala Asp Met Thr Leu
                645                 650                 655
Glu Trp Gln Glu Ser Gly Val Glu Gly Ala Asn Arg Phe Leu Lys Arg
            660                 665                 670
Val Trp Lys Leu Val Tyr Glu His Thr Ala Lys Gly Asp Val Ala Ala
            675                 680                 685
Leu Asn Val Asp Ala Leu Thr Glu Asn Gln Lys Ala Leu Arg Arg Asp
            690                 695                 700
Val His Lys Thr Ile Ala Lys Val Thr Asp Asp Ile Gly Arg Arg Gln
705                 710                 715                 720
Thr Phe Asn Thr Ala Ile Ala Ala Ile Met Glu Leu Met Asn Lys Leu
                725                 730                 735
Ala Lys Ala Pro Thr Asp Gly Glu Gln Asp Arg Ala Leu Met Gln Glu
            740                 745                 750
Ala Leu Leu Ala Val Val Arg Met Leu Asn Pro Phe Thr Pro His Ile
            755                 760                 765
Cys Phe Thr Leu Trp Gln Glu Leu Lys Gly Glu Gly Asp Ile Asp Asn
            770                 775                 780
Ala Pro Trp Pro Val Ala Asp Glu Lys Ala Met Val Glu Asp Ser Thr
785                 790                 795                 800
Leu Val Val Val Gln Val Asn Gly Lys Val Arg Ala Lys Ile Thr Val
                805                 810                 815
Pro Val Asp Ala Thr Glu Glu Gln Val Arg Glu Arg Ala Gly Gln Glu
            820                 825                 830
His Leu Val Ala Lys Tyr Leu Asp Gly Val Thr Val Arg Lys Val Ile
            835                 840                 845
Tyr Val Pro Gly Lys Leu Leu Asn Leu Val Val Gly
            850                 855                 860
```

<210> SEQ ID NO 93
<211> LENGTH: 860
<212> TYPE: PRT
<213> ORGANISM: Artificial
<220> FEATURE:
<223> OTHER INFORMATION: mutant synthetase

<400> SEQUENCE: 93

```
Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Phe Glu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365
```

-continued

Asp Leu Ser Gln Gln Ala Leu Thr Glu Lys Gly Val Leu Phe Asn Ser
370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Arg Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Thr Ile
                515                 520                 525

Gly Gly Ile Glu His Ala Ile Met Gly Leu Leu Tyr Phe Arg Phe Phe
530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
                595                 600                 605

Gly His Glu Leu Val Tyr Thr Gly Met Ser Lys Met Ser Lys Ser Lys
610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
                675                 680                 685

Leu Asn Val Asp Ala Leu Thr Glu Asn Gln Lys Ala Leu Arg Arg Asp
690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
                755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
            805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly
850                 855                 860

<210> SEQ ID NO 94
<211> LENGTH: 860
<212> TYPE: PRT
<213> ORGANISM: Artificial
<220> FEATURE:
<223> OTHER INFORMATION: mutant synthetase

<400> SEQUENCE: 94

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Gly Glu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

-continued

```
Lys Val Ala Glu Ala Glu Met Ala Thr Met Glu Lys Lys Gly Val Asp
        290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
                340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Arg Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Leu Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
690                 695                 700

Val His Lys Thr Ile Ala Lys Val Thr Asp Asp Ile Gly Arg Arg Gln
```

-continued

```
            705                 710                 715                 720
        Thr Phe Asn Thr Ala Ile Ala Ala Ile Met Glu Leu Met Asn Lys Leu
                        725                 730                 735

Ala Lys Ala Pro Thr Asp Gly Glu Gln Asp Arg Ala Leu Met Gln Glu
                        740                 745                 750

Ala Leu Leu Ala Val Val Arg Met Leu Asn Pro Phe Thr Pro His Ile
                        755                 760                 765

Cys Phe Thr Leu Trp Gln Glu Leu Lys Gly Glu Gly Asp Ile Asp Asn
                        770                 775                 780

Ala Pro Trp Pro Val Ala Asp Glu Lys Ala Met Val Glu Asp Ser Thr
        785                 790                 795                 800

Leu Val Val Val Gln Val Asn Gly Lys Val Arg Ala Lys Ile Thr Val
                        805                 810                 815

Pro Val Asp Ala Thr Glu Glu Gln Val Arg Glu Arg Ala Gly Gln Glu
                        820                 825                 830

His Leu Val Ala Lys Tyr Leu Asp Gly Val Thr Val Arg Lys Val Ile
                        835                 840                 845

Tyr Val Pro Gly Lys Leu Leu Asn Leu Val Val Gly
                850                 855                 860

<210> SEQ ID NO 95
<211> LENGTH: 860
<212> TYPE: PRT
<213> ORGANISM: Artificial
<220> FEATURE:
<223> OTHER INFORMATION: mutant synthetase

<400> SEQUENCE: 95

Met Gln Glu Gln Tyr Arg Pro Glu Glu Ile Glu Ser Lys Val Gln Leu
        1               5                   10                  15

His Trp Asp Glu Lys Arg Thr Phe Glu Val Thr Glu Asp Glu Ser Lys
                        20                  25                  30

Glu Lys Tyr Tyr Cys Leu Ser Gly Trp Pro Tyr Pro Ser Gly Arg Leu
                        35                  40                  45

His Met Gly His Val Arg Asn Tyr Thr Ile Gly Asp Val Ile Ala Arg
                50                  55                  60

Tyr Gln Arg Met Leu Gly Lys Asn Val Leu Gln Pro Ile Gly Trp Asp
        65              70                  75                  80

Ala Phe Gly Leu Pro Ala Glu Gly Ala Ala Val Lys Asn Asn Thr Ala
                        85                  90                  95

Pro Ala Pro Trp Thr Tyr Asp Asn Ile Ala Tyr Met Lys Asn Gln Leu
                        100                 105                 110

Lys Met Leu Gly Phe Gly Tyr Asp Trp Ser Arg Glu Leu Ala Thr Cys
                        115                 120                 125

Thr Pro Glu Tyr Tyr Arg Trp Glu Gln Lys Phe Phe Thr Glu Leu Tyr
                        130                 135                 140

Lys Lys Gly Leu Val Tyr Lys Lys Thr Ser Ala Val Asn Trp Cys Pro
        145                 150                 155                 160

Asn Asp Gln Thr Val Leu Ala Asn Glu Gln Val Ile Asp Gly Cys Cys
                        165                 170                 175

Trp Arg Cys Asp Thr Lys Val Glu Arg Lys Glu Ile Pro Gln Trp Phe
                        180                 185                 190

Ile Lys Ile Thr Ala Tyr Ala Asp Glu Leu Leu Asn Asp Leu Asp Lys
                        195                 200                 205

Leu Asp His Trp Pro Asp Thr Val Lys Thr Met Gln Arg Asn Trp Ile
```

```
            210                 215                 220
Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
                260                 265                 270

Glu Asn Asn Pro Glu Leu Ala Ala Phe Ile Asp Glu Cys Arg Asn Thr
            275                 280                 285

Lys Val Ala Glu Ala Glu Met Ala Thr Met Glu Lys Lys Gly Val Asp
            290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
                340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
            370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
            450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ala Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Leu Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
            610                 615                 620

Asn Asn Gly Ile Asp Pro Gln Val Met Val Glu Arg Tyr Gly Ala Asp
625                 630                 635                 640
```

-continued

Thr Val Arg Leu Phe Met Met Phe Ala Ser Pro Ala Asp Met Thr Leu
            645                 650                 655

Glu Trp Gln Glu Ser Gly Val Glu Gly Ala Asn Arg Phe Leu Lys Arg
        660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ile Met Glu Leu Met Asn Lys Leu
            725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
            805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly
            850                 855                 860

<210> SEQ ID NO 96
<211> LENGTH: 860
<212> TYPE: PRT
<213> ORGANISM: Artificial
<220> FEATURE:
<223> OTHER INFORMATION: mutant synthetase

<400> SEQUENCE: 96

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Trp Ser Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
            85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

-continued

```
Lys Lys Gly Leu Val Tyr Lys Thr Ser Ala Val Asn Trp Cys Pro
145                 150                 155                 160

Asn Asp Gln Thr Val Leu Ala Asn Glu Gln Val Ile Asp Gly Cys Cys
            165                 170                 175

Trp Arg Cys Asp Thr Lys Val Glu Arg Lys Glu Ile Pro Gln Trp Phe
        180                 185                 190

Ile Lys Ile Thr Ala Tyr Ala Asp Glu Leu Leu Asn Asp Leu Asp Lys
            195                 200                 205

Leu Asp His Trp Pro Asp Thr Val Lys Thr Met Gln Arg Asn Trp Ile
210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Ala Ile
        515                 520                 525

Gly Gly Ile Glu His Ala Ile Met Gly Leu Leu Tyr Phe Arg Phe Phe
    530                 535                 540

His Lys Leu Met Arg Asp Ala Gly Met Val Asn Ser Asp Glu Pro Ala
545                 550                 555                 560
```

```
Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860

<210> SEQ ID NO 97
<211> LENGTH: 860
<212> TYPE: PRT
<213> ORGANISM: Artificial
<220> FEATURE:
<223> OTHER INFORMATION: mutant synthetase

<400> SEQUENCE: 97

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Gly Thr Pro Tyr Pro Ser Gly Arg Leu
        35                  40                  45

His Met Gly His Val Arg Asn Tyr Thr Ile Gly Asp Val Ile Ala Arg
    50                  55                  60
```

-continued

```
Tyr Gln Arg Met Leu Gly Lys Asn Val Leu Gln Pro Ile Gly Trp Asp
 65                  70                  75                  80

Ala Phe Gly Leu Pro Ala Glu Gly Ala Ala Val Lys Asn Asn Thr Ala
             85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
        290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
        370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
        450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
```

```
                        485                 490                 495
Ser Trp Trp Tyr Ala Arg Tyr Thr Cys Pro Gln Tyr Lys Glu Gly Met
                    500                 505                 510
Leu Asp Ser Glu Ala Ala Asn Tyr Trp Leu Pro Val Asp Ile Leu Ile
                515                 520                 525
Gly Gly Ile Glu His Ala Ile Met Gly Leu Leu Tyr Phe Arg Phe Phe
            530                 535                 540
His Lys Leu Met Arg Asp Ala Gly Met Val Asn Ser Asp Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
                580                 585                 590
Val Glu Arg Asp Glu Lys Gly Arg Ile Val Lys Ala Lys Asp Ala Ala
                595                 600                 605
Gly His Glu Leu Val Tyr Thr Gly Met Ser Lys Met Ser Lys Ser Lys
            610                 615                 620
Asn Asn Gly Ile Asp Pro Gln Val Met Val Glu Arg Tyr Gly Ala Asp
625                 630                 635                 640
Thr Val Arg Leu Phe Met Met Phe Ala Ser Pro Ala Asp Met Thr Leu
                    645                 650                 655
Glu Trp Gln Glu Ser Gly Val Glu Gly Ala Asn Arg Phe Leu Lys Arg
                660                 665                 670
Val Trp Lys Leu Val Tyr Glu His Thr Ala Lys Gly Asp Val Ala Ala
                675                 680                 685
Leu Asn Val Asp Ala Leu Thr Glu Asn Gln Lys Ala Leu Arg Arg Asp
690                 695                 700
Val His Lys Thr Ile Ala Lys Val Thr Asp Asp Ile Gly Arg Arg Gln
705                 710                 715                 720
Thr Phe Asn Thr Ala Ile Ala Ala Ile Met Glu Leu Met Asn Lys Leu
                725                 730                 735
Ala Lys Ala Pro Thr Asp Gly Glu Gln Asp Arg Ala Leu Met Gln Glu
                740                 745                 750
Ala Leu Leu Ala Val Val Arg Met Leu Asn Pro Phe Thr Pro His Ile
                755                 760                 765
Cys Phe Thr Leu Trp Gln Glu Leu Lys Gly Glu Gly Asp Ile Asp Asn
                770                 775                 780
Ala Pro Trp Pro Val Ala Asp Glu Lys Ala Met Val Glu Asp Ser Thr
785                 790                 795                 800
Leu Val Val Val Gln Val Asn Gly Lys Val Arg Ala Lys Ile Thr Val
                    805                 810                 815
Pro Val Asp Ala Thr Glu Glu Gln Val Arg Glu Arg Ala Gly Gln Glu
                820                 825                 830
His Leu Val Ala Lys Tyr Leu Asp Gly Val Thr Val Arg Lys Val Ile
                835                 840                 845
Tyr Val Pro Gly Lys Leu Leu Asn Leu Val Val Gly
                850                 855                 860

<210> SEQ ID NO 98
<211> LENGTH: 860
<212> TYPE: PRT
<213> ORGANISM: Artificial
<220> FEATURE:
<223> OTHER INFORMATION: mutant synthetase
```

```
<400> SEQUENCE: 98

Met Glu Glu Gln Tyr Arg Pro Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Ala Asn Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65              70                  75                  80

Ala Phe Gly Leu Pro Ala Glu Gly Ala Ala Val Lys Asn Asn Thr Ala
            85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145             150                 155                 160

Asn Asp Gln Thr Val Leu Ala Asn Glu Gln Val Ile Asp Gly Cys Cys
            165                 170                 175

Trp Arg Cys Asp Thr Lys Val Glu Arg Lys Glu Ile Pro Gln Trp Phe
        180                 185                 190

Ile Lys Ile Thr Ala Tyr Ala Asp Glu Leu Leu Asn Asp Leu Asp Lys
    195                 200                 205

Leu Asp His Trp Pro Asp Thr Val Lys Thr Met Gln Arg Asn Trp Ile
210             215                 220

Gly Arg Ser Glu Gly Val Glu Ile Thr Phe Asn Val Asn Asp Tyr Asp
225             230                 235                 240

Asn Thr Leu Thr Val Tyr Thr Thr Arg Pro Asp Thr Phe Met Gly Cys
            245                 250                 255

Thr Tyr Leu Ala Val Ala Ala Gly His Pro Leu Ala Gln Lys Ala Ala
        260                 265                 270

Glu Asn Asn Pro Glu Leu Ala Ala Phe Ile Asp Glu Cys Arg Asn Thr
    275                 280                 285

Lys Val Ala Glu Ala Glu Met Ala Thr Met Glu Lys Lys Gly Val Asp
290             295                 300

Thr Gly Phe Lys Ala Val His Pro Leu Thr Gly Glu Glu Ile Pro Val
305             310                 315                 320

Trp Ala Ala Asn Phe Val Leu Met Glu Tyr Gly Thr Gly Ala Val Met
            325                 330                 335

Ala Val Pro Gly His Asp Gln Arg Asp Tyr Glu Phe Ala Ser Lys Tyr
        340                 345                 350

Gly Leu Asn Ile Lys Pro Val Ile Leu Ala Ala Asp Gly Ser Glu Pro
    355                 360                 365

Asp Leu Ser Gln Gln Ala Leu Thr Glu Lys Gly Val Leu Phe Asn Ser
370                 375                 380

Gly Glu Phe Asn Gly Leu Asp His Glu Ala Ala Phe Asn Ala Ile Ala
385             390                 395                 400

Asp Lys Leu Thr Ala Met Gly Val Gly Glu Arg Lys Val Asn Tyr Arg
            405                 410                 415
```

```
Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
            450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
            485                 490                 495

Cys Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Gly Ile
            515                 520                 525

Gly Gly Ile Glu His Ala Ile Met Thr Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
            610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
            690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
            770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830
```

His Leu Val Ala Lys Tyr Leu Asp Gly Val Thr Val Arg Lys Val Ile
                835                 840                 845

Tyr Val Pro Gly Lys Leu Leu Asn Leu Val Val Gly
    850                 855                 860

<210> SEQ ID NO 99
<211> LENGTH: 860
<212> TYPE: PRT
<213> ORGANISM: Artificial
<220> FEATURE:
<223> OTHER INFORMATION: mutant synthetase

<400> SEQUENCE: 99

Met Glu Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
                20                  25                  30

Glu Lys Tyr Tyr Cys Leu Ser Ala Asn Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

```
Ala Val Pro Gly His Asp Gln Arg Asp Tyr Glu Phe Ala Ser Lys Tyr
            340                 345                 350
Gly Leu Asn Ile Lys Pro Val Ile Leu Ala Ala Asp Gly Ser Glu Pro
        355                 360                 365
Asp Leu Ser Gln Gln Ala Leu Thr Glu Lys Gly Val Leu Phe Asn Ser
    370                 375                 380
Gly Glu Phe Asn Gly Leu Asp His Glu Ala Ala Phe Asn Ala Ile Ala
385                 390                 395                 400
Asp Lys Leu Thr Ala Met Gly Val Gly Glu Arg Lys Val Asn Tyr Arg
                405                 410                 415
Leu Arg Asp Trp Gly Val Ser Arg Gln Arg Tyr Trp Gly Ala Pro Ile
            420                 425                 430
Pro Met Val Thr Leu Glu Asp Gly Thr Val Met Pro Thr Pro Asp Asp
            435                 440                 445
Gln Leu Pro Val Ile Leu Pro Glu Asp Val Val Met Asp Gly Ile Thr
    450                 455                 460
Ser Pro Ile Lys Ala Asp Pro Glu Trp Ala Lys Thr Thr Val Asn Gly
465                 470                 475                 480
Met Pro Ala Leu Arg Glu Thr Asp Thr Phe Asp Thr Phe Met Glu Ser
                485                 490                 495
Cys Trp Ile Tyr Ala Arg Tyr Thr Cys Pro Gln Tyr Lys Glu Gly Met
            500                 505                 510
Leu Asp Ser Glu Ala Ala Asn Tyr Trp Leu Pro Val Asp Ile Gly Ile
        515                 520                 525
Gly Gly Ile Glu His Ala Ile Met Thr Leu Leu Tyr Phe Arg Phe Phe
    530                 535                 540
His Lys Leu Met Arg Asp Ala Gly Met Val Asn Ser Asp Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
            580                 585                 590
Val Glu Arg Asp Glu Lys Gly Arg Ile Val Lys Ala Lys Asp Ala Ala
        595                 600                 605
Gly His Glu Leu Val Tyr Thr Gly Met Ser Lys Met Ser Lys Ser Lys
    610                 615                 620
Asn Asn Gly Ile Asp Pro Gln Val Met Val Glu Arg Tyr Gly Ala Asp
625                 630                 635                 640
Thr Val Arg Leu Phe Met Met Phe Ala Ser Pro Ala Asp Met Thr Leu
                645                 650                 655
Glu Trp Gln Glu Ser Gly Val Glu Gly Ala Asn Arg Phe Leu Lys Arg
            660                 665                 670
Val Trp Lys Leu Val Tyr Glu His Thr Ala Lys Gly Asp Val Ala Ala
        675                 680                 685
Leu Asn Val Asp Ala Leu Thr Glu Asn Gln Lys Ala Leu Arg Arg Asp
    690                 695                 700
Val His Lys Thr Ile Ala Lys Val Thr Asp Asp Ile Gly Arg Arg Gln
705                 710                 715                 720
Thr Phe Asn Thr Ala Ile Ala Ile Met Glu Leu Met Asn Lys Leu
                725                 730                 735
Ala Lys Ala Pro Thr Asp Gly Glu Gln Asp Arg Ala Leu Met Gln Glu
            740                 745                 750
Ala Leu Leu Ala Val Val Arg Met Leu Asn Pro Phe Thr Pro His Ile
```

-continued

```
                755                 760                 765
Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Val Arg Glu Arg Ala Gly Gln Glu
                820                 825                 830

His Leu Val Ala Lys Tyr Leu Asp Gly Val Thr Val Arg Lys Val Ile
                835                 840                 845

Tyr Val Pro Gly Lys Leu Leu Asn Leu Val Val Gly
850                 855                 860

<210> SEQ ID NO 100
<211> LENGTH: 860
<212> TYPE: PRT
<213> ORGANISM: Artificial
<220> FEATURE:
<223> OTHER INFORMATION: mutant synthetase

<400> SEQUENCE: 100

Met Glu Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
                20                  25                  30

Glu Lys Tyr Tyr Cys Leu Ser Ala Asn Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
```

```
                260                 265                 270
Glu Asn Asn Pro Glu Leu Ala Ala Phe Ile Asp Glu Cys Arg Asn Thr
            275                 280                 285
Lys Val Ala Glu Ala Glu Met Ala Thr Met Glu Lys Lys Gly Val Asp
        290                 295                 300
Thr Gly Phe Lys Ala Val His Pro Leu Thr Gly Glu Ile Pro Val
305                 310                 315                 320
Trp Ala Ala Asn Phe Val Leu Met Glu Tyr Gly Thr Gly Ala Val Met
                325                 330                 335
Ala Ala Pro Gly His Asp Gln Arg Asp Tyr Glu Phe Ala Ser Lys Tyr
            340                 345                 350
Gly Leu Asn Ile Lys Pro Val Ile Leu Ala Ala Asp Gly Ser Glu Pro
        355                 360                 365
Asp Leu Ser Gln Gln Ala Leu Thr Glu Lys Gly Val Leu Phe Asn Ser
    370                 375                 380
Gly Glu Phe Asn Gly Leu Asp His Glu Ala Ala Phe Asn Ala Ile Ala
385                 390                 395                 400
Asp Lys Leu Thr Ala Met Gly Val Gly Glu Arg Lys Val Asn Tyr Arg
                405                 410                 415
Leu Arg Asp Trp Gly Val Ser Arg Gln Arg Tyr Trp Gly Ala Pro Ile
            420                 425                 430
Pro Met Val Thr Leu Glu Asp Gly Thr Val Met Pro Thr Pro Asp Asp
        435                 440                 445
Gln Leu Pro Val Ile Leu Pro Glu Asp Val Val Met Asp Gly Ile Thr
    450                 455                 460
Ser Pro Ile Lys Ala Asp Pro Glu Trp Ala Lys Thr Thr Val Asn Gly
465                 470                 475                 480
Met Pro Ala Leu Arg Glu Thr Asp Thr Phe Asp Thr Phe Met Glu Ser
                485                 490                 495
Cys Trp Ile Tyr Ala Arg Tyr Thr Cys Pro Gln Tyr Lys Glu Gly Met
            500                 505                 510
Leu Asp Ser Glu Ala Ala Asn Tyr Trp Leu Pro Val Asp Ile Gly Ile
        515                 520                 525
Gly Gly Ile Glu His Ala Ile Met Thr Leu Leu Tyr Phe Arg Phe Phe
    530                 535                 540
His Lys Leu Met Arg Asp Ala Gly Met Val Asn Ser Asp Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
            580                 585                 590
Val Glu Arg Asp Glu Lys Gly Arg Ile Val Lys Ala Lys Asp Ala Ala
        595                 600                 605
Gly His Glu Leu Val Tyr Thr Gly Met Ser Lys Met Ser Lys Ser Lys
    610                 615                 620
Asn Asn Gly Ile Asp Pro Gln Val Met Val Glu Arg Tyr Gly Ala Asp
625                 630                 635                 640
Thr Val Arg Leu Phe Met Met Phe Ala Ser Pro Ala Asp Met Thr Leu
                645                 650                 655
Glu Trp Gln Glu Ser Gly Val Glu Gly Ala Asn Arg Phe Leu Lys Arg
            660                 665                 670
Val Trp Lys Leu Val Tyr Glu His Thr Ala Lys Gly Asp Val Ala Ala
        675                 680                 685
```

```
Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
                755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
                820                 825                 830

His Leu Val Ala Lys Tyr Leu Asp Gly Val Thr Val Arg Lys Val Ile
                835                 840                 845

Tyr Val Pro Gly Lys Leu Leu Asn Leu Val Val Gly
    850                 855                 860

<210> SEQ ID NO 101
<211> LENGTH: 860
<212> TYPE: PRT
<213> ORGANISM: Artificial
<220> FEATURE:
<223> OTHER INFORMATION: mutant synthetase

<400> SEQUENCE: 101

Met Glu Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Gly Lys
                20                  25                  30

Glu Lys Tyr Tyr Cys Leu Ser Trp Ser Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
                100                 105                 110

Lys Met Leu Gly Phe Gly Tyr Asp Trp Ser Arg Glu Leu Ala Thr Cys
            115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
                180                 185                 190
```

```
Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Ala Ser Arg Pro Asp Thr Phe Met Gly Cys
                245                 250                 255

Thr Tyr Leu Ala Val Ala Ala Gly His Pro Leu Ala Gln Lys Ala Ala
                260                 265                 270

Glu Asn Asn Pro Glu Leu Ala Ala Phe Ile Asp Glu Cys Arg Asn Thr
                275                 280                 285

Lys Val Ala Glu Ala Glu Met Ala Thr Met Glu Lys Lys Gly Val Asp
                290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
                340                 345                 350

Gly Leu Asn Ile Lys Pro Val Ile Leu Ala Ala Asp Gly Ser Glu Pro
                355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Cys Trp Ile Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Ala Ile
                515                 520                 525

Gly Gly Ile Glu His Ala Ile Met Gly Leu Leu Tyr Phe Arg Phe Phe
530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
                595                 600                 605
```

```
Gly His Glu Leu Val Tyr Thr Gly Ile Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Val Glu Gly Ala Asn Arg Phe Leu Lys Arg
            660                 665                 670

Ala Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
850                 855                 860

<210> SEQ ID NO 102
<211> LENGTH: 15
<212> TYPE: PRT
<213> ORGANISM: Artificial
<220> FEATURE:
<223> OTHER INFORMATION: tryptic peptide from enhanced GFP

<400> SEQUENCE: 102

Phe Ser Val Ser Gly Glu Gly Glu Gly Asp Ala Thr Tyr Gly Lys
1               5                   10                  15

<210> SEQ ID NO 103
<211> LENGTH: 15
<212> TYPE: PRT
<213> ORGANISM: Artificial
<220> FEATURE:
<223> OTHER INFORMATION: tryptic peptide from enhanced GFP
<220> FEATURE:
<221> NAME/KEY: MISC_FEATURE
<222> LOCATION: (13)..(13)
<223> OTHER INFORMATION: X is tyrosine, p-methoxy-L-phenylalanine,
      p-acetyl-L-phenylalanine, p-benzoyl-L-phenylalanine,
      p-iodo-L-phenylalanine, p-azido-L-phenylalanine, or
      p-propargyloxyphenylalanine

<400> SEQUENCE: 103

Phe Ser Val Ser Gly Glu Gly Glu Gly Asp Ala Thr Xaa Gly Lys
```

```
<210> SEQ ID NO 104
<211> LENGTH: 55
<212> TYPE: DNA
<213> ORGANISM: Homo sapiens

<400> SEQUENCE: 104
agcgctccgg tttttctgtg ctgaacctca ggggacgccg acacacgtac acgtc          55

<210> SEQ ID NO 105
<211> LENGTH: 25
<212> TYPE: DNA
<213> ORGANISM: Artificial
<220> FEATURE:
<223> OTHER INFORMATION: 5'-flanking sequence

<400> SEQUENCE: 105
gatccgaccg tgtgcttggc agaac                                            25

<210> SEQ ID NO 106
<211> LENGTH: 12
<212> TYPE: DNA
<213> ORGANISM: Artificial
<220> FEATURE:
<223> OTHER INFORMATION: 3'-flanking sequence

<400> SEQUENCE: 106
gtcctttttt tg                                                          12
```

GENETIC INCORPORATION OF UNNATURAL AMINO ACIDS INTO PROTEINS IN MAMMALIAN CELLS

CROSS-REFERENCE TO RELATED APPLICATIONS

This application is a 371 application of PCT/US2007/022232, filed Oct. 17, 2007, which claims priority to U.S. Provisional Patent Application Ser. No. 60/853,008, filed Oct. 18, 2006, and U.S. Provisional Patent Application Ser. No. 60/923,458, filed Apr. 12, 2007, the disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. GM62159 awarded by the National Institutes of Health. The government has certain rights in the invention.

FIELD OF THE INVENTION

The invention is in the field of translation biochemistry. The invention relates to compositions and methods for making and using orthogonal tRNAs, orthogonal aminoacyl-tRNA synthetases, and pairs thereof, that incorporate unnatural amino acids into proteins. The invention also relates to methods of producing proteins in cells using such pairs and the proteins produced by the methods.

BACKGROUND OF THE INVENTION

Methods have been previously described to incorporate unnatural amino acids site-specifically into proteins in mammalian cells. Chemically aminoacylated suppressor tRNAs have been microinjected or electroporated into CHO cells and neurons, respectively, and used to suppress nonsense amber mutations with a series of unnatural amino acids (Monahan et al. (2003), "Site-specific incorporation of unnatural amino acids into receptors expressed in Mammalian cells," Chem Biol 10:573-580). However, the use of the aminoacylated tRNA as a stoichiometric reagent severely limits the amount of protein that can be produced.

Alternatively, heterologous suppressor tRNA/aaRS pairs that do not cross react with host tRNAs, aaRSs or amino acids (orthogonal tRNA/aaRSs) have been engineered to incorporate unnatural amino acids selectively into proteins. For example, Yokoyama and coworkers modified a Bacillus stearothermophilus amber suppressor tRNA$_{CUA}^{Tyr}$ (BstRNA$_{CUA}^{Tyr}$) and E. coli tyrosyl-tRNA synthetase (Ec-TyrRS) to incorporate 3-iodo-L-tyrosine into proteins in CHO cells (Sakamoto et al. (2002), "Site-specific incorporation of an unnatural amino acid into proteins in mammalian cells," Nucleic Acids Res 30:4692-4699). Similarly, Zhang and coworkers engineered an orthogonal Bacillus subtilis suppressor tRNA/tryptophanyl-tRNA synthetase pair to incorporate 5-hydroxytryptophan into proteins in mammalian cells with high fidelity (Zhang et al. (2004), "Selective incorporation of 5-hydroxytryptophan into proteins in mammalian cells," Proc Natl Acad Sci USA 101:8882-8887).

However, the use of structure-based mutagenesis to generate aaRS variants that aminoacylate an amino acid whose side chain differs significantly from that of the wild type substrate requires mutations of multiple active site residues which are difficult to predict a priori (Zhang et al. (2002), "Structure-based design of mutant Methanococcus jannaschii tyrosyl-tRNA synthetase for incorporation of O-methyl-L-tyrosine," Proc Natl Acad Sci USA 99:6579-6584; Turner et al. (2005), "Structural characterization of a p-acetylphenylalanyl aminoacyl-tRNA synthetase," J Am Chem Soc 127:14976-14977; Turner et al. (2006), "Structural plasticity of an aminoacyl-tRNA synthetase active site," Proc Natl Acad Sci USA 103:6483-6488). Moreover, the engineered mutant may still recognize host amino acids, as is the case with a mutant aaRS that charges its cognate tRNA$_{CUA}^{Tyr}$ with 3-iodo-L-tyrosine (Sakamoto et al. (2002), "Site-specific incorporation of an unnatural amino acid into proteins in mammalian cells," Nucleic Acids Res 30:4692-4699; and Kiga et al. (2002), "An engineered Escherichia coli tyrosyl-tRNA synthetase for site-specific incorporation of an unnatural amino acid into proteins in eukaryotic translation and its application in a wheat germ cell-free system," Proc Natl Acad Sci USA 99:9715-9720).

Alternatively, one can attempt to evolve aaRSs with altered specificities directly in mammalian cells. For example, Wang and coworkers recently used somatic hypermutation in a human B cell line to directly evolve a monomeric red fluorescent protein with enhanced photostability and far-red emissions (Wang et al. (2004), "Evolution of new nonantibody proteins via iterative somatic hypermutation," Proc Natl Acad Sci USA 101:16745-16749). However, somatic hypermutation introduces random mutations in the whole protein, which may be less effective than genetic diversity created by targeted mutagenesis of the active site when evolving variants with altered substrate specificity. The latter, however, is limited by difficulties in generating large stable libraries in mammalian cells.

Orthogonal Translation Technology

A general methodology has been developed for the in vivo site-specific incorporation of structurally diverse unnatural amino acids with non-native physical, chemical and biological properties into proteins in prokaryotic organisms and yeast. These methods rely on orthogonal protein translation components that recognize a suitable selector codon to insert a desired unnatural amino acid at a defined position in a gene of interest during polypeptide translation in vivo. These methods utilize an orthogonal tRNA (O-tRNA) that recognizes a selector codon (e.g., a nonsense amber codon), and where a corresponding specific orthogonal aminoacyl-tRNA synthetase (an O-RS) specifically charges the O-tRNA with the unnatural amino acid. These components do not cross-react with any of the endogenous tRNAs or RSs in the host organism (i.e., the engineered tRNA and RS are orthogonal).

Using this technique in E. coli host systems, functional amber and frameshift suppressor tRNA/aaRS pairs have been derived from a Methanococcus jannaschii tRNA$^{Tyr}$/TyrRS pair, an archaeal tRNA$^{Glu}$/Pyrococcus horikoshii glutamyl-tRNA synthetase pair, and an archaeal tRNA$^{Lys}$/Pyrococcus horikoshii lysyl-tRNA synthetase pair. In Saccharomyces cerevisiae (S. cerevisiae), functional tRNA$_{CUA}$/aaRS pairs have been derived from the corresponding E. coli tRNA$^{Tyr}$/TyrRS and tRNA$^{Leu}$/leucyl-tRNA synthetase pairs. Directed evolution of these suppressor tRNA/aaRS pairs using a combination of positive and negative selections has allowed the efficient, highly selective in vivo incorporation of a large number of diverse unnatural amino acids in E. coli and S. cerevisiae. These include fluorescent, glycosylated, sulfated, metal-ion-binding, and redox-active amino acids, as well as amino acids with novel chemical and photochemical reactivity. This methodology provides a powerful tool for exploring protein structure and function in vitro and in vivo, and for generating proteins, e.g., therapeutic proteins, with new or enhanced properties. The extension of this methodology to mammalian cells, for example primate and rodent cell lines, would significantly enhance the utility of this technology.

The practice of using orthogonal translation systems that are suitable for in vivo production of proteins that comprise one or more unnatural amino acid is generally known in the art. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004 and WO 2006/110182, filed Oct. 27, 2005, entitled "ORTHOGONAL TRANSLATION COMPONENTS FOR THE VIVO INCORPORATION OF UNNATURAL AMINO ACIDS." Each of these applications is incorporated herein by reference in its entirety.

Additional discussion of orthogonal translation systems is also found in, for example, Wang et al. (2001), "Expanding the genetic code of *Escherichia coli,*" *Science* 292:498-500; Wang and Schultz (2002), "Expanding the Genetic Code," *Chem. Commun. (Camb.)* 1:1-11; Alfonta et al. (2003), "Site-Specific Incorporation of a Redox-Active Amino Acid into Proteins," *J Am Chem Soc* 125:14662-14663; Santoro et al. (2003), "An archaebacteria-derived glutamyl-tRNA synthetase and tRNA pair for unnatural amino acid mutagenesis of proteins in *Escherichia coli,*" *Nucleic Acids Res* 31:6700-6709; Chin et al. (2003), "An expanded eukaryotic genetic code," *Science* 301, 964-967; Chin et al. (2003), "Progress toward an expanded eukaryotic genetic code," *Chem Biol* 10, 511-519; and Wu et al. (2004), "A genetically encoded photocaged amino acid," *J Am Chem Soc* 126, 14306-14307; Summerer et al. (2006), "A Genetically Encoded Fluorescent Amino Acid," *PNAS* 103(26):9785-9789; Anderson et al. (2004), "An expanded genetic code with a functional quadruplet codon," *Proc Natl Acad Sci USA* 101:7566-7571; Zhang et al. (2004), "A new strategy for the synthesis of glycoproteins," *Science* 303, 371-373; Wang and Schultz "Expanding the Genetic Code," *Angewandte Chemie Int. Ed.,* 44(1):34-66 (2005); Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); Wang et al., "Expanding the Genetic Code," *Annu. Rev. Biophys. Biomol. Struct.,* 35:225-249 (2006); Xie and Schultz (2006), "A Chemical Toolkit for Proteins—an Expanded Genetic Code," *Nat. Rev. Mol. Cell. Biol.,* 7(10): 775-782; Summerer et al. (2006), "A Genetically Encoded Fluorescent Amino Acid," *Proc Natl Acad Sci USA* 103, 9785-9789; Wang et al. (2006), "A Genetically Encoded Fluorescent Amino Acid," *J Am Chem Soc* 128, 8738-8739; and Liu and Schultz (2006), "Recombinant Expression of Selectively Sulfated Proteins in *E. coli,*" *Nat. Biotechnol.,* 24(11): 1436-1440. The content of each of these publications above is hereby incorporated by reference.

There is a need in the art for the development of improved orthogonal translation components that incorporate unnatural amino acids into proteins in mammalian cell host systems, for example in primate and rodent host cell systems, where a desired unnatural amino acid is incorporated at defined positions. There is a need in the art for improved methods for screening and identifying orthogonal translation components (e.g., mutant aminoacyl-tRNA synthetase enzymes) that can function in mammalian cells, such as rodent cells and human cells. The invention described herein fulfills these and other needs, as will be apparent upon review of the following disclosure.

SUMMARY OF THE INVENTION

The present invention provides a general approach that allows unnatural amino acids with diverse physicochemical and biological properties to be genetically encoded in mammalian cells, e.g., rodent cells and primate cells. Mutant *Escherichia coli* (*E. coli*) aminoacyl-tRNA synthetases (RS) are first evolved in yeast to selectively utilize the unnatural amino acid of interest. The mutant RS together with an amber suppressor tRNA from a eubacteria, e.g., *Bacillus stearothermophilus* (*B. stearothermophilus*), are then used to site-specifically incorporate the unnatural amino acid into proteins in the mammalian cells in response to an amber nonsense codon. Ten unnatural amino acids (the unnatural amino acids provided in FIG. 1) were independently incorporated into model proteins expressed in Chinese Hamster Ovary (CHO) cells or human 293T cells with efficiencies up to 1 µg protein per $2 \times 10^7$ cells. Mass spectrometry confirmed a high translational fidelity for the unnatural amino acid. This methodology can facilitate the introduction of biological probes into proteins for cellular studies and may ultimately facilitate the synthesis of therapeutic proteins containing unnatural amino acids in mammalian cells such as rodent cells and primate cells.

The invention provides compositions and methods for incorporating unnatural amino acids into a growing polypeptide chain in response to a selector codon, e.g., an amber stop codon, in vivo in a host cell such as a rodent host cell or a primate host cell. These compositions include the host cells, as well as pairs of orthogonal-tRNAs (O-tRNAs) and orthogonal aminoacyl-tRNA synthetases (O-RSs) that do not interact with the host cell translation machinery. That is to say, the O-tRNA is not charged (or not charged to a significant level) with an amino acid (natural or unnatural) by an endogenous host cell aminoacyl-tRNA synthetase. Similarly, the O-RSs provided by the invention do not charge any endogenous tRNA with an amino acid (natural or unnatural) to a significant or detectable level. These novel compositions permit the production of large quantities of proteins having translationally incorporated unnatural amino acids in mammalian host cell systems.

In some aspects, the invention provides translation systems. These systems comprise (a) a mammalian host cell such as a rodent or primate host cell, comprising (b) a first orthogonal aminoacyl-tRNA synthetase (O-RS), (c) a first orthogonal tRNA (O-tRNA), and (d) a first unnatural amino acid, where the first O-RS preferentially aminoacylates the first O-tRNA with the first unnatural amino acid. The unnatural amino acid can be, but not limited by:
p-methoxyphenylalanine (pMpa);
p-acetylphenylalanine (pApa);
p-benzoylphenylalanine (pBpa);
p-iodophenylalanine (pIpa);
p-azidophenylalanine (pAzpa);
p-propargyloxyphenylalanine (pPpa);
α-aminocaprylic acid;
o-nitrobenzylcysteine (o-NBC);
1,5-dansylalanine; and
o-nitrobenzylserine (o-NBS).

In some aspects, the O-RS preferentially aminoacylates the O-tRNA with said unnatural amino acid with an efficiency that is at least 50% of the efficiency observed for a translation system comprising that same O-tRNA, the unnatural amino acid, and an aminoacyl-tRNA synthetase comprising an amino acid sequence selected from SEQ ID NO: 57-101.

The translation systems can use components derived from a variety of sources. In one embodiment, the first O-RS is derived from an *E. coli* aminoacyl-tRNA synthetase, e.g., a wild-type *E. coli* tyrosyl or leucyl-tRNA synthetase. In some embodiments, the O-tRNA comprises or is encoded by SEQ ID NO: 3. The O-RS used in the system can comprise the amino acid sequence of SEQ ID NOS: 57-101, and conservative variants of that sequence. In some aspects, the host cell can comprise one or more polynucleotides that encode components of the translation system, including the O-RS or O-tRNA. In some embodiments, the polynucleotide encoding the O-RS comprises a nucleotide sequence selected from SEQ ID NO: 8-56.

In some aspects, the translation system further comprises a nucleic acid encoding a protein of interest, where the nucleic acid has at least one selector codon that is recognized by the O-tRNA.

In some aspects, the translation system (i.e., the host cell) incorporates a second orthogonal pair (that is, a second O-RS and a second O-tRNA) that utilizes a second unnatural amino acid, so that the system is now able to incorporate at least two different unnatural amino acids at different selected sites in a polypeptide. In this dual system, the second O-RS preferentially aminoacylates the second O-tRNA with a second unnatural amino acid that is different from the first unnatural amino acid, and the second O-tRNA recognizes a selector codon that is different from the selector codon recognized by the first O-tRNA.

The mammalian host cell used in the translation system is not particularly limited, as long as the O-RS and O-tRNA retain their orthogonality in their host cell environment. The host cell can be a rodent host cell such as a mouse cell or a rat cell. When the host cell is a primate cell, the cell can be, e.g., a human host cell, chimpanzee host cell, bonobo host cell, gorilla host cell, orangutan host cell, gibbon host cell, macaque host cell, tamarin host cell or a marmoset host cell. The host cell can be, for example, a CHO cell or a human 293T.

In other aspects, the invention provides methods for producing proteins of interest having one or more unnatural amino acids at selected positions. These methods utilize the translation systems described above. Generally, these methods start with the step of providing a translation system comprising: (i) a first unnatural amino acid (e.g., an unnatural amino acid of FIG. 1); (ii) a first orthogonal aminoacyl-tRNA synthetase (O-RS); (iii) a first orthogonal tRNA (O-tRNA), wherein the O-RS preferentially aminoacylates the O-tRNA with the unnatural amino acid; and, (iv) a nucleic acid encoding the protein of interest, where the nucleic acid comprises at least one selector codon that is recognized by the first O-tRNA, and where the position of selector codon in the nucleic acid corresponds to the selected position in the protein of interest. All of these system components are contained in a suitable host cell, e.g., a rodent cell or a primate cell. The methods for producing a protein with an unnatural amino acid entail generally culturing the host cell in the presence of all the components of the translation system described above. In these methods, the unnatural amino acid can be selected from (but not limited to):

p-methoxyphenylalanine (pMpa);
p-acetylphenylalanine (pApa);
p-benzoylphenylalanine (pBpa);
p-iodophenylalanine (pIpa);
p-azidophenylalanine (pAzpa);
p-propargyloxyphenylalanine (pPpa);
α-aminocaprylic acid;
o-nitrobenzylcysteine (o-NBC);
1,5-dansylalanine; and
o-nitrobenzylserine (o-NBS).

In some aspects of these methods, the O-RS preferentially aminoacylates the O-tRNA with the unnatural amino acid with an efficiency that is at least 50% of the efficiency observed for a translation system comprising that same O-tRNA, the unnatural amino acid, and an aminoacyl-tRNA synthetase (O-RS) comprising an amino acid sequence selected from SEQ ID NOs: 57-101.

This methods can be widely applied using a variety of reagents. In some embodiments of the methods, the O-tRNA comprises or is encoded by SEQ ID NO: 3. In some embodiments, a polynucleotide encoding the O-RS and/or the O-tRNA is provided. In some embodiments, the O-RS is derived from an *E. coli* aminoacyl-tRNA synthetase, such as a wild-type *E. coli* tyrosyl or leucyl-tRNA synthetase. In some embodiments, the providing step includes providing an O-RS comprising an amino acid sequence selected from SEQ ID NOS: 57-101, and conservative variants thereof. In some aspects of these methods, a polynucleotide that encodes the O-RS is provided. For example, the polynucleotide encoding the O-RS can comprise a nucleotide sequence selected from SEQ ID NO: 8-56.

In some embodiments of these methods, the providing the O-RS entails mutating an amino acid binding pocket of a wild-type aminoacyl-tRNA synthetase by site-directed mutagenesis, and selecting a resulting O-RS that preferentially aminoacylates the O-tRNA with the unnatural amino acid. The selecting step can comprises positively selecting and negatively selecting for the O-RS from a pool of resulting aminoacyl-tRNA synthetase molecules following site-directed mutagenesis.

These methods can also be modified to incorporate more than one unnatural amino acid into a protein. In those methods, a second orthogonal translation system is employed in conjunction with the first translation system, where the second system has different amino acid and selector codon specificities. For example, the providing step can include providing a second O-RS and a second O-tRNA, where the second O-RS preferentially aminoacylates the second O-tRNA with a second unnatural amino acid that is different from the first unnatural amino acid, and where the second O-tRNA recognizes a selector codon in the nucleic acid that is different from the selector codon recognized by the first O-tRNA.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl or leucyl derived orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any tRNA that is designated as a substrate for a tyrosyl-tRNA synthetase, or (6) a conservative variant of any example tRNA that is designated as a substrate for a tyrosyl-tRNA synthetase. The tyrosyl-tRNA can exist charged with an amino acid, or in an uncharged state. It is also to be understood that a "tyrosyl-O-tRNA" optionally is charged (aminoacylated) by a cognate synthetase with an amino acid other than tyrosine, respectively, e.g., with an unnatural amino acid. Indeed, it will be appreciated that a tyrosyl-O-tRNA of the invention is advantageously used to insert essentially any amino acid, whether natural or unnatural, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS provided herein. For example, the O-RS can be a conservative variant of a tyrosyl-O-RS of FIG. 16, and/or can be at least 50%, 60%, 70%, 80%, 90%, 95%, 98%, 99% or more identical in sequence to an O-RS of FIG. 16 (SEQ ID NOS: 57-101).

Orthogonal leucyl-tRNA: As used herein, an orthogonal leucyl-tRNA (leucyl-O-tRNA) is a tRNA that is orthogonal to a translation system of interest, where the tRNA is: (1) identical or substantially similar to a naturally occurring leucyl-tRNA, (2) derived from a naturally occurring leucyl-tRNA by natural or artificial mutagenesis, (3) derived by any process that takes a sequence of a wild-type or mutant leucyl-tRNA sequence of (1) or (2) into account, (4) homologous to a wild-type or mutant tyrosyl-tRNA; (5) homologous to any tRNA that is designated as a substrate for a leucyl-tRNA synthetase, or (6) a conservative variant of any example tRNA that is designated as a substrate for a leucyl-tRNA synthetase. The leucyl-tRNA can exist charged with an amino acid, or in an uncharged state. It is also to be understood that a "leucyl-O-tRNA" optionally is charged (aminoacylated) by a cognate synthetase with an amino acid other than leucine, respectively, e.g., with an unnatural amino acid. Indeed, it will be appreciated that a leucyl-O-tRNA of the invention is advantageously used to insert essentially any amino acid, whether natural or unnatural, into a growing polypeptide, during translation, in response to a selector codon.

Orthogonal leucyl-amino acid synthetase: As used herein, an orthogonal leucyl amino acid synthetase (leucyl-O-RS) is an enzyme that preferentially aminoacylates the leucyl-O-tRNA with an amino acid in a translation system of interest. The amino acid that the leucyl-O-RS loads onto the leucyl-O-tRNA can be any amino acid, whether natural, unnatural or artificial, and is not limited herein. The synthetase is optionally the same as or homologous to a naturally occurring leucyl amino acid synthetase, or the same as or homologous to a synthetase designated as an O-RS provided herein. For example, the O-RS can be a conservative variant of a leucyl-O-RS of FIG. 16, and/or can be at least 50%, 60%, 70%, 80%, 90%, 95%, 98%, 99% or more identical in sequence to an O-RS of FIG. 16.

Cognate: The term "cognate" refers to components that function together, or have some aspect of specificity for each other, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, typically by allowing the incorporation of an amino acid in response to a stop codon (i.e., "read-through") during the translation of a polypeptide. In some aspects, a selector codon of the invention is a suppressor codon, e.g., a stop codon (e.g., an amber, ocher or opal codon), a four base codon, a rare codon, etc.

Suppression activity: As used herein, the term "suppression activity" refers, in general, to the ability of a tRNA (e.g., a suppressor tRNA) to allow translational read-through of a codon (e.g., a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various methods by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatived lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a mammalian cell, e.g., a rodent cell or a primate cell.

Unnatural amino acid: As used herein, the term "unnatural amino acid" refers to any amino acid, modified amino acid, and/or amino acid analogue, that is not one of the 20 common naturally occurring amino acids or seleno cysteine or pyrrolysine. For example, see the unnatural amino acids provided in FIG. 1.

Derived from: As used herein, the term "derived from" refers to a component that is isolated from or made using a specified molecule or organism, or information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Positive selection or screening marker: As used herein, the term "positive selection or screening marker" refers to a marker that, when present, e.g., expressed, activated or the like, results in identification of a cell, which comprises the trait, e.g., a cell with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokaryote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma, although historically considered "bacteria," are sometimes given separate classifications under the Kingdom Monera.

Eubacteria: As used herein, the terms "eubacteria" and "bacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans and other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus thermophilus, Bacillus subtilis* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum* and *Thermoplasma volcanium*.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS, or a conservative variant of that O-RS, will aminoacylate a cognate O-tRNA with an unnatural amino acid, e.g., an unnatural amino acid of FIG. 1. In this example, the O-RS and the conservative variant O-RS do not have the same amino acid sequences. The conservative variant can have, e.g., one variation, two variations, three variations, four variations, or five or more variations in sequence, as long as the conservative variant is still complementary to (e.g., functions with) the cognate corresponding O-tRNA or O-RS.

In some embodiments, a conservative variant O-RS comprises one or more conservative amino acid substitutions compared to the O-RS from which it was derived. In some embodiments, a conservative variant O-RS comprises one or more conservative amino acid substitutions compared to the O-RS from which it was derived, and furthermore, retains O-RS biological activity; for example, a conservative variant O-RS that retains at least 10% of the biological activity of the parent O-RS molecule from which it was derived, or alternatively, at least 20%, at least 30%, or at least 40%. In some preferred embodiments, the conservative variant O-RS retains at least 50% of the biological activity of the parent O-RS molecule from which it was derived. The conservative amino acid substitutions of a conservative variant O-RS can occur in any domain of the O-RS, including the amino acid binding pocket.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 1 provides the chemical structures and nomenclature of the unnatural amino acids p-methoxyphenylalanine (pMpa), p-acetylphenylalanine (pApa), p-benzoylphenylalanine (pBpa), p-iodophenylalanine (pIpa), p-azidophenylalanine (pAzpa), p-propargyloxyphenylalanine (pPpa), α-aminocaprylic acid, o-nitrobenzylcysteine (o-NBC), 1,5-dansylalanine and o-nitrobenzylserine (o-NBS). Most of these unnatural amino acids have variably been referred to using various alternative nomenclatures, which are also indicated in the figure.

FIG. 13A provides panels with green fluorescence images of Invitrogen™ T-REx™ CHO cells transiently transfected with different constructs. In the first panel, cells were transfected with pcDNA4-GFP. In the second panel, cells were transfected with pcDNA4-EcTyrRS and pcDNA4-GFP37TAG. In the third panel, cells were transfected with pUC18-3BstRNA$_{CUA}^{Tyr}$ and pcDNA4-GFP37TAG. In the fourth panel, cells were transfected with pUC18-3BstRNA$_{CUA}^{Tyr}$, pcDNA4-EcTyrRS and pcDNA4-GFP37TAG. FIG. 13B provides panels with green fluorescence images of Invitrogen™ T-REx™ 293 cells transiently transfected with different constructs. The constructs used in the various panels were identical to that shown in FIG. 13A.

FIG. 16 provides nucleotide and amino acid sequences.

DETAILED DESCRIPTION OF THE INVENTION

Figure 2:
FIG. 2 shows a Western blot analysis of full-length GFP expression in Invitrogen™ T-REx™ CHO cells using orthogonal BstRNA$_{CUA}^{Tyr}$ and EcTyrRS pairs. The cells were cotransfected with plasmids pcDNA4-GFP37TAG, pcDNA4-EcTyrRS variant and pUC18-3BstRNA$_{CUA}^{Tyr}$ and grown in the presence or absence of unnatural amino acids. The first lane is wild type GFP expression in T-rex CHO cells that were transiently transfected with pcDNA4-GFP. The second lane is full-length expression of GFP37TAG suppressed by wild type EcTyrRS together with BstRNA$_{CUA}^{Tyr}$. The following lanes are full-length expression of GFP37TAG suppressed by EcTyrRS variants together with BstRNA$_{CUA}^{Tyr}$ in the presence or absence of unnatural amino acids. pMpaRS represents pMpa-tRNA synthetase, etc. A 40 μg aliquot of the cell lysate for each reaction (10 μg cell lysate was loaded into the first lane) was analyzed with anti-c-myc antibody. The concentrations of unnatural amino acids for protein expression were 10 mM for pMpa, 10 mM for pApa, 1 mM for pBpa, 8 mM for pIpa, 5 mM for pAzpa and 1 mM for pPpa.

The present invention provides a general methodology that allows for the rapid screening and isolation of mutant aminoacyl-tRNA synthetase enzymes (RS) that have the ability to charge a suitable orthogonal suppressor tRNA with unnatural amino acids with diverse physicochemical and biological properties in mammalian cell host systems, and further, where the screening method does away with the need for slow and technically challenging screening in mammalian cells. In these methods, mutant *Escherichia coli* (*E. coli*) aminoacyl-tRNA synthetases (RS) are evolved in yeast to selectively utilize the unnatural amino acid of interest. The same mutant RS together with an amber suppressor tRNA from *Bacillus stearothermophilus* (*B. stearothermophilus*) are then used to site-specifically incorporate the unnatural amino acid into protein of interest in mammalian cells in response to an selector codon (e.g., an amber nonsense codon). The incorporation of the unnatural amino acid into the protein is programmed to occur at any desired position by engineering the polynucleotide encoding the protein of interest to contain the selector codon that signals the incorporation of the unnatural amino acid.

The present invention also provides novel translation systems, where the systems comprise host cells that have hereto not been contemplated. For example, a translation system of the invention includes (i) an unnatural amino acid, (ii) an orthogonal tRNA (O-tRNA), (iii) an orthogonal aminoacyl-tRNA synthetase (O-RS) derived from a eubacterial aminoacyl-tRNA synthetase, typically an *E. coli* RS, and (iv) a mammalian host cell that contains these components, where the mammalian host cell can be a rodent cell (e.g., a mouse cell or a rat cell), or a primate cell, i.e., any cell belonging to any of the groups commonly termed simians (including apes, humans and Old World monkeys), New World monkeys and pro-simians (e.g., lemurs). Human cells find particular use with the invention. However, it is not intended that the invention be limited to the host cells listed above, as other host cells also find use with the invention.

The invention also provides methods for producing a protein having at least one unnatural amino acid at a selected position, where the methods use the translation systems described above. The methods result in the incorporation of the unnatural amino acid by programming the incorporation of the unnatural amino acid at the site of a selector codon during protein translation.

The invention provides a general approach in which mutant RSs (originally evolved in *S. cerevisiae*) together with an amber suppressor from a suitable eubacteria, e.g., *B. stearothermophilus*, are used to incorporate a wide variety of unnatural amino acids into proteins in mammalian host cells, such as rodent cells and primate cells. As a proof of principle, this methodology was successfully employed to site specifically incorporate a total of ten different unnatural amino acids into model proteins in response to amber nonsense codons with excellent fidelity and good efficiencies in Chinese hamster ovary (CHO) and human 293T host cells. For example, unnatural amino acids were independently incorporated into green fluorescent protein (GFP) expressed in CHO cells with efficiencies up to 1 μg protein per $2 \times 10^7$ cells. Mass spectrometry confirmed a high translational fidelity for the unnatural amino acid. This methodology should facilitate the introduction of biological probes into proteins for cellular studies and may ultimately facilitate the synthesis of therapeutic proteins containing unnatural amino acids in mammalian cells.

In some aspects, to demonstrate (but not to limit) the present invention, the disclosure herein demonstrates that the unnatural amino acid moiety can be incorporated into various model proteins in mammalian host cells. It is not intended that the incorporation of the unnatural amino acid be limited to any particular protein of interest. From the present disclosure, it will be clear that the incorporation of the various unnatural amino acids into particular proteins of interest is advantageous for a wide variety of proteins and for a wide variety of purposes.

It is noted that the genes that control the expression of the mutant *E. coli* aminoacyl-tRNA synthetases (O-RSs) that are evolved in yeast and the O-tRNA can not be used immediately in mammalian host cells (e.g., rodent or human cells). These genes must be reengineered with suitable regulatory elements to drive their expression in the mammalian cell background. The yeast transcription regulatory elements originally associated with the O-tRNA and O-RS genes would be ineffective (or at best not optimal) for use in the mammalian cells. One of skill in the art recognizes this point. Mammalian cell gene expression elements are well characterized and readily available for use in recombinant constructs for the purpose of optimizing (e.g., maximizing) the gene sequences with which they are associated.

Unnatural Amino Acids Finding Use with the Invention

The invention provides orthogonal translation systems that have the ability to produce polypeptides comprising unnatural amino acids in mammalian host cell systems, for example, primate and rodent host cell systems. The unnatural amino acids that are employed in these translation systems is not particularly limited. Generally, the unnatural amino acids that find use with the invention are those that can be utilized by an *E. coli* derived mutant aminoacyl-tRNA synthetase to charge a corresponding orthogonal tRNA in a *Saccharomyces cerevisiae* (*S. cerevisiae*) yeast host cell system. For example, as utilized herein, the following unnatural amino acids find use with the invention:
p-methoxyphenylalanine (pMpa)
p-acetylphenylalanine (pApa)
p-benzoylphenylalanine (pBpa)
p-iodophenylalanine (pIpa)
p-azidophenylalanine (pAzpa)
p-propargyloxyphenylalanine (pPpa)

The structures of each of these six unnatural amino acids is shown in FIG. 1. These amino acids can also be known by alternative nomenclatures and various abbreviations, which are also shown in FIG. 1. As shown in the Examples, these six unnatural amino acids were independently incorporated into green fluorescent protein (GFP) in human and rodent host cells using *E. coli* derived O-RS species that were originally screened and isolated using yeast host cell systems.

In addition to those listed above, still other unnatural amino acids also find use with the invention. The unnatural amino acids listed below have previously been used successfully by *E. coli* derived orthogonal RS's to charge an O-tRNA in yeast host cell systems. These unnatural amino acids include:

α-aminocaprylic acid
o-nitrobenzylcysteine (o-NBC)
1,5-dansylalanine
o-nitrobenzylserine The structures of these unnatural amino acids and their various alternative nomenclatures and abbreviations are shown in FIG. 1.

The successful use of all these unnatural amino acids in yeast host cells is described, for example, in Chin et al. (2003), "An expanded eukaryotic genetic code," *Science* 301:964-967; Deiters et al. (2003), "Adding amino acids with novel reactivity to the genetic code of *Saccharomyces cerevisiae*," *J Am Chem Soc* 125:11782-11783; Summerer et al. (2006), "A Genetically Encoded Fluorescent Amino Acid," *PNAS* 103(26):9785-9789; WO 2005/003294 to Deiters et al., "UNNATURAL REACTIVE AMINO ACID GENETIC CODE ADDITIONS," filed Apr. 16, 2004; WO 2006/034410 to Deiters et al., "ADDING PHOTOREGULATED AMINO ACIDS TO THE GENETIC CODE," filed Sep. 21, 2005; and WO 2006/110182, filed Oct. 27, 2005, entitled "ORTHOGONAL TRANSLATION COMPONENTS FOR THE VIVO INCORPORATION OF UNNATURAL AMINO ACIDS."

Host Cells Finding Use with the Invention

The present invention provides novel translation systems, where the systems utilize host cells that have hereto not been contemplated. For example, a translation system of the invention includes (i) an unnatural amino acid, (ii) an orthogonal tRNA (O-tRNA), (iii) an orthogonal aminoacyl-tRNA synthetase (O-RS) derived from an *E. coli* aminoacyl-tRNA synthetase, and (iv) a mammalian host cell that contains these components, where the mammalian host cell can be a rodent cell (e.g., a mouse cell or a rat cell), or a primate cell, i.e., any cell belonging to any of the groups commonly termed simians (including apes, humans and Old World monkeys), New World monkeys and pro-simians (e.g., lemurs). Human cells find particular use with the invention. The animal cell lines finding use with the invention can be derived from any tissue from the animal. It is not intended that the invention be limited to the host cells listed above, as other host cells also find use with the invention.

As used herein, the term "host cell" also includes a plurality of individual cells, commonly referred to as a "cell line," and in this case, a "host cell line."

The host cells used for the production of polypeptides that contain at least one unnatural amino acid can be any type of host cell, but some host cells find particular use. For example, some host cell types can be used to produce polypeptides that find use in the production of recombinant therapeutic polypeptides.

When the host cell is a rodent cell, the type of rodent cell is not particularly limited. As described in the Examples, Chinese hamster ovary (CHO) cells can be used as host cells. CHO cells are widely adapted and are a well established system for the expression of recombinant proteins. However, it is not intended that the invention be limited to this rodent cell type. Indeed, one of skill in the art knows a vast array of rodent cell lines that can be used as host cells for recombinant protein production.

Rodent cell lines include any cell line derived from the mammalian order Rodentia, and includes, but not limited to, true mice, rats, hamsters, chipmunks, beavers and squirrels. Rodent cell lines include cell lines derived from the common house mouse, *Mus musculus*, and any and all strains thereof. Similarly, rodent cell lines include cell lines derived from the rat, e.g., any species of the genus *Rattus*, such as *Rattus norvegicus* (Norwegian rat) and *Rattus rattus* (the black rat), and any and all strains thereof.

The host cell of the invention can be a primate cell. The type of primate cell is not particularly limited. As described in the Examples, human embryonic kidney cells (also known as HEK cells, HEK 293 or just 293) can be used as host cells. 293 cells are widely adapted and are a well established system for the expression of recombinant proteins. However, it is not intended that the invention be limited to this human cell type. Indeed, one of skill in the art knows a vast array of human and other primate cell lines that can be used as host cells for recombinant protein production.

Primate cell lines include any cell line derived from the mammalian order Primate, and includes, but not limited to (i) simians, which include Old World monkeys apes, including humans), (ii) New World monkeys and (iii) prosimians (e.g., lemurs). The primate cell line can be derived from any primate species. For example, but not limited to, the primate cell lines can be derived from chimpanzees, baboons, marmosets, macaques, and African green monkeys (e.g., the COS-1 cell line).

The table below provides a non-exhaustive list of primate species from which derived cells lines find use with the invention.

| Species | Common Name |
| --- | --- |
| *Pan troglodytes schweinfurthii* | Eastern chimpanzee |
| *Pan troglodytes* | Chimpanzee |
| *Pan paniscus* | Bonobo |
| *Pan troglodytes verus* | Western chimpanzee |
| *Gorilla gorilla* | Western lowland gorilla |
| *Pongo pygmaeus abelii* | Sumatran orangutan |
| *Pongo pygmaeus pygmaeus* | Bornean orangutan |
| *Hylobates* sp. | gibbon sp. |
| *Macaca arctoides* | stump-tailed macaque |
| *Macaca fascicularis* | Long-tailed macaque |
| *Cercopithecus mitis albogularis* | blue monkey |
| *Macaca fascicularis* | Long-tailed macaque |
| *Macaca mulatta* | Rhesus macaque |
| *Macaca sylvanus* | Barbary macaque |
| *Pan troglodytes verus* | Western chimpanzee |
| *Papio hamadryas anubis* | Olive baboon |
| *Papio* sp. | baboon sp. |
| *Saguinus oedipus* | Cotton top tamarin |
| *Callithrix jacchus* | Common marmoset |
| *Pan paniscus* | Bonobo |
| *Homo sapiens* | human |

Cell lines derived from these primate species can be found, for example, on the websites for the Research Infrastructure to Promote Primate Molecular Biology (INPRIMAT; Barcelona, Spain) and the Biomedical Primate Research Centre (BPRC; Rijswijk, The Netherlands).

The use of human cell lines for the production of recombinant polypeptides is well established and within the scope of the present invention. The human host cell lines can be from any source, and can be derived from any tissue. Human cell lines suitable for the production of recombinant proteins are widely known, and are available from a large number of commercial and private sources well know to one of skill in the art.

Furthermore, host cell lines derived from other diverse mammalian species are also within the scope of the invention. These include bovine (cattle), porcine (swine), ovine (sheep), canine (dog), equine (horse) and caprine (goat) cell lines. Cell lines derived from these species are known in the art, and are readily available to one of average skill in the art.

Rodent cell lines, primate cell lines, and numerous other cell lines from other mammalian groups, and materials and methods for the culture of these animal cell lines, are well established in the art, and are widely available from a number of sources. For example, see the American Type Culture Collection (ATCC; Manassas, Va.) for extensive listings of available cell lines. Cell culture media is available from a variety of sources, for example, GIBCO® brand (Invitrogen™) cell culture media and Mediatech, Inc. culture media by Cellgro®. Furthermore, the de novo establishment of new cell lines (primary cell lines or established cell lines) also finds use with the invention as host cells for the production of recombinant proteins having at least one unnatural amino acid.

O-RS Species Finding Use with the Invention

The present invention provides novel orthogonal translation systems, where the systems have the ability to produce polypeptides comprising unnatural amino acids in mammalian host cells that have not been previously contemplated, for example, primate and rodent host cell systems. A translation system of the invention includes (i) an unnatural amino acid, (ii) an orthogonal tRNA (O-tRNA), (iii) an orthogonal aminoacyl-tRNA synthetase (O-RS) derived from an E. coli aminoacyl-tRNA synthetase, and (iv) a mammalian host cell that contains these components, where the mammalian host cell can be, for example, a rodent cell (e.g., a mouse cell or a rat cell), or a primate cell, (e.g., a human cell or a mouse cell). The invention also provides methods for producing a protein having at least one unnatural amino acid at a selected position, where the methods use the translation systems described above. The methods result in the incorporation of the unnatural amino acid in the mammalian host cell by programming the incorporation of the unnatural amino acid at a selector codon during protein translation.

The O-RS species finding use with the invention are not particularly limited, but generally has the following properties. An O-RS finding use with the invention is generally derived from an E. coli aminoacyl-tRNA synthetase, such as a wild-type E. coli leucyl-tRNA synthetase (Ec LeuRS; amino acid sequence provided at SEQ ID NO: 4, and polynucleotide sequence provided at SEQ ID NO: 5) or a wild-type E. coli tyrosyl-tRNA synthetase (Ec TyrRS; amino acid sequence provided at SEQ ID NO: 6, and polynucleotide sequence provided at SEQ ID NO: 7). The mutant O-RS species finding use with the invention (e.g., synthetases derived from the SEQ ID NOS: 4 or 6) are originally evolved and selected in a Saccharomyces cerevisiae (S. cerevisiae) yeast host cell system.

A large number of such O-RS species that find use with the invention are known in the art. In S. cerevisiae, functional tRNA$_{CUA}$/RS pairs have been successfully derived from the corresponding E. coli tRNA$^{Tyr}$/TyrRS and tRNA$^{Leu}$/leucyl-tRNA synthetase pairs. See, for example, Chin et al., "An Expanded Eukaryotic Genetic Code," Science 301, 964-967 (2003); Chin et al., "Progress Toward an Expanded Eukaryotic Genetic Code," Chem Biol 10, 511-519 (2003); Deiters et al. (2003), "Adding amino acids with novel reactivity to the genetic code of Saccharomyces cerevisiae," J Am Chem Soc 125:11782-11783; Summerer et al. (2006), "A Genetically Encoded Fluorescent Amino Acid," PNAS 103(26):9785-9789; and Wu et al., "A Genetically Encoded Photocaged Amino Acid," J Am Chem Soc 126, 14306-14307 (2004)). See also WO 2005/003294 to Deiters et al., "UNNATURAL REACTIVE AMINO ACID GENETIC CODE ADDITIONS," filed Apr. 16, 2004; WO 2006/034410 to Deiters et al., "ADDING PHOTOREGULATED AMINO ACIDS TO THE GENETIC CODE," filed Sep. 21, 2005; and WO 2006/110182, filed Oct. 27, 2005, entitled "ORTHOGONAL TRANSLATION COMPONENTS FOR THE VIVO INCORPORATION OF UNNATURAL AMINO ACIDS." Each of these references is incorporated by reference in their entirety. This teaching in the art also provides sufficient guidance for the construction of additional O-RS species that find use with the invention.

Examples of O-RS species that find use with the invention are provided in FIG. 16. The polynucleotide sequences that encode the O-RSs are provided in SEQ ID NOS: 8-56. The corresponding O-RS polypeptide sequences are provided in SEQ ID NOS: 57-101. It is noted that a full length O-RS is not necessarily required for the RS to be operative in the invention. Expression of only an RS active site fragment can be sufficient for use with the invention, as shown in some of the sequences in FIG. 16. Each of the O-RS sequences in FIG. 16 is known in the art, as described in the references cited herein.

It is not intended that the invention be limited to the use of the O-RS provided in FIG. 16. Any O-RS species identified herein that finds use with the invention can serve as a template for the derivation is still other O-RS species that can be used with the invention, for example, by making conservative amino acid substitutions within the existing O-RS species. The number of substitutions that are allowed is not limited, with the condition that the newly derived O-RS retains biological activity to preferentially aminoacylate the corresponding O-tRNA with the unnatural amino acid.

The biological activity of an O-RS can be expressed as a percentage of the biological activity of another "reference" O-RS that is shown to be of use with the invention. For example, an O-RS finding use with the invention can include an O-RS that preferentially aminoacylates an O-tRNA with an unnatural amino acid with an efficiency that is at least 50% of the efficiency observed for a "reference" translation system comprising the O-tRNA, the unnatural amino acid, and an aminoacyl-tRNA synthetase (RS) of known sequence. The selection of the threshold activity is arbitrary, and the value of "50%" serves only as an example. Indeed, an O-RS finding use with the invention can include an O-RS that preferentially aminoacylates an O-tRNA with an unnatural amino acid with an efficiency that is at least 20%, 30%, 40%, 50%, 60%, 70%, 80%, 90%, 95%, 98% or 99% of the efficiency observed for a "reference" translation system.

O-tRNA Species Finding Use with the Invention

The mutant O-RS species finding use with the invention are originally evolved and selected in a yeast host cell system. The O-RS species that are evolved in the yeast host cell system function in conjunction with a suitable O-tRNA that is preferentially aminoacylated by the O-RS with the unnatural amino acid. For example, suppressor O-tRNA species that function in the yeast host system can be, e.g., the tRNA of SEQ ID NOS: 1 or 2.

In contrast, the translation systems of the present invention use a different O-tRNA that is orthogonal in a mammalian host cell (such as a rodent cell or a primate cell). For example, an O-tRNA finding use with the invention can be the *Bacillus stearothermophilus* amber suppressor tyrosyl-tRNA$_{CUA}$ (Bs-tRNATyrCUA), as provided in SEQ ID NO: 3. It is not intended that the invention be limited to this one tRNA species, as variants of this tRNA sequence, other tRNAs derived from *Bacillus stearothermophilus*, as well as tRNA species derived from other organisms (e.g., other eubacterial species) are also contemplated.

Orthogonal tRNA/Aminoacyl-tRNA Synthetase Technology

An understanding of the novel compositions and methods of the present invention requires an understanding of the activities associated with orthogonal tRNA and orthogonal aminoacyl-tRNA synthetase pairs. In order to add additional unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthogonal pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated (or is poorly aminoacylated, i.e., charged) by endogenous synthetases. For example, in an *E. coli* host system, an orthogonal pair will include an aminoacyl-tRNA synthetase that does not cross-react with any of the endogenous tRNA, e.g., which there are 40 in *E. coli*, and an orthogonal tRNA that is not amino-acylated by any of the endogenous synthetases, e.g., of which there are 21 in *E. coli*.

The general principles of orthogonal translation systems that are suitable for making proteins that comprise one or more unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; International Application No. PCT/US2005/039210, filed on Oct. 27, 2005, entitled "ORTHOGONAL TRANSLATION COMPONENTS FOR THE IN VIVO INCORPORATION OF UNNATURAL AMINO ACIDS;" and U.S. Provisional Application Ser. No. 60/783,497, entitled "SYSTEMS FOR THE EXPRESSION OF ORTHOGONAL TRANSLATION COMPONENTS IN EUBACTERIAL HOST CELLS," filed Mar. 17, 2006. Each of these applications is incorporated herein by reference in its entirety. For discussion of orthogonal translation systems that incorporate unnatural amino acids, and methods for their production and use, see also, Wang and Schultz "Expanding the Genetic Code," *Angewandte Chemie Int. Ed.*, 44(1):34-66 (2005); Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); and Wang et al., "Expanding the Genetic Code," *Annu. Rev. Biophys. Biomol. Struct.*, 35:225-249 (2006); the contents of which are each incorporated by reference in their entirety.

Orthogonal Translation Systems

Orthogonal translation systems generally comprise cells (which can be mammalian cells such as rodent cells or primate cells) that include an orthogonal tRNA (O-tRNA), an orthogonal aminoacyl tRNA synthetase (O-RS), and an unnatural amino acid, where the O-RS aminoacylates the O-tRNA with the unnatural amino acid. An orthogonal pair of the invention can include an O-tRNA, e.g., a suppressor tRNA, a frameshift tRNA, or the like, and a cognate O-RS. The orthogonal systems of the invention can typically comprise O-tRNA/O-RS pairs, either in the context of a host cell or without the host cell. In addition to multi-component systems, the invention also provides individual components, for example, orthogonal aminoacyl-tRNA synthetase polypeptides (e.g., SEQ ID NOs: 57-101), and the polynucleotides that encodes those polypeptides (e.g., SEQ ID NOs: 8-56).

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily charged, which results in blocking production of a polypeptide that would otherwise be translated from the nucleic acid. In an orthogonal pair system, the O-RS aminoacylates the O-tRNA with a specific unnatural amino acid. The charged O-tRNA recognizes the selector codon and suppresses the translational block caused by the selector codon.

In some aspects, an O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to the suppression efficiency of an O-tRNA comprising or encoded by a polynucleotide sequence as set forth in the sequence listing herein.

In some embodiments, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In some aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

The host cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain preferred aspects, the cell can include one or more additional O-tRNA/O-RS pairs, where the additional O-tRNA is loaded by the additional O-RS with a different unnatural amino acid. For example, one of the O-tRNAs can recognize a four base codon and the other O-tRNA can recognize a stop codon. Alternately, multiple different stop codons or multiple different four base codons can be used in the same coding nucleic acid.

As noted, in some embodiments, there exists multiple O-tRNA/O-RS pairs in a cell or other translation system, which allows incorporation of more than one unnatural amino acid into a polypeptide. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, where the second O-tRNA recognizes a different selector codon, e.g., an opal codon, a four-base codon, or the like. Desirably, the different orthogonal pairs are derived from different sources, which can facilitate recognition of different selector codons.

In certain embodiments, systems comprise a cell such as a mammalian cell, including but not limited to rodent and primate cells, that includes an orthogonal tRNA (O-tRNA), an orthogonal aminoacyl-tRNA synthetase (O-RS), an unnatural amino acid and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/O-RS pair and an unnatural amino acid as described herein.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases. A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention desirably mediates incorporation of an unnatural amino acid into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a β-galactosidase reporter assay can be used, e.g., a derivatized lacZ plasmid (where the construct has a selector codon in the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Examples of O-tRNAs finding use with the invention are set forth in the sequence listing herein, for example, see FIG. 16 and SEQ ID NO: 3. The disclosure herein also provides guidance for the design of additional equivalent O-tRNA species. In an RNA molecule, such as an O-RS mRNA, or O-tRNA molecule, Thymine (T) is replace with Uracil (U) relative to a given sequence (or vice versa for a coding DNA), or complement thereof. Additional modifications to the bases can also be present to generate largely functionally equivalent molecules.

The invention also encompasses conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing or FIG. 16, and desirably, are other than wild type tRNA molecules.

The composition comprising an O-tRNA can further include an orthogonal aminoacyl-tRNA synthetase (O-RS), where the O-RS preferentially aminoacylates the O-tRNA with an unnatural amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell.

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof, e.g., of the O-tRNA of SEQ ID NO: 3.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding additional sequences to the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in mammalian cells such as rodent cells and primate cells, a synthetase and/or a tRNA is chosen that does not display close sequence similarity to the host organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense (e.g., stop) or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous E. coli synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In some aspects of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O—RS pair that loads an unnatural amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco, J. A., et al., (1993) *Production and fluorescence-activated cell sorting of Escherichia coli expressing a functional antibody fragment on the external surface. Proc Natl Acad Sci USA.* 90:10444-8.

Additional methods for producing a recombinant orthogonal tRNA can be found, e.g., in International Application Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100(10): 5676-5681.

Orthogonal Aminoacyl-tRNA Synthetase (O-RS)

An O-RS of the invention preferentially aminoacylates an O-tRNA with an unnatural amino acid, in vitro or in vivo. An O-RS of the invention can be provided to the translation system, e.g., a cell, by a polypeptide that includes an O-RS and/or by a polynucleotide that encodes an O-RS or a portion thereof. For example, an example O-RS comprises an amino acid sequence selected from SEQ ID NOs: 57-101, or a conservative variation thereof. In another example, an O-RS, or a portion thereof, is encoded by a polynucleotide sequence that encodes an amino acid sequence in the sequence listing or examples herein, or a complementary polynucleotide sequence thereof. See, e.g., the polynucleotides of SEQ ID NOs: 8-56.

Methods for identifying an orthogonal aminoacyl-tRNA synthetase (O-RS), e.g., an O-RS, for use with an O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled unnatural amino acid). The active RS that more efficiently aminoacylates the second set of tRNAs compared to the first set of tRNAs is typically selected, thereby providing an efficient (e.g., optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soil (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O-RS can be further manipulated to alter substrate specificity of the synthetase, so that only a desired unnatural amino acid, but not any of the common 20 amino acids, are charged to the O-tRNA. Methods to generate an orthogonal aminoacyl-tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In some aspects of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE." See also, Wang and Schultz "Expanding the Genetic Code," *Angewandte Chemie Int. Ed.*, 44(1):34-66 (2005), the content of which is incorporated by reference in its entirety.

Source and Host Organisms

The orthogonal translational components (O-tRNA and O-RS) of the invention can be derived from any organism (or a combination of organisms) for use in a host translation system from any other species, with the caveat that the O-tRNA/O-RS components and the host system work in an orthogonal manner. It is not a requirement that the O-tRNA and the O-RS from an orthogonal pair be derived from the same organism. In some aspects, the orthogonal components are derived from *E. coli* genes (i.e., eubacteria) for use in mammalian host systems (e.g., rodent or primate host systems).

For example, the orthogonal O-tRNA can be derived from an Archae organism, e.g., an *archaebacterium*, such as *Methanococcus jannaschii*, *Methanobacterium thermoautotrophicum*, *Halobacterium* such as *Haloferax volcanii* and *Halobacterium* species NRC-1, *Archaeoglobus fulgidus*, *Pyrococcus furiosus*, *Pyrococcus horikoshii*, *Aeuropyrum pernix*, *Methanococcus maripaludis*, *Methanopyrus kandleri*, *Methanosarcina mazei* (Mm), *Pyrobaculum aerophilum*, *Pyrococcus abyssi*, *Sulfolobus solfataricus* (Ss), *Sulfolobus tokodaii*, *Thermoplasma acidophilum*, *Thermoplasma volcanium*, or the like, or a *eubacterium*, such as *Escherichia coli*, *Thermus thermophilus*, *Bacillus subtilis*, *Bacillus stearothermphilus*, or the like, while the orthogonal O-RS can be derived from an organism or combination of organisms, e.g., an *archaebacterium*, such as *Methanococcus jannaschii*, *Methanobacterium thermoautotrophicum*, *Halobacterium* such as *Haloferax volcanii* and *Halobacterium* species NRC-1, *Archaeoglobus fulgidus*, *Pyrococcus furiosus*, *Pyrococcus horikoshii*, *Aeuropyrum pernix*, *Methanococcus maripaludis*, *Methanopyrus kandleri*, *Methanosarcina mazei*, *Pyrobaculum aerophilum*, *Pyrococcus abyssi*, *Sulfolobus solfataricus*, *Sulfolobus tokodaii*, *Thermoplasma acidophilum*, *Thermoplasma volcanium*, or the like, or a *eubacterium*, such as *Escherichia coli*, *Thermus thermophilus*, *Bacillus subtilis*, *Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a mammalian cell such as a rodent cell or primate cell, to produce a polypeptide with an unnatural amino acid. The mammalian host cell used is not particularly limited. Compositions of mammalian cells comprising translational components of the invention are also a feature of the invention.

See also, International Application Publication Number WO 2004/094593, entitled "EXPANDING THE EUKARYOTIC GENETIC CODE," filed Apr. 16, 2004, for screening O-tRNA and/or O-RS in one species for use in another species.

Although orthogonal translation systems (e.g., comprising an O-RS, an O-tRNA and an unnatural amino acid) can utilize cultured host cells to produce proteins having unnatural amino acids, it is not intended that an orthogonal translation system of the invention require an intact, viable host cell. For example, a orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one unnatural amino acid, using these different selector codons.

In one embodiment, the methods involve the use of a selector codon that is a stop codon for the incorporation of an unnatural amino acid in vivo in a cell. For example, an O-tRNA is produced that recognizes the stop codon and is aminoacylated by an O-RS with an unnatural amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), 5',3' *Exonuclease in phosphorothioate-based oligonucleotide-directed mutagenesis*. Nucleic Acids Res, 791-802. When the O-RS, O-tRNA and the nucleic acid that encodes a polypeptide of interest are combined, e.g., in vivo, the unnatural amino acid is incorporated in response to the stop codon to give a polypeptide containing the unnatural amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of unnatural amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNA$^{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.* 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense readthrough and frameshift suppression at other unwanted sites. Four base codons have been used as selector codons in a variety of orthogonal systems. See, e.g., WO 2005/019415; WO 2005/007870 and WO 2005/07624. See also, Wang and Schultz "Expanding the Genetic Code," *Angewandte Chemie Int. Ed.,* 44(1):34-66 (2005), the content of which is incorporated by reference in its entirety. While the examples below utilize an amber selector codon, four or more base codons can be used as well, by modifying the examples herein to include four-base O-tRNAs and synthetases modified to include mutations similar to those previously described for various unnatural amino acid O-RSs.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

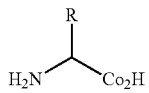

I

An unnatural amino acid is typically any structure having Formula I wherein the R group is any substituent other than one used in the twenty natural amino acids. See e.g., *Biochemistry* by L. Stryer, 3rd ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Although the unnatural amino acids shown in FIG. 1 are of primary interest in the Examples described herein, it is not intended that the invention be strictly limited to these structure. Indeed, a variety of easily-derived, structurally related analogs can be readily produced that retain the principle characteristics of the structures from which they were derived (i.e., the structures shown in FIG. 1), and also are specifically recognized by the aminoacyl-tRNA synthetases references herein (e.g., the O-RSs of SEQ ID NOS: 57-101). It is intended that these related amino acid analogues are within the scope of the invention.

In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides unnatural amino acids having the general structure illustrated by Formula IV below:

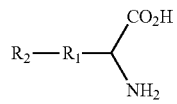

IV

An unnatural amino acid having this structure is typically any structure where $R_1$ is a substituent used in one of the twenty natural amino acids (e.g., tyrosine or phenylalanine) and $R_2$ is a substituent. Thus, this type of unnatural amino acid can be viewed as a natural amino acid derivative.

In addition to the unnatural amino acid structures shown in FIG. 1, unnatural amino acids can also optionally comprise modified backbone structures, e.g., as illustrated by the structures of Formula II and III:

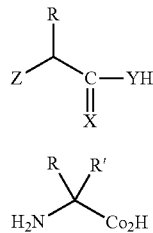

II

III wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

In some aspects, the invention utilizes unnatural amino acids in the L-configuration. However, it is not intended that the invention be limited to the use of L-configuration unnatural amino acids. It is contemplated that the D-enantiomers of these unnatural amino acids also find use with the invention.

The unnatural amino acids finding use with the invention are not strictly limited to the unnatural amino acids shown in FIG. 1. One of skill in the art will recognize that a wide variety of unnatural analogs of naturally occurring amino acids are easily derived. For example, but not limited to, unnatural amino acids derived from phenylalanine or tyrosine are readily produced. Tyrosine analogs include, e.g., para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenylalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, sulfotyrosine, p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenyalanine (DHP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are disclosed in the references cited herein. See also, Published International Applications WO 2004/094593, entitled "EXPANDING THE EUKARYOTIC GENETIC CODE;" and International Application PCT/US2005/039210, entitled "ORTHOGONAL TRANSLATION COMPONENTS FOR THE VIVO INCORPORATION OF UNNATURAL AMINO ACIDS," filed Oct. 27, 2005.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In Vivo Incorporation of Unnatural Amino Acids;" Matsoukas et al., (1995) *J. Med. Chem.*, 38, 4660-4669; King and Kidd (1949) "A New Synthesis of Glutamine and of γ-Dipeptides of Glutamic Acid from Phthylated Intermediates," *J. Chem. Soc.*, 3315-3319; Friedman and Chatterrji, (1959) "Synthesis of Derivatives of Glutamine as Model Substrates for Anti-Tumor Agents," *J. Am. Chem. Soc.* 81, 3750-3752; Craig et al. (1988) "Absolute Configuration of the Enantiomers of 7-Chloro-4 [[4-(diethylamino)-1-methylbutyl]amino]quinoline (Chloroquine)," *J. Org. Chem.* 53, 1167-1170; Azoulay et al., (1991) "Glutamine analogues as Potential Antimalarials," *Eur. J. Med. Chem.* 26, 201-5; Koskinen and Rapoport, (1989) "Synthesis of 4-Substituted Prolines as Conformationally Constrained Amino Acid Analogues,". *J. Org. Chem.* 54, 1859-1866; Christie and Rapoport, (1985) "Synthesis of Optically Pure Pipecolates from L-Asparagine. Application to the Total Synthesis of (+)-Apovincamine through Amino Acid Decarbonylation and Iminium Ion Cyclization," *J. Org. Chem.* 1989:1859-1866; Barton et al., (1987) "Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives," *Tetrahedron Lett.* 43:4297-4308; and, Subasinghe et al., (1992) "Quisqualic acid analogues: synthesis of beta-heterocyclic 2-aminopropanoic acid derivatives and their activity at a novel quisqualate-sensitized site," *J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) *Progress toward the evolution of an organism with an expanded genetic code. PNAS* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), "Rapid evolution of a protein in vitro by DNA shuffling," *Nature* 370(4):389-391; and, Stemmer, (1994), "DNA shuffling by random fragmentation and reassembly: In vitro recombination for molecular evolution," *Proc. Natl. Acad. Sci. USA*, 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature*, 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA*, 96: 3562-67, and Ostermeier et al. (1999), "Incremental Truncation as a Strategy in the Engineering of Novel Biocatalysts," *Biological and Medicinal Chemistry*, 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology*, 20(7): 707-712; and Zhang et al. (2002) "Genome shuffling leads to rapid phenotypic improvement in bacteria" *Nature*, February 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of *Corynebacterium* 2,5-diketo-D-gluconic acid reductase for use in vitamin C biosynthesis" *Biochemistry*, 41(20), 6226-36; Selivonova et al. (2001) "Rapid Evolution of Novel Traits in Microorganisms" *Applied and Environmental Microbiology*, 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Unnatural Amino Acids

The invention provides compositions and methods for producing orthogonal components for incorporating the unnatural amino acids shown in FIG. 1 into a growing polypeptide chain in response to a selector codon, e.g., an amber stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate an unnatural amino acid into growing polypeptide chains.

A composition of the invention includes an orthogonal aminoacyl-tRNA synthetase (O-RS), where the O-RS preferentially aminoacylates an O-tRNA with an unnatural amino acid of FIG. 1. In certain embodiments, the O-RS comprises an amino acid sequence selected from SEQ ID NO: 57-101, and conservative variations thereof. In certain embodiments of the invention, the O-RS preferentially aminoacylates the O-tRNA over any endogenous tRNA with an the particular unnatural amino acid, where the O-RS has a bias for the O-tRNA, and where the ratio of O-tRNA charged with an unnatural amino acid to the endogenous tRNA charged with the same unnatural amino acid is greater than 1:1, and more preferably where the O-RS charges the O-tRNA exclusively or nearly exclusively.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 3) and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA in the absence of an O-RS. In some aspects, the suppression efficiency of the O-RS and the O-tRNA together is at least 45% of the suppression efficiency of an orthogonal leucyl or tyrosyl-tRNA synthetase pair derived from E. coli.

A composition that includes an O-tRNA can optionally include a host cell (e.g., a mammalian cell such as a rodent cell or a primate cell), and/or a complete translation system.

A cell (e.g., a rodent cell or a primate cell) comprising a translation system is also provided by the invention, where the translation system includes an orthogonal-tRNA (O-tRNA); an orthogonal aminoacyl-tRNA synthetase (O-RS); and, an unnatural amino acid provided in FIG. 1. Typically, the O-RS preferentially aminoacylates the O-tRNA over any endogenous tRNA with the unnatural amino acid, where the O-RS has a bias for the O-tRNA, and where the ratio of O-tRNA charged with the unnatural amino acid to the endogenous tRNA charged with the unnatural amino acid is greater than 1:1, and more preferably where the O-RS charges the O-tRNA exclusively or nearly exclusively. The O-tRNA recognizes the first selector codon, and the O-RS preferentially aminoacylates the O-tRNA with an unnatural amino acid. In one embodiment, the O-tRNA comprises or is encoded by a polynucleotide sequence as set forth in SEQ ID NO: 3, or a complementary polynucleotide sequence thereof. In one embodiment, the O-RS comprises an amino acid sequence selected from SEQ ID NOs: 57-101, and conservative variations thereof.

A cell of the invention can optionally further comprise an additional different O-tRNA/O-RS pair and a second unnatural amino acid, e.g., where this O-tRNA recognizes a second selector codon and this O-RS preferentially aminoacylates the corresponding O-tRNA with the second unnatural amino acid, where the second amino acid is different from the first unnatural amino acid. Optionally, a cell of the invention includes a nucleic acid that comprises a polynucleotide that encodes a polypeptide of interest, where the polynucleotide comprises a selector codon that is recognized by the O-tRNA.

In certain embodiments, a host cell of the invention is a mammalian cell (such as a rodent cell or a primate cell) that includes an orthogonal-tRNA (O-tRNA), an orthogonal aminoacyl-tRNA synthetase (O-RS), an unnatural amino acid, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with the unnatural amino acid with an efficiency that is greater than the efficiency with which the O—RS aminoacylates any endogenous tRNA.

In certain embodiments of the invention, an O-tRNA of the invention comprises or is encoded by a polynucleotide sequence as set forth in the sequence listings (e.g., SEQ ID NO: 3) or examples herein, or a complementary polynucleotide sequence thereof. In certain embodiments of the invention, an O-RS comprises an amino acid sequence as set forth in the sequence listings, or a conservative variation thereof. In one embodiment, the O-RS or a portion thereof is encoded by a polynucleotide sequence encoding an amino acid as set forth in the sequence listings or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention (e.g., SEQ ID NOs: 8-56) includes an artificial (e.g., man-made, and not naturally occurring) polynucleotide comprising a nucleotide sequence encoding a polypeptide as set forth in the sequence listings herein, and/or is complementary to or that polynucleotide sequence. A polynucleotide of the invention can also include a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that is orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges an O-tRNA with an unnatural amino acid are also provided. For example, methods include subjecting a population of cells of a first species to a selection, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a host cell (e.g., in a mammalian cell such as a rodent cell or a primate cell, or the like) having the unnatural amino acid at a selected position are also a feature of the invention. For example, a method includes growing, in an appropriate medium, a cell, where the cell comprises a nucleic acid that comprises at least one selector codon and encodes a protein, providing the unnatural amino acid, and incorporating the unnatural amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O—RS) that preferentially aminoacylates the O-tRNA with the unnatural amino acid. A protein produced by this method is also a feature of the invention.

The invention also provides compositions that include proteins, where the proteins comprise an unnatural amino acid. In certain embodiments, the protein comprises an amino acid sequence that is at least 75% identical to that of a known protein, e.g., a therapeutic protein, a diagnostic protein, an industrial enzyme, or portions thereof. Optionally, the composition comprises a pharmaceutically acceptable carrier.

Nucleic Acid and Polypeptide Sequences and Variants

As described herein, the invention provides for polynucleotide sequences encoding, e.g., O-tRNAs and O-RSs, and polypeptide amino acid sequences, e.g., O-RSs, and, e.g., compositions, systems and methods comprising said polynucleotide or polypeptide sequences. Examples of said sequences, e.g., O-tRNA and O-RS amino acid and nucleotide sequences are disclosed herein (see FIG. 16, e.g., SEQ ID NOs: 3 and 8-101). However, one of skill in the art will appreciate that the invention is not limited to those sequences disclosed herein, e.g., in the Examples and sequence listing. One of skill will appreciate that the invention also provides many related sequences with the functions described herein, e.g., polynucleotides and polypeptides encoding conservative variants of an O-RS disclosed herein. General methodology for the construction and analysis of orthogonal synthetase species (O-RS) that are able to aminoacylate an O-tRNA with an unnatural amino acid in a yeast host system are known in the art.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence selected from SEQ ID NOS: 8-56, and a polynucleotide that is complementary to or that encodes a polynucleotide sequence thereof. A polynucleotide of the invention also includes any polynucleotide that encodes an O-RS amino acid sequence selected from SEQ ID NOS: 57-101. Similarly, an artificial nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide also includes an artificial polynucleotide that is, e.g., at least 75%, at least 80%, at least 90%, at least 95%, at least 98% or more identical (but not 100% identical) to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

| Conservative Amino Acid Substitutions | | | | |
|---|---|---|---|---|
| Nonpolar and/ or Aliphatic Side Chains | Polar, Uncharged Side Chains | Aromatic Side Chains | Positively Charged Side Chains | Negatively Charged Side Chains |
| Glycine | Serine | Phenyl- alanine | Lysine | Aspartate |
| Alanine | Threonine | | Arginine | Glutamate |
| Valine | Cysteine | Tyrosine | Histidine | |
| Leucine | Methionine | Tryptophan | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to a nucleic acid represented by SEQ ID NOS: 8-56, under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization of the probe to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes, Part I, Chapter 2, "Overview of principles of hybridization and the strategy of nucleic acid probe assays," (Elsevier, N.Y.), as well as in Current Protocols in Molecular Biology, Ausubel et al., eds., Current Protocols, a joint venture between Greene Publishing Associates, Inc. and John Wiley & Sons, Inc., (supplemented through 2004); Hames and Higgins (1995) Gene Probes 1, IRL Press at Oxford University Press, Oxford, England, and Hames and Higgins (1995) Gene Probes 2, IRL Press at Oxford University Press, Oxford, England, provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook et al., Molecular Cloning—A Laboratory Manual (3rd Ed.), Vol. 1-3, Cold Spring Harbor Laboratory, Cold Spring Harbor, N.Y., 2001, for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes, Part I, Chapter 2, "Overview of principles of hybridization and the strategy of nucleic acid probe assays," (Elsevier, N.Y.), Hames and Higgins (1995) Gene Probes 1, IRL Press at Oxford University Press, Oxford, England, and Hames and Higgins (1995) Gene Probes 2, IRL Press at Oxford University Press, Oxford, England. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention or related nucleic acids.

Similarly, the invention includes a polypeptide which comprises a unique subsequence in a polypeptide selected from the sequences of O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2006).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), *J. Mol. Biol.* 215:403-410). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul (1993), *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology volume* 152, Academic Press, Inc., San Diego, Calif.; Sambrook et al., *Molecular Cloning—A Laboratory Manual* (3rd Ed.), Vol. 1-3, Cold Spring Harbor Laboratory, Cold Spring Harbor, N.Y., 2001, and *Current Protocols in Molecular Biology*, Ausubel et al., eds., *Current Protocols*, a joint venture between Greene Publishing Associates, Inc. and John Wiley & Sons, Inc., (supplemented through 2006). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode an unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman and Smith, *Gene* 8:81 (1979); Roberts, et al., *Nature,* 328:731 (1987); Schneider et al., *Protein Expr. Purif.* 6435:10 (1995); Berger and Kimmel, *Guide to Molecular Cloning Techniques, Methods in Enzymology volume* 152, Academic Press, Inc., San Diego, Calif.; Sambrook et al., *Molecular Cloning—A Laboratory Manual* (3rd Ed.), Vol. 1-3, Cold Spring Harbor Laboratory, Cold Spring Harbor, N.Y., 2001, and *Current Protocols in Molecular Biology*, Ausubel et al., eds., *Current Protocols*, a joint venture between Greene Publishing Associates, Inc. and John Wiley & Sons, Inc., (supplemented through 2006). The vector can be, for example, in the form of a plasmid, a bacterium, a virus, a naked polynucleotide, or a conjugated polynucleotide. The vectors are introduced into cells and/or microorganisms by standard methods including electroporation (From et al. (1985), *Proc. Natl. Acad. Sci. USA* 82, 5824), infection by viral vectors, high velocity ballistic penetration by small particles with the nucleic acid either within the matrix of small beads or particles, or on the surface (Klein et al. (1987), *Nature* 327:70-73), and/or the like.

Bacteria and bacteriophage useful for cloning are widely known to one of skill in the art, and are available from a variety of sources. See, for example, the American Type Culture Collection (ATCC; Manassas, Va.) and *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook et al., *Molecular Cloning—A Laboratory*

*Manual* (3rd Ed.), Vol. 1-3, Cold Spring Harbor Laboratory, Cold Spring Harbor, N.Y., 2001, and *Current Protocols in Molecular Biology*, Ausubel et al., eds., *Current Protocols*, a joint venture between Greene Publishing Associates, Inc. and John Wiley & Sons, Inc., (supplemented through 2006), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, Third Edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.) and Atlas and Parks (eds) *The Handbook of Microbiological Media* (1993) CRC Press, Boca Raton, Fla.

Proteins and Polypeptides of Interest

Methods of producing a protein in a cell with an unnatural amino acid at a specified position are also a feature of the invention. For example, a method includes growing, in an appropriate medium, the cell, where the cell comprises a nucleic acid that comprises at least one selector codon and encodes a protein; and, providing the unnatural amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. A protein produced by this method is also a feature of the invention.

In certain embodiments, the O-RS comprises a bias for the aminoacylation of the cognate O-tRNA over any endogenous tRNA in an expression system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The invention also provides compositions that include proteins, where the proteins comprise an unnatural amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O-RS pairs or individual components of the invention can then be used in a host system's translation machinery, which results in an unnatural amino acid being incorporated into a protein. International Publication Numbers WO 2004/094593, filed Apr. 16, 2004, entitled "EXPANDING THE EUKARYOTIC GENETIC CODE," and WO 2002/085923, entitled "IN VIVO INCORPORATION OF UNNATURAL AMINO ACIDS," describe this process, and are incorporated herein by reference. For example, when an O-tRNA/O-RS pair is introduced into a host, e.g., a rodent or primate cell, the pair leads to the in vivo incorporation of an unnatural amino acid (e.g., the unnatural amino acids of FIG. 1) into a proteins in response to a selector codon. The unnatural amino acid that is added to the system can be a synthetic amino acid, such as a derivative of a phenylalanine or tyrosine, which can be exogenously added to the growth medium. Optionally, the compositions of the present invention can be in an in vitro translation system, or in an in vivo system(s).

A cell of the invention provides the ability to synthesize proteins that comprise unnatural amino acids in large useful quantities. In some aspects, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises an unnatural amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 mL to about 100 L). The production of large quantities (e.g., greater that that typically possible with other methods, e.g., in vitro translation) of a protein in a cell including at least one unnatural amino acid is a feature of the invention.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), incorporation of labels or reactive groups, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology*, 4:645-652.

In some aspects of the invention, a composition includes at least one protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is an unnatural amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid can be found, but not limited to, those in International Publications WO 2004/094593, filed Apr. 16, 2004, entitled "EXPANDING THE EUKARYOTIC GENETIC CODE;" and, WO 2002/085923, entitled "IN VIVO INCORPORATION OF UNNATURAL AMINO ACIDS." Examples of therapeutic, diagnostic, and other proteins that can be modified to comprise one or more unnatural amino acids include, but are not limited to, e.g., hirudin, Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Caspace, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Procaspace-3, Procaspace-9, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of unnatural amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acids) include biologically active proteins such as hirudin, cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2002 catalogue and price list), and the corresponding protein sequences and genes and, typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest.

Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid using compositions and methods of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., Plasmodia), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

To make a protein that includes an unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising unnatural amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Use of O-tRNA and O-RS and O-tRNA/O-RS Pairs

The compositions of the invention and compositions made by the methods of the invention optionally are in a cell. The O-tRNA/O-RS pairs or individual components of the invention can then be used in a host system's translation machinery, which results in an unnatural amino acid being incorporated into a protein. International Publication Number WO 2002/085923 by Schultz, et al., entitled "IN VIVO INCORPORATION OF UNNATURAL AMINO ACIDS," describes this process and is incorporated herein by reference. For example, when an O-tRNA/O-RS pair is introduced into a host, e.g., *Escherichia coli* or yeast, the pair leads to the in vivo incorporation of an unnatural amino acid, which can be exogenously added to the growth medium, into a protein, e.g., a myoglobin test protein or a therapeutic protein, in response to a selector codon, e.g., an amber nonsense codon. Optionally, the compositions of the invention can be in an in vitro translation system, or in a cellular in vivo system(s). Proteins with the unnatural amino acid can be used in any of a wide range of applications. For example, the unnatural moiety incorporated into a protein can serve as a target for any of a wide range of modifications, for example, crosslinking with other proteins, with small molecules such as labels or dyes and/or biomolecules. With these modifications, incorporation of the unnatural amino acid can result in improved therapeutic proteins and can be used to alter or improve the catalytic function of enzymes. In some aspects, the incorporation and subsequent modification of an unnatural amino acid in a protein can facilitate studies on protein structure, interactions with other proteins, and the like.

Kits

Kits are also a feature of the invention. For example, a kit for producing a protein that comprises at least one unnatural amino acid in a rodent or primate cell is provided, where the kit includes at least one container containing a polynucleotide sequence encoding an O-tRNA, and/or a polynucleotide sequence encoding an O-RS, and/or an O-RS polypeptide. In one embodiment, the kit further includes the unnatural amino acid. In another embodiments, the kit further comprises instructional materials for producing the protein comprising the unnatural amino acid.

EXAMPLES

The following examples are offered to illustrate, but not to limit the claimed invention. One of skill will recognize a variety of non-critical parameters that may be altered without departing from the scope of the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Technical Limitations of Nonsense Suppression in Mammalian Cells by Non-Mammalian Translation Components One strategy to genetically encode unnatural amino acids in mammalian cells would be to adapt the existing mutant tRNA/aaRS pairs that have been generated in *Escherichia coli* or *Saccharomyces cerevisiae* host systems. Because the tRNA$^{Tyr}$ identity elements in *E. coli*, which include the variable arm and G1:C72 base pair in the acceptor stem, are distinct from those in mammalian cells (Wang and Schultz (2004), "Expanding the genetic code," *Angew Chem Int Ed Engl* 44:34-66; and Bonnefond et al. (2005), "Evolution of the tRNA(Tyr)/TyrRS aminoacylation systems," *Biochimie* 87:873-883), the tRNA/aaRS pairs that have been used in bacteria are unfortunately not likely to be orthogonal in eukaryotic cells. In contrast, tRNAs in *S. cerevisiae* and mammalian cells are processed similarly and have the same identity elements (Bonnefond et al. (2005), "Evolution of the tRNA(Tyr)/TyrRS aminoacylation systems," *Biochimie* 87:873-883). Moreover, because the translational machinery of *S. cerevisiae* is also homologous to that of higher eukaryotes, it is possible that one can transfer a modified orthogonal tRNA/aaRS pair evolved in *S. cerevisiae* into mammalian cells. Indeed, Yokoyama and coworkers used an EcTyrRS variant that was evolved in *S. cerevisiae* to accept p-benzoyl-L-phenylalanine (pBpa) to incorporate this photoreactive amino acid into human Grb2 protein in CHO cells (Hino et al. (2005), "Protein photo-cross-linking in mammalian cells by site-specific incorporation of a photoreactive amino acid," *Nat Methods* 2, 201-206). Unfortunately, functionally active *E. coli* tRNA$_{CUA}^{Tyr}$ does not express well in mammalian cells, severely limiting the yields of mutant protein (Sakamoto et al. (2002) "Site-specific incorporation of an unnatural amino acid into proteins in mammalian cells," *Nucleic Acids Res* 30:4692-4699).

Example 2

Creation of Novel Nonsense Suppression Systems in Mammalian Cells

To overcome the limitations in orthogonal tRNA expression described above, the present invention provides a general system that allows for the transfer of mutant suppressor tRNA/aaRS pairs evolved in yeast to be used in mammalian cells. This method and the novel orthogonal systems are demonstrated herein to efficiently introduce a number of unnatural amino acids into green fluorescent protein (GFP) in both rodent CHO host cells and primate (human) 293T host cells. Although these two cell types were used experimentally, the invention is widely applicable to mammalian host cells from diverse species.

Creation of a Novel Mammalian Nonsense Suppression System

The tRNAs in eukaryotes are transcribed by RNA polymerase III, which recognizes two conserved intragenic transcriptional control elements, namely, the A and B boxes (Sprague, *Transcription of Eukaryotic tRNA Genes*, AMS Press, Washington, D.C.; 1994). *E. coli* tRNA$^{Tyr}$ only has a B box element, and it has been shown that the introduction of a pseudo-A box results in a non-functional tRNA that is not recognized by EcTyrRS (Sakamoto et al., "Site-specific incorporation of an unnatural amino acid into proteins in mammalian cells," *Nucleic Acids Res* 30:4692-4699 (2002)). Unlike *E. coli* tRNA$^{Tyr}$, the tRNA$^{Tyr}$ from *Bacillus stearothermophilus* (which has similar identity elements and is still charged by EcTyrRS; Bedouelle, "Recognition of tRNA(Tyr) by tyrosyl-tRNA synthetase," *Biochimie* 72, 589-598 (1990)) has naturally occurring internal A and B boxes. Thus, this tRNA together with EcTyrRS are capable of functioning as an orthogonal tRNA/aaRS pair in mammalian cells (Sakamoto et al. (2002), "Site-specific incorporation of an unnatural amino acid into proteins in mammalian cells," *Nucleic Acids Res* 30:4692-4699).

Construction and Expression of an Amber Suppressor Orthogonal tRNA

To afford an amber suppressor BstRNA$_{CUA}^{Tyr}$, the trinucleotide anticodon of BstRNA$^{Tyr}$ was changed to C(34) UA. Since G34 of prokaryotic tRNA$^{Tyr}$ is only a weak identity element of TyrRS (Hou and Schimmel (1989), "Modeling with in vitro kinetic parameters for the elaboration of transfer RNA identity in vivo," *Biochemistry* 28:4942-4947), the G34C mutant should not significantly affect the binding of EcTyrRS to BstRNA$_{CUA}^{Tyr}$. Furthermore, nonsense amber suppression should be better tolerated in mammalian cells than opal or ochre suppression due to the lower occurrence of the TAG stop codon in mammalian genomes (TAG, 23%; TAA, 30%; TGA, 47% in *Homo sapiens*). Since expression of the BstRNA$_{CUA}^{Tyr}$ gene in eukaryotes also depends on the 5' flanking sequence, the 5' flanking sequence of human tRNA$^{Tyr}$ was added to BstRNA$_{CUA}{}^{Tyr}$ to enhance its transcription in mammalian cells. To further increase transcription of BstRNA$_{CUA}{}^{Tyr}$, a gene cluster containing three tandem repeats of the BstRNA$_{CUA}{}^{Tyr}$ gene was constructed and this gene cluster was inserted into the pUC18 plasmid to afford pUC18-3BstRNA$_{CUA}{}^{Tyr}$. The Northern blot analysis of isolated total tRNAs from CHO cells transfected with pUC18-3BstRNA$_{CUA}{}^{Tyr}$ showed a two-fold higher level of BstRNA$_{CUA}{}^{Tyr}$ than cells transfected with a pUC18 plasmid containing only one copy of BstRNA$_{CUA}{}^{Tyr}$.

Expression of an Orthogonal Synthetase

Next, the wild type EcTyrRS gene was inserted into the mammalian expression vector pcDNA4/TO/myc-His A to afford pcDNA4-EcTyrRS in which expression is controlled by a tetracycline (Tet)-regulated CMV promoter. The use of an inducible expression was intended to lower possible toxicity due to heterologous expression of EcTyrRS in mammalian cells.

Demonstration of a Functional EcTyrRS/BstRNA$_{CUA}{}^{Tyr}$ Orthogonal Pair

The ability of the resulting suppressor BstRNA$_{CUA}{}^{Tyr}$/EcTyrRS pair to efficiently suppress an amber codon mutation at position Y37 of model protein green fluorescent protein, GFP (GFP37TAG) was assayed in mammalian cells. Because Y37 is located at the surface of GFP and distal from the fluorophore, the introduction of an unnatural amino acid at this position is not expected to affect the folding and fluorescent properties of the protein (Ormo et al. (1996), "Crystal structure of the *Aequorea victoria* green fluorescent protein," *Science* 273:1392-1395). Moreover, amber suppression of GFP37TAG results in expression of full-length GFP, providing a rapid qualitative assay of amber suppression efficiency. The mutant GFP37TAG gene was inserted into pcDNA4/TO/myc-His A to afford pcDNA4-GFP37TAG in which GFP is fused to myc and 6×His epitopes at C-terminus and under the control of a Tet-regulated promoter.

Figure 13A:
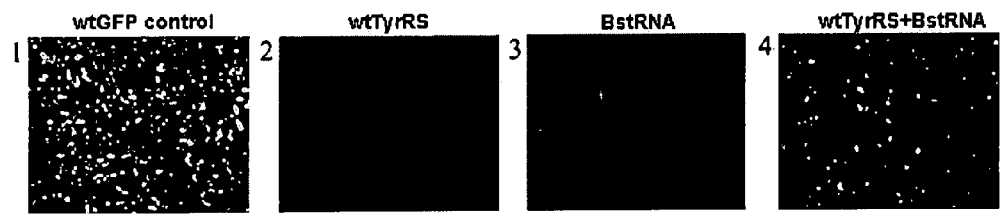
FIGS. 13A and 13B illustrate that amber suppression is dependent upon both the EcTyrRS and BstRNA$_{CUA}^{Tyr}$ genes in both Invitrogen™ T-REx™ CHO and Invitrogen™ T-REx™ 293 cells.
Figure 13B:
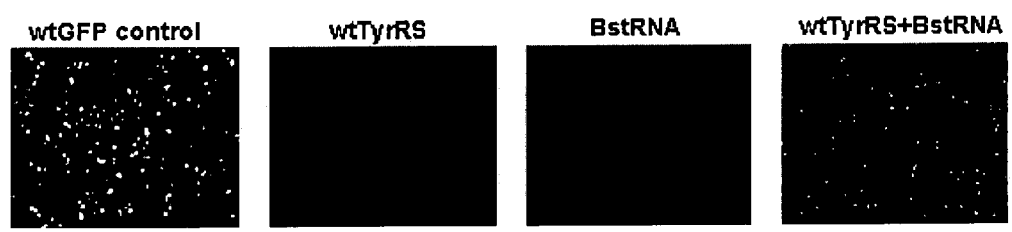

The ability of the BstRNA$_{CUA}{}^{Tyr}$/EcTyrRS pair to suppress the nonsense amber codon of GFP37TAG was examined in both Invitrogen™ T-REx™ rodent CHO and human 293 cells. Both cell lines constitutively express the tetracycline repressor and are suitable for Tet-regulated expression of proteins using the pcDNA4/TO/myc-His A plasmid. Cells were grown to 80-90% confluency (Invitrogen™ T-REx™ CHO cells were grown in F12 media containing 10% FBS, 1% Pen-Strep, 2 mM of L-glutamine, and 10 µg/ml of blasticidin; Invitrogen™ T-REx™ 293 cells were grown in DMEM containing 10% FBS, 1% Pen-Strep, 2 mM of L-glutamine, and 5 µg/ml of blasticidin) and transiently transfected with 3 µg of plasmids per 2×10$^6$ cells using FuGENE® 6 from Roche Applied Science (0.5 µg of pUC18-3BstRNA$_{CUA}{}^{Tyr}$, 0.5 µg of pcDNA4-EcTyrRS, and 2 µg of pcDNA4-GFP37TAG; pUC18-3BstRNA$_{CUA}{}^{Tyr}$ or pcDNA4-EcTyrRS was replaced with the same amount of pUC18 when they are not present). Protein expression was induced by the addition of 1 µg/ml tetracycline six hours after transfection, and cells were grown at 37° C. for two days. In both cell lines, the expression of full length GFP is dependent upon the presence of both BstRNA$_{CUA}{}^{Tyr}$ and EcTyrRS genes (see FIGS. 13A and 13B). When transfected with pcDNA4-GFP37TAG and pcDNA4-EcTyrRS or pUC18-3BstRNA$_{CUA}{}^{Tyr}$ alone, cells did not exhibit green fluorescence. These experiments demonstrate that BstRNA$_{CUA}{}^{Tyr}$ is charged only by EcTyrRS and that the BstRNA$_{CUA}{}^{Tyr}$/EcTyrRS pair can function efficiently to suppress a nonsense amber codon in primate cells and rodent cells.

Example 3

Demonstration of System Universality Using Six Unnatural Amino Acids

The generality of this orthogonal system was determined. In this test system, the ability of BstRNA$_{CUA}{}^{Tyr}$ and six EcTyrRS variants to incorporate a variety of corresponding unnatural amino acids into GFP37TAG in both Invitrogen™ T-REx™ CHO and 293 cell lines was determined. The six EcTyrRS variants were previously evolved in *S. cerevisiae* to encode the following unnatural amino acids:

p-methoxy-L-phenylalanine (pMpa)

p-acetyl-L-phenylalanine (pApa)

p-benzoyl-L-phenylalanine (pBpa)

p-iodo-L-phenylalanine (pIpa)

p-azido-L-phenylalanine (pAzpa)

p-propargyloxyphenylalanine (pPpa)

The structures of these unnatural amino acids are shown in FIG. 1; structures 1 through 6. The selection and isolation of the synthetase variants are described in, for example, Chin et al. (2003), "An expanded eukaryotic genetic code," *Science* 301:964-967; Deiters et al. (2003), "Adding amino acids with novel reactivity to the genetic code of *Saccharomyces cerevisiae*," *J Am Chem Soc* 125:11782-11783; WO 2005/003294 to Deiters et al., "UNNATURAL REACTIVE AMINO ACID GENETIC CODE ADDITIONS," filed Apr. 16, 2004; and WO 2006/034410 to Deiters et al., "ADDING PHOTOREGULATED AMINO ACIDS TO THE GENETIC CODE," filed Sep. 21, 2005.

Figure 14:
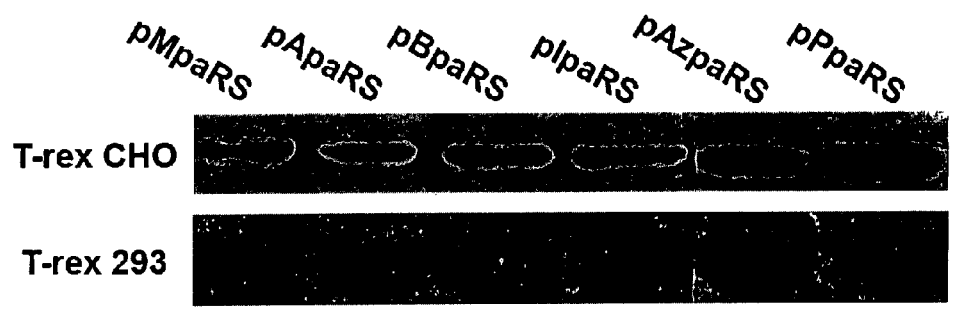
FIG. 14 provides a Western blot analysis of expression of six EcTyrRS variants in Invitrogen™ T-REx™ CHO and 293 cells. A 40 μg aliquot of the cell lysate for each reaction was analyzed with anti-c-myc antibody. The expression of EcTyrRS variants is not affected by the active site mutations. The variants express equally in both T-REx™ CHO and T-REx™ 293 cell lines.

Each of the six EcTyrRS genes was inserted into pcDNA4/TO/myc-His A to afford a pcDNA4-EcTyrRS derivative, and expression of the aaRS in T-REx™ CHO and 293 cells was verified by Western blot analysis (FIG. 14). All six EcTyrRS variants show similar expression levels in both T-REx™ CHO and T-REx™ 293 cell lines.

Figure 3:
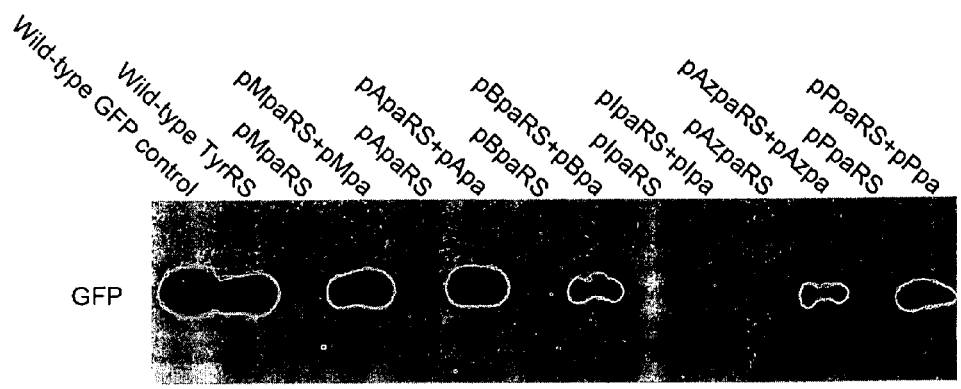
FIG. 3 shows a Western blot analysis of full-length GFP expression in Invitrogen™ T-REx™ 293 cells using orthogonal BstRNA$_{CUA}^{Tyr}$ and EcTyrRS pairs as described in FIG. 2. A 20 μg aliquot of the cell lysate for each reaction (5 μg for the control reaction) was analyzed with anti-His-HRP antibody. The reagents, concentrations of unnatural amino acids and lane designations were the same as described in FIG. 2.

The ability of the six EcTyrRS variants together with BstRNA$_{CUA}{}^{Tyr}$ to suppress the amber codon in GFP37TAG was then tested in the presence and absence of unnatural amino acids in the growth media. Transient transfection of cells with plasmids was carried out as described for wild type EcTyrRS. Six hours after transfection, the media were replaced by the fresh media containing 1 µg/ml tetracycline and supplemented with the corresponding unnatural amino acid (pMpa, 10 mM; pApa, 10 mM; pBpa, 1 mM; pIpa, 8 mM; pAzpa, 5 mM; or pPpa, 1 mM). Cells were then grown 24 hours for T-REx™ CHO cell lines and 48 hours for T-REx™ 293 cell lines before harvesting. In both T-REx™ CHO and 293 cells, the expression of full length GFP37TAG was dependent upon the presence of unnatural amino acids in the growth media as indicated in FIG. 2 and FIG. 3. In the absence of unnatural amino acids, no GFP expression (<1%) was detected, indicating that EcTyrRS variants specifically charge BstRNA$_{CUA}{}^{Tyr}$ with their cognate unnatural amino acids with high fidelity. A low expression level of GFP containing pIpa was observed in T-REx™ CHO cells and no GFP expression containing pIpa was detected in T-REx™ 293 cells, possibly due to the cellular toxicity of pIpa (in the presence of 8 mM pIpa, T-REx™ 293 cells die in 6 hours).

Example 4

Figure 4A:
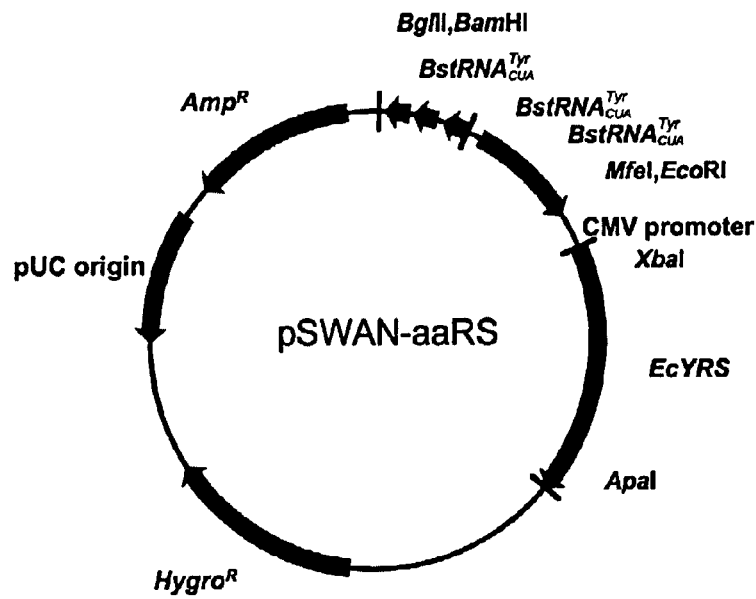
FIG. 4A provides a plasmid map of pSWAN-pMpaRS.

Improved Plasmid Expression System for the Expression of Orthogonal Components to Incorporate p-Methoxy-L-Phenylalanine Because heterologous expression of p-methoxy-L-phenylalanine-tRNA synthetase (pMpaRS) did not show any apparent cellular toxicity under the growth conditions used, the plasmid containing the pMpaRS gene was modified to encode (a) three tandem repeats of the BstRNA$_{CUA}^{Tyr}$ gene, and (b) the pMpaRS gene (pSWAN-pMpaRS in FIG. 4A).

Figure 4B:
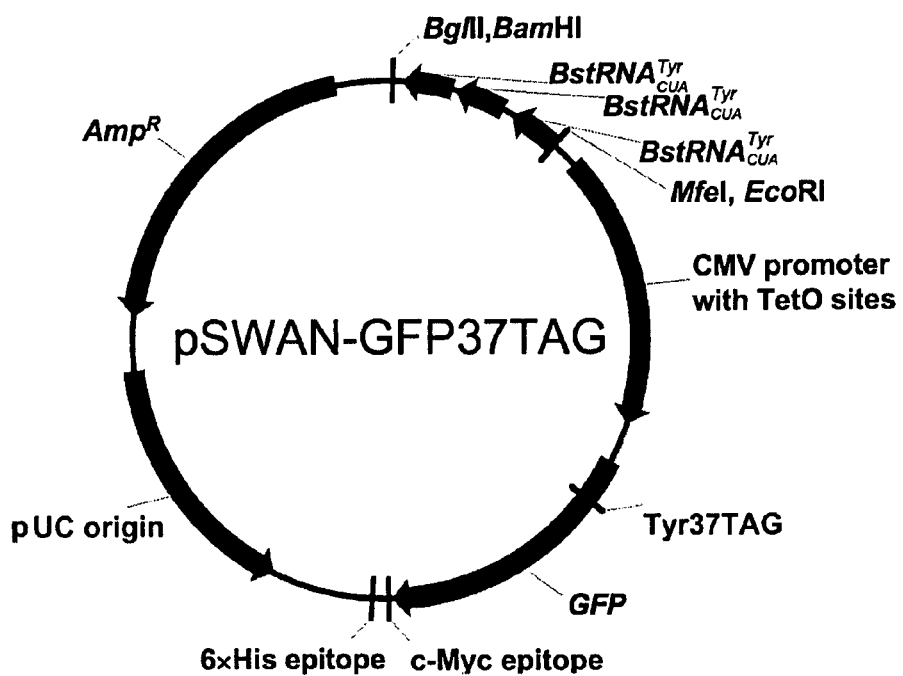
FIG. 4B provides a plasmid map of pSWAN-GFP37TAG.

The pMpaRS gene was inserted directly after the non-regulated CMV promoter for efficient and continuous expression of pMpaRS. Another plasmid (pSWAN-GFP37TAG in FIG. 4B) containing both three tandem repeats of the BstRNA$_{CUA}^{Tyr}$ gene and the GFP37TAG gene was also constructed. The gene encoding GFP37TAG was inserted after a Tet-regulated CMV promoter to minimize potential read-through of the nonsense amber codon caused by endogenous amber suppression in mammalian cells. These two plasmids were then assayed for their suppression efficiency. Because both plasmids contain three tandem repeats of the BstRNA$_{CUA}^{Tyr}$ gene, varying the ratio of the two plasmids to increase the suppression level is not expected to change the total amount of the BstRNA$_{CUA}^{Tyr}$ gene transfected into cells. Under optimized transfection conditions (0.5 µg of pSWAN-pMpaRS and 2.5 µg pSWAN-GFP37TAG per 2×10$^6$ cells), the suppression level is roughly two-fold higher than that using the three plasmids pUC18-3BstRNA$_{CUA}^{Tyr}$, pcDNA4-pMpaRS, and pcDNA4-GFP37TAG (the suppression level was determined by the number of fluorescent cells). Cells were grown for 1-2 days after induction and kept viable before harvesting. The yield of mutant GFP containing pMpa (GFP-pMpa) was also quantified. In the presence of 10 mM pMpa in the growth media, 1 µg of mutant GFP can be obtained from 2×10$^7$ adhesive T-REx™ CHO cells.

Example 5

Mass Spectroscopy and Fidelity Analysis

To further characterize GFP-pMpa, the mutant protein was expressed in T-REx™ CHO cells transiently transfected with both pSWAN-pMpaRS and pSWAN-GFP37TAG. The protein was purified using an anti-myc antibody agarose column and then separated by SDS-PAGE. The GFP-pMpa band from the SDS-PAGE gel was digested with trypsin and analyzed by nanoscale reversed-phase liquid chromatography/mass spectrometry/mass spectrometry (nano-RP LC/MS/MS). In parallel, wild type GFP was purified from cells transfected with pcDNA4-GFP and subjected to the same analysis.

Figure 5:
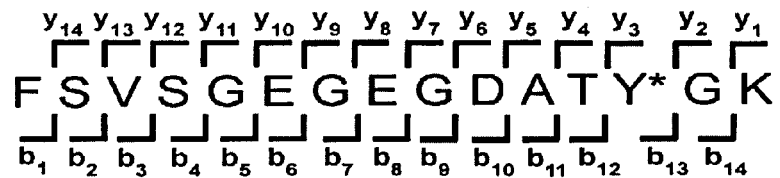
FIG. 5 provides the amino acid sequence of the wild type GFP and GFP-pMpa peptides. Y* denotes tyrosine in wild type GFP or pMpa in GFP-pMpa. The y- and b-type ions generated during fragmentation of the peptide FSVSGEGEGDATY*GK (SEQ ID NO: 103) are shown.
Figure 6:
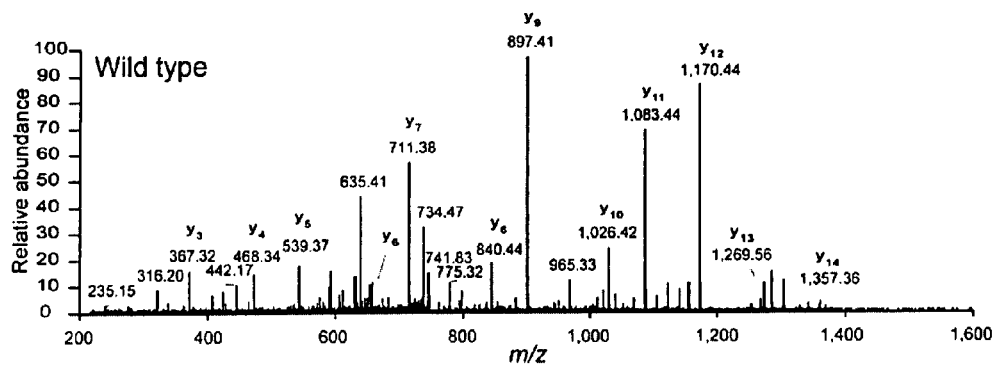
FIG. 6 provides an annotated tandem MS spectra of the wild type GFP peptide FSVSGEGEGDATY*GK (SEQ ID NO: 103) provided in FIG. 5. For comparison and clarity, only the abundant Y*-ion series are annotated as well as the $b_{13}$ ion that locates pMpa unambiguously at position 37. Proteins were purified by anti-myc affinity column and analyzed by SDS-PAGE. The GFP bands were excised for the MS analysis.
Figure 7:
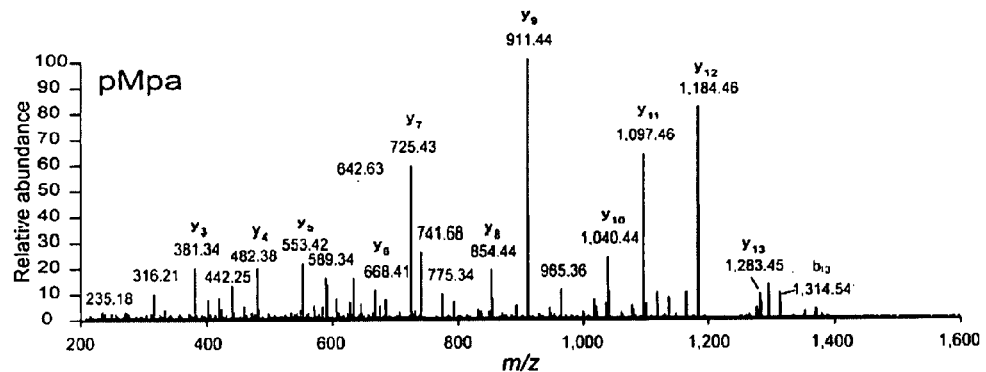
FIG. 7 provides an annotated tandem MS spectra of the FSVSGEGEGDATY*GK (SEQ ID NO: 103) peptide from GFP-pMpa. Tandem MS spectra of the Y*-ion series exhibit the expected mass shift of 14 Da.

The tandem mass spectra of the tryptic Y37 containing fragments of:

```
FSVSGEGEGDATY*GK   (see FIG. 5 and SEQ ID NO: 103)
``` where Y* denotes either tyrosine or pMpa from the mutant protein reveals intense pMpa peaks, indicating efficient incorporation of pMpa (see FIG. 6 and FIG. 7). The Y* containing ions ($y_3$ to $y_{14}$) all have a mass shift of 14 Da in comparison to wild type GFP, which matches exactly the mass difference between tyrosine and pMpa. The mass shift of y ion series together with the observation of an identical mass shift of the $b_{13}$ ion in FIG. 7 unambiguously assigns the site of pMpa incorporation to position 37 of GFP.

Figure 8:
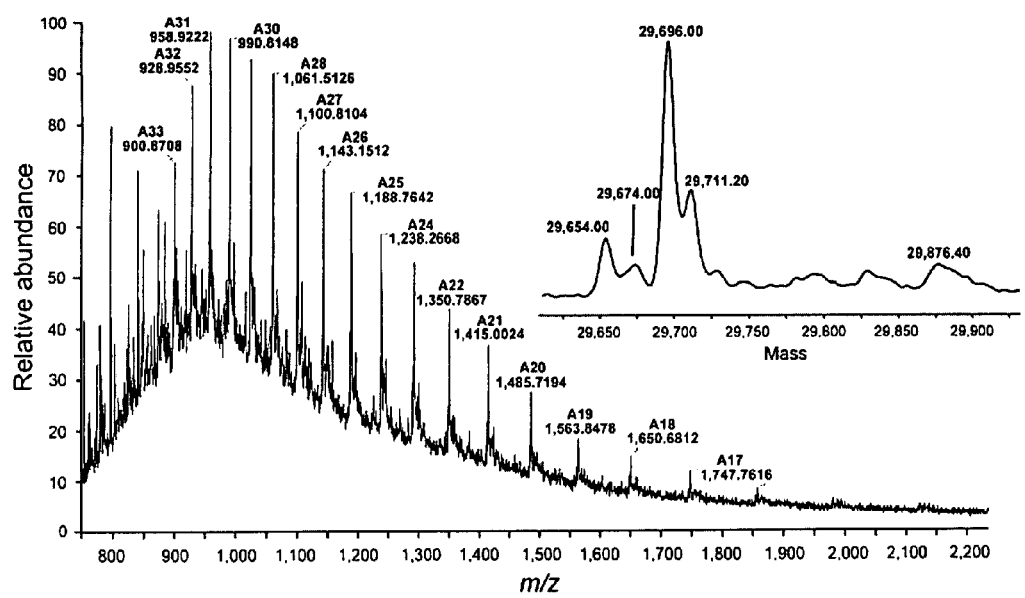
FIG. 8 provides an intact protein ESI TOF-MS spectrum of affinity purified GFP-pMpa. The deconvoluted charge state envelope (shown in the figure insert) shows one major component of 29696 Da, which matches the expected mass of the modified protein minus the N-terminal methionine and plus acetylation (theoretical mass 29696.52) within experimental error. The smaller feature at 29654 Da is assigned to GFP-pMpa minus the N-terminal methionine. The two side bands are likely due to nonspecific modification.
Figure 9:
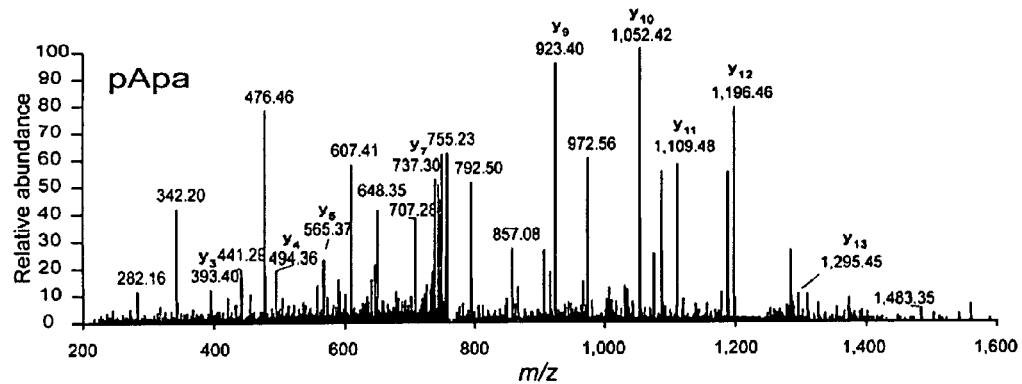
FIG. 9 provides a tandem MS spectra of mutant GFP containing pApa. The Y*-ions exhibit a 26 Da mass shift with respect to the same ions in the spectrum of wild type GFP.
Figure 10:
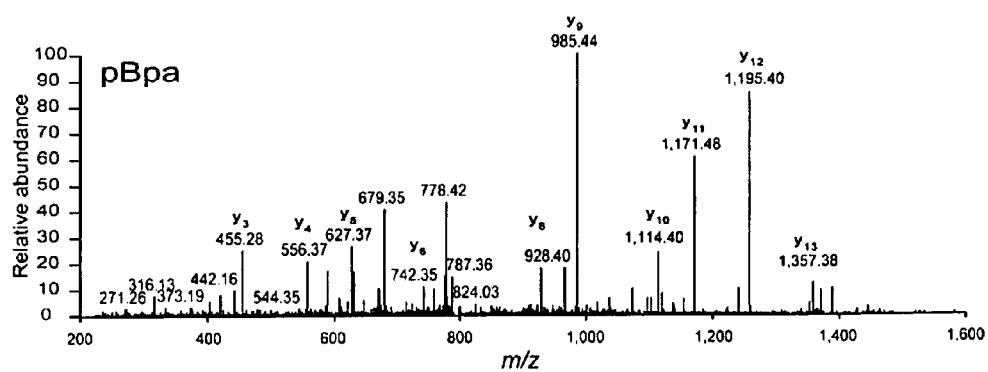
FIG. 10 provides a tandem MS spectrum of mutant GFP containing pBpa. The characteristic mass shift of 86 Da between mutant GFP and wild type GFP is clearly observed.
Figure 11:
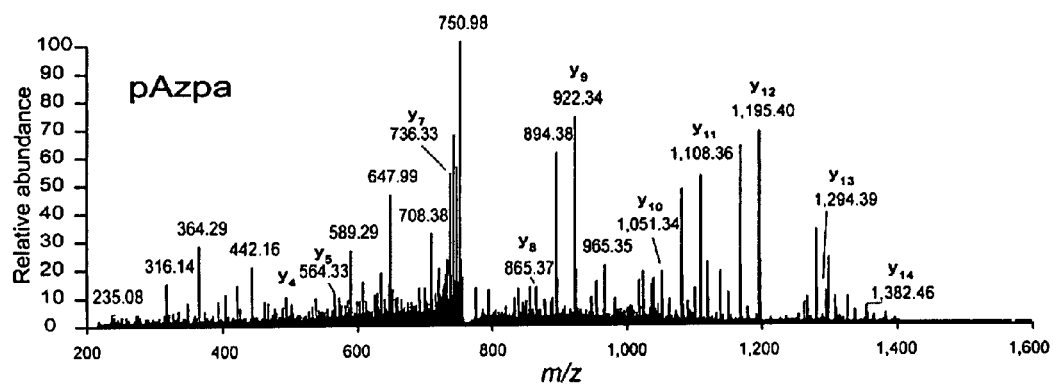
FIG. 11 provides a tandem MS spectrum of mutant GFP containing pAzpa. Most of pAzpa decays to pAmpa (p-aminophenylalanine; see FIG. 15 for tandem MS spectra of tryptic pAmpa containing fragment). However, the characteristic mass shift of 25 Da of Y*-ions in comparison to signals of wild type GFP is still clearly observed.
Figure 12:
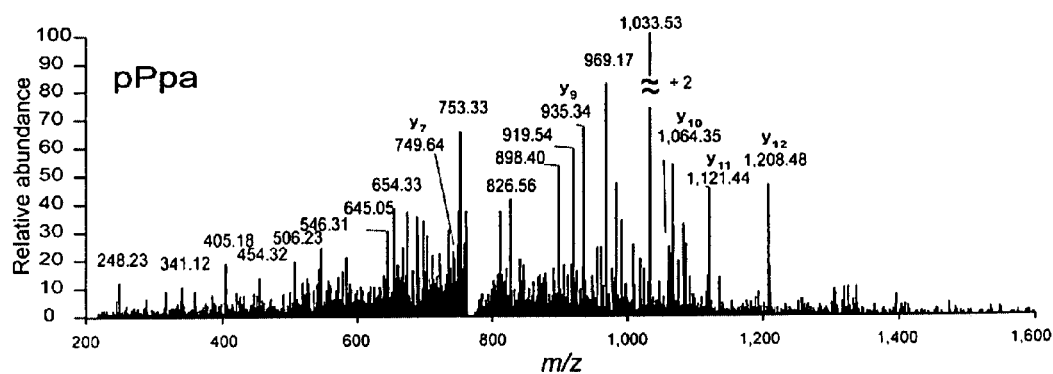
FIG. 12 provides a tandem MS spectrum of mutant GFP containing pPpa. The signals of the pPpa fragment are largely swamped by background. Despite this, it is still identified with good discrimination by database searching of the spectrum against MSDB. The stronger Y*-ions are observed with a characteristic mass shift of 38 Da.

The ratios of the MS peaks of pMpa containing peptides to those of tyrosine containing peptides were also obtained. Integration of the single ion chromatograms of the precursor ions of:

```
FSVSGEGEGDATY*GK   (see FIG. 5 and SEQ ID NO: 103)
``` suggests high fidelity for incorporation of pMpa (>99.9%). An estimate based on monitoring the three most abundant fragment ions ($y_9$, $y_{11}$, and $y_{12}$) in the tandem MS data suggests an even greater purity (99.93%). To acquire the masses of the parent protein, the mutant protein purified by anti-myc antibody column was subjected to analysis with ESI TOF-MS. The theoretical mass of the acetylated mutant protein missing the N-terminal methionine is 29,696.00 Da, which is in good agreement with the major component of 29,696.0 Da observed in the charged-state deconvoluted ESI TOF-MS spectrum in FIG. 8. A smaller feature at 29,654.0 Da is assigned to the mass of GFP-pMpa lacking N-terminal acetylation. No wild type GFP signals or signals indicating incorporation of multiple pMpas were detected. This result further confirms the selective incorporation of pMpa at position 37 of GFP.

Example 6

Improved Plasmid Expression Systems for the Expression of Orthogonal Components that Incorporate pApa, pBpa, pIpa, pAzpa and pPpa Plasmids were reengineered to afford other pSWAN-EcTyrRS variant two-plasmid systems by subcloning the genes that encode the various synthetase variants. These synthetase variants were as follows:

p-acetyl-L-phenylalanine-tRNA synthetase (pApaRS)

p-benzoyl-L-phenylalanine-tRNA synthetase (pBpaRS)

p-iodo-L-phenylalanine-tRNA synthetase (pIpaRS)

p-azido-L-phenylalanine-tRNA synthetase (pAzpaRS)

p-propargyloxyphenylalanine-tRNA synthetase (pPpaRS)

Transient transfection of T-REx™ CHO and 293 cells with the pSWAN-EcTyrRS variants and pSWAN-GFP37TAG (0.5 µg of pSWAN-EcTyrRS variant and 2.5 µg of pSWAN-GFP37TAG per 2×10$^6$ cells) all afforded roughly two-fold higher suppression levels than for the three plasmids pUC18-3BstRNA$_{CUA}^{Tyr}$, pcDNA4-EcTyrRS variant, and pcDNA4-GFP37TAG (with the exception of the pIpa specific variant). Mutant GFPs containing pApa, pBpa, pAzpa or pPpa were also expressed in T-REx™ CHO cells transfected with the pSWAN-EcTyrRS variants and pSWAN-GFP37TAG and grown in media containing the corresponding unnatural amino acid (pApa, 10 mM; pBpa, 1 mM; pAzpa, 5 mM; or pPpa, 1 mM) for 1-2 days, and purified using an anti-myc antibody column. The yields of the mutant proteins containing pApa and pAzpa were close to that for pMpa (~1 µg per 2×10$^7$ cells), and the yields of mutant proteins containing pBpa and pPpa were somewhat lower (~0.7 µg per 2×10$^7$ cells). Because the expression levels of EcTyrRS variants in T-REx™ CHO cells are similar, the lower yield of the mutant proteins containing pBpa and pPpa may be due to the low concentrations of unnatural amino acids in the media.

The mutant GFP proteins were also subjected to analysis with nano-RP LC/MS/MS to obtain tandem MS of the tryptic fragments of:

FSVSGEGEGDATY*GK.    (FIG. 5 and SEQ ID NO: 103)

Figure 15:
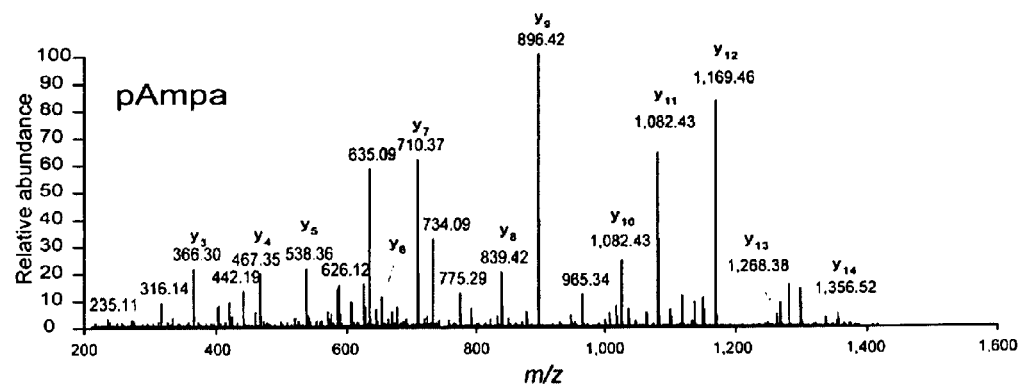
FIG. 15 provides an annotated tandem MS spectra of the peptide FSVSGEGEGDATY*GK (SEQ ID NO: 103) from mutant GFP containing pAzpa. Y* denotes pAmpa (p-aminophenylalanine). For clarity only the Y*-ion series is annotated. Most of the pAzpa decayed to pAmpa as the signal strength for the pAzpa peptide is quite weak (see FIG. 11) and the detectable mass 1 Da mass difference between fragments of wild type GFP and those of mutant GFP containing pAzpa.

Tandem MS data (FIGS. 9-12) clearly showed the incorporation of the unnatural amino acids at position 37 of GFP. The mutant GFP containing pAzpa was only weakly detectable. A closer look at the data revealed the presence of the p-aminophenylalanine (pAmpa) containing peptide instead (FIG. 15), which is not surprising considering the chemical reactivity and photo-instability of the azido group (pAmpa has previously been observed from MS analysis of pAzpa containing peptides; Chin et al. (2003), "Progress toward an expanded eukaryotic genetic code," Chem Biol 10, 511-519). A trace amount of the wild type peptide in the pBpa sample was identified, but the signals were too weak for accurate quantitation of the pBpa/tyrosine ratio. No wild type signals could be detected in the pApa, pAzpa, and pPpa samples. The data from all five mutant proteins indicate the high selectivity and fidelity of the incorporation of unnatural amino acids.

Example 7

Discussion/Conclusions

In the mammalian genome, the occurrence of amber stop codons is higher (23% in humans), in comparison to E. coli (7%). Therefore, amber suppression might be toxic to cells if essential proteins are not terminated correctly. Yokoyama and coworkers showed that inducible expression of the mutant EcTyrRS that charges its cognate tRNA with 3-iodo-L-tyrosine minimizes possible cellular toxicity resulting from background incorporation of endogenous tyrosine by the mutant aaRS in the absence of 3-iodo-L-tyrosine. The present invention described herein provides a solution to this problem. All EcTyrRS variants were previously evolved from a two-step positive/negative selection scheme in S. cerevisiae, which removes aaRS variants that incorporate endogenous amino acids. Cotransfection of cells with a pSWAN-EcTyrRS variant and pSWAN-GFP37TAG did not lead to observable read-through of the nonsense amber codon in GFP37TAG in the absence of unnatural amino acids, suggesting that the tRNA/aaRS pairs do not efficiently suppress natural TAG stop codons in the absence of unnatural amino acids. Cell lines stably expressing tRNA and aaRS proteins should therefore be viable in the absence of unnatural amino acids. Since there is no endogenous amber suppression observed, the expression of the target protein containing unnatural amino acids also does not require induction. Creation of stable cell lines maintaining the tRNA, aaRS, and target protein genes will allow efficient production of the target protein containing the unnatural amino acid when cells are supplemented with the unnatural amino acid. In the presently described proof-of-principle experiments, the host mammalian cells survived three days after the addition of unnatural amino acids, which is likely sufficient for recombinant protein expression.

These studies have successfully been extended to other unnatural amino acids, including 1,5-danyslalanine, o-nitrobenzylcysteine and α-aminocaprylic acid. It is not intended that the invention be limited to the cell lines or unnatural amino acids described herein.

Example 8

Photoregulated Protein Sequences in Mammalian Cells

In some embodiments of the claimed translation systems and methods, the unnatural amino acid is a photoregulated amino acid, such as o-nitrobenzylserine, o-nitrobenzylcysteine, α-aminocaprylic acid, and the like. Photoregulated amino acids (e.g., photochromic, photocleavable, photoisomerizable, etc.) can be used to spatially and temporally control a variety of biological process, e.g., by directly regulating the activity of enzymes, receptors, ion channels or the like, or by modulating the intracellular concentrations of various signaling molecules. See, e.g., Shigeri et al., *Pharmacol. Therapeut.*, 2001, 91:85+; Curley, et al., *Pharmacol. Therapeut.*, 1999, 82:347+; Curley, et al., *Curr. Op. Chem. Bio.*, 1999, 3:84+; "Caged Compounds" *Methods in Enzymology*, Marriott, G., Ed, Academic Press, NY, 1998, V. 291; Adams, et al., *Annu. Rev. Physiol.*, 1993, 55:755+; and Bochet, et al., *J. Chem. Soc., Perkin* 1, 2002, 125+.

To increase the transcription level of Amber suppressor tRNA derived from E. coli tRNALeu, the suppressor tRNA was put under control of 5'- and 3'-flanking sequence of human initiator tRNA$^{Met}$. The over transcribed Amber suppressor tRNA together with a mutant E. coli leucyl-tRNA synthetase specific for o-nitrobenzylcysteine was used to site-specifically incorporate this unnatural amino acid into a human procaspase-3 active site in Chinese Hamster Ovary cells and human 293T cells. The expression of the protein in the presence of o-nitrobenzylcysteine followed by exposure of the cells to UV light for 5 min triggered cell death, indicating that UV light induced cleavage of the nitrobenzyl group from the unnatural cysteine residue and recovered the activity of procaspase-3, which triggered cell apoptosis.

This experiment confirms that the selective substitution of active site cysteine with o-nitrobenzylcysteine in a protein in living mammalian cells can be used, for example, to spatially control the protein activity by using, e.g., UV light. Similar results can be obtained for proteins with different reactive site groups (for example, employment of o-nitrobenzylserine in the active site residues of serine proteases). Further details regarding photocaged or photoregulated amino acids can be found in PCT publication WO 2006/034410 by Dieters et al. (Mar. 30, 2006), titled "Adding Photoregulated Amino Acids to the Genetic Code," the contents of which are incorporated herein in their entirety.

Example 9

Materials and Methods: Mammalian Cell Transfection and Western Blot Analysis

Both T-REx™ CHO and T-REx™ 293 cells (Invitrogen™) constitutively express the tetracycline repressor, which regulates the expression of genes inserted into the pcDNA4/TO/myc-His A plasmid. T-REx™ CHO cells were grown in F-12 (Invitrogen™), 10% FBS (Invitrogen™), 1% Pen-Strep (Invitrogen™), 2 mM L-glutamine (Invitrogen™), and 10 µg/ml blasticidin (Invitrogen™) at 37° C. in a humidified atmosphere of 5% $CO_2$; T-REx™ 293 cells were grown in Gibco D-MEM media (Invitrogen™), 10% FBS, 1% Pen-Strep, 2 mM L-glutamine, and 5 µg/ml blasticidin at 37° C. in a humidified atmosphere of 5% $CO_2$. Cells were grown to 80-90% confluency in Costar® 6-well cell culture clusters and then transfected with plasmids using FuGENE® 6 (Roche Applied Science) (9 µl FuGENE®+3

μg plasmids). Six hours after transfection, the media were replaced by fresh media that contained 1 μg/ml of tetracycline.

To test amber suppression of EcTyrRS variants in the presence of their corresponding unnatural amino acids, the unnatural amino acids were also added to the fresh media. The concentrations of unnatural amino acids in the media were 10 mM for pMpa (Bachem, Inc), 10 mM for pApa (Synchem, Inc); 1 mM for pBpa (Bachem, Inc), 8 mM for pIpa (Bachem, Inc), 5 mM for pAzpa (Bachem, Inc), and 1 mM for pPpa. Chiral pure pPpa was synthesized as described previously (Deiters et al. (2003), "Adding amino acids with novel reactivity to the genetic code of *Saccharomyces cerevisiae*," *J Am Chem Soc* 125:11782-11783). T-REx™ CHO cells were grown for 24 hours after addition of tetracycline and then harvested; T-REx™ 293 cells were harvested after 48-hour incubation.

For Western blot analysis, harvested cells were lysed in RIPA buffer (Upstate Biotechnology/Millipore) with a 1:100 dilution of protease inhibitor cocktail (Sigma). The supernatant was fractionated by SDS-PAGE under denatured condition and transferred to a 0.45 μm nitrocellulose membrane (Invitrogen™). For T-REx™ CHO cells, the proteins immobilized on the membrane were probed with anti-myc antibody (Invitrogen™; 1:5000 dilution) as the primary antibody and anti-mouse IgG-HRP (Invitrogen™) as the secondary antibody. Chemiluminescence was then detected with PIERCE ECL Western Blotting substrate. For T-REx™ 293 cells, the membranes were probed with anti-His-HRP (Invitrogen™; 1:5000 dilution) and then detected with PIERCE ECL Western Blotting substrate.

Materials and Methods: Bacterial Cell Transfection

Top 10 *E. coli* cells (Invitrogen™) were used for cloning, maintaining, and amplifying plasmids. Pfx high-fidelity DNA polymerase (Invitrogen™) was used for polymerase chain reaction (PCR). FuGENE® 6 (Roche Applied Science) was used as the transfection reagent. All plasmids were verified by sequencing.

Example 10

Materials and Methods: Plasmid Constructions pUC18-3BstRNA$_{CUA}^{Tyr}$

The BstRNA$_{CUA}^{Tyr}$ gene was constructed by annealing four oligodeoxynucleotides (Integrated DNA Technologies, Inc). The gene consists of the corresponding tRNA sequence lacking the 3'-CCA and the 5'-flanking sequence of the human tRNA$^{Tyr}$ gene:

```
                                       (SEQ ID NO: 104)
AGCGCTCCGGTTTTCTGTGCTGAACCTCAGGGGACGCCGACACACGTAC

ACGTC
```

Two restriction sites—EcoRI at the 5'-end and BamHI at the 3'-end, were incorporated into the synthetic DNA duplex, which was then inserted into pUC18 to afford pUC18-BstRNA$_{CUA}^{Tyr}$. The BstRNA$_{CUA}^{Tyr}$ gene in pUC-BstRNA$_{CUA}^{Tyr}$ was then amplified by PCR. The amplified BstRNA$_{CUA}^{Tyr}$ containing a BglII restriction site at the 5'-end and a BamHI site at the 3'-end was inserted into the BamHI restriction site of pUC18-BstRNA$_{CUA}^{Tyr}$ to afford pUC18-2BstRNA$_{CUA}^{Tyr}$. The plasmid pUC18-2BstRNA$_{CUA}^{Tyr}$ only contains one BamHI restriction site that was used to incorporate another copy of BstRNA$_{CUA}^{Tyr}$ to afford pUC18-3BstRNA$_{CUA}^{Tyr}$. EcTyrRS and its six variants were all amplified from pEcTyrRS/tRNA$_{CUA}$ (Chin et al. (2003), "An expanded eukaryotic genetic code," *Science* 301:964-967) by PCR and then inserted into the XbaI and ApaI sites of the pcDNA4/TO/myc-His A plasmid (Invitrogen™) to afford the pcDNA4-EcTyrRS vectors. EcTyrRS genes were placed after two tetracycline operator sequences and the CMV promoter, which confer the tetracycline regulated gene expression in Invitrogen™ T-REx™ cell lines. They were also linked to a c-myc epitope for Western blot analysis. The mutations in six EcTyrRS variants were:

pMpaRS: Y37V/D182S/F183M
pApaRS: Y371/D182G/F183M/L186A
pBpaRS: Y37G/D182G/F183Y/L186M
pIpaRS: Y371/D183S/F183M
pAzpaRS: Y37L/D182S/F183M/L186A
pPpaRS: Y37S/D182T/F183M/L186V pcDNA4-EcTyrRS and pcDNA4-GFP37TAG pcDNA4-GFP was created by inserting wild type enhanced GFP gene into the XbaI and ApaI sites of vector pcDNA4/TO/myc-His A. In pcDNA4-GFP, the GFP gene was ligated with a myc epitope and 6×His tags at the C-terminus for Western blot analysis and affinity purification of the expressed protein. The plasmid pcDNA4-GFP37TAG, in which the triple codon of Y37 is mutated to TAG amber codon, was generated by a QuikChange® site-directed mutagenesis kit (Stratagene).

pSWAN-EcTyrRS Variants and pSWAN-GFP37TAG

To construct pSWAN-EcTyrRS variants, 3BstRNA$_{CUA}^{Tyr}$ was isolated from pUC18-3BstRNA$_{CUA}^{Tyr}$ using BamHI and EcoRI restriction enzymes and inserted into the BglII and MfeI sites of pcDNA3.1/hygro (+) (Invitrogen™) to afford pcDNA-3BstRNA$_{CUA}^{Tyr}$. The genes encoding the six EcTyrRS variants were then inserted into the XbaI and ApaI sites of pcDNA-3BstRNA$_{CUA}^{Tyr}$ to afford pSWAN-EcTyrRS variants. To create pSWAN-GFP37TAG, a pSWAN-EcTyrRS vector was amplified and digested with the MluI and PciI restriction enzymes. The digested fragments were separated by agarose gel electrophoresis and the fragment containing 3BstRNA$_{CUA}^{Tyr}$ was purified by QIAquick® gel purification kit (QIAGEN®). The pcDNA4-GFP37TAG fragment from the CMV promoter to the BGH polyA site were amplified by PCR, digested with the MluI and PciI restriction enzymes, and then ligated with the pSWAN-EcTyrRS fragment containing 3BstRNA$_{CUA}^{Tyr}$ to afford pSWAN-GFP37TAG (~4000 bp).

Example 11

Materials and Methods: Protein Expression and Purification pSWAN-EcTyrRS variants and pSWAN-GFP37TAG were used to express mutant GFPs containing unnatural amino acids. T-REx™ CHO cells (Invitrogen™) were grown in 75 cm$^2$ tissue culture flasks (BD Biosciences) to 80-90% confluency and transfected with 2 μg of pSWAN-EcTyrRS and 10 μg pSWAN-GFP37TAG using 601 FuGENE® 6. After overnight incubation, the media were changed to the fresh media containing the unnatural amino acid (pMpa, 10 mM; pApa, 10 mM; pBpa, 1 mM; pAzpa, 5 mM; and pPpa, 1 mM) and 1 μg/ml tetracycline. Cells were then grown for 1-2 days at 37° C. before harvesting, and then lysed with RIPA lysis buffer. The supernatant from the cell lysate was dialyzed against and equilibrated with PBS buffer before loading onto an anti-myc antibody agarose column (Sigma). The column was washed with 15 column volumes of PBS buffer and then eluted with 0.1 M ammonium hydroxide. The purified proteins were neutralized with 0.1 M acetic acid and analyzed by SDS-PAGE. The bands corresponding to GFP were excised for mass spectrometric analysis. To determine the yield and acquire intact protein mass spectra, the protein was concentrated to ~0.1 mg/ml after elution.

Example 12

Materials and Methods: Proteolysis

Proteolysis of affinity purified proteins (performed for wild-type and pBpa samples) was carried out by overnight incubation of proteins at 37° C. with sequencing-grade modified trypsin (Promega) using a substrate/enzyme ratio of 10:1 (wt/wt) based on the estimated protein concentration in 100 mM triethylammonium bicarbonate buffer (pH 8.5). In-gel digestions (performed for pMpa, pAzpa, pApa, and pPpa samples) were performed according to a modified EMBL procedure (see the website for EMBL, Heidelberg, Germany, Bioanalytical Research Group). Briefly, gel slices were excised to approximately 1 mm×1 mm cubes, washed for 5 minutes with water, 15 minutes with acetonitrile, and dried in a vacuum centrifuge before being rehydrated at 0° C. for 30 minutes with 12.5 ng/μl of sequencing-grade modified trypsin in 50 mM triethylammonium bicarbonate buffer (pH 8.5). Excess buffer was removed and 20 μl of 50 mM triethylammonium bicarbonate buffer (pH 8.5) was added to the gel slices before incubating at 37° C. overnight. Peptides were extracted from the gel slices as described in the protocol.

Example 13

Materials and Methods: Nano-RP LC/MS/MS

Nano-RP LC/MS/MS was performed with an HPLC pump, autosampler (Agilent Technologies, Palo Alto, Calif.), and an LTQ Orbitrap hybrid mass spectrometer (ThermoElectron, San Jose, Calif.). Tryptic digests were loaded with a pressure bomb onto a 75 μm i.d. precolumn packed with 4 cm of 5-μm Monitor C18 particles (Column Engineering, Ontario, Calif.) at a flow rate of approximately 2 μl/min. The precolumn was then connected to the HPLC pump and after several minutes of washing with solvent A the analytical column with integrated emitter tip (360 μm O.D.×75 μm i.d; 10 cm of 5 μM C18, ~5-μm tip) was connected in series. The chromatographic profile was from 100% solvent A (0.1% aqueous acetic acid) to 50% solvent B (0.1% acetic acid in acetonitrile) in 40 min; the flow rate through the analytical column was ca. 100 nl/min.

For data-dependent experiments, the mass spectrometer was programmed to first record a high-resolution Orbitrap scan then a full-scan ion trap spectrum (m/z 500-2,000). This was followed by 10 data-dependent MS/MS scans (relative collision energy=35%; 3-Da isolation window) triggered of the ion-trap scan and finally two targeted MS/MS scans. The first targeted MS/MS scan was set to isolate and fragment the doubly charged precursor ion of the predicted unnatural amino acid modified peptide (FSVSGEGEGDATY*GK; SEQ ID NO: 103).

The second targeted MS/MS scan was always set to isolate and fragment the doubly-charge precursor ion of the wild-type peptide:

(FSVSGEGEGDATYGK; SEQ ID NO: 102)

at m/z 752.3. The raw data were searched against the MSDB database using MASCOT (Matrixscience, London, UK) for protein identification and to find the scans containing the target peptides with the unnatural amino acids as variable modification. To estimate fidelity at Y*37 of GFP-pMpa, single ion chromatograms (doubly charged precursor ions at m/z 752.3 for the wt and 759.3 for pMpa) and selected ion chromatograms ($y_9$, $y_{11}$, and $y_{12}$) were integrated using the Xcalibur software package (ThermoElectron, San Jose, Calif.).

Intact protein mass spectra were acquired on an automated LC/MS system (Waters, Milford, Mass.) consisting of a capillary LC with auto-sampler and a QTOF2 mass spectrometer. GFP-pMpa (0.1 mg/ml) was loaded onto a reversed-phase protein Captrap (Michrom Bioresources, Auburn, Calif.) for desalting with 0.1% acetic acid in water and eluted with 80% acetonitrile/0.1% acetic acid at 5 μl/min into the ESI source of the mass spectrometer. Summing, smoothing, and deconvolution of the spectra with the MaxEnt1 algorithm were performed using the MassLynx (Waters, Milford, Mass.) software package.

Example 14

Promoters for Mammalian Transcription

Strong promoters for tRNA transcription in mammalian cells include 5' flanking sequence for the *E. coli* suppressor tRNA$^{Leu5}$(CUA) GATCCGACCGTGTGC TTGGCAGAAC (SEQ ID NO: 105) and 3' flanking sequence GTCCTTTTTTTG (SEQ ID NO: 106) for the *E. coli* suppressor tRNA$^{Leu5}$(CUA).

While the foregoing invention has been described in some detail for purposes of clarity and understanding, it will be clear to one skilled in the art from a reading of this disclosure that various changes in form and detail can be made without departing from the true scope of the invention. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A translation system comprising:
(a) a first unnatural amino acid selected from the group consisting of:
   i) p-methoxyphenylalanine (pMpa);
   ii) p-acetylphenylalanine (pApa);
   iii) p-benzoylphenylalanine (pBpa);
   iv) p-iodophenylalanine (pIpa);
   v) p-azidophenylalanine (pAzpa);
   vi) p-propargyloxyphenylalanine (pPpa);
   vii) α-aminocaprylic acid;
   viii) o-nitrobenzylcysteine (o-NBC);
   ix) 1,5-dansylalanine; and
   x) o-nitrobenzylserine (o-NBS);
(b) a first orthogonal tRNA (O-tRNA) derived from a *Bacillus stearothermophilus* tRNA wherein the O-tRNA is a suppressor O-tRNA and wherein the O-tRNA comprises or is encoded by the polynucleotide sequence set forth in SEQ ID NO: 3;
(c) a first orthogonal aminoacyl-tRNA synthetase (O-RS) derived from an *Escherichia coli* aminoacyl-tRNA synthetase, wherein said O-RS preferentially aminoacylates said first O-tRNA with said unnatural amino acid when in the presence of both said unnatural amino acid and a natural amino acid, wherein said O-RS does not aminoacylate said first O-tRNA with an endogenous amino acid in the absence of said unnatural amino acid, and wherein the first O-tRNA recognizes a selector codon present in a nucleic acid encoding a polypeptide of interest and wherein the first O-RS comprises an amino acid sequence selected from the group of amino acid sequences set forth in SEQ ID NOS: 57-101, and conservative variants thereof, which conservative variants are at least 90% identical to an amino acid sequence selected from the group of SEQ ID NOS: 57-101 and preferentially aminoacylate said first O-tRNA with said first unnatural amino acid with an efficiency that is at least 50% of the efficiency observed for a translation system comprising said first O-tRNA, said unnatural amino acid, and an aminoacyl-tRNA synthetase comprising an amino acid sequence selected from SEQ ID NOS: 57-101; and,
(d) a host cell comprising (a), (b) and (c),
   wherein the host cell is a rodent cell or a primate cell, and wherein at least 0.7 µg of the polypeptide of interest comprising the unnatural amino acid is obtained from 2 ×10$^7$ host cells.

2. The translation system of claim 1, wherein said host cell further comprises a nucleic acid encoding a protein of interest, said nucleic acid comprising at least one selector codon, wherein said selector codon is recognized by said first O-tRNA.

3. The translation system of claim 2, wherein said host cell further comprises a second unnatural amino acid that is different from the first unnatural amino acid, a second O-RS and a second O-tRNA, wherein the second O-RS preferentially aminoacylates the second O-tRNA with the second unnatural amino acid, and wherein the second O-tRNA recognizes a selector codon encoded by the nucleic acid that is different from the selector codon recognized by the first O-tRNA.

4. The translation system of claim 1, wherein said host cell comprises a polynucleotide encoding said first O-RS.

5. The translation system of claim 4, wherein said polynucleotide comprises a nucleotide sequence selected from the nucleotide sequences set forth in SEQ ID NOS: 8-56.

6. The translation system of claim 1, wherein said host cell comprises a polynucleotide encoding said first O-tRNA.

7. The translation system of claim 1, wherein said rodent host cell is selected from a rat host cell and a mouse host cell.

8. The translation system of claim 1, wherein said primate host cell is selected from the group consisting of human host cell, chimpanzee host cell, bonobo host cell, gorilla host cell, orangutan host cell, gibbon host cell, macaque host cell, tamarin host cell and marmoset host cell.

9. The translation system of claim 1, wherein said rodent host cell is a CHO host cell.

10. The translation system of claim 1, wherein said primate host cell is a 293T host cell.

\* \* \* \* \*

UNITED STATES PATENT AND TRADEMARK OFFICE
CERTIFICATE OF CORRECTION

PATENT NO. : 9,624,485 B2
APPLICATION NO. : 12/311545
DATED : April 18, 2017
INVENTOR(S) : Liu et al.

Page 1 of 1

It is certified that error appears in the above-identified patent and that said Letters Patent is hereby corrected as shown below:

On the Title Page

Column 1, Lines 16-22, the paragraph STATEMENT AS TO RIGHTS OF INVENTIONS MADE UNDER FEDERALLY SPONSORED RESEARCH AND DEVELOPMENT should be changed to:
-- STATEMENT OF GOVERNMENT LICENSE RIGHTS
This invention was made with government support under grant number GM062159 awarded by the National Institutes of Health. The government has certain rights in the invention. --

Signed and Sealed this
Seventh Day of April, 2020

Andrei Iancu
*Director of the United States Patent and Trademark Office*